US012370195B2

(12) United States Patent
Smith et al.

(10) Patent No.: US 12,370,195 B2
(45) Date of Patent: **\*Jul. 29, 2025**

(54) ORAL COMPOSITIONS OF MK2 PATHWAY INHIBITOR FOR TREATMENT OF IMMUNE CONDITIONS

(71) Applicant: ACLARIS THERAPEUTICS, INC., Wayne, PA (US)

(72) Inventors: Walter Smith, St. Louis, MO (US); Joseph Monahan, Eureka, MO (US); Edward Hellriegel, Barto, PA (US); David Gordon, Ardmore, PA (US); Heidi Hope, St. Louis, MO (US); John Robert Springer, Wentzville, MO (US); Gary A. Decrescenzo, Parkville, MO (US)

(73) Assignee: Aclaris Therapeutics, Inc., Wayne, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/504,778

(22) Filed: Nov. 8, 2023

(65) Prior Publication Data

US 2024/0197732 A1 Jun. 20, 2024

Related U.S. Application Data

(63) Continuation of application No. 17/214,532, filed on Mar. 26, 2021, now Pat. No. 11,844,801.

(60) Provisional application No. 63/149,230, filed on Feb. 13, 2021, provisional application No. 63/140,116, filed on Jan. 21, 2021, provisional application No. 63/138,672, filed on Jan. 18, 2021, provisional application No. 63/136,967, filed on Jan. 13, 2021, provisional application No. 63/136,080, filed on Jan. 11, 2021, provisional application No. 63/128,523, filed on Dec. 21, 2020, provisional application No. 63/126,173, filed on Dec. 16, 2020, provisional application No. 63/076,689, filed on Sep. 10, 2020, provisional application No. 63/053,903, filed on Jul. 20, 2020, provisional application No. 63/024,160, filed on May 13, 2020, provisional application No. 63/022,298, filed on May 8, 2020, provisional application No. 63/022,301, filed on May 8, 2020, provisional application No. 63/018,954, filed on May 1, 2020, provisional application No. 63/015,241, filed on Apr. 24, 2020, provisional application No. 63/000,746, filed on Mar. 27, 2020.

(51) Int. Cl.
| | |
|---|---|
| *A61K 31/506* | (2006.01) |
| *A61K 9/00* | (2006.01) |
| *A61K 9/20* | (2006.01) |
| *A61K 45/06* | (2006.01) |
| *A61P 11/00* | (2006.01) |
| *A61P 31/14* | (2006.01) |
| *A61P 37/06* | (2006.01) |
| *C07D 401/14* | (2006.01) |

(52) U.S. Cl.
CPC .......... *A61K 31/506* (2013.01); *A61K 9/0053* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 45/06* (2013.01); *A61P 11/00* (2018.01); *A61P 31/14* (2018.01); *A61P 37/06* (2018.01); *C07D 401/14* (2013.01); *C07B 2200/13* (2013.01)

(58) Field of Classification Search
CPC .................................................. A61K 31/506
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 7,067,540 B2 | 6/2006 | Devadas et al. | |
| 7,345,054 B2 | 3/2008 | Hale et al. | |
| 7,893,061 B2 | 2/2011 | White | |
| 9,115,089 B2 | 8/2015 | Hockerman et al. | |
| 9,636,333 B2 | 5/2017 | Hockerman et al. | |
| 11,844,801 B2 \* | 12/2023 | Smith ................. | A61K 9/2018 |
| 2002/0016471 A1 | 2/2002 | Salituro et al. | |
| 2005/0176775 A1 | 8/2005 | Devadas et al. | |
| 2006/0187368 A1 | 8/2006 | Kim et al. | |
| 2007/0003993 A1 | 1/2007 | Kritzman et al. | |
| 2007/0167621 A1 | 7/2007 | Durley | |
| 2009/0030017 A1 | 1/2009 | Hanada et al. | |
| 2012/0142709 A1 | 6/2012 | Selness et al. | |
| 2012/0252830 A1 | 10/2012 | Coppola et al. | |
| 2013/0143906 A1 | 6/2013 | Selness et al. | |
| 2014/0364442 A1 | 12/2014 | Hockerman et al. | |

(Continued)

FOREIGN PATENT DOCUMENTS

| | | |
|---|---|---|
| JP | 2005255675 A | 9/2005 |
| WO | 200017175 A1 | 3/2000 |

(Continued)

OTHER PUBLICATIONS

McMahon et al.(2000).\*
Pinedo et al.(2000).\*
Takebe et al. "Regulation of p38 MAPK Phosphorylation Inhibits Chondrocyte Apoptosis in Response to Heat Stress or Mechanical Stress" 2011, International J. Molecular Medicine 27:329-335.
Tonkiha et al. "Synthesis of 7,8-Dihydro-9H-Pyrido[3,2-b][1,4]Diazepin-8-Ones and 2,3-Dihydro-1 H-1,5-Benzodiazepines n Reactions of 4-Hydroxycoumarin and 4-Hydroxy-6-Methyl-2H-Pyran-2-One with Aromatic O-Diamines" 2005, Latvijas imijas Zumals 1:51-60.

(Continued)

*Primary Examiner* — Paul V Ward
(74) *Attorney, Agent, or Firm* — DLA Piper LLP

(57) ABSTRACT

The present disclosure relates to oral compositions of Compound I or a derivative thereof. Methods of use for treating an inflammatory condition are also disclosed.

24 Claims, 34 Drawing Sheets

(56) References Cited

U.S. PATENT DOCUMENTS

| | | |
|---|---|---|
| 2015/0352092 A1 | 12/2015 | Hockerman et al. |
| 2019/0169127 A1 | 6/2019 | Lin et al. |
| 2021/0338669 A1 | 11/2021 | Smith et al. |
| 2023/0242505 A1 | 8/2023 | DeCrescenzo et al. |

FOREIGN PATENT DOCUMENTS

| | | |
|---|---|---|
| WO | 200071535 A1 | 11/2000 |
| WO | 200242292 A2 | 5/2002 |
| WO | 2003068230 A1 | 8/2003 |
| WO | 2004014859 A2 | 2/2004 |
| WO | 2004024078 A2 | 3/2004 |
| WO | 2004087677 A2 | 10/2004 |
| WO | 2005018557 A2 | 3/2005 |
| WO | 2005077050 A2 | 8/2005 |
| WO | 2006109876 A1 | 10/2006 |
| WO | 2007006591 A2 | 1/2007 |
| WO | 2007081901 A2 | 7/2007 |
| WO | 2007141200 A1 | 12/2007 |
| WO | 2008062905 A2 | 5/2008 |
| WO | 2008073306 A1 | 6/2008 |
| WO | 2008153942 A1 | 12/2008 |
| WO | 2009012277 A1 | 1/2009 |
| WO | 2009156484 A2 | 12/2009 |
| WO | 2011003007 A1 | 1/2011 |
| WO | 2011003012 A1 | 1/2011 |
| WO | 2011003021 A1 | 1/2011 |
| WO | 2012078684 A1 | 6/2012 |
| WO | 2014197846 A1 | 12/2014 |
| WO | 2021022186 A1 | 2/2021 |
| WO | 2021178449 A1 | 9/2021 |
| WO | 2021195562 A1 | 9/2021 |

OTHER PUBLICATIONS

U.S. Department of Health and Human Services Food and Drug Administration Center for Drug Evaluation and Research, (2002). Guidance for Industry: Food-Effect Bioavailability and Fed Bioequivalence Studies. Office of Training and Communications Division of Drug Information, HFD-240.
Wang et al. "Selective Inhibition of the p38α MAPK-MK2 Axis Inhibits Inflammatory Cues Including Inflammasome Priming Signals" 2018, J. Experimental Medicine, 215(5): 1315-1325.
Yong et al. "The p38 MAPK Inhibitors for the Treatment of Inflammatory Diseases and Cancer" 2009, Expert Opinion on Investigational Drugs, 18(12):1893-1905.
Aclaris, "Empowering Patients Through Revelationary Science" Sep. 27, 2019, Aclaris Therapeutics Research & Development Day, retrieved from the internet: URL: https://www.sec.gov/Archives/edgar/data/1557746/000155837019008709/ex-99d1.htm.
Anderson J., et al., "Rheumatoid Arthritis Disease Activity Measures: American College of Rheumatology Recommendations for Use in Clinical Practice," Arthritis Care & Research, May 2012, vol. 64, No. 5, pp. 640-647, DOI:10.1002/acr.21649, 17 Pages.
Banker G.S., et al., "Modern Pharmaceutics," Drugs and the Pharmaceutical Sciences (cover and TOC), 4th Edition, 2002, vol. 121, 5 Pages.
Beals et al."Magnetic Resonance Imaging of the Hand and Wrist in a Randomized, Double-blind, Multicenter, Placebo—Controlled Trial of Infliximab for Rheumatoid Arthritis: Comparison of Dynamic Contrast Enhanced Assessments With Semi—Quantitative Scoring" 2017, PLoS one 12(12):e0187297.
Bihorel et al. "Population Pharmacokinetic Modeling of LY2189102 After Multiple Intravenous and Subcutaneous Administrations" Sep. 2014, The AAPS J. 16(5):1009-1017.
Boehm et al. "New Inhibitors of p38 Kinase" 2000, Expert Opinion in Therapeutic Patents 10(1):25-37.
Bradham et al. "p38 MPK in Development and Cancer" Apr. 15, 2006, Cell Cycle 5(8):824-828.
Burnette et al. "SD0006: A Potent, Selective and Orally Available Inhibitor of P38 Kinase" Jul. 4, 2009, Pharmacology 84(1):42-60.
Caira et al. "Crystalline Polymorphism of Organic Compounds" Jan. 1, 1998, Topics in Current Chemistry 198:163-208.
Davidson et al. "Discovery and Characterization of a Substrate Selective p38alpha Inhibitor" 2004, Biochemistry 43(37):11658-11671.
Deady et al. "Studies on the Synthesis of Benzimidazo{2,1-a]isoquinolines" Jun. 30, 1998, Australian J. Chemsitry 51 (10):941-945.
Dimitri et al. "The p38 Mitogen-Activated Protein Kinase Cascade Modulates T Helper Type 17 Differentiation and Functionality in Multiple Sclerosis" 2015, Immunology 146:251-263.
Dodeller et al. "The p38 Mitogen-activated Protein Kinaase Signalling Cascade in CD4 T Cells" Feb. 17, 2006, Arthritis Research & Therapy 8(205):11 Pages, Retrieved from the Internet: http://arthritis-research.com/content/8/2/205.
Gracey et al. "TYK2 Inhibition Reduces Type 3 Immunity and Modifies Disease Progression in Murine Spondyloarthritis" Apr. 2020, The J. Clinical Investigation 130(4):1863-1878.
Gura et al. "Systems for Identifying New Drugs are Often Faulty" Nov. 7, 1997, Science 278(5340):1041-1042.
Han et al. "Attenuation of Mitochondrial and Nuclear p38alpha Signaling: a novel mechanism of estrogen Neuroprotection in cerebral Ischemia" Jan. 15, 2015, Mol. Cell Endocrinol, 400:21-31, 11 Pages.
Hill et al. "Pamapimod, a Novel p38 Mitogen-Activated Protein Kinase Inhibitor: Preclinical analysis of Efficacy and Selectivity" Sep. 4, 2008, J. Pharmacology and Experimental Therapeutics 327(3):610-619.
International Search Report and Written Opinion for PCT/US2014/041381 dated Sep. 9, 2014, 7 Pages.
International Search Report and Written Opinion for PCT/US2020/044558 dated Oct. 28, 2020, 8 Pages.
International Search Report and Written Opinion for PCT/US2021/024482 dated Jun. 8, 2021, 8 Pages.
Japan Office Action and Written Opinion for JP21518407 dated Aug. 7, 2018 (with English Translation).
Japan Office Action and Written Opinion for JP21518407 dated Oct. 15, 2019 (with English Translation).
Japan Office Action for JP21518407 dated Mar. 20, 2018 (with English Translation).
Johnson et al. "Relationships Between Drug Activity and NCI Preclinical in Vitro and in Vivo Models and early Clinical Trials" 2001, British J. Cancer, 84(10):1424-1431.
Kato et al. "Ketene and Its Derivatives. Viii. Reactions of Diketene With Amino Heterocycles" 1964, Yakugaku Zasshi 34(12):1201-1205.
Kato et al. "Studies on Ketene and Its Derivatives. Vi. Reaction of Diketene With Aminopyridines and Their N-oxides" 1964, Chem. Pharm. Bull., 12(8): 910-916.
Kato et al., "Studies on Ketene and its derivatives. XLVI. Mass Spectrometric studies of 3-Acetyl-4-hydroxy-6-methyl-1-pyridyl-2-pyridones and N-Pyridy1-2, 6-dimethyl1-4-pyrone-3-carboxamides" 1972, Chem. Pharm. Bull. 20(1):133-141.
Kumphune et al. "Inhibition of p38 MAPK Activation Protects Cardiac Mitochondria from Ischemia/Reperfusion Injury" Apr. 16, 2015, Pharmaceutical Biology 53(12):1831-1841.
Liu et al. "Proline-Rich Tyrosine Kinase 2 and Src Kinase Signaling Transduce Monosodium Urate Crystal-Induced Nitric Oxide Production and Matrix Metalloproteinase 3 Expression in Chondrocytes" Jan. 2004, Arthritis Rheumatism 50(1):247-258.
Macrae et al. "Mercury 4.0: From Visualization to Analysis, Design and Prediction" Feb. 1, 2020, J. Applied Crystallography 53:226-235.
Marumo et al. "p38 Mitogen-activated Protein Kinase Determines the Susceptibility to Cigarette Smoke-induced Emphysema in Mice" 2014, Pulmonary Medicine 14(79): 14 Pages.
McMahon "VEGF Receptor Signaling in Tumor Angiogenesis" 2000, The Oncologist 5(Suppl. 1):3-10.
Murali et al. "Inhibition of the Stromal p38MAPK/MK2 Pathway Limits Breast Cancer Metastases and Chemotherapy-Induced Bone Loss" Oct. 1, 2018, Cancer Research 78(19):5618-5630.

(56) References Cited

OTHER PUBLICATIONS

Nyirenda et al. "TLR2 Stimulation Drives Human Naive and Effector Regulatory T Cells into a Th17-Like Phenotype with Reduced Suppressive Function" Sep. 2021, J. Immunology 187(5):2278-2290.

Office Action for U.S. Appl. No. 14/298,610 mailed Dec. 3, 2014.

Office Action for U.S. Appl. No. 14/298,610 mailed May 7, 2014.

O'Sullivan et al. "NF-KappaB and p38 MAPK Inhibition Improve Survival in Endotoxin Shock and in a Cecal Ligation and Juncture Model of Sepsis in Combination With Antibiotic Therapy" Mar. 2009, J. Surg. Res. 152(1):46-53 (abstract only).

Pearce et al. "Failure Modes in Anticancer Drug Discovery and Development" 2008, Cancer Drug Design and Discovery, Edited by Stephen Neidle Ch. 18:424-435.

Pecharsky et al. "Fundamentals of powder diffraction and structural characterization of materials 2nd Ed." 2009, New fork: Springer, ISBN 978-0-387-09579-0. OCLC 314182615 (cover and TOC only).

Perterfy et al. "Monitoring Cartilage Loss in the Hands and Wrists in Rheumatoid Arthritis With Magnetic Resonance Imaging in a Multi-center Clinical Trial: Impress (NCT00425932)" 2013, Arthritis Research & Therapy 15(R44): 10 Pages.

Pinedo et al. "Translational Research: The Role of VEGF in Tumor Angiogenesis" 2000, The Oncologist 5(Suppl 1):1-2.

Prevoo et al. "Modified Disease Activity Scores that Include Twenty-Eight Joints" Jan. 1995, Arthritis & Rheumatism 38(1):44-48.

Sato et al. "Synthesis of 1,3-Dioxin-4-Ones and their use in Synthesis: XI. 2,2-Dimethyl-1,3-Dioxin-4-One as a Synthetic Equivalent of Formylketene: Synthesis of Heterocyclic Compounds" 1986, Chemical and Pharmaceutical Bulletin 34(2):621-627.

Shao et al. "Synthesis of d3-Poziotinib Hydrochloride and Stability of Liver Microsomes in Vitro" Jul. 15, 2019, Journal of Yantai University 32(03):220-225.

Sherlock et al. "Antiallergy agents. 1. Substituted 1,8-naphthyridin-2(1H)-ones as inhibitors of SRS-A release" 1988, J. Medicinal Chemistry 31(11):2108-2121.

Simone "Oncology: Introduction 20th Ed." 1996, Feb. 3, 1997, Cecil Textbook of Medicine 1:1004-1010.

Smolen et al. "Validity and Reliability of the Twenty-eight-joint Count for the Assessment of Rheumatoid Arthritis Activity" Jan. 1995, Arthritis Rheumatology 38(1):38-43.

Stout et al. "X-Ray Structure Determination: A Practical Guide" 1968, Macmillan Company, New York TOC. Ch.3:7 Pages (Cover only).

Strasser et al. "Substrate-based Kinase Activity Inference Identifies MK2 as Driver of Colitis" 2019, Integrative Biology 11(7):301-314.

\* cited by examiner (*) = All placebo samples (all time points)

(*) = All placebo samples (all time points)

(*) = All placebo samples (all time points)

(*) = All placebo samples (all time points)

ORAL COMPOSITIONS OF MK2 PATHWAY INHIBITOR FOR TREATMENT OF IMMUNE CONDITIONS

CROSS-REFERENCE TO RELATED APPLICATIONS

This application is a continuation of U.S. patent application Ser. No. 17/214,532; now U.S. Pat. No. 11,844,801, issued Dec. 19, 2023, which claims the benefit of U.S. Provisional Patent Application Ser. No. 63/000,746, filed on Mar. 27, 2020; Ser. No. 63/015,241, filed on Apr. 24, 2020; Ser. No. 63/018,954, filed on May 1, 2020; Ser. No. 63/022,301, filed on May 8, 2020, Ser. No. 63/022,298, filed on May 8, 2020, Ser. No. 63/024,160 filed on May 13, 2020, Ser. No. 63/053,903, filed on Jul. 20, 2020, Ser. No. 63/076,689, filed on Sep. 10, 2020, Ser. No. 63/126,173, filed on Dec. 16, 2020, Ser. No. 63/128,523, filed on Dec. 21, 2020; Ser. No. 63/136,080, filed on Jan. 11, 2021, Ser. No. 63/136,967, filed on Jan. 13, 2021, Ser. No. 63/138,672, filed on Jan. 18, 2021, Ser. No. 63/140,116, filed on Jan. 21, 2021, and Ser. No. 63/149,230, filed on Feb. 13, 2021, each of which is hereby incorporated by reference in its entirety.

SUMMARY

The present disclosure is directed to a method of treating an inflammatory condition comprising administering to a human subject having an inflammatory condition, an oral dose of 5 mg/day to 300 mg/day of Compound I having the following structure:

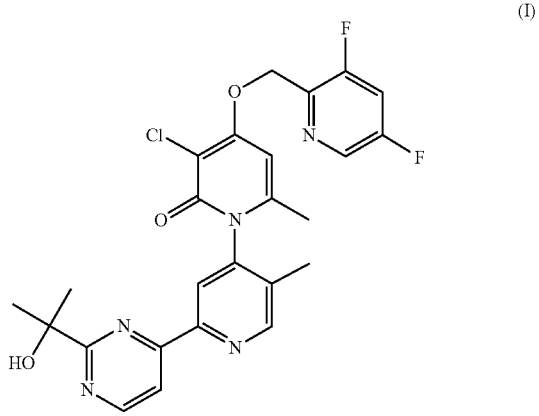 [SMILES: Cc1cnc(-c2ccnc(C(C)(C)O)n2)cc1-n1c(C)cc(OCc2ncc(F)cc2F)c(Cl)c1=O]

(I)

or a derivative thereof to treat said inflammatory condition.

The present disclosure is further directed to oral pharmaceutical compositions comprising Compound I or a derivative thereof, where the oral compositions comprise 5 mg to 300 mg of Compound I and a pharmaceutically acceptable carrier.

As used throughout this disclosure, recitation of "Compound I" encompasses atropisomer compounds (P)-I and (M)-I as disclosed below in any molar ratio from 4:1 ((P)-I:(M)-I) to 999:1, and also includes embodiments where Compound (P)-I is substantially free from Compound (M)-I. Compounds (P)-I and (M)-I can be in any form (e.g., free base, crystalline form, etc.) as described herein.

BRIEF DESCRIPTION OF THE DRAWINGS

FIGS. 4A-4E also show mean (±SEM) levels of pHSP27 (FIG. 4A, bottom), TNF-α (FIG. 4B, bottom), IL-1β (FIG. 4C, bottom), IL-8 (FIG. 4D, bottom), IL-6 (FIG. 4E, bottom) in subjects administered 10 mg, 30 mg, 50 mg, 80 mg, and 120 mg twice daily, comparing day 1 pre-dosing values (set to 100%) with day 7 values 4 hours after dosing (approximate $C_{max}$) and 12 hours after dosing ($C_{trough}$).

FIG. 7B are graphs showing mean (+/−std. dev.) plasma concentration-time profiles of ATI-450 dosed at 120 mg BID. FIG. 7C are graphs showing the plasma concentration-time profiles of ATI-450 in individual subjects at days 1 (left) and 7 (right) following 120 mg BID dosing.

Figure 13A:
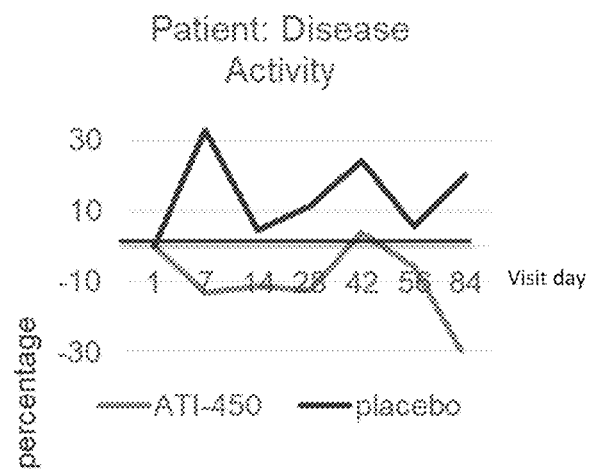
FIGS. 13A-13D are graphs showing median percent change in patient visual analog scale (VAS) for disease activity (FIG. 13A), patient VAS for arthritic pain (FIG.
Figure 13B:
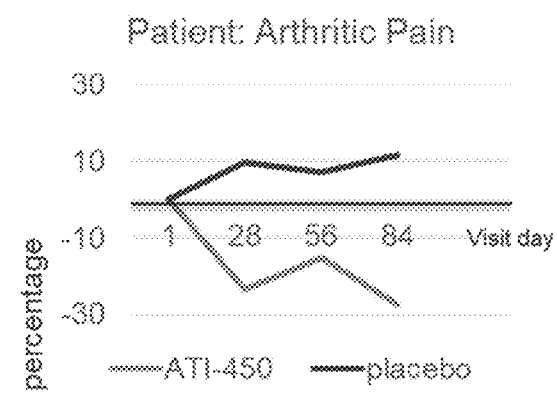
Figure 13C:
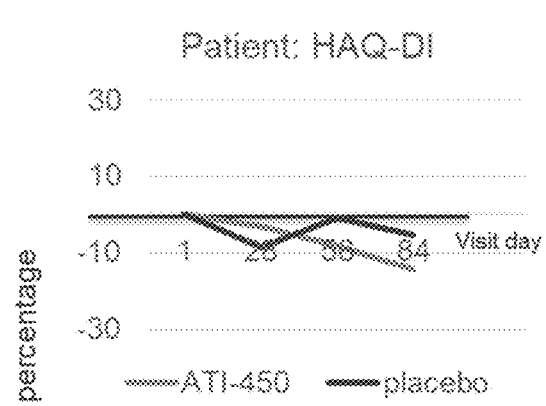

13B), Health Assessment Questionnaire (HAQ) Disability Index (DI) (FIG. 13C), and physician VAS scores for disease activity (FIG. 13C).

Figure 14:
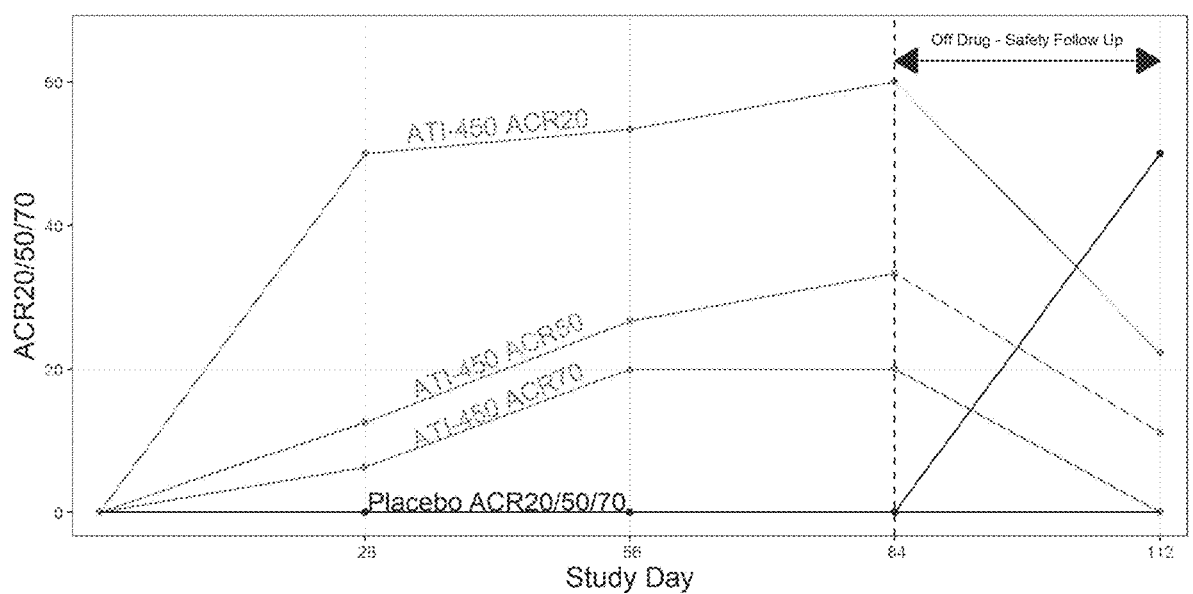

FIG. 14 shows the ACR20/50/70 response over the course of the study (through day 112) for placebo and ATI-450 (50 mg/BID) treatment groups.

Figure 15:
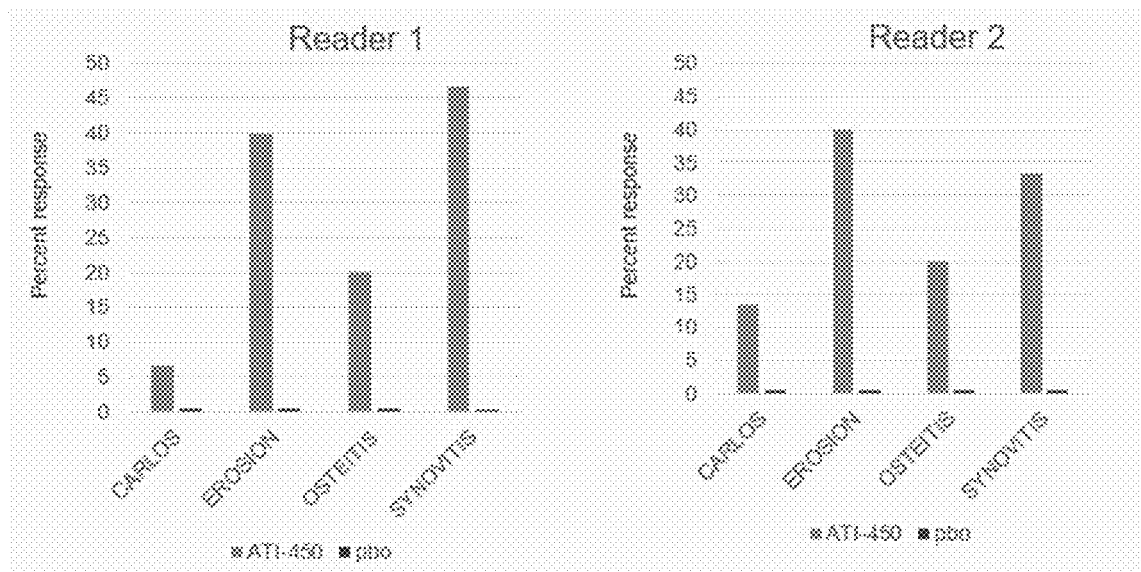

FIG. 15 is a graph showing the percent of patients responsive to ATI-450 treatment as assessed by the Hand-Wrist MRI RAMRIS. The RAMRIS provides sub-scores for CARLOS (cartilage loss), erosion, osteitis, synovitis, and the graph of FIG. 15 is showing percent responsiveness in these endpoints by treatment and hand. A patient was deemed responsive if at least a 1-point improvement in any hand was observed.

Figure 16:
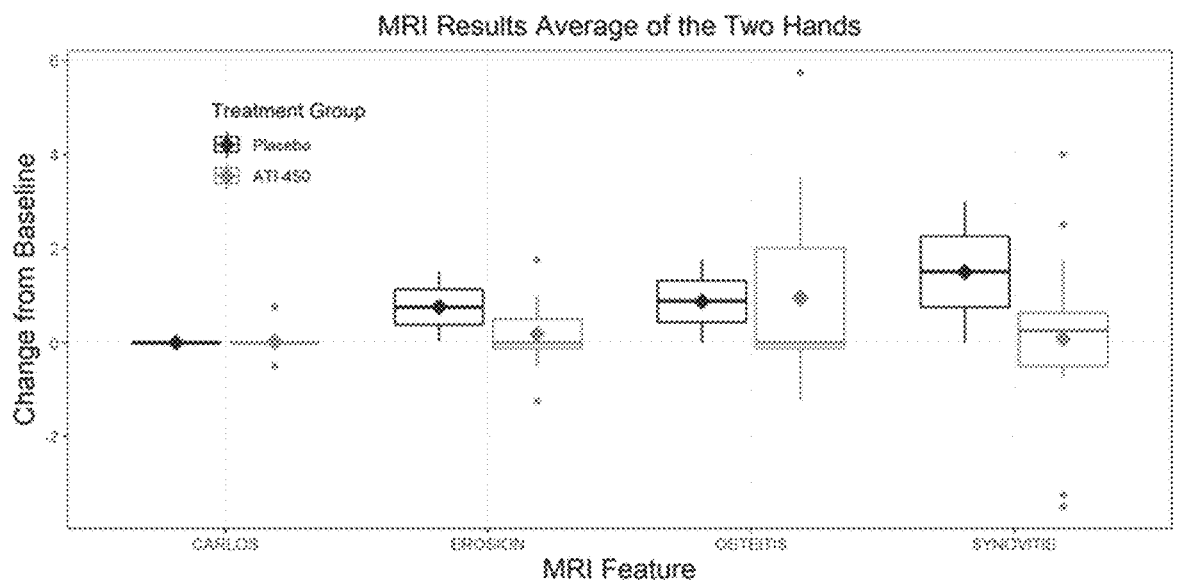

FIG. 16 is a graph showing the change in baseline at day 84 for CARLOS, erosion, osteitis, and synovitis endpoints in placebo and ATI-450 (50 mg BID) patients. The data represents the average of both hands as assessed by the Hand-Wrist MRI RAMRIS. Diamonds represent mean values.

Figure 17:
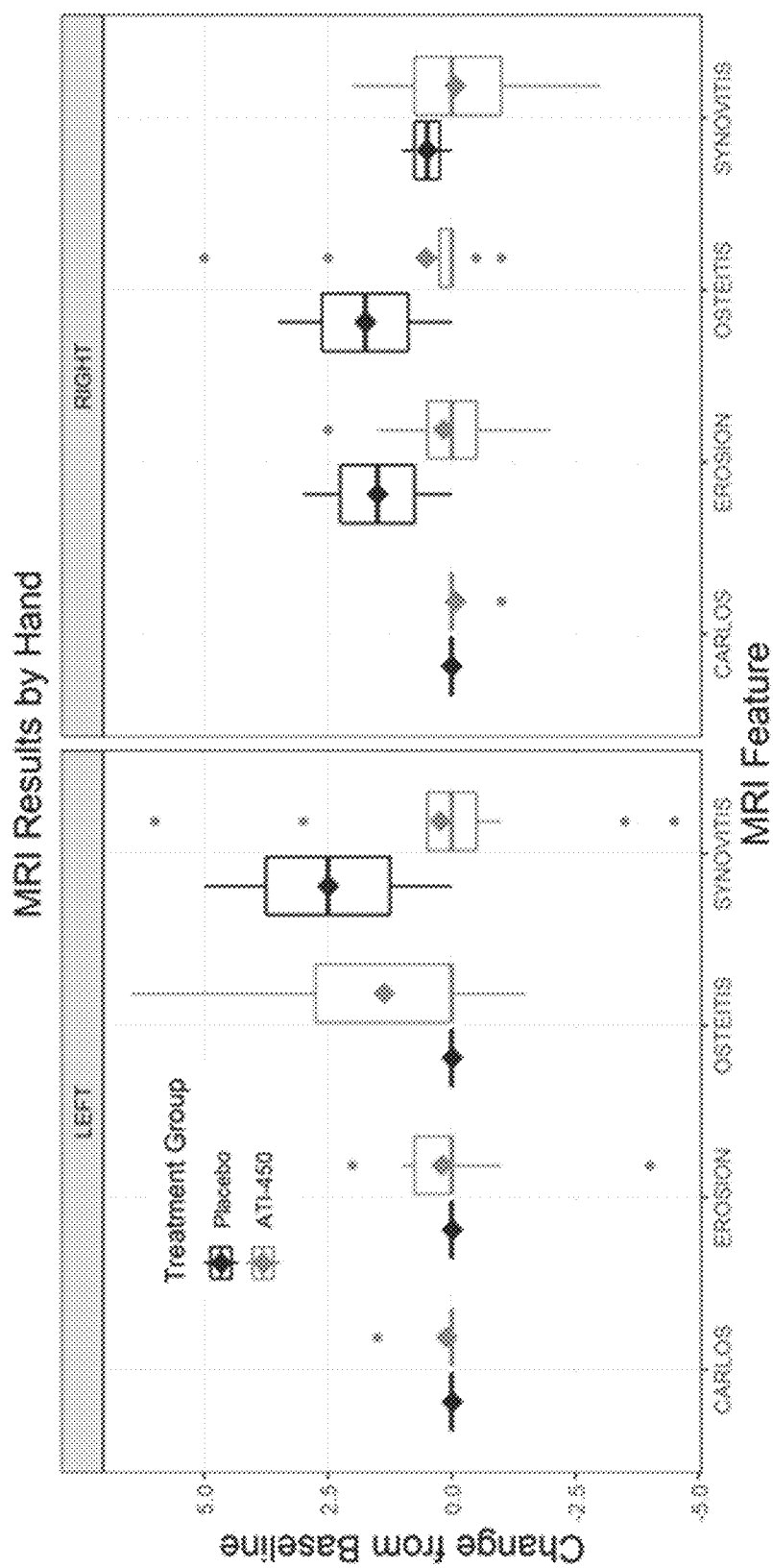

FIG. 17 is a graph showing the change in baseline at day 84 for CARLOS, erosion, osteitis, and synovitis endpoints for each hand in placebo and ATI-450 (50 mg BID) patients. The data the average of each hand as assessed by the Hand-Wrist MRI RAMRIS. Diamonds represent mean values.

Figure 18A:
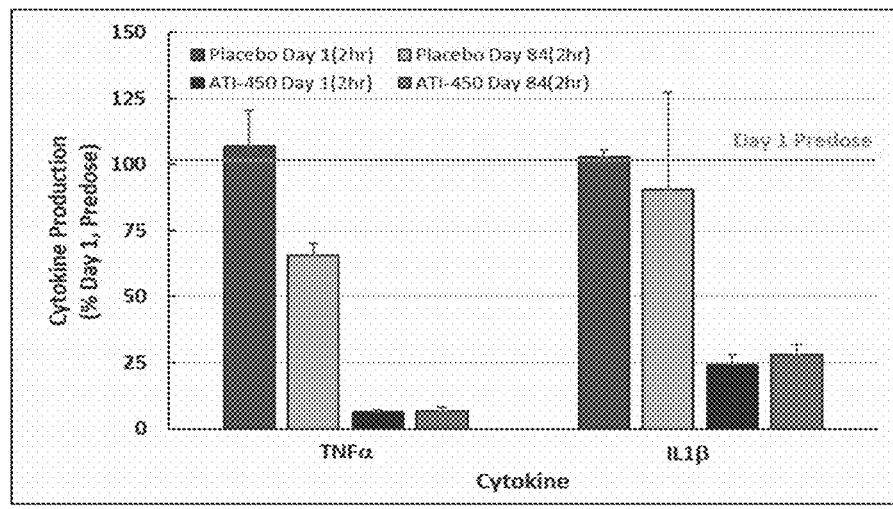
Figure 18B:
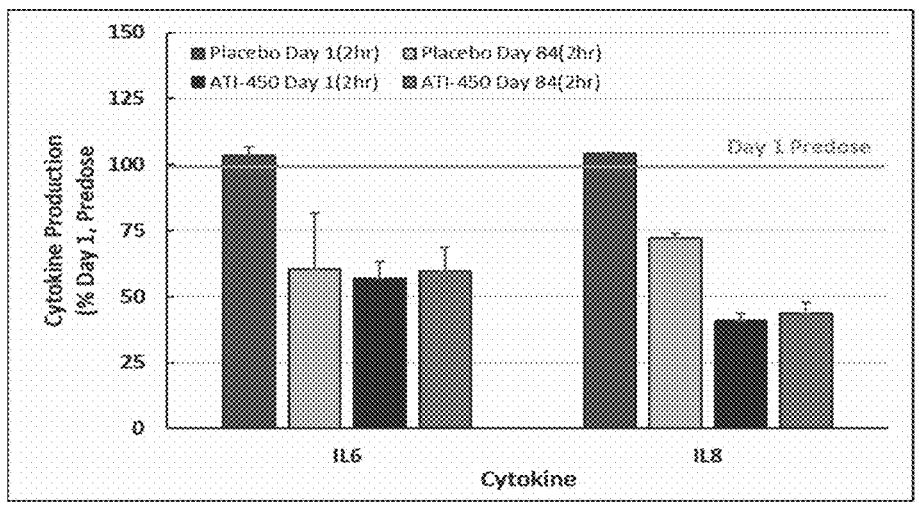

FIGS. 18A-18B are a graphs showing ex vivo LPS-stimulated cytokines, including TNF-α and IL-1β (FIG. 18A) and IL-6 and IL-8 (FIG. 18B), at day 1 versus day 84 in blood samples from patient in placebo and ATI-450 (50 mg/BID) treatment groups.

Figure 19A:
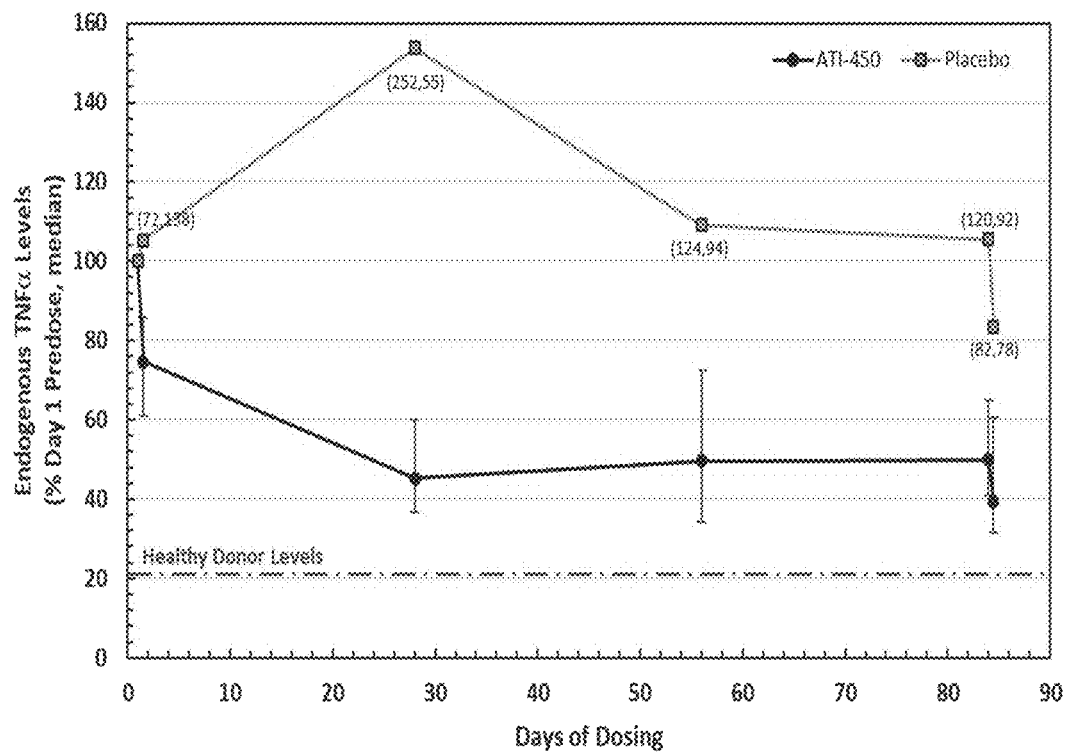
Figure 19B:
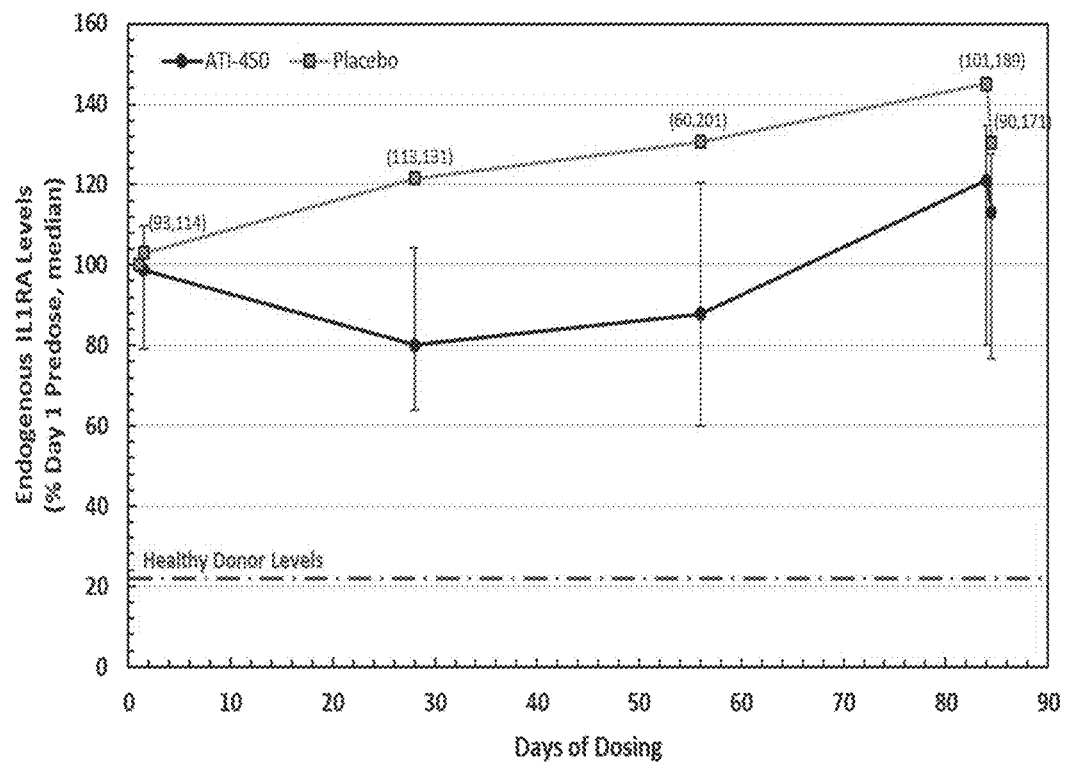

FIGS. 19A-19B show the impact of ATI-450 treatment (50 mg/BID) on endogenous plasma levels of the pro-inflammatory cytokine, TNF-α (FIG. 19A), and the anti-inflammatory cytokine, IL-1RA (FIG. 19B), at days 1, 28, 56, and 84 of treatment.

FIGS. 20A-20D shows the impact of ATI-450 treatment (50 mg/BID) on endogenous plasma levels of TNF-α (FIG. 20A), IL-8 (FIG. 20B), IL-6 (FIG. 20C), and MIP1β (FIG. 20D) at days 1, 28, 56, and 84 of treatment.

Figure 21:
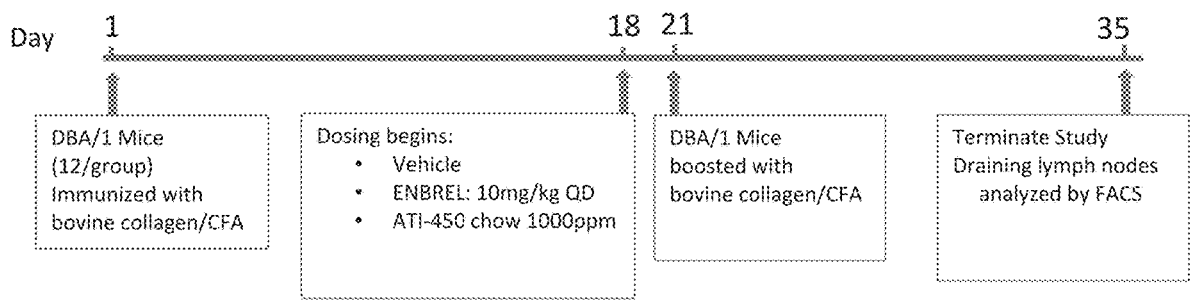
Figure 21:
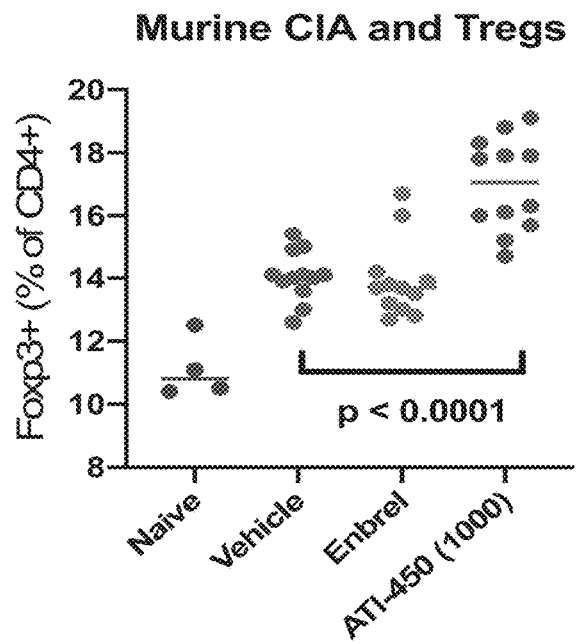

FIG. 21 is a graph showing ATI-450 mediated increase in T regulatory (Treg) cells in a murine collagen-induced arthritis model. The timeline above the graph depicts timing and dose of ATI-450 and ENBREL® (tumor necrosis factor inhibitor) in mice following collagen administration. Treg cells were identified as Foxp3$^+$/CD4$^+$ cells.

Figure 22A:
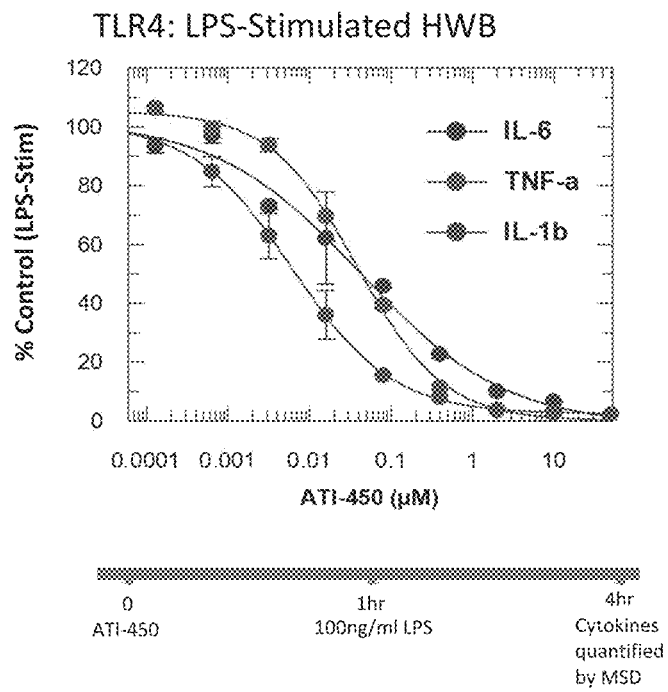
Figure 22B:
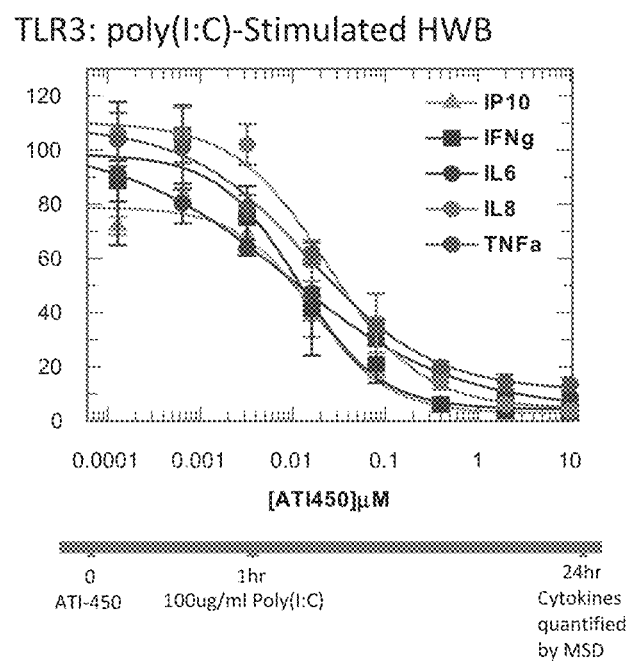
Figure 22C:
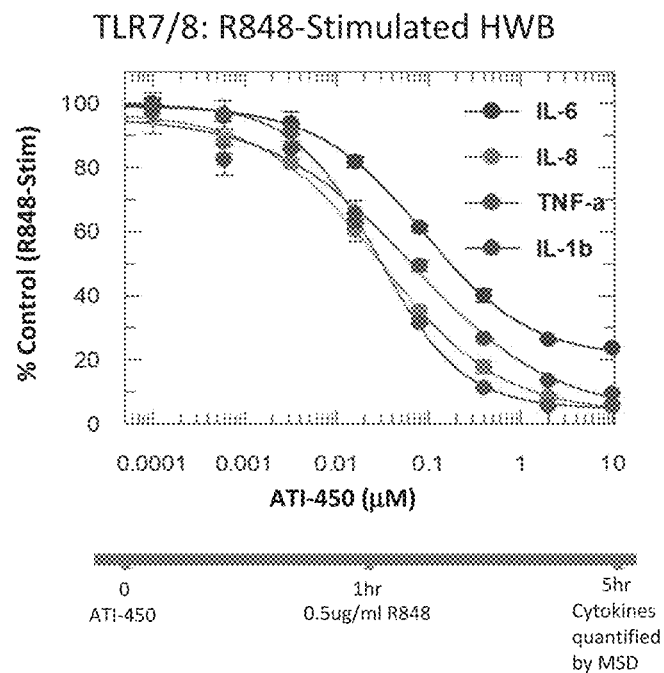

FIGS. 22A-22C are graphs showing ATI-450 inhibition of TLR4 mediated cytokine release (FIG. 22A), TLR3 mediated cytokine release (FIG. 22B), and TLR7,8 mediated cytokine release (FIG. 22C).

Figure 23:
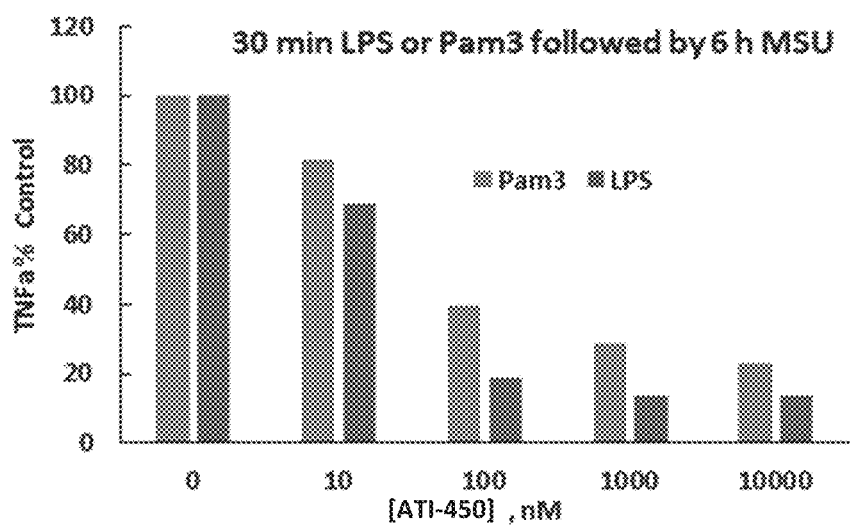

FIG. 23 is a graph showing that ATI-450 dose-dependently inhibits TLR2 mediated induction of TNF-α production.

Figure 24:
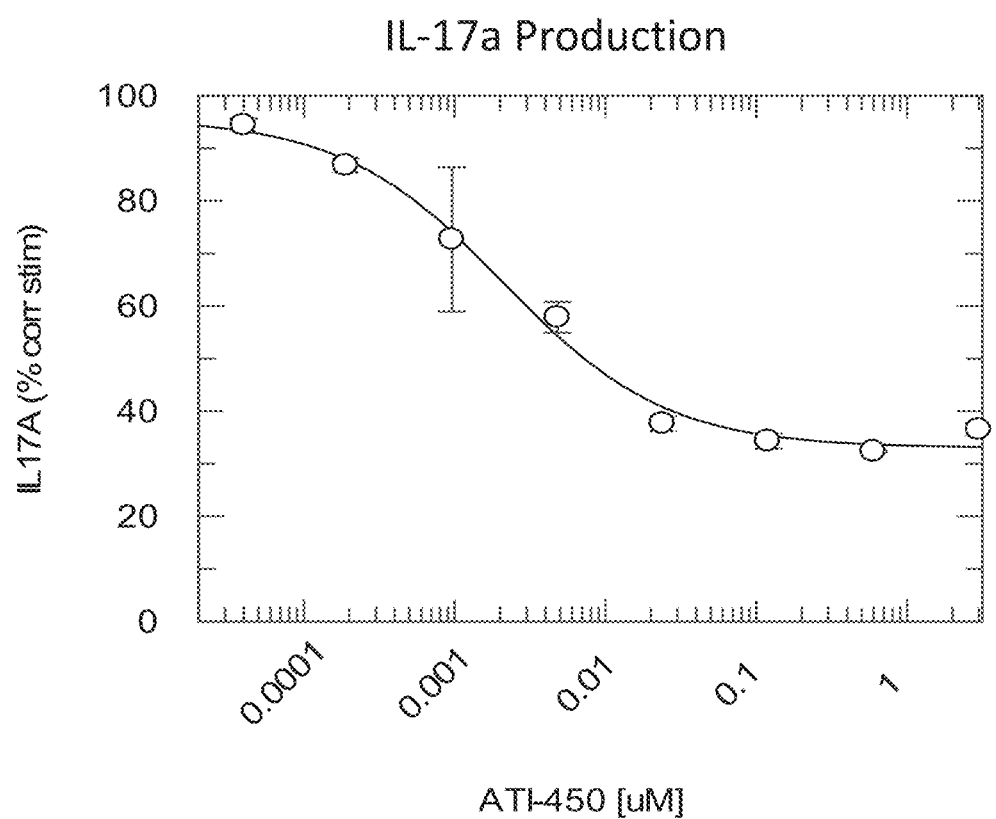

FIG. 24 shows that ATI-450 inhibits IL-17A production in TH17 cells.

Figure 25:
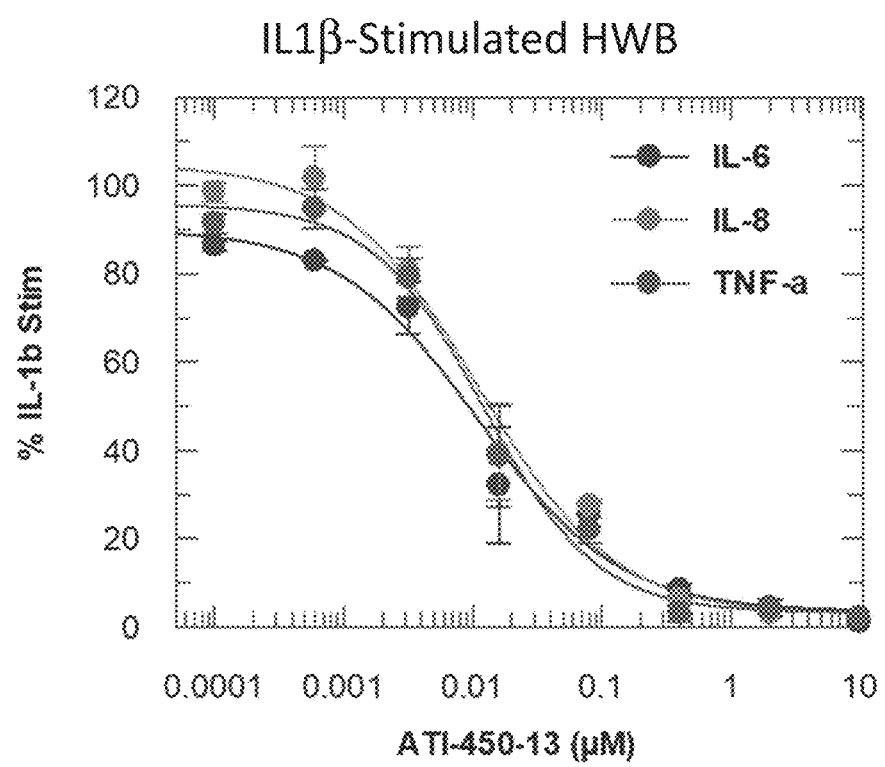

FIG. 25 shows that ATI-450 inhibits IL-1β stimulated TNF-α, Il-6, and IL-8 production.

Figure 26A:
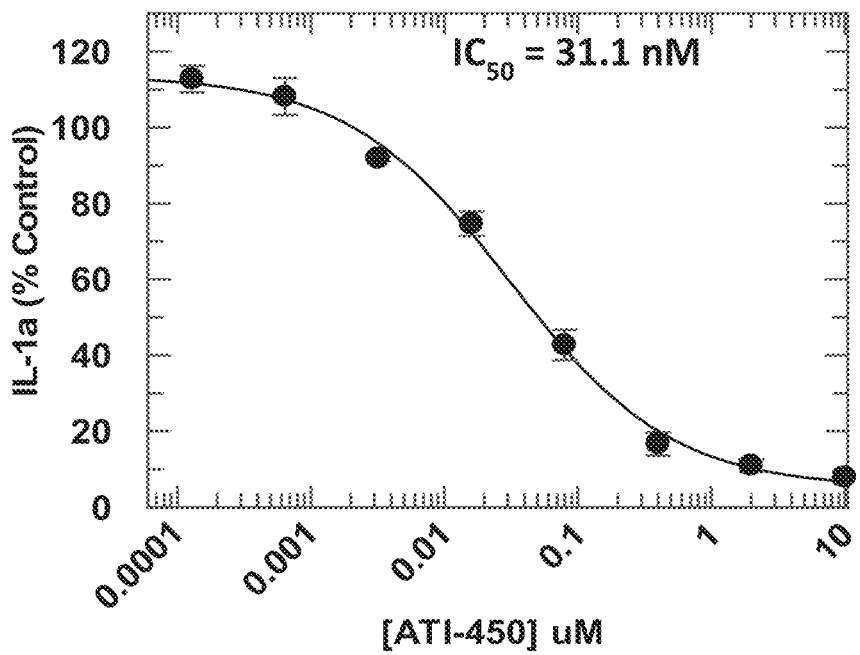
Figure 26B:
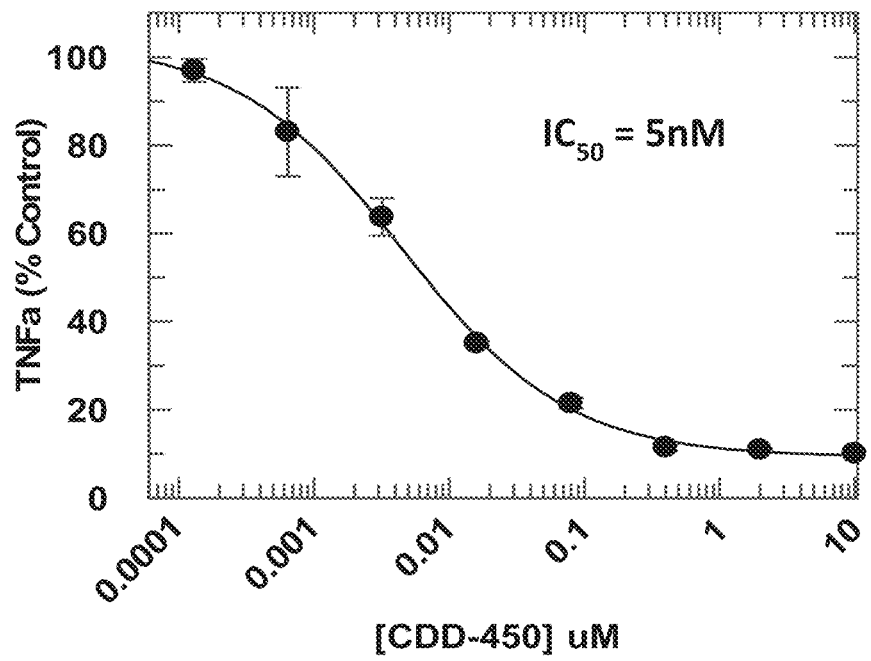

FIGS. 26A-26B show that ATI-450 inhibits both IL-1α biosynthesis in human peripheral blood mononuclear cells (FIG. 26A) and IL-1α activity in neutrophils (FIG. 26B).

Figure 27:
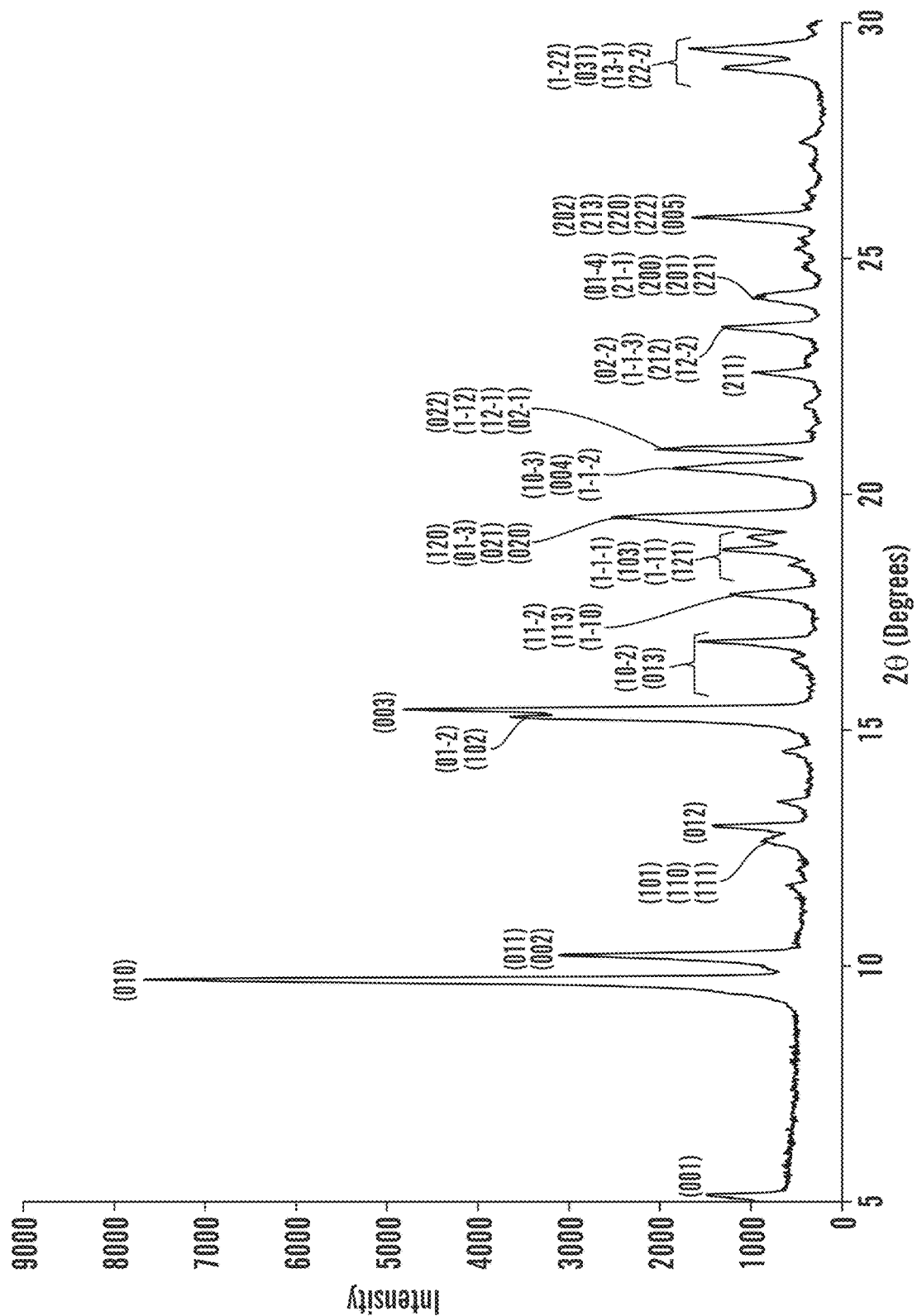

FIG. 27 shows a PXRD of Compound (P)-I.

Figure 28:
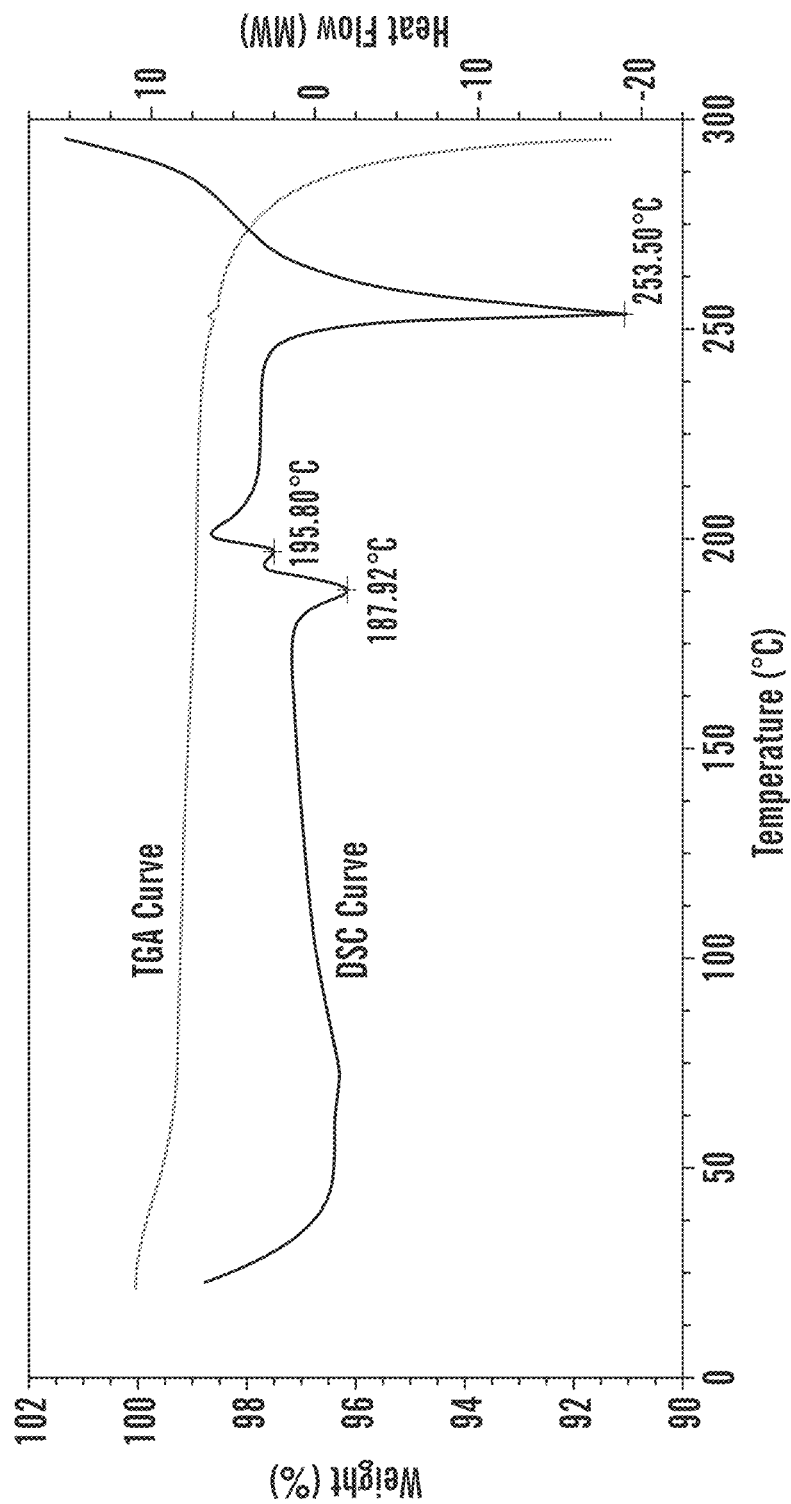

FIG. 28 shows TGA (top trace) and DSC (bottom trace) curves for Compound (P)-I.

DETAILED DESCRIPTION

Definitions

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

As used herein and in the appended claims, the singular forms "a," "an," and "the" include plural reference unless the context clearly dictates otherwise. Thus, for example, reference to a "MK2 inhibitor" is a reference to one or more MK2 inhibitors and equivalents thereof known to those skilled in the art, and so forth.

The transitional term "comprising," which is synonymous with "including," "containing," or "characterized by," is inclusive or open-ended and does not exclude additional, non-recited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. The compositions and methods of the present disclosure can comprise, consist essentially of, or consist of, the components or steps disclosed.

As used herein, the term "about" means plus or minus 10% of the numerical value of the number with which it is being used. Therefore, about 50% means in the range of 45%-55%.

"Administering" when used in conjunction with a therapeutic means to administer a therapeutic to a patient whereby the therapeutic positively impacts the tissue to which it is targeted. Thus, as used herein, the term "administering", when used in conjunction with a MK2 inhibitor compound, can include, but is not limited to, providing a MK2 inhibitor compound into or onto the target tissue; providing a MK2 inhibitor compound systemically to a patient by, e.g., oral administration whereby the therapeutic reaches the target tissue.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

The term "substantially free" as used herein, alone or in combination, refers to the absence of isomers within the limits of detection of analytical methods such as nuclear magnetic resonance (NMR), gas chromatography/mass spectroscopy (GC/MS), high performance liquid chromatography (HPLC), or liquid chromatography/mass spectroscopy (LC/MS).

The term "condition" as used herein is intended to be generally synonymous, and is used interchangeably with, the terms "disorder," "syndrome," and "disease", in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"MK2 inhibitor" is used herein to refer to a compound that exhibits an $IC_{50}$ with respect to mitogen-activated protein kinase-activated protein kinase 2 ("MK2") activity of no more than about 100 μM and more typically not more than about 50 μM, as measured in the MK2 enzyme assays. $IC_{50}$ is the concentration of inhibitor which reduces the activity of an enzyme (e.g., MHK2) to half-maximal level. Compounds disclosed herein have been discovered to exhibit inhibition against MK2. In some embodiments, the compounds will exhibit an $IC_{50}$ with respect to MK2 of no more than about 1 nM. In some embodiments, the compounds will exhibit an $IC_{50}$ with respect to MK2 of no more than about 1 μM. In some embodiments, the compounds will exhibit an $IC_{50}$ with respect to MK2 of about 1 μM to about 50 μM. In certain embodiments, compounds will exhibit an $IC_{50}$ with respect to MK2 of no more than about 10 μM; in further embodiments, compounds will exhibit an $IC_{50}$ with respect to MK2 of no more than about 5 μM; in yet further embodiments, compounds will exhibit an $IC_{50}$ with respect to MK2 of not more than about 1 μM; in yet further embodiments, compounds will exhibit an $IC_{50}$ with respect to MK2 of not more than about 300 nM, as measured in the MK2 assay described herein.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

Suitable pharmaceutically acceptable acid addition salts of the compounds of embodiments herein may be prepared from an inorganic acid or an organic acid. All of these salts may be prepared by conventional means from the corresponding compound of embodiments herein by treating, e.g., the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases suitable for the formulations as described herein include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X–) is associated with the positive charge of the N atom. X– may be an anion of various mineral acids (e.g., chloride, bromide, iodide, sulfate, nitrate, phosphate), or an anion of an organic acid (e.g., acetate, maleate, fumarate, citrate, oxalate, succinate, tartrate, malate, mandelate, trifluoroacetate, methanesulfonate, p-toluenesulfonate). $X^-$ is preferably an anion selected from chloride, bromide, iodide, sulfate, nitrate, acetate, maleate, oxalate, succinate or trifluoroacetate. More preferably $X^-$ is chloride, bromide, trifluoroacetate or methanesulfonate.

The compounds of embodiments herein may exist in both non-solvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethyl sulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

In some embodiments herein one solvent molecule can be associated with one molecule of the compound described herein, such as a hydrate. In some embodiments, more than one solvent molecule may be associated with one molecule of the compound described herein, such as a dihydrate. Additionally, in some embodiments herein less than one solvent molecule may be associated with one molecule of the compound described herein, such as a hemihydrate. Furthermore, solvates of embodiments herein are contemplated as solvates of the compound described herein that retain the biological effectiveness of the non-solvate form of the compounds.

Embodiments herein also includes isotopically-labeled compounds of embodiments herein, wherein one or more atoms is replaced by an atom having the same atomic number, but an atomic mass or mass number different from the atomic mass or mass number usually found in nature.

Examples of isotopes suitable for inclusion in the compounds of embodiments herein include isotopes of hydrogen, such as $^2$H and $^3$H carbon, such as $^{11}$C, $^{13}$C and $^{14}$C, chlorine, such as $^{31}$Cl, fluorine, such as $^{18}$F, iodine, such as $^{123}$I and $^{125}$I, nitrogen, such as $^{13}$N and 15N, oxygen, such as $^{15}$O, $^{17}$O and $^{18}$O, phosphorus, such as $^{32}$P, and sulfur, such as $^{35}$S. Certain isotopically-labeled compounds of embodiments herein, e.g., those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, e.g., increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or $^2$H) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope (the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The term "subject" as used herein and interchangeably with "patient", includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In another embodiment, the subject is a research animal such as a rodent, dog, or non-human primate. In certain embodiments, the subject is a non-human transgenic animal such as a transgenic mouse or transgenic pig.

The phrase "therapeutically effective" is intended to qualify the amount of active ingredients used in the treatment of a disease or disorder or on the effecting of a clinical endpoint.

The term "therapeutically acceptable" refers to those compounds, and a derivative thereof, which are suitable for use in contact with the tissues of patients without undue toxicity, irritation, and allergic response, are commensurate with a reasonable benefit/risk ratio, and are effective for their intended use.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

Embodiments herein are directed to oral pharmaceutical compositions that inhibit MK2 activity and methods of treatment that involve administering to a subject in need thereof an oral dose of the MK2 inhibitor compound. Some embodiments include methods for the treatment of diseases in a subject in need thereof that comprise orally administering the MK2 inhibitor compound described herein.

The oral compositions disclosed herein possess a specific MK2 inhibitor which prevents p38 MAP Kinase mediated inflammatory signaling, and thus, can be used in the treatment or prophylaxis of a disease or condition in which p38 MAP Kinase inflammatory signaling plays an active role. Thus, embodiments provide oral pharmaceutical compositions comprising the MK2 inhibitor disclosed herein together with a pharmaceutically acceptable carrier, as well as methods for using the compounds and compositions. Certain embodiments provide methods for inhibiting p38 MAP kinase inflammatory signaling using compounds of embodiments herein. Other embodiments provide methods for treating a p38 MAP Kinase-mediated disorder in a patient in need of such treatment, comprising administering to said patient a therapeutically effective amount of a MK2 inhibitor compound or composition comprising the same according to the present disclosure. Also provided is the use of the specific MHK2 inhibitor disclosed herein for use in the manufacture of a medicament for the treatment of a disease or condition ameliorated by the inhibition of p38 MAP Kinase.

Also provided are embodiments wherein any embodiment described herein may be combined with any one or more of these embodiments, provided the combination is not mutually exclusive.

Oral Compositions

Embodiments herein are directed to pharmaceutical compositions formulated for oral administration ("oral pharmaceutical composition"), comprising about 5 mg to about 300 mg of Compound I as shown below

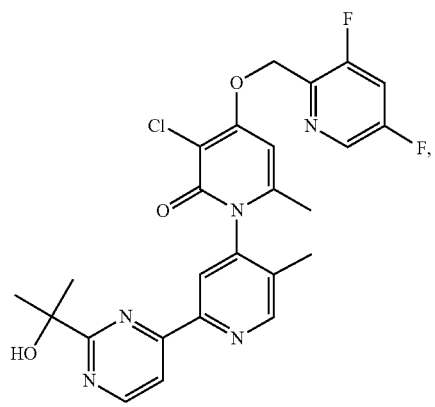

(I)

or a derivative thereof, and a pharmaceutically acceptable carrier.

Compound I is also referred to herein by its chemical name, i.e., 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

Compound I may be prepared according to the methods described in U.S. Pat. No. 9,115,089, which is hereby incorporated by reference in its entirety. Compound I may also be obtained from Aclaris Therapeutics, Inc. (640 Lee Road, Suite 200, Wayne, PA 19087, USA).

There are two atropisomers of 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one, which are depicted below as Compound (P)-I ((P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one) and Compound (M)-I ((M)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one).

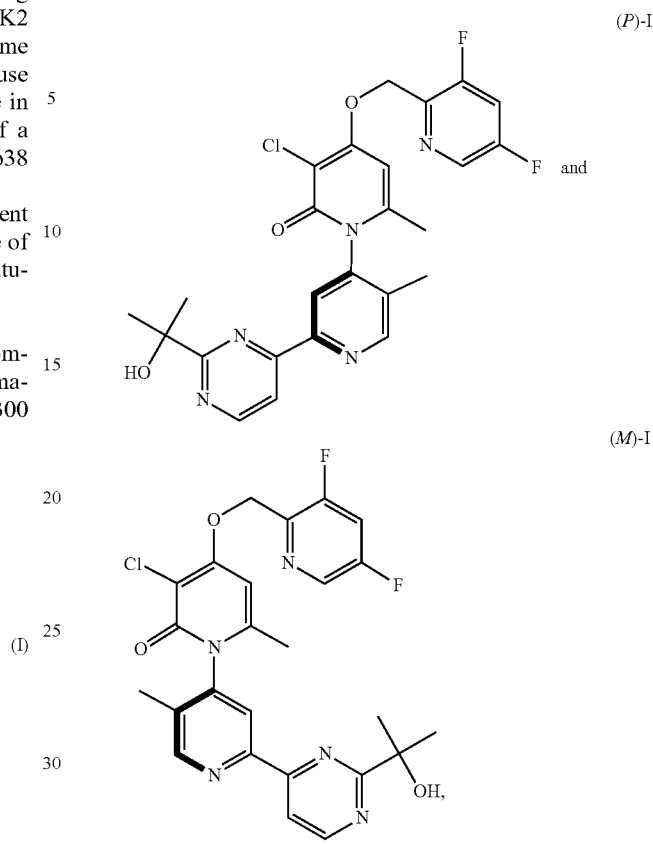

The term "atropisomerism" refers to a type of isomerism resulting from hindered rotation around a single bond due to steric strain of the substituents. This phenomenon creates stereoisomers which display axial chirality. Atropisomers may be separated (resolved) via supercritical fluid chromatography using a mobile phase of carbon dioxide and ethanol/methanol. Chiral resolution of the P and M atropisomers of 3-chloro-4-((3,5-difluoropyridin-2-yl)methoxy)-2'-(2-(2-hydroxypropan-2-yl)pyrimidin-4-yl)-5', 6-dimethyl-2H-[1,4'-bipyridin]-2-one is described in the Examples herein.

As used throughout this disclosure, recitation of "Compound I" encompasses atropisomer compounds (P)-I and (M)-I as depicted above in any molar ratio from 4:1 ((P)-I:(M)-I) to 999:1 and also includes embodiments where Compound (P)-I is substantially free from Compound (M)-I. Compounds (P)-I and (M)-I can be in any form (e.g., free base, crystalline form, etc.) as described herein.

In any embodiment, Compound I of the oral composition as disclosed herein comprises Compound (P)-I and Compound (M)-I in a molar ratio of about 4:1 ((P)-I:(M)-I) to about 999:1. In any embodiment, the molar ratio of (P)-I to (M)-I is about 4.3:1, about 4.6:1, about 4.9:1, about 5.25:1, about 5.7:1, about 6.1:1, about 6.7:1, about 7.3:1, about 8.1:1, about 9:1, about 10:1, about 11.5:1, about 13.3:1, about 15.7:1, about 19:1, about 24:1, about 32.3:1, about 49:1, about 91:1, about 110.1:1, about 124:1, about 141.9:1, about 165.7:1, about 199:1, about 249:1, about 332.3:1, about 399:1, about 499:1, and about 999:1. In a preferred embodiment, the molar ratio of (P)-I to (M)-I is about 399:1.

Said another way, in any embodiment, Compound I of the oral composition as disclosed herein comprises at least 80 mol % of Compound (P)-I. In any embodiment the oral composition as disclosed herein comprises at least 81 mol % of Compound (P)-I, at least 82 mol % of Compound (P)-I, at least 83 mol % of Compound (P)-I, at least 84 mol % of Compound (P)-I, at least 85 mol % of Compound (P)-I, at least 86 mol % of Compound (P)-I, at least 87 mol % of Compound (P)-I, at least 88 mol % of Compound (P)-I, at least 89 mol % of Compound (P)-I, at least 90 mol % of Compound (P)-I, at least 91 mol % of Compound (P)-I, at least 92 mol % of Compound (P)-I, at least 93 mol % of Compound (P)-I, at least 94 mol % of Compound (P)-I, at least 95 mol % of Compound (P)-I, at least 96 mol % of Compound (P)-I, at least 97 mol % of Compound (P)-I, at least 98 mol % of Compound (P)-I, at least 99 mol % of Compound (P)-I, at least 99.1 mol % of Compound (P)-I, at least 99.2 mol % of Compound (P)-I, at least 99.3 mol % of Compound (P)-I, at least 99.4 mol % of Compound (P)-I, at least 99.5 mol % of Compound (P)-I, at least 99.6 mol % of Compound (P)-I, at least 99.7 mol % of Compound (P)-I, at least 99.8 mol % of Compound (P)-I, at least 99.9 mol % of Compound (P)-I. In a preferred embodiment the oral composition as disclosed herein comprises at least 99.75 mol % of Compound (P)-I. In any embodiment, Compound I of the oral composition as disclosed herein comprises Compound (P)-I substantially free from Compound (M)-I.

In any embodiment, the oral pharmaceutical composition disclosed herein comprises 10 mg of Compound I. In any embodiment, the oral pharmaceutical composition disclosed herein comprises 40 mg of Compound I. In any embodiment, the oral pharmaceutical composition disclosed herein comprises 50 mg of Compound I. In any embodiment, the oral pharmaceutical composition disclosed herein comprises 60 mg of Compound I. In any embodiment, the oral pharmaceutical composition disclosed herein comprises 80 mg of Compound I. In any embodiment, the oral pharmaceutical composition disclosed herein comprises 100 mg of Compound I. In any embodiment, the oral pharmaceutical composition disclosed herein comprises 120 mg of Compound I. In any embodiment, the oral pharmaceutical composition disclosed herein comprises 160 mg of Compound I. In any embodiment, the oral pharmaceutical composition disclosed herein comprises 200 mg of Compound I. In any embodiment, the oral pharmaceutical composition disclosed herein comprises 240 mg of Compound I.

In any embodiment, the oral pharmaceutical compositions described herein comprise Compound I in an amount of about 5 mg to about 200 mg. In any embodiment, Compound I is present in the pharmaceutical composition as described herein in an amount of about 5 mg to about 300 mg, about 7.5 mg to about 300 mg, about 10 mg to about 300 mg, about 12.5 mg to about 300 mg, about 15 mg to about 300 mg, about 17.5 mg to about 300 mg, about 20 mg to about 300 mg, about 22.5 mg to about 300 mg, about 25 mg to about 300 mg, about 27.5 mg to about 300 mg, about 30 mg to about 300 mg, about 32.5 mg to about 300 mg, about 35 mg to about 300 mg, about 37.5 mg to about 300 mg, about 40 mg to about 300 mg, about 42.5 mg to about 300 mg, about 45 mg to about 300 mg, about 47.5 mg to about 300 mg, about 50 mg to about 300 mg, about 50 mg to about 290 mg, about 50 mg to about 280 mg, about 50 mg to about 270 mg, about 50 mg to about 260 mg, about 50 mg to about 250 mg, about 50 mg to about 240 mg, about 50 mg to about 230 mg, about 50 mg to about 220 mg, about 50 mg to about 210 mg, about 50 mg to about 200 mg about 50 mg to about 190 mg, about 50 mg to about 180 mg, about 50 mg to about 170 mg, about 50 mg to about 160 mg, about 50 mg to about 150 mg, about 50 mg to about 140 mg, about 50 mg to about 130 mg, about 50 mg to about 120 mg, about 50 mg to about 110 mg, about 50 mg to about 100 mg, about 50 mg to about 90 mg, about 50 mg to about 80 mg, about 50 mg to about 70 mg, about 50 mg to about 60 mg, about 40 mg to about 50 mg, about 30 mg to about 60 mg, about 20 mg to about 70 mg, about 15 mg to about 80 mg, about 10 mg to about 90 mg, about 5 mg to about 100 mg, or any amount in between. In a preferred embodiment, the oral pharmaceutical compositions described herein comprise Compound I in an amount of about 50 mg to about 240 mg.

In any embodiment, Compound I is present in the pharmaceutical composition as described herein in an amount of about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 92.5 mg, 95 mg, 97.5 mg, 100 mg, 105 mg, 107.5 mg, 110 mg, 112.5 mg, 115 mg, 117.5 mg, 120 mg, 122.5 mg, 125 mg, 127.5 mg, 130 mg, 132.5 mg, 135 mg, 137.5 mg, 140 mg, 142.5 mg, 145 mg, 147.5 mg, 150 mg, 152.5 mg, 155 mg, 157.5 mg, 160 mg, 162.5 mg, 165 mg, 167.5 mg, 170 mg, 172.5 mg, 175 mg, 177.5 mg, 180 mg, 182.5 mg, 185 mg, 187.5 mg, 190 mg, 192.5 mg, 195 mg, 197.5 mg, 200 mg, 200 mg, 205 mg, 207.5 mg, 210 mg, 212.5 mg, 215 mg, 217.5 mg, 220 mg, 222.5 mg, 225 mg, 227.5 mg, 230 mg, 232.5 mg, 235 mg, 237.5 mg, 240 mg, 242.5 mg, 245 mg, 247.5 mg, 250 mg, 252.5 mg, 255 mg, 257.5 mg, 260 mg, 262.5 mg, 265 mg, 267.5 mg, 270 mg, 272.5 mg, 275 mg, 277.5 mg, 280 mg, 282.5 mg, 285 mg, 287.5 mg, 290 mg, 292.5 mg, 295 mg, 297.5 mg, or 300 mg. In preferred embodiments, Compound I is present in the pharmaceutical composition as described herein in an amount of 50 mg, 80 mg, 100 mg, 120 mg, 160 mg, or 240 mg.

In any embodiment, Compound I of the oral composition as disclosed herein comprises a free base. In any embodiment, Compound I of the oral composition as disclosed herein comprises a pharmaceutically acceptable salt.

In any embodiment, Compound I of the oral composition comprises Compound (P)-I and Compound (M)-I as disclosed herein in the free base form. In any embodiment, Compound I of the oral composition comprises Compound (P)-I and Compound (M)-I as disclosed herein in form of pharmaceutically acceptable salts.

In any embodiment, the pharmaceutically acceptable salt is an acid addition salt. Suitable acid addition salts include those formed with both organic and inorganic acids. Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

In any embodiment, the pharmaceutically acceptable salt is a basic addition salt. Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In any embodiment, Compound I of the oral compositions is a non-solvated form or in a solvated form. In any embodiment herein one solvent molecule can be associated with one molecule of Compound I described herein, such as a hydrate. In some embodiments, more than one solvent molecule may be associated with one molecule of Compound I as described herein, such as a dihydrate. Additionally, in some embodiments herein less than one solvent molecule may be associated with one molecule of Compound I described herein, such as a hemihydrate. Furthermore, solvates of embodiments herein are contemplated as solvates of Compound I as described herein that retain the biological effectiveness of the non-solvate form of Compound I.

In any embodiment, Compound 1 of the oral composition is a deuterated derivative. As used herein, the term deuterated derivative embraces compounds of embodiments herein where in a particular position at least one hydrogen atom is replaced by deuterium. Deuterium (D or $^2$H) is a stable isotope of hydrogen which is present at a natural abundance of 0.015 molar %.

In any embodiment, Compound I of the oral composition as disclosed herein comprises Compound (P)-I (free base) in a crystalline form. In any embodiment, the crystalline form of Compound (P)-I is crystalline Form A as disclosed and characterized herein.

For example, the crystalline form A of Compound (P)-I of the oral composition may be characterized by its PXRD pattern. Thus, in any embodiment, the crystalline Form A of Compound (P)-I is characterized by an PXRD pattern having a peak expressed in degrees 2θ at about 9.78±0.2. In any embodiment, the crystalline Form A of Compound (P)-I is characterized by an PXRD pattern having peaks expressed in degrees 2θ at 9.78±0.2 and 15.51±0.2. In any embodiment, the crystalline Form A of Compound (P)-I is characterized by an PXRD pattern having peaks expressed in degrees 2θ at 9.78±0.2, 15.51±0.2, 19.6±0.2, and 25.92±0.2. In any embodiment, the crystalline Form A of Compound (P)-I is characterized by an PXRD pattern having peaks expressed in degrees 2θ at 9.78±0.2, 15.34±0.2, 15.51±0.2, 19.6±0.2, 20.57±0.2, 21.01±0.2, 25.92±0.2, 29.05±0.2, and 29.48±0.2. In any embodiment, the crystalline Form A of Compound (P)-I is characterized by an PXRD pattern of FIG. 27.

The crystalline Form A of Compound (P)-I of the oral composition disclosed herein may be additionally or alternatively characterized by thermogravimetric analysis (TGA). Samples of crystalline Form A of (P)-I yielded a TGA curve revealing that, in the sample analyzed, negligible weight loss was observed. Weight loss (0.7%) is observed between 25° C. and 256° C. by TGA for freebase crystalline Form A, suggesting that crystalline form A of (P)-I is substantially anhydrous.

The crystalline form A of (P)-I may additionally or alternatively be characterized by differential scanning calorimetry (DSC). Thus, in any embodiment, the crystalline Form A of Compound (P)-I is characterized by a DSC plot comprising an initial endothermic melting event with an onset temperature of about 188° C., followed by an exothermic recrystallization event at about 196° C., with a final sharp endothermic melting event at about 254° C.

In any embodiment, the oral composition of the present disclosure comprises Compound I as disclosed herein formulated by admixture with a pharmaceutically acceptable carrier or excipient. In certain embodiments, the pharmaceutical compositions include the therapeutically effective amount of Compound I and a physiologically acceptable diluent or carrier. In certain embodiments, the pharmaceutical composition further includes one or more additional therapeutic components and/or adjuvants.

In any embodiment, the oral compositions disclosed herein may further comprise pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for preparation and administration are known in the art and an artisan can refer to various pharmacologic references for guidance. For example, Banker, G. S., & Rhodes, C. T. (2002). *Modern pharmaceutics*. New York: Marcel Dekker.; and Goodman, L. S., Brunton, L. L., Chabner, B., & Knollmann, B. C. (2011). *Goodman & Gilman's pharmacological basis of therapeutics*. New York: McGraw-Hill. can be consulted.

The oral pharmaceutical compositions as disclosed herein can be formulated readily by combining Compound I with pharmaceutically acceptable carriers well known in the art. Such carriers enable the compounds of embodiments herein to be formulated as nanoparticles, nanoparticle suspension, tablets, troches, pills, dragees, capsules, powders, liquids, gels, syrups, slurries, suspensions and the like, for oral ingestion by a subject to be treated. Oral compositions can also be prepared using a fluid carrier for use as a mouthwash, wherein the compound in the fluid carrier is applied orally and swished and expectorated or swallowed. Pharmaceutical preparations for oral administration can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropyl methylcellulose (HPMC), sodium carboxymethylcellulose (CMC), and polyvinylpyrrolidone (PVP). If desired, disintegrating agents can be added, such as, but not limited to, the cross-linked PVP, agar, or alginic acid or a salt thereof such as sodium alginate.

Dragee cores can be provided with suitable coatings. For this purpose, concentrated sugar solutions can be used, which can optionally contain gum arabic, talc, PVP, carbopol gel, polyethylene glycol (PEG), and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredient in an admixture with one or more fillers (e.g., lactose), one or more binders (e.g., starches), and/or one or more lubricants (e.g., talc or magnesium stearate) and, optionally, one or more stabilizers. In soft capsules, the active compound can be dissolved or suspended in suitable liquids, such as fatty oils, liquid paraffin, or liquid PEG. In addition, stabilizers can be added. All compositions for oral administration should be in dosages (e.g., about 5 mg to about 300 mg) suitable for such administration.

In some embodiments, the oral compositions may take the form of, e.g., lozenges, tablets or capsules prepared by conventional means with pharmaceutically acceptable excipients such as binding agents (e.g., pregelatinized maize starch, PVP or HPMC); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, e.g., sugars, films or enteric coatings. Additionally, the pharmaceutical compositions containing Compound I as disclosed herein can be in any form suitable for oral use, including, e.g., troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

In one embodiment, the oral pharmaceutical composition as disclosed herein is a tablet. Tablets may contain Compound I in admixture with non-toxic pharmaceutically acceptable excipients which are suitable for the manufacture of tablets. These excipients may be e.g., inert diluents, such as calcium carbonate, sodium carbonate, lactose, calcium phosphate or sodium phosphate; granulating and disintegrating agents (e.g., corn starch, or alginic acid); binding agents (for example starch, gelatin or acacia); and lubricating agents (for example magnesium stearate, stearic acid or talc). The tablets may be uncoated or they may be coated by known techniques to delay disintegration and absorption in the gastrointestinal tract and thereby provide a sustained action over a longer period. In some embodiments, the tablet is formulated for immediate release. In some embodiments, the tablet is formulated for controlled release. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. The pharmaceutical compositions described herein may also be in the form of oil-in-water emulsions.

In some embodiments, the oral composition comprises Compound I and a buffer. In some embodiments, the buffer may be selected from the group consisting of citric acid monohydrate, sodium phosphate, water, and a combination thereof. In some embodiments, the oral composition comprises Compound I and a stabilizer. In some embodiments, the stabilizer is selected from a group consisting of povidone, sodium benzoate, water, sodium lauryl sulfate, and a combination thereof. In some embodiments, the oral composition further includes a buffer, an acid, sodium benzoate, sodium phosphate, citric acid, or a combination thereof. In some embodiments, the oral composition comprises Compound I and a stabilizer and a buffer. In some embodiments, the oral composition further comprises a lubricant, a pH modifier, a binder, a diluent, a granulating agent, a glidant, a disintegrant, a filler, a sorbent, an anti-adherent, a coloring agent, a compression aid, a coating material, a sweetener, a preservative, an antioxidant, or a combination thereof. In some embodiments, Compound I is in a therapeutically effective amount (e.g., about 5 mg to about 200 mg). In some embodiments, the oral composition is a suspension, tablet, capsule, nanoparticle powder, nanoparticle suspension, cachet, pellet, pill, powder, granules, or a combination thereof.

In some embodiments, the lubricant may be selected from the group consisting of stearic acid or its salts (e.g., magnesium stearate, calcium stearate), sodium lauryl sulfate, PEG, mineral oil, sodium benzoate, glyceryl palmitostearate, glyceryl behenate, sodium stearyl fumarate, and a combination thereof.

In some embodiments, the pH modifier may be an acid (e.g., hydrochloric acid, acetic acid, citric acid, phosphoric acid, sulfuric acid, or a combination thereof).

In some embodiments, the binder may be selected from the group consisting of a natural or synthetic polymer (e.g., starches, sugars, sugar alcohols, or cellulose derivatives) such as gelatin, glucose, lactose, sorbitol, xylitol, maltitol, methyl cellulose, microcrystalline cellulose (MCC), ethyl cellulose, HPMC, hydroxypropyl cellulose (HPC), starch, PVP, PEG, sodium alginate, CMC, and a combination thereof.

In some embodiments, the compression aid may be selected from the group consisting of silicified microcrystalline cellulose, microcrystalline cellulose, a physical mixture of MCC-colloidal silicon dioxide, and a combination thereof.

In some embodiments, the disintegrant may be selected from the group consisting of starch, cellulose derivatives and alginates, PVP, croscarmellose sodium, sodium starch glycolate, and a combination thereof.

In some embodiments, the filler may be selected from the group consisting of lactose, sucrose, glucose, mannitol, sorbitol, calcium carbonate, magnesium stearate, plant cellulose, dibasic calcium phosphate, dibasic sodium phosphate, vegetable fats and oils, and a combination thereof.

In some embodiments, the diluent may be selected from the group consisting of sugar compounds (e.g., sucrose, lactose, dextrin, glucose, sorbitol, or the like), inorganic compounds (e.g., silicates, calcium salts, or magnesium salts), sodium chloride, potassium chloride, and a combination thereof.

In some embodiments, the preservative may be selected from the group consisting of an antioxidant (e.g., vitamin A, vitamin E, vitamin C, retinyl palmitate, and selenium), an amino acid (e.g., cysteine, or methionine), citric acid, sodium citrate, a synthetic preservative (e.g., a paraben such as methyl paraben or propyl paraben), and a combination thereof.

In some embodiments, the glidant may be selected from the group consisting of colloidal anhydrous silicon and other silica compounds, such as fumed silica, magnesium carbonate, colloidal silicon dioxide (AEROSIL®), cornstarch, talc, and a combination thereof.

In some embodiments the oral composition comprising Compound I is a capsule. In some embodiments, the capsule comprises an inner coating made from a high fat emulsion. In some embodiments the capsule comprises a high fat coating that is either on the inside or the outside of the capsule. In some embodiments the capsule comprises HPMC. In some embodiments, the capsule may be a HPMC capsule. In some embodiments, the capsule may be enteric coated. In some embodiments, the capsule may be a silica capsule, such as silica sold under the trade name SYLOID®. In some embodiments, the capsule comprises cyclodextrin. In some embodiments, the capsule may be a cyclodextrin complex enteric capsule.

In some embodiments the oral formulation comprising Compound I is a tablet. In some embodiments the tablet contains Compound I in the form of nanoparticles. In some embodiments, the tablet may be coated. In some embodiments, the tablet may be coated with an enteric coating. In some embodiments, the tablet may be coated with a coating selected from a sugar coating, film coating, organic film coating, aqueous film coating, pan coating, dip coating, electrostatic coating, compression coating, plasticizer dry coating, heat dry coating, electrostatic dry coating, or the like. Some ingredients used for coating may include aqueous acrylic enteric system such as that sold under the trade name ACRYL-EZE®, film coating system sold under the trade name OPADRY®, HPMC, methyl hydroxyethyl cellulose, ethylcellulose, povidone, cellulose acetate phthalate, acrylate polymers (such as those sold under the trade name EUDRAGIT® L & EUDRAGIT® S), HPMC phthalate, or a combination thereof.

In some embodiments the oral composition comprises Compound I in the form of a nanoparticle suspension (nanosuspension). In some embodiments, the nanosuspension comprises Compound I, a stabilizer, and a buffer. In some embodiments, the nanosuspension may further comprise a pH modifier. In some embodiments, the pH modifier may be selected from a group consisting of hydrochloric acid, acetic acid, citric acid, phosphoric acid, sulfuric acid, and a combination thereof. In some embodiments, the pH modifier may be hydrochloric acid. In some embodiments, the hydrochloric acid may be 1.0N hydrochloric acid. In some embodiments, the stabilizer may be selected from the group consisting of povidone, sodium lauryl sulfate, sodium benzoate, WFI quality water such as that sold under the tradename HYCLONE™, or a combination thereof. In some embodiments, the buffer solution may include WFI quality water, sodium phosphate (dibasic, 7-hydrate, crystal), citric acid monohydrate, or a combination thereof.

The nanoparticle suspension may be manufactured by suspending particles of the active in the excipients, reducing particles to the desired particle size using grinding media in a mill, and then diluting the suspension to the final volume. In some embodiments, the grinding media used may be selected from ceramic, agate, silicon nitride, sintered corundum, zirconia, stainless steel, chrome steel, Cr—Ni steel, tungsten carbide, glass (yttrium-stabilized), cross-linked polystyrene resins, plastic polyamide, pearls, or a combination thereof. In some embodiments, the mill may be a stationary agitated vessel or a recirculating mill.

A tablet may be manufactured by spraying the nanosuspension (above) onto sucrose to form a spray granulate intermediate, granulating the spray granulate intermediate with excipients to form a final granulation, and compressing the final granulation to form a tablet. The sucrose could be any sugar, including, e.g., glucose, fructose, maltose, galactose, lactose, or the like. In some embodiments, the excipients for the tablet formulation may include lactose monohydrate, PVP, silicified microcrystalline cellulose (e.g., sold under the trade name PROSOLV® SMCC HD 90), magnesium stearate, or a combination thereof. In some embodiments, the tablet comprises about 5 mg to about 300 mg of Compound I.

In some embodiments the oral composition as described herein is a dry powder. In some embodiments, the dry powder may be encapsulated or made into a suspension. In some embodiments, the suspension may be a nanoparticle suspension or a milled suspension.

In some embodiments, liquid preparations for oral administration may take the form of, e.g., elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE® or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers (e.g., PEG).

The compositions can further include one or more additional pharmaceutical agents such as an anti-inflammatory drug, an anti-atherosclerotic drug, an immunosuppressive drug, an immunomodulatory drug, a cytostatic drug, an angiogenesis inhibitor, a kinase inhibitor, a cytokine blocker, and an inhibitor of cell adhesion molecules.

Methods of Use

Another aspect of the present disclosure relates a method for treating an inflammatory condition in a subject in need thereof. This method comprises administering, to a human subject having an inflammatory condition, an oral dose of 5 mg/day to 300 mg/day of Compound I, i.e., Compound (P)-I and (M)-I in any molar ratio as described supra and in any form (e.g., free form, crystalline form) as described supra. A particularly useful oral dose of Compound I for use in the methods described herein comprises an oral dose of 100 mg/day to 240 mg/day of Compound I comprising greater than 80 mol % of Compound (P)-I.

Suitable inflammatory conditions that can be treated in accordance with the methods disclosed herein include any inflammatory condition involving the p38 MAP kinase-mediated inflammatory signaling. In some embodiments the inflammatory condition is a chronic inflammatory condition. In some embodiments, the inflammatory condition is an acute inflammatory condition. In some embodiments, the inflammatory condition is an autoinflammatory condition. In some embodiments, the inflammatory condition is an autoimmune condition. In some embodiments, the inflammatory condition is inflammasomopathy.

For example, in any embodiment, the methods and compositions disclosed herein are suitable for treating chronic or acute inflammatory or autoimmune gastrointestinal disorders, inflammatory or autoimmune skin disorders, neuroinflammatory disorders, inflammatory heart disease, inflammatory lung diseases, inflammatory myopathies, inflammatory bone disorders or diseases, periodic fever syndromes, as well as pain or pruritus associated with any aforementioned disease.

Compound I, in any embodiment, also be used to treat scarring/fibrotic diseases or disorders and various types of cancers and hyper proliferative disorders.

For example, in any embodiment, the methods and compositions disclosed herein are suitable for treating inflammatory arthritis, such as rheumatoid arthritis (RA), spondyloarthritis such as ankylosing spondylitis, psoriatic arthritis, reactive arthritis and Reiter's syndrome, juvenile rheumatoid arthritis (JIA), systemic-onset juvenile rheumatoid arthritis, idiopathic arthritis (JIA) (including systemic (SJIA)), and gout; cryopyrin-associated autoinflammatory syndromes (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), including emphysema, chronic bronchitis, and asthma (allergic and non-allergic); inflammatory skin conditions, including, but not limited to hidradenitis suppurativa (HS), psoriasis, such as plaque psoriasis, pyoderma gangrenosum, IL-17 associated skin condition, pruritus; colitis from an inflammatory bowel disease (IBD) such as Crohn's disease or ulcerative colitis and inflammatory bowel disease-associated arthritis; pericarditis, including acute pericarditis, recurrent pericarditis, and chronic pericarditis; pulmonary inflammation or fibrosis, including idiopathic pulmonary fibrosis and interstitial lung disease; metastatic breast cancer, and pancreatic cancer.

In any embodiment, the methods and compositions disclosed herein are suitable for treating Familial Mediterranean Fever (FMF); tumor necrosis factor receptor-associated periodic syndrome (TRAPS); adult-onset Still's disease; pyoderma gangrenosum; bone-resorption disorders (such as those associated with cancer (e.g., breast cancer)); metastatic melanoma; Castleman disease; and chronic atypical neutrophilic dermatosis with lipodystrophy (CANDLE).

In some embodiments, the condition that is treated in accordance with the methods described here is pruritus, which may be associated with any other condition, for example, pruritus associated with hidradenitis suppurativa, pruritus associated with inflammation, pruritus associated with rheumatoid arthritis, pruritus associated with psoriasis, and pruritus associated with TH17-associated inflammation.

In any embodiment, the methods and compositions disclosed herein are suitable for treating Lyme disease; cytokine release syndrome (CRS); acute respiratory distress syndrome (ARDS); chronic or acute bronchitis; epidermolysis bullosa (EB); bullous pemphigoid; juvenile dermatomyositis; inflammatory vitiligo (including marginal); pemphigus vulgaris; enterocolitis; polymyositis; myositis, bone cancer; lung cancer; inflammatory bone disorders such as chronic recurrent multi osteomyelitis (CRMO), Synovitis, acne, pustulosis, hyperostosis, and osteitis (SAPHO) syndrome, Majeed syndrome, deficiency of interleukin-1 receptor antagonist (DIRA) and cherubism; bone resorption (such as is associated with an autoimmune disease); neuroinflammatory diseases such as Alzheimer's disease (AD), Parkinson's disease (PD), multiple sclerosis (MS), acute disseminated encephalomyelitis (ADEM), acute optic neuritis (AON), transverse myelitis, and neuromyelitis optical (NMO); Behcet's disease; endotoxic shock (e.g., toxic shock syndrome (TSS) and other systemic gram-negative bacterial infections); enthesitis; polyarteritis nodosa (PAN); chronic pain; polymyalgia rheumatica; chronic allograft rejection; Sjogren's syndrome; and Schnitzler's syndrome (SchS).

In any embodiment, the condition that is treated in accordance with the methods described here is arthritis, such as inflammatory arthritis, rheumatoid arthritis (RA), spondyloarthritis such as ankylosing spondylitis, psoriatic arthritis, reactive arthritis and Reiter's syndrome, juvenile rheumatoid arthritis (JIA), systemic-onset juvenile rheumatoid arthritis, idiopathic arthritis (JIA) (including systemic (SJIA)), gout, and inflammatory bowel disease-associated arthritis.

In any embodiment, the condition to be treated is rheumatoid arthritis, ankylosing spondylitis, or psoriatic arthritis.

In any embodiment, the condition that is treated is an inflammatory skin condition, such as, hidradenitis suppurativa, psoriasis, such as plaque psoriasis, pyoderma gangrenosum, an IL-17 related inflammatory skin condition, and a IL-1α related inflammatory skin condition.

In any embodiment, the condition to be treated is cryopyrin associated periodic syndrome (CAPS), including MWS, NOMIDS, and FCAS.

In any embodiment, the condition to be treated is irritable bowel disease, including colitis, Crohn's disease and ulcerative colitis.

In any embodiment, the condition to be treated is cytokine release syndrome, for example, CAR-T cell induced cytokine release syndrome, and acute respiratory distress syndrome.

In any embodiment, the condition to be treated is cancer, including, but not limited to, metastatic breast cancer, pancreatic cancer, colorectal cancer and lung cancer.

In any embodiment, the condition to be treated is chronic obstructive pulmonary diseases (COPD), including emphysema, chronic bronchitis, and asthma (allergic and non-allergic).

In any embodiment, the condition to be treated is pulmonary fibrosis, including idiopathic pulmonary fibrosis and interstitial lung disease.

Other conditions that may be treated in accordance with the methods and compositions disclosed herein include inflammatory and/or autoimmune conditions such as allergic and non-allergic asthma, pancreatitis, autoimmune encephalomyelitis, autoimmune myositis, giant-cell arteritis, episcleritis, glomerulonephritis, Hashimoto's thyroiditis, keratitis, lupus nephritis, myocarditis, enteritis, neutrophilic eccrine hidradentitis, nonalcoholic steatohepatitis, periodontitis, polychondritis, primary sclerosing cholangitis, schleritis, sinusitis, small vessel vasculitis, large vessel vasculitis, Takayasu's arteritis, atopic dermatitis, autoimmune and inflammatory hepatitis, autoimmune atrophic gastritis, autoimmune orchitis, bronchiolitis, bronchioligis obliterans, carditis, chortitis, esophagitis, hepatitis C, optic neurotis, uveitis, tinea capitis, acne vulgaris, and hypophysitis, lupus, myasthenia gravis, pernicious anemia, type I diabetes, Addison's disease, Chagas disease, peripheral neuropathy, hypoxia or ischemia induced inflammation, autoimmune nephropathy, cicatricial pemphigoid, Goodpasture's Disease, Graves' disease, histiocytoid neutrophilic dermatosis, hypereosinophilic syndrome, stimulator of interferon genes-associated vasculopathy with onset in infancy (SAVI), Churg-Strauss syndrome, Guillain-Barret syndrome, immune-mediated glomerulonephritis, linear IgA disease, sarcoidosis, sympathetic ophthalmia, and type 3 hypersensitivity reaction disease.

Other conditions that may be treated in accordance with the methods and compositions disclosed herein include any condition where MK2 inhibition is therapeutically beneficial, such as cancer (e.g., head/neck cancer, bladder cancer, intestinal cancer, non-small cell lung cancer, astrocytoma, small cell lung cancer, colon cancer, colorectal cancer, esophageal cancer, fibrotic cancers, hepatic cancers, leukemia, kidney cancer, larynx cancer, multiple myeloma, Merkel cell carcinoma, mouth or pharynx cancer, nerve cancer, non-melanoma skin cancer, ovarian cancer, prostate cancer, renal cancer, seminoma, squamous cell carcinoma, stomach cancer, schwannoma, teratocarcinoma, testicular cancer, osteosarcoma, rhabdomyosarcoma, Wegener's granulomatosis, keratocanthoma, Kaposi's sarcoma, glioblastoma, glioma, t-cell lymphoma, throat cancer, thyroid cancer, thyroid follicular cancer, and uterine cancer), fibrotic conditions (e.g., atrial fibrosis, cardiac fibrosis, cystic fibrosis, endomyocardial fibrosis, hepatic fibrosis, idiopathic myelofibrosis (IMF), mediastinal fibrosis, myelofibrosis, nephrogenic systemic fibrosis, renal fibrosis, retroperitoneal fibrosis, fibroadenomas, fibromyalgia, fibrosarcomas, fibrosclerosis, fibroids, fibroma, fibrosing alopecia, glomerulosclerosis, juvenile scleroderma, membranous glomerulopathy, sc leroderma, and cardiac-allograft vasculopathy), and gastrointestinal fibrosis), retinopathy, cirrhosis, and keratopathy.

As described supra, the oral composition suitable for administration in accordance with the methods described herein comprises a therapeutically effective amount (e.g., about 50 mg/day to about 300 mg/day) of Compound I (i.e., in a molar ratio of Compound (P)-I Compound (M)-I) of 4:1 to 999:1) or an oral pharmaceutical composition comprising the same.

The specific dose level for any particular patient will depend upon a variety of factors including the activity of the specific compound employed, the age, body weight, general health, sex, diet, time of administration, rate of excretion, drug combination, the precise disorder being treated, and the severity of the indication or condition being treated.

In some embodiments, administration of Compound I (i.e., in a molar ratio of Compound (P)-I:Compound (M)-I) of 4:1 to 999:1) or an oral pharmaceutical composition comprising the same is effective to cause at least partial remission of the symptoms that characterize the disease. In some embodiments, administration of one or more of the presently disclosed oral compositions of embodiments herein is effective to cause at least full remission of the symptoms that characterize the disease.

In any embodiment, administration of a composition comprising Compound I as described herein is effective to cause inhibition of p38 MAP kinase-mediated pro-inflammatory, but not anti-inflammatory signaling. In some embodiments, administration of one or more of the presently disclosed oral compositions of embodiments herein is effective to cause inhibition of MK2 inflammatory signaling. Inhibition of p38 MAP kinase and MK2 mediated inflammatory signaling can be measured or assessed by in vivo serum levels of one or more inflammatory cytokines, including, but not limited to TNF-$\alpha$, IL-1$\beta$, IL-6, IL-8, IFN$\gamma$, IL-17, IL-18, IL-1$\alpha$, and MIP1$\beta$. Thus in any embodiment, administration of a composition comprising Compound I, in particular, a composition comprising at least 80 mol %, at least 90 mol %, at least 95 mol %, or at least 99 mol % of Compound (P)-I at the dosages described herein (e.g., 100 mg/day, 160 mg/day, or 240 mg/day) reduces the in vivo serum levels of one or more cytokines selected from TNF-$\alpha$, IL-1$\beta$, IL-6, IL-8, IFN$\gamma$, IL-17, IL-18, IL-1$\alpha$, and MIP1$\beta$ in a subject as compared to the in vivo serum levels of the corresponding cytokines prior to treatment of the subject with the composition comprising Compound I.

In one embodiment, the inflammatory condition to be treated in accordance with the methods and compositions comprising Compound I described herein is arthritis, in particular moderate to severe rheumatoid arthritis. In some embodiments, treatment of a subject having moderate to severe rheumatoid arthritis in accordance with the methods and compositions comprising Compound I as described herein, alone or in combination with methotrexate, is effective to inhibit progression of joint damage, improve synovitis, or both as assessed by magnetic resonance imaging (MRI).

In some embodiments, treatment of a subject having moderate to severe rheumatoid arthritis in accordance with the methods and compositions comprising Compound I as described herein, alone or in combination with methotrexate, is effective to reduce high sensitivity C-reactive protein (hsCRP) levels in the subject. In some embodiments, hsCRP is reduced relative to the baseline level (i.e., the hsCRP level prior to treatment) by at least 10%, by at least 20%, by at least 30%, by at least 40%, or by greater than 40%. Preferably, treatment with the Compound I reduced hsCRP levels by greater than 40% relative to baseline.

In some embodiments, treatment of a subject having moderate to severe rheumatoid arthritis in accordance with the methods and compositions comprising Compound I as described herein, alone or in combination with methotrexate, is effective to reduce the subject's Disease Activity Score for 28 Joint Count (DAS28). The DAS28 consists of a composite score of the following variables: tender joint count, swollen joint count, CRP, and Patient's Global Assessment of Disease Activity score. Interpretation of the DAS28 (CRP) disease activity measure is on a scale of 0 to 9.4, where: <2.6 is considered remission, ≥2.6 to <3.2 is considered low/minimal, ≥3.2 to ≤5.1 is considered moderate, and >5.1 is considered high/severe (Anderson et al., "Rheumatoid arthritis disease activity measures: American College of Rheumatology recommendations for use in clinical practice," *Arthritis Care Res* (Hoboken) 64(5):640-7 (2012), which is hereby incorporated by reference in its entirety). Thus, in some embodiments, treatment of moderate to severe rheumatoid arthritis in accordance with the methods and compositions comprising Compound I as described herein is effective to reduce the DAS28(CRP) score to ≤3.2 over the course of treatment as an indicator of low disease activity of remission. In some embodiments, treatment of severe rheumatoid arthritis in accordance with the methods and compositions comprising Compound I as described herein is effective to reduce the DAS28(CRP) score to <2.6 over the course of treatment as an indicator of remission.

In some embodiments, treatment of a subject having moderate to severe rheumatoid arthritis in accordance with the methods and compositions comprising Compound I as described herein, alone or in combination with methotrexate, is effective to achieve at least 20% improvement in the swollen and tender joints counts and an improvement of least 20% in at least 3 of the following 5 measures: (i) Patient's Global Assessment of Disease Activity (VAS), (ii) Patient's Assessment of Arthritis Pain (VAS), (iii) Patient's Assessment of Physical Function/Health Assessment Questionnaire-Disability Index (HAQ-DI), (iv) Physician's Global Assessment of Disease Activity (VAS), (v) Acute phase reactant as measured by hsCRP. In some embodiments, treatment with compositions comprising Compounds I as describe herein, alone or in combination with methotrexate, is effective to achieve at least 50% improvement in the swollen and tender joints counts and an improvement of least 50% in at least 3 of the 5 above noted measures. In some embodiments, treatment with compositions comprising Compound I as describe herein, alone or in combination with methotrexate, is effective to achieve at least 70% improvement in the swollen and tender joints counts and an improvement of least 70% in at least 3 of the 5 above noted measures.

In some embodiments, treatment of a subject having moderate to severe rheumatoid arthritis in accordance with the methods and compositions comprising Compound I as described herein, alone or in combination with methotrexate, is effective to significantly reduce predosing levels of one or more inflammatory cytokines. In some embodiments, treatment of a subject having severe rheumatoid arthritis with a composition comprising Compound I, alone or in combination with methotrexate, is effective to significantly reduce predosing levels of one or more of TNF-α, IL-6, IL-8, IL-1β, and MIP1β. In any embodiment, the aforementioned cytokine levels are reduced by least 10%, at least 15%, at least 20%, at least 30%, at least 40%, at least 50%, at least 60%, at least 70%, or greater than 75% following administration of a composition comprising Compound I as disclosed in the Examples herein.

In some embodiments, treatment of a subject having moderate to severe active psoriatic arthritis in accordance with the methods and compositions comprising Compound I as described herein, alone or in combination with methotrexate, is effective to achieve at least a 20% reduction (improvement) compared with baseline in tender joint count (TJC), swollen joint count (SJC), and an improvement of least 20% in at least at least 3 of the 5 remaining ACR core set measures: (i) patient's assessment of pain, (ii) patient's global assessment of disease activity (PtGA); (iii) physician's global assessment of disease activity (PhGA), (iv) Health Assessment Questionnaire-Disability Index (HAQ-DI), and (iv) high sensitivity C-reactive protein (hsCRP).

In some embodiments, treatment of a subject having moderate to severe active psoriatic arthritis in accordance with the methods and compositions comprising Compound I as described herein, alone or in combination with methotrexate, is effective to achieve a static Investigator Global Assessment (sIGA) of Psoriasis of 0 or 1 and at least a 2-point improvement from baseline (pre-treatment) sIGA levels.

In some embodiments, treatment of a subject having moderate to severe active psoriatic arthritis in accordance with the methods and compositions comprising Compound I as described herein, alone or in combination with methotrexate, is effective to achieve a psoriasis area severity index (PASI) 75 response (for participants with at least a 3% BSA psoriasis as baseline).

In some embodiments, treatment of a subject having moderate to severe active psoriatic arthritis in accordance with the methods and compositions comprising Compound I as described herein, alone or in combination with methotrexate, is effective to achieve minimal disease activity (MDA), determined based on meeting 5 of 7 outcome measures: TJC≤1; SJC≤1; PASI≤1 or BSA-Ps≤3%; Patient's Assessment of Pain NRS≤1.5; PtGA-Disease Activity NRS≤2.0; HAQ-DI score≤0.5; and tender entheseal points ≤1.

In some embodiments, treatment of a subject having moderate to severe active psoriatic arthritis in accordance with the methods and compositions comprising Compound I as described herein, alone or in combination with methotrexate, is effective to significantly reduce predosing levels of one or more of TNF-α, IL-1β, IL-6, IL-8, IFNγ, IL 17, IL-18, IL-1α and MIP1β. In any embodiment, the aforementioned cytokine levels are reduced by least 10%, at least 15%, at least 20%, at least 30%, at least 40%, at least 50%, at least 60%, at least 70%, or greater than 75% following administration of a composition comprising Compound I.

In some embodiments, treatment of a subject having moderate to severe Hidradenitis Suppurativa (HS) in accordance with the methods and compositions comprising Compound I as described herein, alone or in combination with antibiotics, is effective to achieve a Hidradenitis Suppurativa Clinical Response (HiSCR) during the course of treatment, where HiSCR is defined as at least a 50% reduction from baseline in the total abscess and inflammatory nodule (AN) count, with no increase in abscess or draining fistula counts.

In some embodiments, treatment of a subject having moderate to severe Hidradenitis Suppurativa (HS) in accordance with the methods and compositions comprising Compound I as described herein, alone or in combination with antibiotics, is effective to achieve at least 30% reduction from baseline (pre-treatment) level in Numerical Rating Scale (NRS30) in Patient's Global Assessment of Skin Pain (PGA Skin Pain) during the course of treatment.

In some embodiments, treatment of a subject having moderate to severe Hidradenitis Suppurativa (HS) in accordance with the methods and compositions comprising Compound I as described herein, alone or in combination with antibiotics, is effective to achieve at least 25% decrease in AN counts with a minimum increase of 2 relative to baseline over the treatment period.

In some embodiments, treatment of a subject having moderate to severe Hidradenitis Suppurativa (HS) in accordance with the methods and compositions comprising Compound I as described herein, alone or in combination with antibiotics, is effective to achieve at least one or more of the following: increase from baseline in Dermatology Life Quality Index (DLQI) with treatment (the DLQI is a 10-item validated questionnaire used to assess the impact of HS disease symptoms and treatment on quality of life (QoL); decrease from baseline in HS-related swelling assessed based on the Hidradenitis Suppurativa Symptom Assessment (HSSA) with treatment (HSSA is a 9-item patient reported outcome (PRO) questionnaire developed to assess the symptoms of HS on a 0 to 11-point NRS, where 0 represents no symptoms and 10 represents extreme symptom experience); decrease from baseline in HS-related odor assessed based on the HSSA over 12-weeks; change from baseline in HS-related worst drainage assessed based on the HSSA with treatment.

In some embodiments, treatment of a subject having moderate to severe Hidradenitis Suppurativa (HS) in accordance with the methods and compositions comprising Compound I as described herein, alone or in combination with antibiotics, is effective to achieve decrease from baseline in one or more endogenous cytokine levels selected from TNF-α IL-1β, IL-6, IL-8, IFNγ, IL 17, IL-18, MIP1β, and IL-1α. In any embodiment, the aforementioned cytokine levels are reduced by least 10%, at least 15%, at least 20%, at least 30%, at least 40%, at least 50%, at least 60%, at least 70%, or greater than 75% following administration of a composition comprising Compound I.

In some embodiments, treatment of a subject having a Cryopyrin-associated Periodic Syndrome (CAPS) (e.g., Familial Cold Autoinflammatory Syndrome, Muckle-Wells Syndrome, or Neonatal Onset Multisystem Inflammatory Disease) in accordance with the methods and compositions comprising Compound I as described herein, is effective to cause disease remission as defined by one or both of (i) a Physician Global Assessment (PGA) score of absent or minimal, and (ii) a high sensitivity C-reactive protein (hsCRP) and serum amyloid A (SAA) value within the normal range (≤10 mg/L) or within 30 percent of the baseline value.

In some embodiments, treatment of a subject having a Cryopyrin-associated Periodic Syndrome (CAPS) (e.g., Familial Cold Autoinflammatory Syndrome, Muckle-Wells Syndrome, or Neonatal Onset Multisystem Inflammatory Disease) in accordance with the methods and compositions comprising Compound I as described herein, is effective to cause clinical remission as defined by a Physician Global Assessment (PGA) score of absent or minimal.

In some embodiments, treatment of a subject having a Cryopyrin-associated Periodic Syndrome (CAPS) (e.g., Familial Cold Autoinflammatory Syndrome, Muckle-Wells Syndrome, or Neonatal Onset Multisystem Inflammatory Disease) in accordance with the methods and compositions comprising Compound I as described herein, is effective to maintain a mean Key Symptom Score (KSS) of no more than 2 points higher than baseline with treatment. KSS is derived from the patient-administered daily health assessment form (DHAF), and is the average on a 0 to 10 scale (0=None, 10=Very Severe) of 5 separate scales—rash, feeling of fever and chills, joint pain, eye redness and pain, and fatigue.

In some embodiments, treatment of a subject having a Cryopyrin-associated Periodic Syndrome (CAPS) (e.g., Familial Cold Autoinflammatory Syndrome, Muckle-Wells Syndrome, or Neonatal Onset Multisystem Inflammatory Disease) in accordance with the methods and compositions comprising Compound I as described herein, is effective to significantly reduce predosing levels of one or more of TNF-α, IL-6, IL-8, IL-1β, and MIP1β. In any embodiment, the aforementioned cytokine levels are reduced by least 10%, at least 15%, at least 20%, at least 30%, at least 40%, at least 50%, at least 60%, at least 70%, or greater than 75% following administration of a composition comprising Compound I.

In any embodiment, the oral compositions of Compound I described herein may be administered at a first dose to prevent progression, at a second dose to induce remission, and/or a third dose to prevent the disease and/or maintain remission of the disease. Such doses may be the same dose, a lower dose, or a higher dose. The dose may be administered more frequently, less frequently or at the same frequency. In some embodiments, the dose may be administered in combination with another therapy, a therapeutic, an adjuvant, or the like.

As described supra, subjects suitable for treatment in accordance with the methods described herein include, humans and non-human vertebrates such as wild, domestic, and farm animals. In some embodiments, the subject described herein is an animal. In some embodiments, the subject is a mammal. In come embodiments, the subject is a human. In some embodiments, the subject is a non-human animal. In some embodiments, the subject is a non-human mammal.

Dosing Regimen

Compound I, i.e., Compound (P)-I and (M)-I in any molar ratio as described supra and in any form (e.g., free form, crystalline form) as described supra, or an oral pharmaceutical composition comprising the same is administered in an amount effective to inhibit p38 MAP Kinase-mediated inflammatory signaling in a subject in need thereof. Subjects in need of such therapy are disclosed above. In some embodiments, the subject is one having an inflammatory condition, e.g., a chronic inflammatory condition, an acute inflammatory condition, an immune-inflammatory condition, an autoimmune condition, or an inflammasomopathy. In accordance with the methods disclosed herein, a therapeutically effective amount comprises 5 mg/day to 300 mg/day of Compound I. The dosage to be administered to a particular subject will depend on the characteristics of the particular subject being treated, e.g., the particular subject treated, age, weight, health, types of concurrent treatment, if any, and frequency of treatments, and can be easily determined by one of skill in the art (e.g., by the clinician).

In any embodiment, 10 mg/day of Compound I is administered to a subject having a condition disclosed herein. In any embodiment, 40 mg/day of Compound I is administered to a subject having a condition disclosed herein. In any embodiment, 50 mg/day of Compound I is administered to a subject having a condition disclosed herein. In any embodiment, 60 mg/day of Compound I is administered to a subject having a condition disclosed herein. In any embodiment, 80 mg/day of Compound I is administered to a subject having a condition disclosed herein. In any embodiment, 100 mg/day of Compound I is administered to a subject having a condition disclosed herein. In any embodiment, 120 mg/day of Compound I is administered to a subject having a condition disclosed herein. In any embodiment, 160 mg/day of Compound I is administered to a subject having a condition disclosed herein. In any embodiment, 200 mg/day of Compound I is administered to a subject having a condition disclosed herein. In any embodiment, 240 mg/day of Compound I is administered to a subject having a condition disclosed herein.

In any embodiment, the therapeutically effective amount of Compound I is 5 mg/day to 300 mg/day, about 7.5 mg/day to about mg/day, about 10 mg/day to about 300 mg/day, about 12.5 mg/day to about 300 mg/day, about 15 mg/day to about 300 mg/day, about 17.5 mg/day to about 300 mg/day, about 20 mg/day to about 300 mg/day, about 22.5 mg/day to about 300 mg/day, about 25 mg/day to about 300 mg/day, about 27.5 mg/day to about 300 mg/day, about 30 mg/day to about 300 mg/day, about 32.5 mg/day to about 300 mg/day, about 35 mg/day to about 300 mg/day, about 37.5 mg/day to about 300 mg/day, about 40 mg/day to about 300 mg/day, about 42.5 mg/day to about 300 mg/day, about 45 mg/day to about 300 mg/day, about 47.5 mg/day to about 300 mg/day, about 50 mg/day to about 300 mg/day, about 50 mg/day to about 290 mg/day, about 50 mg/day to about 280 mg/day, about 50 mg/day to about 270 mg/day, about 50 mg/day to about 260 mg/day, about 50 mg/day to about 250 mg/day, about 50 mg/day to about 240 mg/day, about 50 mg/day to about 230 mg/day, about 50 mg/day to about 220 mg/day, about 50 mg/day to about 210 mg/day, about 50 mg/day to about 200 mg/day, about 50 mg/day to about 190 mg/day, about 50 mg/day to about 180 mg/day, about 50 mg/day to about 170 mg/day, about 50 mg/day to about 160 mg/day, about 50 mg/day to about 150 mg/day, about 50 mg/day to about 140 mg/day, about 50 mg/day to about 130 mg/day, about 50 mg/day to about 120 mg/day, about 50 mg/day to about 110 mg/day, about 50 mg/day to about 100 mg/day, about 50 mg/day to about 90 mg/day, about 50 mg/day to about 80 mg/day, about 50 mg/day to about 70 mg/day, about 50 mg/day to about 60 mg/day, about 40 mg/day to about 50 mg/day, about 30 mg/day to about 60 mg/day, about 20 mg/day to about 70 mg/day, about 15 mg/day to about 80 mg/day, about 10 mg/day to about 90 mg/day, about 5 mg/day to about 100 mg/day, or any amount in between. In a preferred embodiment the therapeutically effective amount of Compound I is about 100 mg/day to about 240 mg/day.

In some embodiments the therapeutically effective amount of Compound I comprises 5 mg/day, 7.5 mg/day, 10 mg/day, 12.5 mg/day, 15 mg/day 17.5 mg/day, 20 mg/day, 22.5 mg/day, 25 mg/day, 27.5 mg/day, 30 mg/day, 32.5 mg/day, 35 mg/day, 37.5 mg/day, 40 mg/day, 42.5 mg/day, 45 mg/day, 47.5 mg/day, 50 mg/day, 52.5 mg/day, 55 mg/day, 57.5 mg/day, 60 mg/day, 62.5 mg/day, 65 mg/day, 67.5 mg/day, 70 mg/day, 72.5 mg/day, 75 mg/day, 77.5 mg/day, 80 mg/day, 82.5 mg/day, 85 mg/day, 87.5 mg/day, 90 mg/day, 92.5 mg/day, 95 mg/day, 97.5 mg/day, 100 mg/day, 105 mg/day, 107.5 mg/day, 110 mg/day, 112.5 mg/day, 115 mg/day, 117.5 mg/day, 120 mg/day, 122.5 mg/day, 125 mg/day, 127.5 mg/day, 130 mg/day, 132.5 mg/day, 135 mg/day, 137.5 mg/day, 140 mg/day, 142.5 mg/day, 145 mg/day, 147.5 mg/day, 150 mg/day, 152.5 mg/day, 155 mg/day 157.5 mg/day, 160 mg/day, 162.5 mg/day, 165 mg/day, 167.5 mg/day, 170 mg/day, 172.5 mg/day, 175 mg/day, 177.5 mg/day, 180 mg/day, 182.5 mg/day, 185 mg/day, 187.5 mg/day, 190 mg/day, 192.5 mg/day, 195 mg/day, 197.5 mg/day, 200 mg/day, 205 mg/day, 207.5 mg/day, 210 mg/day, 212.5 mg/day, 215 mg/day, 217.5 mg/day, 220 mg/day, 222.5 mg/day, 225 mg/day, 227.5 mg/day, 230 mg/day, 232.5 mg/day, 235 mg/day, 237.5 mg/day, 240 mg/day, 242.5 mg/day, 245 mg/day, 247.5 mg/day, 250 mg/day, 252.5 mg/day, 255 mg/day 257.5 mg/day, 260 mg/day, 262.5 mg/day, 265 mg/day, 267.5 mg/day, 270 mg/day, 272.5 mg/day, 275 mg/day, 277.5 mg/day, 280 mg/day, 282.5 mg/day, 285 mg/day, 287.5 mg/day, 290 mg/day, 292.5 mg/day, 295 mg/day, 297.5 mg/day, 300 mg/day. In preferred embodiments, the therapeutically effective amount of Compound I comprises 100 mg/day, 160 mg/day, or 240 mg/day.

In any embodiment, the oral dose of Compound I that is administered to the subject in accordance with the methods disclosed herein comprises Compound (P)-I and Compound (M)-I in a molar ratio of about 4:1 ((P)-I:(M)-I). In any embodiment, the molar ratio of (P)-I to (M)-I is about 4.3:1, about 4.6:1, about 4.9:1, about 5.25:1, about 5.7:1, about 6.1:1, about 6.7:1, about 7.3:1, about 8.1:1, about 9:1, about 10:1, about 11.5:1, about 13.3:1, about 15.7:1, about 19:1, about 24:1, about 32.3:1, about 49:1, about 91:1, about 110.1:1, about 124:1, about 141.9:1, about 165.7:1, about 199:1, about 249:1, about 332.3:1, about 399:1, about 499:1, and about 999:1. A particularly useful oral dose of Compound I comprises a molar ratio of (P)-I to (M)-I is about 399:1.

In any embodiment, the oral dose of Compound I that is administered to the subject in accordance with the methods disclosed herein comprises at least 80 mol % of Compound (P)-I. In any embodiment the oral composition as disclosed herein comprises at least 81 mol % of Compound (P)-I, at least 82 mol % of Compound (P)-I, at least 83 mol % of Compound (P)-I, at least 84 mol % of Compound (P)-I, at least 85 mol % of Compound (P)-I, at least 86 mol % of Compound (P)-I, at least 87 mol % of Compound (P)-I, at least 88 mol % of Compound (P)-I, at least 89 mol % of Compound (P)-I, at least 90 mol % of Compound (P)-I, at least 91 mol % of Compound (P)-I, at least 92 mol % of Compound (P)-I, at least 93 mol % of Compound (P)-I, at least 94 mol % of Compound (P)-I, at least 95 mol % of Compound (P)-I, at least 96 mol % of Compound (P)-I, at least 97 mol % of Compound (P)-I, at least 98 mol % of Compound (P)-I, at least 99 mol % of Compound (P)-I, at least 99.1 mol % of Compound (P)-I, at least 99.2 mol % of Compound (P)-I, at least 99.3 mol % of Compound (P)-I, at least 99.4 mol % of Compound (P)-I, at least 99.5 mol % of Compound (P)-I, at least 99.6 mol % of Compound (P)-I, at least 99.7 mol % of Compound (P)-I, at least 99.8 mol % of Compound (P)-I, at least 99.9 mol % of Compound (P)-I. A particularly useful oral dose of Compound I comprises at least 99.75 mol % of Compound (P)-I.

In any embodiment, the oral dose of Compound I that is administered to the subject in accordance with the methods disclosed herein comprises Compound (P)-I substantially free from Compound (M)-I.

In any embodiment, the oral dose of Compound I that is administered to the subject in accordance with the methods disclosed herein comprises a free base. In any embodiment, the oral dose of Compound I that is administered to the subject in accordance with the methods disclosed herein comprises a pharmaceutically acceptable salt.

In any embodiment, the oral dose of Compound I that is administered to the subject in accordance with the methods disclosed herein comprises Compound (P)-I and Compound (M)-I as disclosed herein in the free base form. In any embodiment, Compound I of the oral composition comprises Compound (P)-I and Compound (M)-I as disclosed herein in form of pharmaceutically acceptable salts.

In any embodiment, the oral dose of Compound I that is administered to the subject in accordance with the methods disclosed herein comprises Compound (P)-I (free base) in a crystalline form. In any embodiment, the crystalline form of Compound (P)-I is crystalline Form A as disclosed and characterized herein.

For example, the crystalline form A of Compound (P)-I of the oral composition may be characterized by its PXRD pattern. Thus, in any embodiment, the crystalline Form A of Compound (P)-I is characterized by an PXRD pattern having a peak expressed in degrees 2θ at about 9.78±0.2. In any embodiment, the crystalline Form A of Compound (P)-I is characterized by an PXRD pattern having peaks expressed in degrees 2θ at 9.78±0.2 and 15.51±0.2. In any embodiment, the crystalline Form A of Compound (P)-I is characterized by an PXRD pattern having peaks expressed in degrees 2θ at 9.78±0.2, 15.51±0.2, 19.6±0.2, and 25.92±0.2. In any embodiment, the crystalline Form A of Compound (P)-I is characterized by an PXRD pattern having peaks expressed in degrees 2θ at 9.78±0.2, 15.34±0.2, 15.51±0.2, 19.6±0.2, 20.57±0.2, 21.01±0.2, 25.92±0.2, 29.05±0.2, and 29.48±0.2. In any embodiment, the crystalline Form A of Compound (P)-I is characterized by an PXRD pattern of FIG. 27.

The crystalline form A of (P)-I may additionally or alternatively be characterized by differential scanning calorimetry (DSC). Thus, in any embodiment, the crystalline Form A of Compound (P)-I is characterized by a DSC plot comprising an initial endothermic melting event with an onset temperature of about 188° C., followed by an exothermic recrystallization event at about 196° C., with a final sharp endothermic melting event at about 254° C.

In some embodiments, treatment of a subject having an inflammatory condition in accordance with the methods and compositions comprising Compound I as described herein, is effective to achieve a maximum plasma concentration ($C_{max}$) of Compound I of 39±10.4 ng/mL with a median $t_{max}$ (time for Compound I to reach $C_{max}$) of 2.0 hours and time-averaged concentration of Compound I circulating in the plasma (i.e., $AUC_{0-t}$) of 276±77.8 h*ng/mL.

In another embodiment, administration of a composition comprising Compound I to a subject having an inflammatory condition is effective to achieve a $C_{max}$ of 122.0±33.4 with a median $t_{max}$ of 4.0 (range 2.0-4.1) hours and $AUC_{0-t}$ of 1074.0±243.5 h*ng/mL.

In another embodiment, administration of a composition comprising Compound I to a subject having an inflammatory condition is effective to achieve a $C_{max}$ of 160.7±20.4 with a median $t_{max}$ of 3.0 (range 2.0-4.0) hours and $AUC_{0-t}$ of 1430.0±254.0 h*ng/mL.

In another embodiment, administration of a composition comprising Compound I to a subject having an inflammatory condition is effective to achieve a $C_{max}$ of 426.0±110.6 with a median $t_{max}$ of 2.0 (2.0-4.0) hours and $AUC_{0-t}$ of 3489.8±475.7 h*ng/mL.

In another embodiment, administration of a composition comprising Compound I to a subject having an inflammatory condition is effective to achieve a $C_{max}$ of 51.8±15.8 with a median $t_{max}$ of 2.0 (2.0-2.0) hours and $AUC_{0-t}$ of 364.6±110.7 h*ng/mL.

In another embodiment, administration of a composition comprising Compound I to a subject having an inflammatory condition is effective to achieve a $C_{max}$ of 146.5±33.6 with a median $t_{max}$ of 2.0 (1.0-4.0) hours and $AUC_{0-t}$ of 1204.6±309.1 h*ng/mL Preferably, administration of a composition comprising Compound I to a subject having an inflammatory condition is effective to achieve a $C_{max}$ of 219.0±77.8 with a median $t_{max}$ of 3.0 (1.0-4.0) hours and $AUC_{0-t}$ of 2260.3±1074.7 h*ng/mL.

Preferably, administration of a composition comprising Compound I to a subject having an inflammatory condition is effective to achieve a $C_{max}$ of 389±101 with a median $t_{max}$ of 2.0 (2.0-3.0) hours and $AUC_{0-t}$ of 4110±1170 h*ng/mL Preferably, administration of a composition comprising Compound I to a subject having an inflammatory condition is effective to achieve a $C_{max}$ of 417±123 with a median $t_{max}$ of 2.0 (1.0-4.0) hours and $AUC_{0-t}$ of 4270±2130 h*ng/mL In any embodiment a subject having an inflammatory condition is administered 5 mg/day to 300 mg/day of Compound I. In accordance with this embodiment the subject has an inflammatory condition selected from rheumatoid arthritis, hidradenitis suppurativa, gout, plaque psoriasis, psoriatic arthritis, ankylosing spondylitis, pericarditis, including acute pericarditis, recurrent pericarditis, and chronic pericarditis, cryopyrin associated periodic syndrome (CAPS), including Muckle Wells Syndrome and familial cold autoinflammatory syndrome, pyoderma gangrenosum, irritable bowel disease, including Crohn's disease and ulcerative colitis, Stills disease, also referred to as juvenile idiopathic arthritis, atopic dermatitis, acute coronary syndrome, heart failure, and cancer, including, but not limited to, breast cancer, pancreatic cancer, colorectal cancer and lung cancer.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 100 mg of Compound I thereof once daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 160 mg of Compound I once daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 200 mg of Compound I once daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 240 mg of Compound I once daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 50 mg of Compound I twice daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 80 mg of Compound I twice daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 100 mg of Compound I twice daily.

In any embodiment, a subject having inflammatory arthritis, such as rheumatoid arthritis (RA), spondyloarthritis (such as ankylosing spondylitis and psoriatic arthritis), juvenile rheumatoid (JIA) or idiopathic arthritis (JIA) (including systemic (SJIA)), and gout; cryopyrin-associated autoinflammatory syndrome (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), hidradenitis suppurativa (HS); psoriasis, such as plaque psoriasis; colitis from an inflammatory bowel disease (IBD) like Crohn's disease or ulcerative colitis; pericarditis; metastatic breast cancer, and pancreatic cancer is administered an oral composition comprising 120 mg of Compound I twice daily.

In any embodiment, a subject having rheumatoid arthritis is administered orally 50 mg/day to 300 mg/day of Compound I. In some embodiments, the subject having rheumatoid arthritis is administered an oral composition comprising Compound I once a day. In some embodiments, the subject having rheumatoid arthritis is administered a composition comprising Compound I twice a day. In some embodiments, the subject having rheumatoid arthritis is administered an oral composition comprising 10 mg, 30 mg, 50 mg, 80 mg, 100 mg, 120 mg, 160 mg, 200 mg, or 240 mg of Compound I once daily.

In any embodiment, the subject having rheumatoid arthritis is administered an oral composition comprising 100 mg of Compound I once daily.

In any embodiment, the subject having rheumatoid arthritis is administered an oral composition comprising 160 mg of Compound I once daily.

In any embodiment, the subject having rheumatoid arthritis is administered an oral composition comprising 200 mg of Compound I once daily.

In any embodiment, the subject having rheumatoid arthritis is administered an oral composition comprising 240 mg of Compound I once daily.

In any embodiment, the subject having rheumatoid arthritis is administered an oral composition comprising 10 mg, 30 mg, 50 mg, 80 mg, 100 mg, or 120 mg of Compound I twice daily.

In any embodiment, the subject having rheumatoid arthritis is administered an oral composition comprising 50 mg of Compound I twice daily.

In any embodiment, the subject having rheumatoid arthritis is administered an oral composition comprising 80 mg of Compound I twice daily.

In any embodiment, the subject having rheumatoid arthritis is administered an oral composition comprising 100 mg of Compound I twice daily.

In any embodiment, the subject having rheumatoid arthritis is administered an oral composition comprising 120 mg of Compound I twice daily.

The dosage administered is a therapeutically effective amount of the composition sufficient to result in amelioration of a symptom or symptoms, and can vary depending upon known factors such as the pharmacodynamic characteristics of the active ingredient and its mode of administration; age, sex, health and weight of the recipient; nature and extent of symptoms; kind of concurrent treatment, frequency of treatment and the effect desired.

In some embodiments, the oral composition comprising Compound I as described herein can be administered to the subject once (e.g., as a single dose or application). In some embodiments, the oral composition of embodiments herein is administered at least once daily, such as at least two, three or four times daily. In some embodiments, the oral composition of embodiments herein may be administered daily, twice daily, three times daily, weekly, twice weekly, every two weeks, every three weeks, monthly, as needed, or as otherwise directed by a physician. The oral composition of embodiments herein may be administered at any interval to achieve the therapeutically desired effect, e.g., induction or maintenance of remission, prevention or relief of a symptom or symptoms. In some embodiments, the oral composition of embodiments herein may be administered to a subject for a period of 1, 2, 3, 4, 5, 6 days, about a week, about two weeks, about three weeks, about four weeks, about five weeks, about six weeks, about two months, about three months, about four months, about five months, about six months, or a range of any two of these values. In some embodiments, treatment may be continued for at least a week, a month, a year, or as otherwise directed by a physician. In some embodiments, treatment may extend over multiple years, the duration of disease, or the lifetime of the subject. In some embodiments, the oral composition of embodiments herein can be administered once or twice daily to a subject in need thereof for a period of about two to about twenty-eight days, or from about seven to about ten days. The oral composition of embodiments herein can also be administered once, twice, or three times daily to a subject for a period of 1, 2, 3, 4, 5, 6, 7, 8, 9, 10, 11, 12 times per year, or a combination thereof.

In some embodiments the oral composition comprising Compound I as described herein is administered before, after, or with a meal. In some embodiments the oral composition described herein is administered before, after, or with a high fat meal. In some embodiments, the oral composition described herein is administered before, after, or with a standardized high fat meal. In some embodiments, the high-fat meal is a high-calorie, high-fat meal. In some embodiments, the high fat meal follows the FDA guidance on a high-fat meal. In some embodiments, the high-calorie, high-fat meal follows the FDA guidance on a high-fat and high-calorie meal. In some embodiments, the high-fat meal comprises a fat content of about 50% or greater of total caloric content of the meal. See U.S. Department of Health and Human Services Food and Drug Administration Center for Drug Evaluation and Research, (2002). Guidance for Industry: Food-Effect Bioavailability and Fed Bioequivalence Studies. Office of Training and Communications Division of Drug Information, HFD-240. In some embodiments, the high-calorie, high-fat meal comprises a fat content of at least 50% of total caloric content of the meal and a total of about 800 to about 1000 kilocalorie content.

In some embodiments the oral composition described herein is administered following an overnight fast. In some embodiments, the overnight fast is at least about 6 hours, at least about 7 hours, at least about 8 hours, at least about 9 hours, or at least about 10 hours. For example, the oral composition described herein may be administered following a high-fat meal, high-calorie meal following an overnight fast of at least 10 hours.

Combination Therapy

Compound I, i.e., Compound (P)-I and (M)-I in any molar ratio as described supra and in any form (e.g., free form, crystalline form) as described supra, and oral compositions comprising the same can be used alone or in combination with other pharmaceutically active compounds, to treat conditions such as those described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of the oral pharmaceutical composition described herein and one or more additional pharmaceutically active compounds.

In certain instances, it may be appropriate to administer the compositions described here in combination with another pharmaceutical agent. By way of example only, if one of the side effects experienced by a patient upon receiving the composition herein is hypertension, then it may be appropriate to administer an anti-hypertensive agent in combination with the initial pharmaceutical agent. Or, by way of example only, the therapeutic effectiveness of the composition described herein may be enhanced by administration of an adjuvant (e.g., by itself the adjuvant may only have minimal therapeutic benefit, but in combination with another pharmaceutical agent, the overall therapeutic benefit to the patient is enhanced). Or, by way of example only, the benefit experienced by a patient may be increased by administering the composition described herein with another pharmaceutical agent (which also includes a therapeutic regimen) that also has therapeutic benefit. By way of example only, in a treatment for rheumatoid arthritis involving administration of the composition described herein, increased therapeutic benefit may result by also providing the patient with another pharmaceutical agent for rheumatoid arthritis. In any case, regardless of the disease, disorder, or condition being treated, the overall benefit experienced by the patient may simply be additive of the two pharmaceutical compositions or the patient may experience a synergistic benefit.

The combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

In any case, the multiple therapeutic compositions (at least one of which is the composition disclosed herein) may be administered concomitantly in any order or even simultaneously. If simultaneously, the multiple therapeutic compositions may be provided in a single, unified form, or in multiple forms (by way of example only, either as a single pill or as two separate pills). One of the therapeutic compositions may be given in multiple doses, or both may be given as multiple doses. If not simultaneously, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating an inflammatory condition in a human or animal subject in need of such treatment comprising administering to said subject an amount of an oral composition comprising Compound I as disclosed herein in an amount of 5 mg/day to 300 mg/day to reduce or prevent said condition in the subject, in combination with at least one additional agent for the treatment of said disorder that is known in the art. In a related aspect, certain embodiments provide the therapeutic composition disclosed herein in combination with one or more additional pharmaceutically active compounds and a pharmaceutically acceptable carrier for the treatment of the inflammatory condition.

The oral compositions comprising Compound I described herein are also optionally used in combination with other therapeutic reagents that are selected for their therapeutic value for the condition to be treated. In general, the compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified.

In some embodiments, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

In some embodiments, a subject suffering from or at risk of suffering from an inflammatory condition is administered an oral composition comprising Compound I together with one or more agents or compositions known for treating an inflammatory condition in any combination.

Specific, non-limiting examples of possible combination therapies for any of the inflammatory conditions listed supra include the oral composition comprising Compound I as described herein in combination with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™), ketoprofen, oxaprozin (DAYPRO™), diclofenac sodium (VOLTAREN™), diclofenac potassium (CATAFLAM™), etodolac (LODINE™) indomethacin (INDOCIN™), ketorolac (TORADOL™), sulindac (CLINORIL™), tolmetin (TOLECTIN™), meclofenamate (MECLOMEN™), mefenamic acid (PONSTEL™) nabumetone (RELAFEN™) and piroxicam (FELDENE™); (3) immunosuppressants, including but not limited to methotrexate (RHEUMATREX™), leflunomide (ARAVA™), azathioprine (IMURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™) rilonocept (ARCALYST™) and canakinumab (ILARIS™); (7) interleukin-6 inhibitors, including but not limited to tocilizumab (ACTEMRA™); (8) interleukin-17 inhibitors, including but not limited to secukinumab (COSENTYX®; AIN457), ixekizumab (TALTZ®) and brodalimumab; (9) Janus kinase inhibitors, including but not limited to tofacitinib; and (10) syk inhibitors, including but not limited to fostamatinib.

Where a subject is suffering from or at risk of suffering from rheumatoid arthritis or a condition that is associated with rheumatoid arthritis, an oral composition comprising Compound I as described herein is optionally administered together with one or more agents suitable for treating rheumatoid arthritis or a condition that is associated with rheumatoid arthritis in any combination. Examples of therapeutic agents/treatments for inflammatory conditions, such as rheumatoid arthritis or a condition that is associated with rheumatoid arthritis, that can be administered in combination with Compound I include, but are not limited, non-steroidal anti-inflammatory drugs (NSAIDs), steroids (e.g., prednisone), corticosteroids, and disease modifying drugs (DMARDs) such as methotrexate, leflunomide, hydroxychloroquine, sulfasalazine, Janus kinase (JAK) inhibitors (e.g., tofacitinib, upadacitinib, baricitinib, filgotinib, ruxolitinib, oclacitinib, peficitinib, fedratinib, cerdulatinib, gandotinib, lesarturtinib, momelotinib, pacritinib, abrocitinib, and BMS-986165), tumor necrosis factor inhibitors (e.g., adalimumab, etanercept, golimumab, infliximab, certolizumab), anti-B-cell antibodies (e.g., rituximab), anti-IL-6 antibodies (e.g., sarilumab, tocilixumab), interleukin-1 receptor (IL-1) antagonist (e.g., anakinra), and T-cell activation inhibitors (e.g., abatacept).

In any embodiment, Compound I is administered in combination with methotrexate for the treatment of rheumatoid arthritis or other inflammatory condition as described herein.

In any embodiment, Compound I is administered in combination with a JAK inhibitor for the treatment of rheumatoid arthritis or other inflammatory condition as described herein. Suitable JAK inhibitors for administering in combination with Compound I for the treatment of rheumatoid arthritis or any of the other inflammatory conditions disclosed herein include, without limitation, tofacitinib, upadacitinib, baricitinib, filgotinib, ruxolitinib, oclacitinib, peficitinib, fedratinib, cerdulatinib, gandotinib, lesarturtinib, momelotinib, pacritinib, abrocitinib, and BMS-986165.

In any embodiment, Compound I is administered in combination with a TYK2 inhibitor for the treatment of rheumatoid arthritis or other inflammatory condition as described herein. Suitable TYK2 inhibitors for administering in combination with Compound I for the treatment of rheumatoid arthritis or any of the other inflammatory conditions disclosed herein include, without limitation, PF-06826647 (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile), 3-pyridazinecarboxamide, tofacitinib, upadacitinib, deucravacitinib (6-(cyclopropanecarbonylamino)-4-[2-methoxy-3-(1-methyl-1,2,4-triazol-3-yl)anilino]-N-(trideuteriomethyl)pyridazine-3-carboxamide), cerdulatinib, AT9283 (1-Cyclopropyl-3-(3-(5-(morpholinomethyl)-1H-benzo[d]imidazol-2-yl)-1H-pyrazol-4-yl)urea), Nvp-bsk805'2HCl (4-(2,6-difluoro-4-(3-(1-(piperidin-4-yl)-1H-pyrazol-4-yl)quinoxalin-5-yl) benzyl)morpholine dihydrochloride), S-ruxolitinib, gandotinib, pacritinb, baricitinib, filgotinib, izencitinib, NDI-031301 (Akahane et al., Blood 128:1596, 2016), and XL019 ((2R)—N-[4-[2-(4-morpholin-4-ylanilino)pyrimidin-4-yl]phenyl]pyrrolidine-2-carboxamide), brepocitinib ([(1S)-2,2-difluorocyclopropyl]-[(1S,5R)-3-[2-[(1-methylpyrazol-4-yl)amino]pyrimidin-4-yl]-3,8-diazabicyclo [3.2.1]octan-8-yl]methanone), VTX-958 (a selective allosteric TYK2 inhibitor developed by Ventyx Biosciences), and NDI-031407 (a selective TYK2 inhibitor developed by Nimbus Therapeutics and disclosed in Gracey, E., et al. J. Clin. Invest.; 130(4):1863-1878 (2020, which is hereby incorporated by reference in its entirety).

In any embodiment, Compound I is administered in combination with a BTK inhibitor for the treatment of rheumatoid arthritis or other inflammatory condition as described herein. Suitable BTK inhibitors for administering in combination with Compound I for the treatment of rheumatoid arthritis or any of the other inflammatory conditions disclosed herein include, without limitation, ibrutinib, acalabrutinib, fenebrutinib, and zanubrutinib.

In any embodiment, Compound I is administered in combination with an IRAK4, IKKi, tpl2, or CTLA4 inhibitor for the treatment of rheumatoid arthritis or other inflammatory condition as described herein. Suitable IRAK4, IKKi, tpl2, and CTLA4 inhibitors for administering in combination with Compound I for the treatment of rheumatoid arthritis or any of the other inflammatory conditions disclosed herein include, without limitation, N-[1-(2-morpholin-4-ylethyl)benzimidazo]-2-yl]-3-nitrobenzamide, N-(1-phenyl-5-(piperidin-1-ylmethyl)-1H-benzo[d]imidazol-2-yl)-3-(trifluoromethyl), benzamide, ibrutinib, (R)-6-((1,6-naphthyridin-2-yl)amino)-4-(cyclopropylamino)-N-(2-fluoro-3-hydroxy-3-methylbutyl)nicotinamide, N-(4-morpholin-4-ylcyclohexyl)-5-(oxan-4-yl)-7H-pyrrolo[2,3-d]pyrimidin-4-amine, N-(trans-4-morpholinocyclohexyl)-5-(tetrahydro-2H-pyran-4-yl)-7H-pyrrolo[2,3-d]pyrimidin-4-amine, 4-[(4-morpholin-4-ylcyclohexyl)amino]quinazoline-6-carbonitrile, 1-[[(2S,3S,4S)-3-Ethyl-4-fluoro-5-oxo-2-pyrrolidinyl]methoxy]-7-methoxy-6-isoquinolinecarboxamide, 2-(4-fluorophenyl)-6-methyl-4-(3-(trifluoromethyl)phenyl)-1,2-dihydrodipyrazolo[3,4-b:3', 4'-d]pyridin-3(6H)-one, ipilimumab, abatacept, 4-(3-chloro-4-fluoroanilino)-6-(pyridin-3-ylmethylamino)-1,7-naphthyridine-3-carbonitrile, 6-[7-[3-cyano-4-(oxan-4-yloxy)phenyl]furo[3,2-b]pyridin-2-yl]-5-methoxy-N,N-dimethylpyridine-3-carboxamide.

Specific, non-limiting examples of possible combination therapies for the treatment of cancer include the oral composition comprising Compound I as described herein in combination with: (1) alkylating agents, including but not limited to cisplatin (PLATIN™) carboplatin (PARAPLATIN™), oxaliplatin (ELOXATIN™), streptozocin (ZANOSAR™) busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™), ipilimumab (YERVOY™), pembrolizumab (KEYTRUDA™), nivolumab (OPDIVO™), and tremelimumab.

In some embodiments, the oral composition described herein is administered in combination with an additional therapeutic agent selected from a chemotherapeutic or antiproliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, an agent for treating cardiovascular disease, an agent for treating diabetes, an agent for treating immunodeficiency disorders, or any combination thereof.

In any embodiment, Compound I may be administered to a subject having psoriatic arthritis in combination with one or more JAK inhibitors including, but limited to, tofacitinib, upadacitinib, baricitinib, filgotinib, ruxolitinib, oclacitinib, peficitinib, fedratinib, cerdulatinib, gandotinib, lesarturtinib, momelotinib, pacritinib, abrocitinib, and BMS-986165, or BTK inhibitors, including, but not limited to, ibrutinib, acalabrutinib, fenebrutinib, and zanubrutinib. In any embodiment, Compound I may be administered to a subject having psoriatic arthritis in combination with one or more of the following: NSAIDs; one or more DMARDs such as methotrexate, sulfasalazine, leflunomide, abatacept, adalimumab, certolizumab, etanercept, golimumab, infliximab, ixekizumab, secukinumab, tocilizumab, tofacitinib, ustekinumab; one or more immunosuppressants such as azathioprine or cyclosporine; apremilast, or steroid (injection).

In any embodiment, Compound I may be administered to a subject having psoriasis in combination with one or more JAK inhibitors, including, but limited to, tofacitinib, upadacitinib, baricitinib, filgotinib, ruxolitinib, oclacitinib, peficitinib, fedratinib, cerdulatinib, gandotinib, lesarturtinib, momelotinib, pacritinib, abrocitinib, and BMS-986165, or BTK inhibitors including, but not limited to, ibrutinib, acalabrutinib, fenebrutinib, and zanubrutinib. In any embodiment, Compound I may be administered to a subject having psoriasis in combination with one or more of the following: corticosteroids; vitamin D analogues; retinoids; calcineurin inhibitors; salicylic acid; anthralin; cyclosporine; one or more DMARDs such as methotrexate, etanercept, infliximab, adalimumab, ustekinumab, secukinumab, ixekizumab; thioguanine, hydroxyurea, apremilast, coal tar in optional combination with light therapy (e.g., Goeckerman therapy), or any natural or alternative treatments such as aloe extract cream, fish oil, Oregon grape, or essential oils.

In any embodiment, Compound I may be administered to a subject having hidradenitis suppurativa (HS) in combination with one or more JAK inhibitors, including, but not limited to, tofacitinib, upadacitinib, baricitinib, filgotinib, ruxolitinib, oclacitinib, peficitinib, fedratinib, cerdulatinib, gandotinib, lesarturtinib, momelotinib, pacritinib, abrocitinib, and BMS-986165; tumor necrosis factor inhibitors including, but not limited to, adalimumab, etanercept, golimumab, infliximab, certolizumab; IL-1β and IL-1α inhibitors, including, but not limited to, anakinra, rilonacept, canakinumab, gevokizumab, LY2189102 ((Bihorel et al., *AAPS J.* 16(5):1009-1117, 2014), and bermekimab. In any embodiment, Compound I may be administered to a subject having hidradenitis suppurativa (HS) in combination with one or more of the following: antibiotics such as clindamycin, gentamicin, rifampin, doxycycline, minocycline; one or more DMARDs such as methotrexate, adalimumab, infliximab, anakinra, canakinumab, ustekinumab; one or more NSAIDs; one or more retinoids, such as isotretinoin and acetretin; resorcinol (e.g., topical); one or more hormones such as spirolactone, finasteride; or metformin.

In any embodiment, Compound I may be administered to a subject having cryopyrin-associated autoinflammatory syndrome (CAPS) in combination with one or more interleukin-1 receptor antagonists, including but not limited to anakinra (KINERET™), rilonocept (ARCALYST™) and canakinumab (ILARIS™). In some embodiments, the combination of Compound I and IL-1 antagonist is used to induce remission and then remission is maintained with administration of Compound I. In other embodiments, Compound I may be administered to a subject having cryopyrin-associated autoinflammatory syndrome (CAPS) in combination with one or more of the following: rilonacept, canakinumab, anakinra, methotrexate, one or more steroids, or one or more NSAIDs.

These various agents/compositions that are used in combination with the oral compositions described herein can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the oral compositions described herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the oral compositions described herein or the additional pharmaceutical agents, or both.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

EMBODIMENTS OF THE DISCLOSURE

The invention provides also the following non-limiting embodiments.

Embodiment is 1 a method for treating an inflammatory condition that involves administering, to a human subject having an inflammatory condition, an oral dose of 5 mg/day to 300 mg/day of Compound I

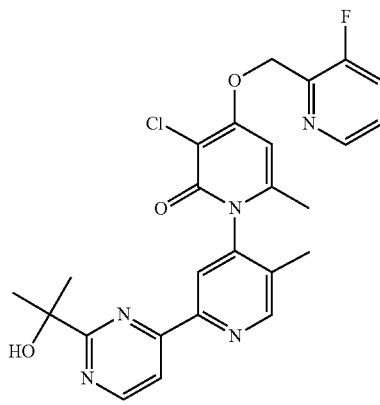

(I)

or a derivative thereof to treat said inflammatory condition.

Embodiment 2 is the method of Embodiment 1, wherein 50 mg/day of the compound is administered to said subject.

Embodiment 3 is the method of Embodiment 1, wherein 100 mg/day of the compound is administered to said subject.

Embodiment 4 is the method of Embodiment 1, wherein 160 mg/day of the compound is administered to said subject.

Embodiment 5 is the method of Embodiment 1, wherein 200 mg/day of the compound is administered to said subject.

Embodiment 6 is the method of Embodiment 1, wherein 240 mg/day of the compound is administered to said subject.

Embodiment 7 is the method of any one of Embodiments 1-6, wherein the compound is administered once a day.

Embodiment 8 is the method of any one of Embodiment 1-6, wherein the compound is administered twice a day.

Embodiment 9 is the method of claim 1, wherein 50 mg of the compound is administered to the subject twice daily.

Embodiment 10 is the method of claim 1, wherein 80 mg of the compound is administered to the subject twice daily.

Embodiment 11 is the method of Embodiment 1, wherein 120 mg of the compound is administered to the subject twice daily.

Embodiment 12 is the method of any one of Embodiments 1-11, wherein Compound I is deuterated.

Embodiment 13 is the method of any one of Embodiments claims 1-12, wherein Compound I comprises the Compound (P)-I

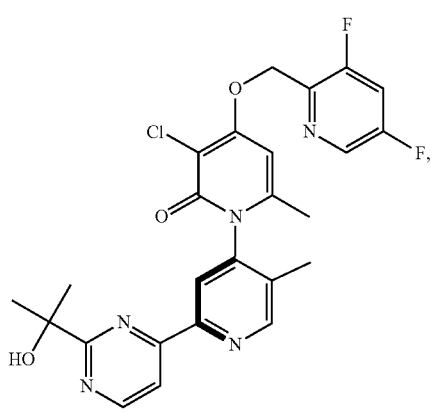

(P)-I and the Compound (M)-I

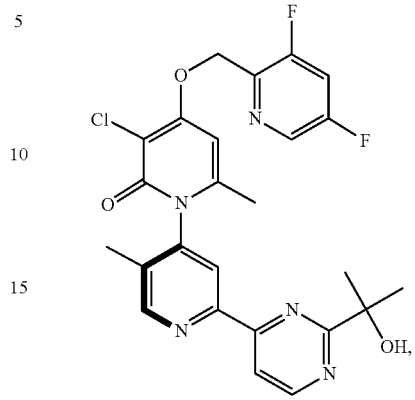

(M)-I in a molar ratio of (P)-I to (M)-I of about 4:1.

Embodiment 14 is the method of Embodiment 13, wherein the molar ratio of (P)-I to (M)-I is about 9:1.

Embodiment 15 is the method of Embodiment 13, wherein the molar ratio of (P)-I to (M)-I is about 99:1.

Embodiment 16 is the method of Embodiment 13, wherein the molar ratio of (P)-I to (M)-I is about 199:1.

Embodiment 17 is the method of Embodiment 13, wherein the molar ratio of (P)-I to (M)-I is about 399:1.

Embodiment 18 is the method of Embodiment 13, wherein the molar ratio of (P)-I to (M)-I is about 999:1.

Embodiment 19 is the method of any one of claims 1-12, wherein Compound I comprises the Compound (P)-I substantially free of Compound (M)-I.

Embodiment 20 is the method of any one of Embodiments claims 1-12, wherein Compound I comprises at least 80 mol % of Compound (P)-I

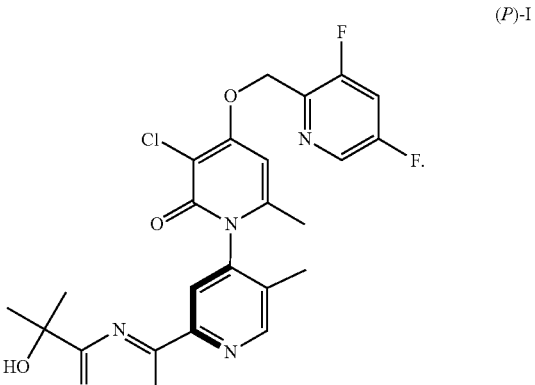

(P)-I

Embodiment 21 is the method of Embodiment 20, wherein Compound I comprises at least 90 mol % of Compound (P)-I.

Embodiment 22 is the method of Embodiment 20, wherein Compound I comprises at least 95 mol % of Compound (P)-I.

Embodiment 23 is the method of Embodiment 20, wherein Compound I comprises at least 99 mol % of Compound (P)-I.

Embodiment 24 is the method of any one of Embodiments 1-23, wherein Compound (P)-I is a free base.

Embodiment 25 is the method of any one of Embodiments 1-23, wherein Compound (P)-I is a pharmaceutically acceptable salt.

Embodiment 26 is the method of any one of Embodiments 1-23, wherein Compound (P)-I is crystalline form.

Embodiment 27 is the method of Embodiment 26, wherein the crystalline form of Compound (P)-I is crystalline Form A characterized by an PXRD pattern having a peak expressed in degrees 2θ at about 9.78±0.2.

Embodiment 28 is the method of Embodiment 26, wherein the crystalline form of Compound (P)-I is the crystalline Form A characterized by an PXRD pattern having peaks expressed in degrees 2θ at 9.78±0.2 and 15.51±0.2.

Embodiment 29 is the method of Embodiment 26, wherein the crystalline form of Compound (P)-I is the crystalline Form A characterized by an PXRD pattern having peaks expressed in degrees 2θ at 9.78±0.2, 15.51±0.2, 19.6±0.2, and 25.92±0.2.

Embodiment 30 is the method of Embodiment 26, wherein the crystalline form of Compound (P)-I is the crystalline Form A characterized by an PXRD pattern having peaks expressed in degrees 2θ at 9.78±0.2, 15.34±0.2, 15.51±0.2, 19.6±0.2, 20.57±0.2, 21.01 0.2, 25.92±0.2, 29.05±0.2, and 29.48±0.2, Embodiment 31 is the method of any one of Embodiments 1-30, wherein the inflammatory condition is rheumatoid arthritis.

Embodiment 32 is the method of any one of Embodiments 1-30, wherein the inflammatory condition is psoriatic arthritis.

Embodiment 33 is the method of any one of Embodiments 1-30, wherein the inflammatory condition is a cryopyrin-associate periodic syndrome.

Embodiment 34 is the method of any one of Embodiments 1-30, wherein the inflammatory condition is Hidradenitis suppurativa.

Embodiment 35 is the method of any one of Embodiments 1-30, wherein the inflammatory condition is selected from the group consisting of psoriasis, juvenile idiopathic arthritis, ulcerative colitis, Crohn's disease, ankylosing spondylitis, pancreatic cancer, metastatic breast cancer, gout, recurrent pericarditis, and idiopathic pulmonary fibrosis.

Embodiment 36 is the method of any one of Embodiments 1-30, wherein the inflammatory condition is selected from spondyloarthritis such as ankylosing spondylitis, psoriatic arthritis, reactive arthritis and Reiter's syndrome, juvenile rheumatoid arthritis (JIA), systemic-onset juvenile rheumatoid arthritis, idiopathic arthritis (JIA) (including systemic (SJIA)), and gout; cryopyrin-associated autoinflammatory syndromes (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), including emphysema, chronic bronchitis, and asthma (allergic and non-allergic), hidradenitis suppurativa (HS); psoriasis, such as plaque psoriasis; colitis from an inflammatory bowel disease (IBD) like Crohn's disease or ulcerative colitis and inflammatory bowel disease-associated arthritis; pericarditis, including acute pericarditis, recurrent pericarditis, and chronic pericarditis; pulmonary inflammation or fibrosis, including idiopathic pulmonary fibrosis; metastatic breast cancer, and pancreatic cancer.

Embodiment 37 is the method of any one of Embodiments 1-30, wherein the inflammatory condition is selected from Familial Mediterranean Fever (FMF); tumor necrosis factor receptor-associated periodic syndrome (TRAPS); adult-onset Still's disease; pyoderma gangrenosum; bone-resorption disorders (such as those associated with cancer (e.g., breast cancer)); metastatic melanoma; Castleman disease; and chronic atypical neutrophilic dermatosis with lipodystrophy (CANDLE).

Embodiment 38 is the method of any one of Embodiments 1-30, wherein the inflammatory condition is pruritus, which may be associated with any other condition, for example, pruritus associated with hidradenitis suppurativa, pruritus associated with inflammation, pruritus associated with rheumatoid arthritis, pruritus associated with psoriasis, and pruritus associated with TH17-associated inflammation.

Embodiment 39 is the method of any one of Embodiments 1-30, wherein the inflammatory condition is selected from Lyme disease; cytokine release syndrome (CRS); acute respiratory distress syndrome (ARDS); chronic or acute bronchitis; epidermolysis bullosa (EB); bullous pemphigoid; juvenile dermatomyositis; inflammatory vitiligo (including marginal); pemphigus vulgaris; enterocolitis; polymyositis; myositis, bone cancer; lung cancer; inflammatory bone disorders such as chronic recurrent multi osteomyelitis (CRMO), Synovitis, acne, pustulosis, hyperostosis, and osteitis (SAPHO) syndrome, Majeed syndrome, deficiency of interleukin-1 receptor antagonist (DIRA) and cherubism; bone resorption (such as is associated with an autoimmune disease); neuroinflammatory diseases such as Alzheimer's disease (AD), Parkinson's disease (PD), multiple sclerosis (MS), acute disseminated encephalomyelitis (ADEM), acute optic neuritis (AON), transverse myelitis, and neuromyelitis optical (NMO); Behcet's disease; endotoxic shock (e.g., toxic shock syndrome (TSS) and other systemic gram-negative bacterial infections); enthesitis; polyarteritis nodosa (PAN); chronic pain; polymyalgia rheumatica; chronic allograft rejection; Sjogren's syndrome; and Schnitzler's syndrome (SchS).

Embodiment 40 is the method of any one of Embodiments 1-30, wherein 50 mg of the compound is administered to a subject having rheumatoid arthritis twice daily.

Embodiment 41 is the method of any one of Embodiments 1-30, wherein 80 mg of the compound is administered to a subject having rheumatoid arthritis twice daily.

Embodiment 42 is the method of any one of Embodiments 1-30, wherein 120 mg of the compound is administered to a subject having rheumatoid arthritis twice daily.

Embodiment 43 is the method of any one of Embodiments 36-38, wherein said administering is carried out under conditions effective to inhibit progression of joint damage, improve synovitis, or both in said subject as assessed by magnetic resonance imaging (MRI).

Embodiment 44 is the method of any one of Embodiments 1-43, wherein said administering is carried out under conditions effective to significantly reduce in vivo serum levels of one or more inflammatory cytokines as compared to in vivo serum levels of the one or more inflammatory cytokines in a subject administered a placebo.

Embodiment 45 is the method of Embodiment 44, wherein the one or more inflammatory cytokines is selected from the group consisting of TNF-α, IL-1β, IL-6, IL-8, IFNγ, IL-17, IL-18, IL-1α and MIP1β.

Embodiment 46 is the method of any one of Embodiments 1-45, wherein said administering is carried out for greater than 12 weeks without tachyphylaxis.

Embodiment 47 is the method of any one of Embodiment 1-45, wherein administering further comprises: administering one or more additional therapeutic agents in conjunction with Compound I.

Embodiment 48 is the method of Embodiment 47, wherein said one or more additional therapeutic agents is administered simultaneously with Compound I.

Embodiment 49 is the method of Embodiment 47, wherein said one or more additional therapeutic agents is administered sequentially with Compound I.

Embodiment 50 is the method of any one of Embodiments 47-49, wherein the one or more additional therapeutic agents is selected from the group consisting of an anti-inflammatory drug, an anti-atherosclerotic drug, an immunosuppressive drug, an immunomodulatory drug, a cytostatic drug, an angiogenesis inhibitor, a kinase inhibitor, a cytokine blocker, and an inhibitor of cell adhesion molecules.

Embodiment 51 is the method of any one of Embodiments 47-49, wherein Compound I as defined in any one of Embodiments 2-30 is administered to a subject having rheumatoid arthritis in conjunction with a JAK inhibitor.

Embodiment 52 is the method of any one of Embodiments 47-49, wherein Compound I as defined in any one of Embodiments 2-30 is administered to a subject having rheumatoid arthritis in conjunction with a TYK2 inhibitor.

Embodiment 53 is the method of any one of Embodiments 47-49, wherein Compound I as defined in any one of Embodiments 2-30 is administered to a subject having rheumatoid arthritis in conjunction with a BTK inhibitor.

Embodiment 54 is the method of any one of Embodiments 47-49, wherein Compound I as defined in any one of Embodiments 2-30 is administered to a subject having rheumatoid arthritis in conjunction with a IRAK4 inhibitor.

Embodiment 55 is the method of any one of Embodiments 47-49, wherein Compound I as defined in any one of Embodiments 2-30 is administered to a subject having rheumatoid arthritis in conjunction with a IKKi inhibitor.

Embodiment 56 is the method of any one of Embodiments 47-49, wherein Compound I as defined in any one of Embodiments 2-30 is administered to a subject having rheumatoid arthritis in conjunction with a tpl2 inhibitor.

Embodiment 57 is the method of any one of Embodiments 47-49, wherein Compound I as defined in any one of Embodiments 2-30 is administered to a subject having rheumatoid arthritis in conjunction with a CTLA4 inhibitor.

Embodiment 58 is the method of any one of Embodiments 1-57, wherein the compound is formulated as a solid dosage form selected from a tablet, a capsule, a lozenge, a sachet, a powder, granules, and orally dispersible film.

Embodiment 59 is the method of Embodiment 58, wherein the solid dosage form is a tablet.

Embodiment 60 is the method of any one of Embodiments 1-59, wherein the compound is administered as an immediate release formulation.

Embodiment 61 is the method of any one of Embodiment 1-59, wherein the compound is administered as a controlled release formulation.

Embodiment 62 is an oral pharmaceutical composition comprising: Compound I

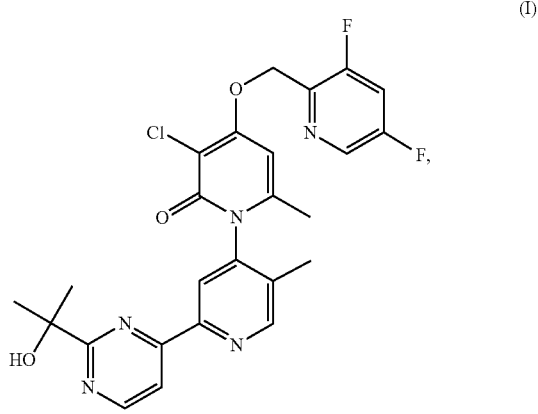 [SMILES: Cc1cnc(-c2ccnc(C(C)(C)O)n2)cc1-n1c(C)cc(OCc2ncc(F)cc2F)c(Cl)c1=O]

or a derivative thereof in an amount of 5 mg to 300 mg, and a pharmaceutically acceptable carrier.

Embodiment 63 is the oral composition of Embodiment 62, wherein said composition comprises 50 mg of Compound I.

Embodiment 64 is the oral composition of Embodiment 62, wherein said composition comprises 80 mg of Compound I.

Embodiment 65 is the oral composition of Embodiment 62, wherein said composition comprises 100 mg of Compound I.

Embodiment 66 is the oral composition of Embodiment 62, wherein said composition comprises 120 mg of Compound I.

Embodiment 67 is the oral composition of Embodiment 62, wherein said composition comprises 160 mg of Compound I.

Embodiment 68 is the oral composition of Embodiment 62, wherein said composition comprises 200 mg of Compound I.

Embodiment 69 is the oral composition of Embodiment 62, wherein said composition comprises 240 mg of Compound I.

Embodiment 70 is the oral composition of any one of Embodiments 62-69, wherein Compound I is deuterated.

Embodiment 71 is the oral composition of any one of Embodiments 62-69 wherein Compound I comprises the Compound (P)-I

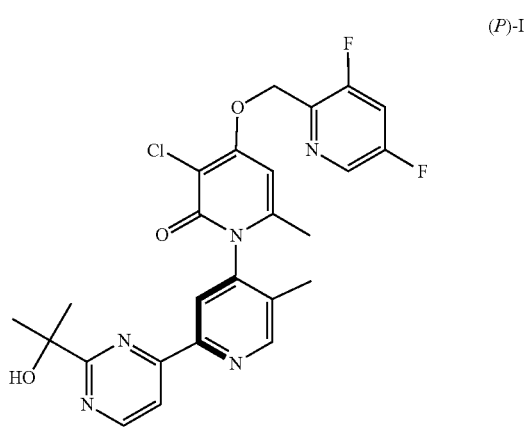

and the Compound (M)-I

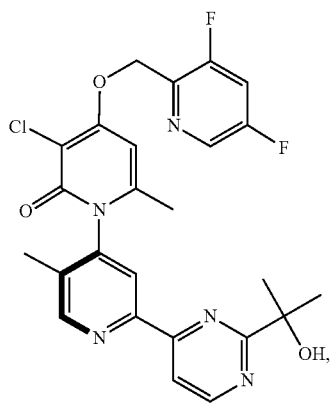

(M)-I in a molar ratio of (P)-I to (M)-I of about 4:1.

Embodiment 72 is the oral composition of Embodiment 71, wherein the molar ratio of (P)-I to (M)-I is about 9:1.

Embodiment 73 is the oral composition of Embodiment 71, wherein the molar ratio of (P)-I to (M)-I is about 99:1.

Embodiment 74 is the oral composition of Embodiment 71, wherein the molar ratio of (P)-I to (M)-I is about 199:1.

Embodiment 75 is the oral composition of Embodiment 71, wherein the molar ratio of (P)-I to (M)-I is about 399:1.

Embodiment 76 is the oral composition of any one of Embodiments 62-69, wherein Compound I comprises the Compound (P)-I substantially free of Compound (M)-I.

Embodiment 77 is the oral composition of any one of Embodiments 62-69, wherein Compound I comprises at least 80 mol % of Compound (P)-I

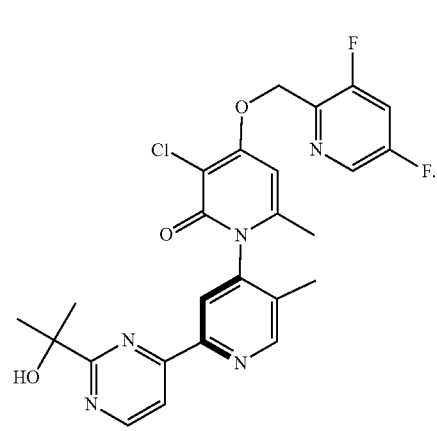

(P)-I

Embodiment 78 is the oral composition of Embodiments 62-69, wherein Compound I comprises at least 90 mol % of Compound (P)-I.

Embodiment 79 is the oral composition of Embodiments 62-69, wherein Compound I comprises at least 95 mol % of Compound (P)-I.

Embodiment 80 is the oral composition of Embodiments 62-69, wherein Compound I comprises at least 99 mol % of Compound (P)-I.

Embodiment 81 is the oral composition of any one of Embodiments 62-80, wherein Compound I (P)-I is a free base.

Embodiment 82 is the oral composition of any one of Embodiments 62-80, wherein Compound I (P)-I is a pharmaceutically acceptable salt.

Embodiment 83 is the oral composition of any one of Embodiments 62-80, wherein Compound I (P)-I is crystalline form.

Embodiment 84 is the oral composition of Embodiment 83, wherein the crystalline form of Compound (P)-I is crystalline Form A characterized by an PXRD pattern having a peak expressed in degrees 2θ at about 9.78±0.2.

Embodiment 85 is the oral composition of Embodiment 83, wherein the crystalline form of Compound (P)-I is the crystalline Form A characterized by an PXRD pattern having peaks expressed in degrees 2θ at 9.78±0.2 and 15.51±0.2.

Embodiment 86 is the oral composition of Embodiment 83, wherein the crystalline form of Compound (P)-I is the crystalline Form A characterized by an PXRD pattern having peaks expressed in degrees 2θ at 9.78±0.2, 15.51±0.2, 19.6±0.2, and 25.92±0.2.

Embodiment 87 is the oral composition of Embodiment 83, wherein the crystalline form of Compound (P)-I is the crystalline Form A characterized by an PXRD pattern having peaks expressed in degrees 2θ at 9.78±0.2, 15.34±0.2, 15.51±0.2, 19.6±0.2, 20.57±0.2, 21.01±0.2, 25.92±0.2, 29.05±0.2, and 29.48±0.2, Embodiment 88 is the oral composition of any one of Embodiments 62-87, wherein said composition is formulated into a solid dosage form selected from a tablet, a capsule, a lozenge, a sachet, a powder, granules, and an orally dispersible film.

Embodiment 89 is the oral composition of any one of Embodiments 62-87, wherein said composition is formulated into a tablet.

Embodiment 90 is the oral composition of any one of Embodiments 62-87, wherein the composition is an immediate release formulation.

Embodiment 91 is the oral composition of any one of Embodiments 62-87, wherein the composition is a controlled release formulation.

EXAMPLES

As described in detail above, 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (i.e., Compound I) exists as a P atropisomer and an M atropisomer. In the Examples and Figures of this disclosure, "ATI-450" refers to the aforementioned compound containing about 99.75 mol % of the P atropisomer and 0.25 mol % of the M atropisomer.

Example 1: Safety, Pharmacokinetics and Pharmacodynamics of Orally Administered ATI-450

ATI-450 is an oral, small molecule inhibitor of the p38α mitogen-activated protein kinase (MAPK)/MAPK-activated protein kinase 2 (MHK2) inflammatory signaling pathway. This Phase 1, single and multiple ascending dose (SAD, MAD), study evaluated ATI-450 for safety, tolerability, pharmacokinetics, and pharmacodynamics. Healthy adults were randomly assigned to SAD (10, 30, 50, 100 mg; n=24) and MAD (10, 30, 50 mg twice daily (BID) for 7 days; n=24) cohorts of ATI-450 or placebo (n=14). Safety and tolerability were evaluated through clinical and laboratory assessments. Blood PK parameters were determined and pharmacodynamic inhibition of ex vivo, endotoxin-induced tumor necrosis factor α (TNF-α), interleukin (IL)-1β, IL-6, IL-8, and phosphorylation of the MK2 substrate, phosphorylated heat shock protein 27 (p-HSP27) was quantitated. The most common adverse events were headache (10/48, 20.8%), dizziness (6/48, 12.5%), upper respiratory tract infection (3/48, 6.3%), and constipation (3/48, 6.3%). ATI-450 had dose proportional pharmacokinetics with a terminal half-life of 9-12 hours in the MAD cohorts on day 7. Dose- and concentration-dependent inhibition of ex vivo stimulated cytokines and target biomarker was observed. On day 7, patients in the 50 mg BID dose cohort recorded mean trough drug levels that were 1.4, 2.5, 2.5, and 2.4 times greater than the $IC_{50}$ for TNF-α, IL-1β, IL-8, and p-HSP27, respectively. Mean $C_{max}$ drug levels were 3.6, 6.4, 6.2, and 6.0 times greater than the $IC_{50}$ for TNF-α, IL-1β, IL-8, and p-HSP27, respectively. IL-6 inhibition >50% was noted for part of the dosing interval. These results support further study of ATI-450 in immuno-inflammatory diseases.

The p38 mitogen-activated protein kinase (p38MAPK) signaling pathway has been a target for therapeutic intervention for inflammatory diseases because of its involvement in the regulation and expression of multiple cytokines (e.g., tumor necrosis factor α [TNF-α], interleukin [IL] 1β, and IL-6) and other inflammatory signals. Small-molecule inhibitors of p38MAPK have been evaluated in clinical trials for the treatment of inflammatory diseases; however, clinical development of these compounds has been limited by toxicity and lack of sustained efficacy. A key challenge with global p38MAPK inhibition is its ubiquitous expression and the broad effects it exerts on cellular physiology as a consequence of the more than 60 substrates that it regulates. Through phosphorylation of these substrates, p38MAPK regulates negative feedback loops and anti-inflammatory pathways, which are both involved in downregulating inflammation; thus, global blockade of p38MAPK pathways may inhibit both pro-inflammatory and anti-inflammatory pathways, limiting its potential efficacy in some disease states. Furthermore, several p38MAPK substrates are involved in the regulation of cellular function and inhibition of these proteins may result in toxicity.

The clinical efficacy achieved with p38MAPK inhibitors has been generally disappointing. Of note, there is evidence in certain autoimmune diseases that p38MAPK inhibitors exhibit tachyphylaxis after multiple treatments, making sustained inhibition of the inflammatory response difficult to achieve in these therapeutic indications. Tachyphylaxis may be explained by the negative feedback and/or anti-inflammatory target substrates described above. Therefore, the approach of targeting key downstream kinase substrates of p38MAPK that specifically regulate inflammatory cytokines to potentially achieve greater specificity for blockade of pathological inflammation has gained interest. MAPK-activated protein kinase 2 (MK2) is a direct downstream substrate of p38MAPK, which has been recognized as a key driver of inflammation. Inflammatory cytokines activated through the p38MAPK/MK2 pathway include TNF-α, IL-1β, IL-6, and IL-8.

The novel approach of selectively inhibiting the p38MAPK/MK2 biomolecular complex instead of p38MAPK alone results in effective blockade of the proinflammatory axis while sparing the anti-inflammatory pathways, negative feedback substrates, and proteins that regulate general cellular function. This approach has the potential to generate safer compounds with greater and more sustained anti-inflammatory efficacy compared with global p38MAPK inhibitors. Unfortunately, directly targeting MK2 has been largely unsuccessful.

ATI-450, a recently developed MK2 inhibitor, has a novel mechanism of action by which it targets the modified p38MAPK ATP binding pocket and juxtaposed MK2 formed upon the interaction between p38MAPK and MK2. The p38MAPK binding site on MK2 is located within the C terminus; thermodynamic studies have shown that the 2 proteins in the complex bind tightly, and deletion of the binding sequence in MK2 abrogates p38-dependent phosphorylation and activation of MK2. Following the formation of the p38MAPK-MK2 biomolecular complex, ATI-450 binds to the interface of the complex with significantly higher affinity than to either kinase alone, thereby selectively inhibiting p38MAPK phosphorylation of MK2 and locking MK2 in an inactive conformation. MK2 regulates inflammatory cytokine mRNA stability and translation through phosphorylation of downstream effectors including adenylate-uridylate-rich element-binding proteins (e.g., tristetraprolin). Therefore, inhibition of p38αMAPK-MK2 blocks downstream MK2-mediated inflammatory actions.

Preclinical animal disease models have been used to predict the potential of ATI-450 as a treatment in several immune-mediated inflammatory diseases. In a rat streptococcal cell wall arthritis model for rheumatoid arthritis, ATI-450 showed joint protective effects and preserved bone mineral density. ATI-450 also was studied in a murine model of neonatal-onset multisystem inflammatory disease (NOMID), which is a severe form of a cryopyrin-associated periodic syndrome; NOMID and other cryopyrin-associated periodic syndromes comprise a spectrum of rare hereditary autoinflammatory disorders in which IL-1β and IL-18 are overproduced. A dramatic attenuation of disease was observed in this transgenic animal model, including a reduction in bone marrow levels of IL-1β in mice treated with ATI-450 relative to those treated with placebo. These preclinical results support clinical development of ATI-450 in humans for autoimmune and autoinflammatory diseases driven by the cytokines TNF-α, IL-1β and IL-6.

As described herein, a first-in-human, Phase 1, randomized, observer-blind, placebo-controlled study was conducted to evaluate the safety, tolerability, PK, and pharmacodynamic (PD) of ATI-450 in single and multiple ascending dose (SAD and MAD) cohorts in healthy subjects. In addition, the study included separate cohorts that evaluated the PK of fed versus fasting administration and of co-administration with methotrexate. Herein is reported the data from the SAD and MAD cohorts.

Results

Study Subjects. In the SAD cohorts, 32 subjects were enrolled, randomized, and included in the safety set. A total of 31 subjects completed the study; 1 subject in the 30 mg ATI-450 cohort withdrew from the study for non-safety reasons after receiving a single dose on day 1 and thus did not complete all study assessments. PK and PD analyses included the 24 subjects who received ATI-450. The majority of subjects in the SAD cohorts were female (84%; Table 1) and ages ranged from 18 to 51 years.

In the MAD cohorts, 30 subjects were enrolled, randomized, and completed the study, and all subjects were included in the safety set; the 24 subjects who received ATI-450 were included in the PK and PD sets. These cohorts were more evenly split between female and male subjects (57% female, 43% male) and ages ranged from 21 to 53 years.

Safety and Tolerability. No clinically significant findings in vital signs, electrocardiograms, or clinical laboratory values were observed. The most common treatment-emergent adverse events (TEAEs) among all study participants are shown in Table 2. In the SAD cohorts, 15 TEAEs were reported by 7 of 24 (29%) subjects who received ATI-450 and 6 TEAEs were reported by 4 of 8 (50%) subjects who received placebo. No deaths or serious adverse events (SAEs) and no discontinuations due to TEAEs occurred. All TEAEs were mild, transient, and resolved without sequelae by the end of the study. Four of 24 (17%) subjects who received ATI 450 reported TEAEs that were considered by the investigator to be related to the study drug (0 subjects in the 10 mg cohort; 2 [33%] subjects in the 30 mg cohort [1 event of nausea and 2 events each of headache and dizziness]; 1 [17%] subject in the 50 mg cohort [1 event of headache]; and 1 subject in the 100 mg cohort [2 events of dizziness]).

In the MAD cohorts, there were 24 TEAEs reported by 12 of 24 (50%) subjects who received ATI-450 and 3 TEAEs reported by 3 of 6 (50%) subjects who received placebo. As in the SAD cohorts, there were no deaths or SAEs and no subjects discontinued the study due to TEAEs; all TEAEs were mild, transient, and resolved without sequelae by the next visit. Nine of 24 (38%) subjects who received ATI-450 reported TEAEs that were considered by the investigator to be related to the study drug (1 of 8 [13%] subjects in the 10 mg BID cohort [1 event of headache], 5 of 8 [63%] subjects in the 30 mg BID cohort [1 event each of blurred vision, constipation, abdominal pain, diarrhea, arthralgia, dizziness, and oropharyngeal pain], and 3 of 8 [38%] subjects in the 50 mg BID cohort [1 event of headache and 2 events of dizziness]). In the placebo group, 2 of 6 (33%) subjects had TEAEs that were considered by the investigator to be related to the study drug (1 event each of vomiting and headache).

Laboratory changes were generally unremarkable. There was a dose dependent reduction in neutrophils observed with the maximum effect in the MAD cohort observed at Day 2 to Day 5. The mean reduction at day 7 in the 50 mg BID group was 24% (3318.4 cells/μL at baseline versus 2514.4 cells/μL at day 7).

Figure 1:
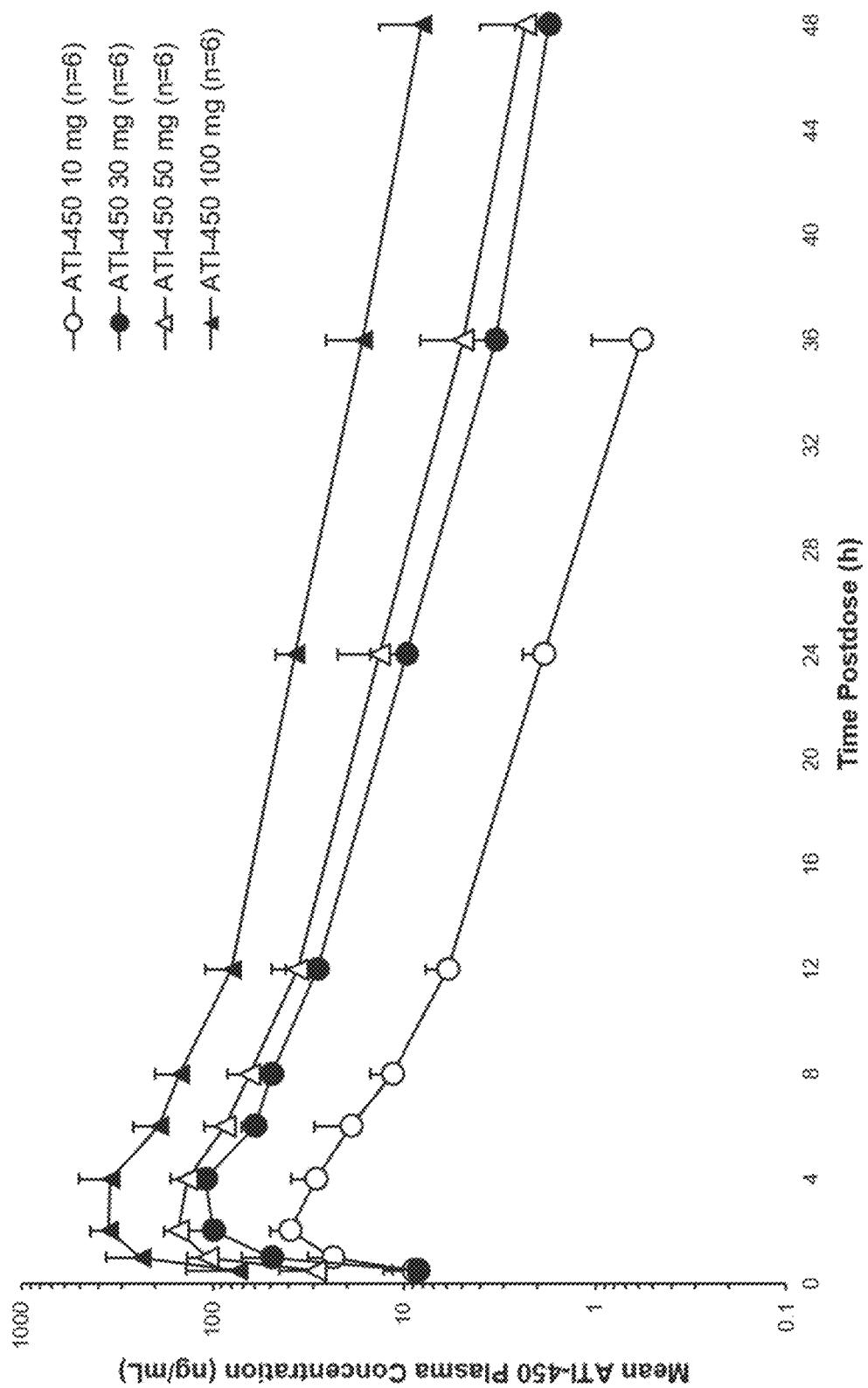
FIG. 1 is a graph showing the mean (SD) plasma concentration-time profiles of ATI-450 after a single dose under fasted conditions, semi-log scale.

Pharmacokinetics—SAD cohorts. As shown in FIG. 1, administration of ATI-450 at single doses of 10 mg, 30 mg, 50 mg, and 100 mg under fasting conditions resulted in ATI-450 post-dose mean plasma concentrations above the lower limit of quantification through 24 hours after dosing at 10 mg and through 48 hours after dosing at all other dose levels. ATI-450 mean plasma concentrations increased with increasing doses (FIG. 1). Systemic exposure increased in a dose-proportional manner across the ATI-450 dose range from 10 to 100 mg, with approximately 10.8-, 12.6-, and 12.8-fold increases in Cmax, AUC0-t, and AUC0-inf, respectively (Table 3). Statistical analysis for dose proportionality using the power model is shown in Table 8, where systemic exposure ($C_{max}$, $AUC_{0-t}$, and $AUC_{0-\infty}$) increased in proportion to ATI-450 dose after single dosing as indicated by the slope estimates near unity and the 90% CIs including unity. ATI-450 concentrations appeared rapidly in plasma, with median $T_{max}$ ranging from 2 to 4 hours across the dose cohorts. Mean $t_{1/2}$ of ATI-450 in plasma ranged from 8.5 to 11.2 hours. $C_{L/F}$, $T_{max}$, and $t_{1/2}$ values showed no clear relation with dose over the dose range of 10 mg to 100 mg. Across the dose cohorts, low inter-subject variability in $C_{max}$, $AUC_{0-\infty}$, and $AUC_{0-t}$ was observed with coefficients of variation ranging from 12.7% to 28.1%.

Table 1, shown below, summarizes the pharmacokinetic data for the SAD cohort fed versus fasting subjects.

TABLE 1

Mean (SD) Pharmacokinetic Parameters of ATI-450 after Single Oral Doses to Healthy Subjects in the Fasted or Fed State (n = 6 per Dose Cohort)

| Dose (mg) | Fed/Fasted State | $C_{max}$ (ng/mL) | $T_{max}^{a}$ (h) | $AUC_{0-\infty}$ (ng · h/mL) | $t_{1/2}$ (h) |
|---|---|---|---|---|---|
| 10 | Fasted | 39.4 (10.4) | 2.0 (2.0, 4.0) | 285.3 (78.4) | 8.5 (3.2) |
| 30 | Fasted | 122.0 (33.4) | 4.0 (2.0, 4.1) | 1102.4 (247.4) | 10.7 (3.3) |
| 50 | Fasted | 160.7 (20.4) | 3.0 (2.0, 4.0) | 1464.7 (269.5) | 9.1 (2.4) |
| 100 | Fasted | 426.0 (110.6) | 2.0 (2.0, 4.0) | 3654.8 (522.9) | 11.2 (5.8) |
| 100 | Fed[b] | 370.7 (101.0) | 6.0 (4.0, 12.0) | 4098.5 (1177.2) | 6.3 (1.6) |

[a] Values are median (min, max)
[b] Subjects received a standardized high-fat, high-calorie breakfast 30 minutes before dose administration.

In the fasted state, ATI-450 was rapidly absorbed ($T_{max}$ of 2.0 hours to 4.0 hours). Approximately dose-proportional increases in mean $C_{max}$ and AUC were observed, indicating linear PK. Moderately slow elimination (terminal $t_{1/2}$ of about 9 to 11 hours) was observed. In the fed state, absorption was delayed (median $T_{max}$ of 6.0 hours versus 2.0 hours), but there did not appear to be any appreciable impact on systemic exposure to ATI-450 ($C_{max}$ was about 9% lower and $AUC_{0-\infty}$ was about 24% higher in the fed state).

Figure 2:
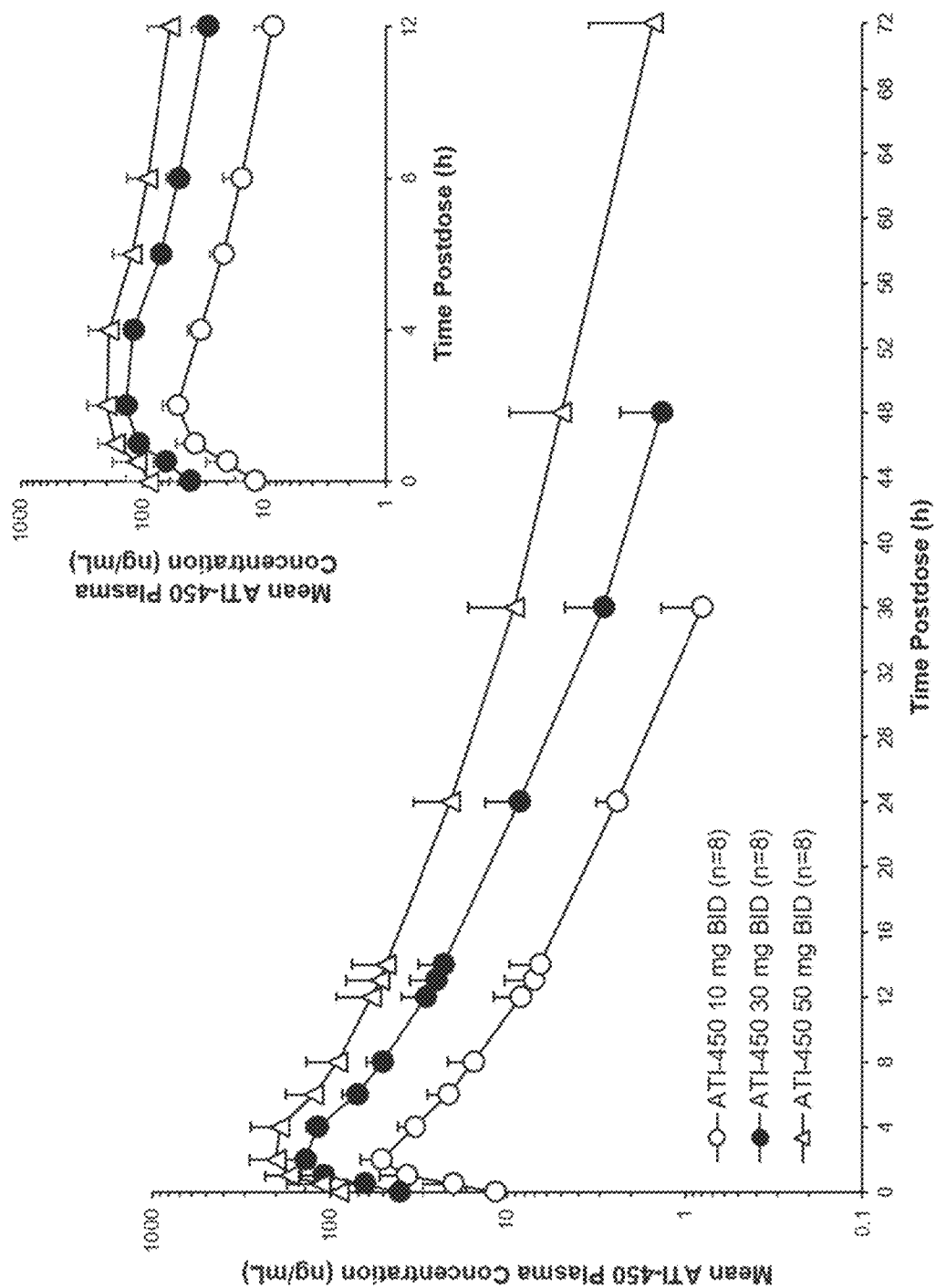
FIG. 2 is a graph showing mean (SD) plasma concentration-time profiles of ATI-450 after 7 days of BID (twice daily) dosing under fasted conditions, semi-log scale.

Pharmacokinetics—MAD cohorts. FIG. 2 shows the mean (SD) plasma concentration-time profiles of ATI-450 from 0 hours to 72 hours after the last dose on day 7, representing dose-proportional PK for the MAD cohorts, and Table 3 shows ATI-450 PK parameters on day 7 after multiple doses. The results obtained after the first dose on day 1 in the MAD cohorts were consistent with those obtained after single doses in the SAD cohorts (data not shown). Tmax appeared to be independent of dose, with median values ranging from 2 to 3 hours following the final dose administration on day 7. Mean $t_{1/2}$ was similar across doses following repeated dose administration (from 9.6 to 11.6 hours). $AUC_{tau}$ and $C_{max}$ increased with escalating doses and there was slight accumulation after multiple doses. Over the dose range of 10 mg to 50 mg BID, $C_{max}$, and $AUC_{tau}$ increased 5.4- and 5.9-fold on day 1, respectively, and 4.2- and 5.2-fold on day 7, respectively. Steady state appeared to be reached by day 2 of administration at all dose levels based on the similarity in the mean $C_{trough}$ of ATI-450 on days 2 through 6. Mean accumulation of ATI-450 after 7 days of BID dosing ranged from 1.17- to 1.57-fold for $C_{max}$ and 1.29- to 1.44-fold for $AUC_{tau}$. The mean values of $t_{1/2}$, CL, and apparent volume of distribution after multiple doses were comparable to those after a single dose, indicating time-independent PK of ATI-450 after 7 days of BID administration. Statistical analysis of dose proportionality on day 7 using the power model is shown in Table 9, where systemic exposure ($C_{max}$, $AUC_{tau}$) following BID administration of ATI-450 increased in proportion to dose over the 5-fold dose range as indicated by the slope estimates near unity and the 90% CIs including unity.

Table 2 below summarizes the PK parameters of ATI-450 on days 1 and 7 of dosing at 10, 30, or 50 mg BID.

TABLE 2

Mean (SD) Pharmacokinetic Parameters of ATI-450 after Twice-daily Oral Doses to Healthy Subjects in the Fasted State (n = 8 per Dose Cohort)

| Day | Dose (mg) | $C_{max}$ (ng/mL) | $T_{max}$[a] (h) | $AUC_{0-12}$ (ng · h/mL) | $t_{1/2}$ (h) |
|---|---|---|---|---|---|
| 1 | 10 | 34.3 (5.7) | 2.0 (2.0, 4.0) | 199.5 (35.9) | NC[b] |
|   | 30 | 126.5 (21.4) | 2.0 (1.0, 4.0) | 680.8 (98.8) | NC |
|   | 50 | 186.7 (66.8) | 2.0 (2.0, 4.0) | 1179.5 (340.1) | NC |
| 7 | 10 | 51.8 (15.8) | 2.0 (2.0, 2.0) | 287.8 (81.5) | 9.6 (2.1) |
|   | 30 | 146.5 (33.6) | 2.0 (1.0, 4.0) | 908.9 (163.1) | 10.3 (3.2) |
|   | 50 | 219.0 (77.8) | 3.0 (1.0, 4.0) | 1507.8 (659.9) | 11.6 (3.7) |

[a]Values are median (min, max)
[b]NC: Not calculable

The PK on day 1 in the MAD cohorts was consistent with PK from the SAD cohorts. Linear (dose- and time-independent) PK after multiple-dosing was observed. Moderately slow elimination (terminal $t_{1/2}$ of about 9-12 hours) was also observed. The trough concentrations were generally similar on days 2 through 7, suggesting that the subjects were at or near steady-state by day 2 of twice-daily administration. Small amount of accumulation (up to 1.4-fold) after multiple dosing Table 3 below summarizes the PK parameters in subjects dosed with methotrexate alone or in combination with ATI-450 as shown.

model are shown in Table 8. Target modulation for ATI-450 was similar to potencies for inhibition of production of 3 of the 4 cytokines, TNF-α, IL-1β, and IL-8, but the potency for inhibition of IL-6 production was lower (less potent). Imax was greatest for p-HSP27, TNF-α, and IL-6, with greater than 96% inhibition, and lower for IL-1β (74%) and IL-8 (57%).

For the 50 mg BID dose MAD cohort, concentrations at $C_{trough}$ were in excess of the relative $IC_{80}$ concentrations (1.4- to 2.4-fold) for the target biomarker p-HSP27 and for 3 of the 4 cytokines (TNF-α, IL-1β, and IL-8), but not for IL-6 (Table 4). TNF-α and IL-1β were inhibited by up to 92.7% and 83.0%, respectively, versus baseline. Plasma levels were greater than the $IC_{50}$ for IL-6 for at least part of the dosing interval. The effects of ATI-450 dose on the relative concentration of each cytokine analyte and the

TABLE 3

Mean (SD) Pharmacokinetic Parameters of ATI-450 and Methotrexate after Oral Administration Alone or in Combination to Healthy Male Subjects in the Fasted State (n = 15)

| Drug | Dose (mg) | Treatment[a] | $C_{max}$ (ng/mL) | $T_{max}$[b] (h) | $AUC_{0-12}$ (ng · h/mL) | $AUC_{0-\infty}$ (ng · h/mL) | $t_{1/2}$ (h) |
|---|---|---|---|---|---|---|---|
| MTX | 7.5 | MTX | 163.3 (35.6) | 1.0 (0.5, 2.5) | NA | 562.2 (102.2) | 3.1 (0.7) |
|  | 7.5 | MTX + ATI-450 | 142.6 (18.6) | 1.5 (1.0, 2.5) | NA | 518.9 (70.2) | 3.0 (0.6) |
| ATI-450 | 50 BID | ATI-450[c] | 219.0 (77.8) | 3.0 (1.0, 4.0) | 1507.8 (659.9) | NA | NC |
|  | 50 BID | ATI-450 + MTX | 182.1 (31.5) | 2.0 (1.0, 4.0) | 1089.5 (262.2) | NA | NC |

[a]Subjects received single 7.5-mg oral doses of MTX on days 1 and 8, single 15-mg oral doses of leucovorin on days 2 and 9, and twice-daily 50-mg oral doses of ATI-450 on days 3-9.
[b]Values are median (min, max).
[c] Values are from the group of subjects (n = 8) administered twice-daily oral doses of ATI-450 at 50 mg during the MAD portion of the study.
MTX: Methotrexate;
NA: Not applicable;
NC: Not calculable.

The pharmacokinetics of MTX was similar with or without ATI-450 exposure. Systemic exposure to ATI-450 appeared to be slightly decreased (about 17% for $C_{max}$ and about 27% for AUC) in the presence of MTX based on a between-group comparison to the 50-mg ATI-450 data from the MAD portion of the study.

Pharmacodynamics

A relationship between concentrations of each analyte and ATI-450 plasma levels was developed and the data were then fit to a nonlinear inhibitory $E_{max}$ model, from which $IC_{50}$ and $IC_{80}$ concentrations were established. The p-HSP27 and cytokine inhibition parameters generated from the biomarker p-HSP27 in the ex vivo stimulated assay, expressed as a percentage of pre-dosing analyte levels (set to 100%) for the 10 mg, 30 mg, and 50 mg BID MAD cohorts on day 7, 4 hours after dosing and 12 hours after dosing, are shown in FIG. 4A-4E, respectively. The 4-hour after dosing day 7 samples reflected approximate steady-state $C_{max}$ ATI-450 concentrations while the 12-hour after dosing day 7 samples reflected steady-state $C_{trough}$ concentrations of the drug. A marked dose-dependent reduction in concentration was observed for all 4 cytokines at the 4-hour time point and persisted through 12 hours. TNF-α, IL-1β, IL-8, and p-HSP27 all demonstrated a reduction in concentration that persisted for the entire dosing interval. Concentration-dependent and dose-dependent modulation of p-HSP27 and inhibition of the 4 cytokines analyzed were demonstrated.

Figure 3:
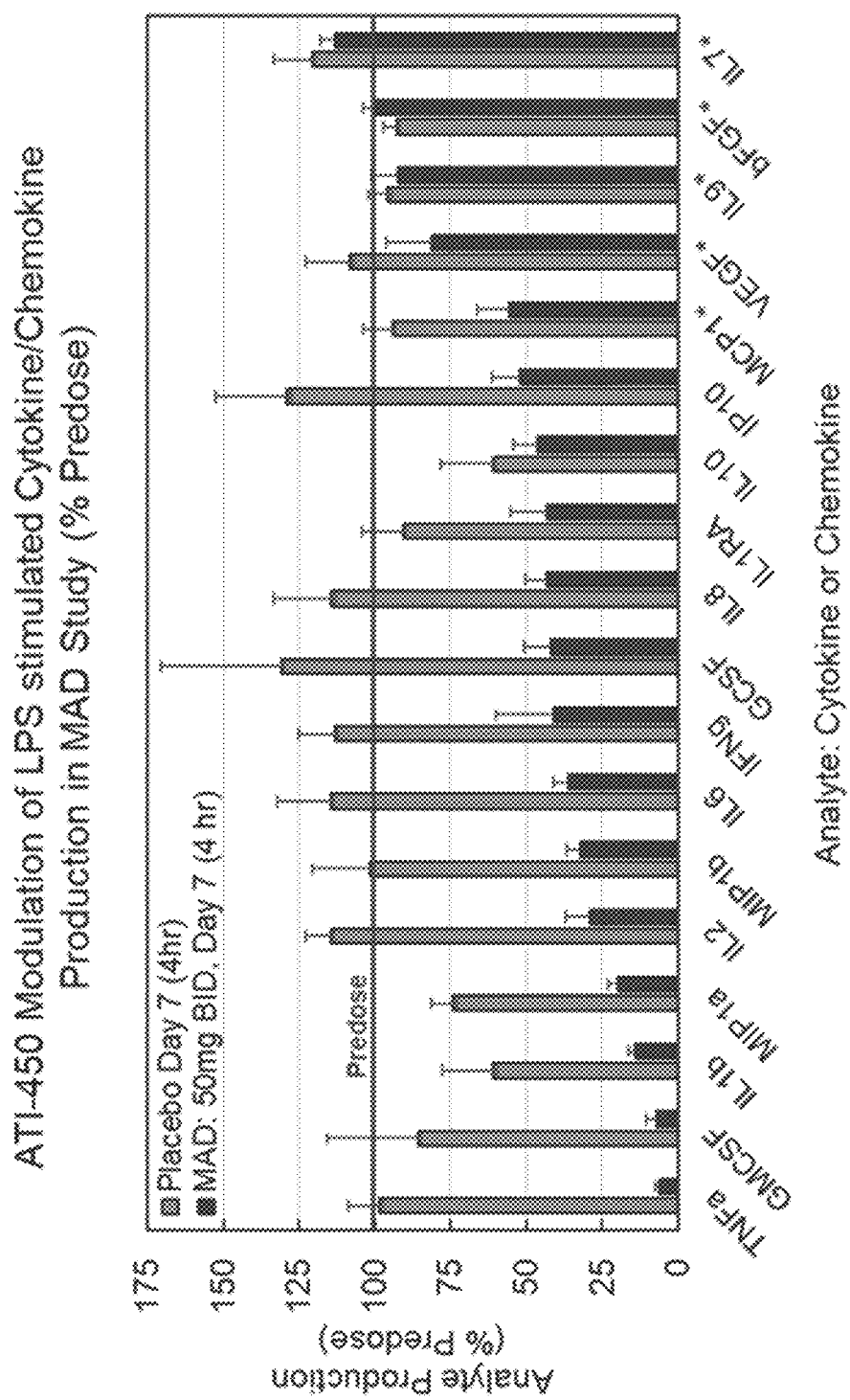
FIG. 3 shows ATI-450 modulation of ex vivo LPS stimulated cytokine/chemokine production in blood samples taken from subjects dosed with placebo or 50 mg/BID ATI-450.
Figure 4A:
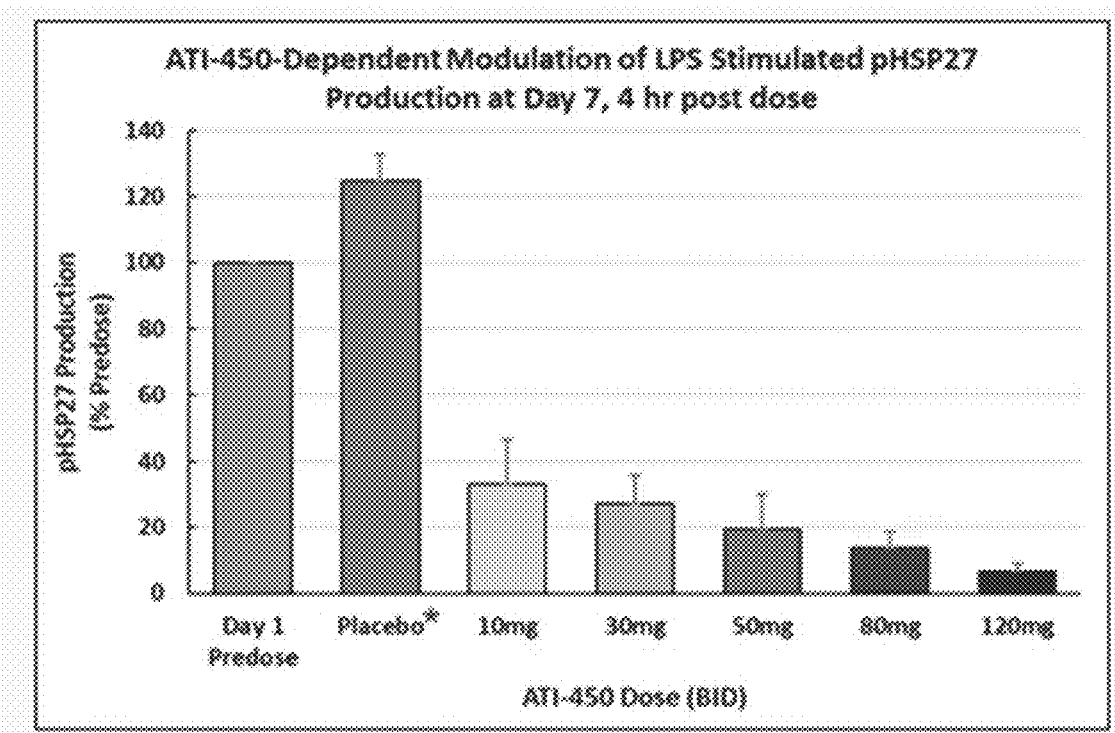
FIGS. 4A-4E are graphs showing ex vivo LPS stimulated production of pHSP27 (FIG. 4A, top), TNF-α (FIG. 4B, top), IL-1β (FIG. 4C, top), IL-8 (FIG. 4D, top), IL-6 (FIG. 4E, top) in Day 7 blood samples taken from subjects dosed with 10 mg, 30 mg, 50 mg, 80 mg, and 120 mg of ATI-450 or placebo.
Figure 4A:
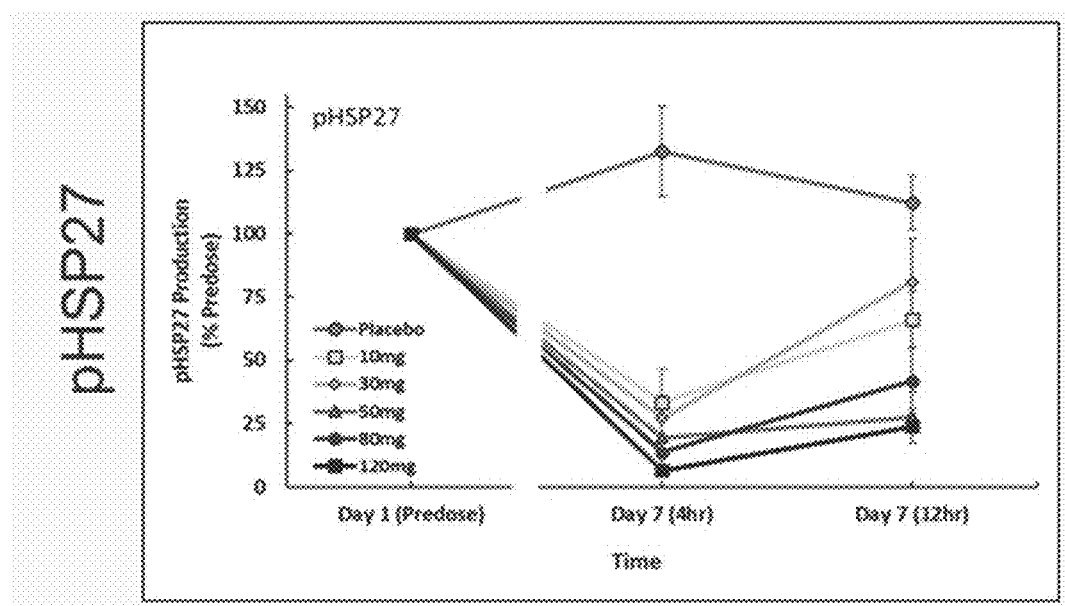
Figure 4B:
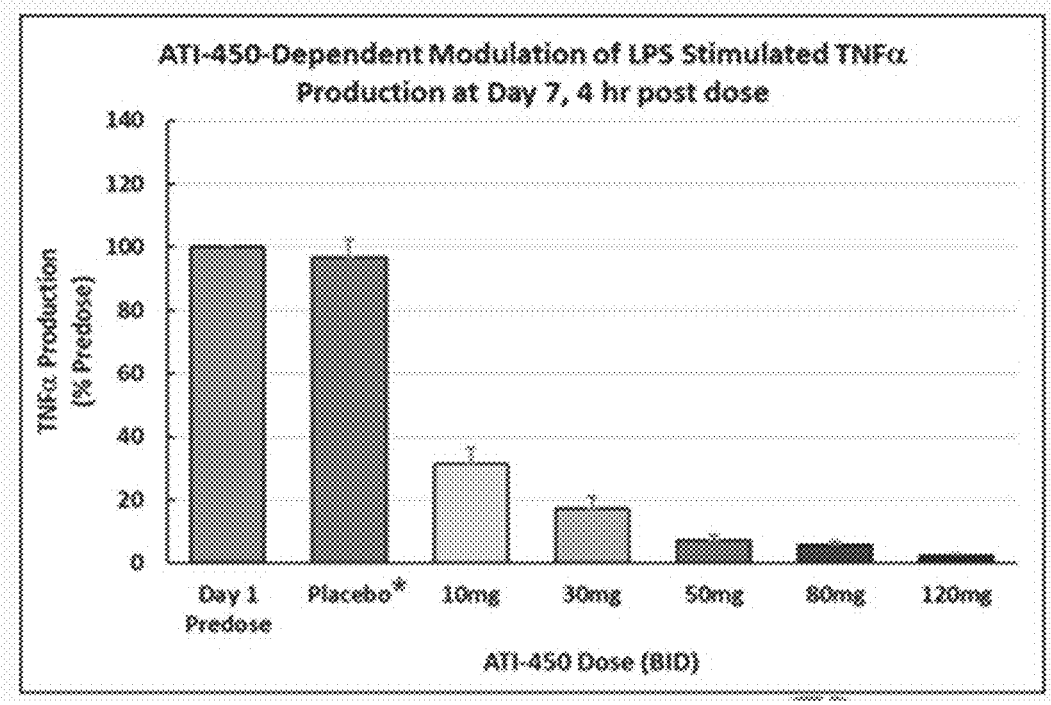
Figure 4B:
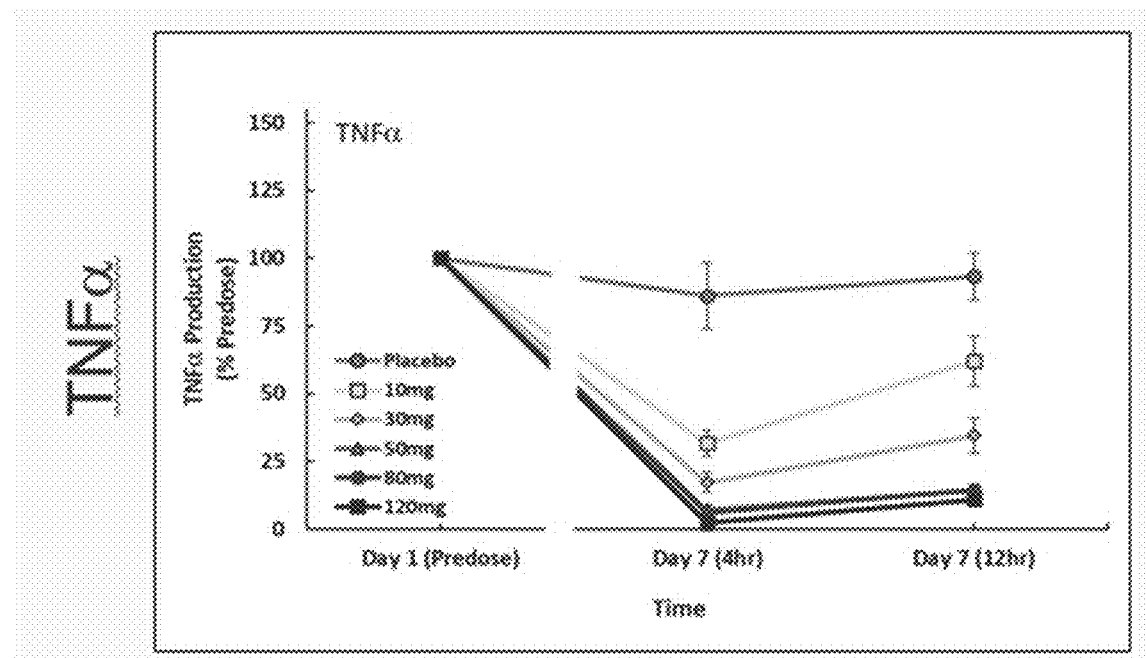
Figure 4C:
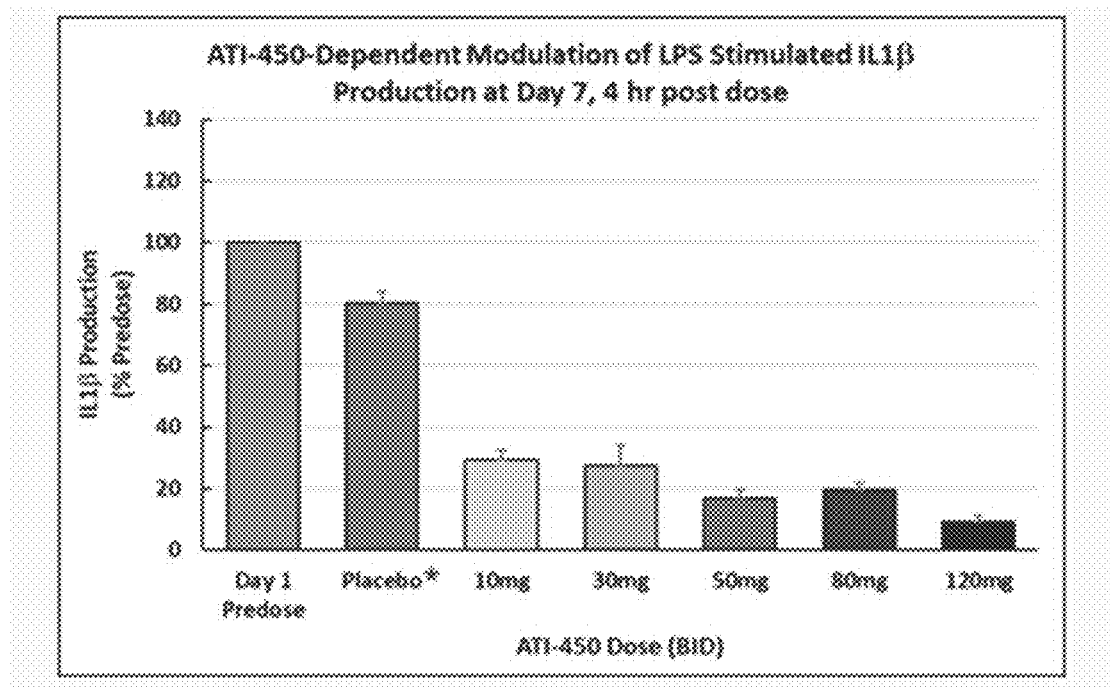
Figure 4C:
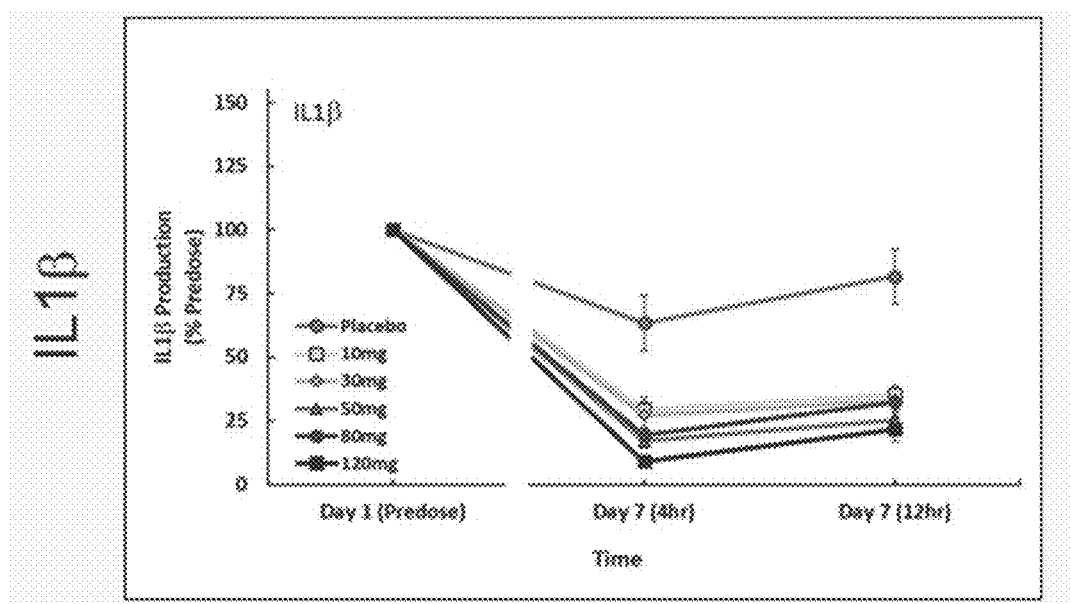
Figure 4D:
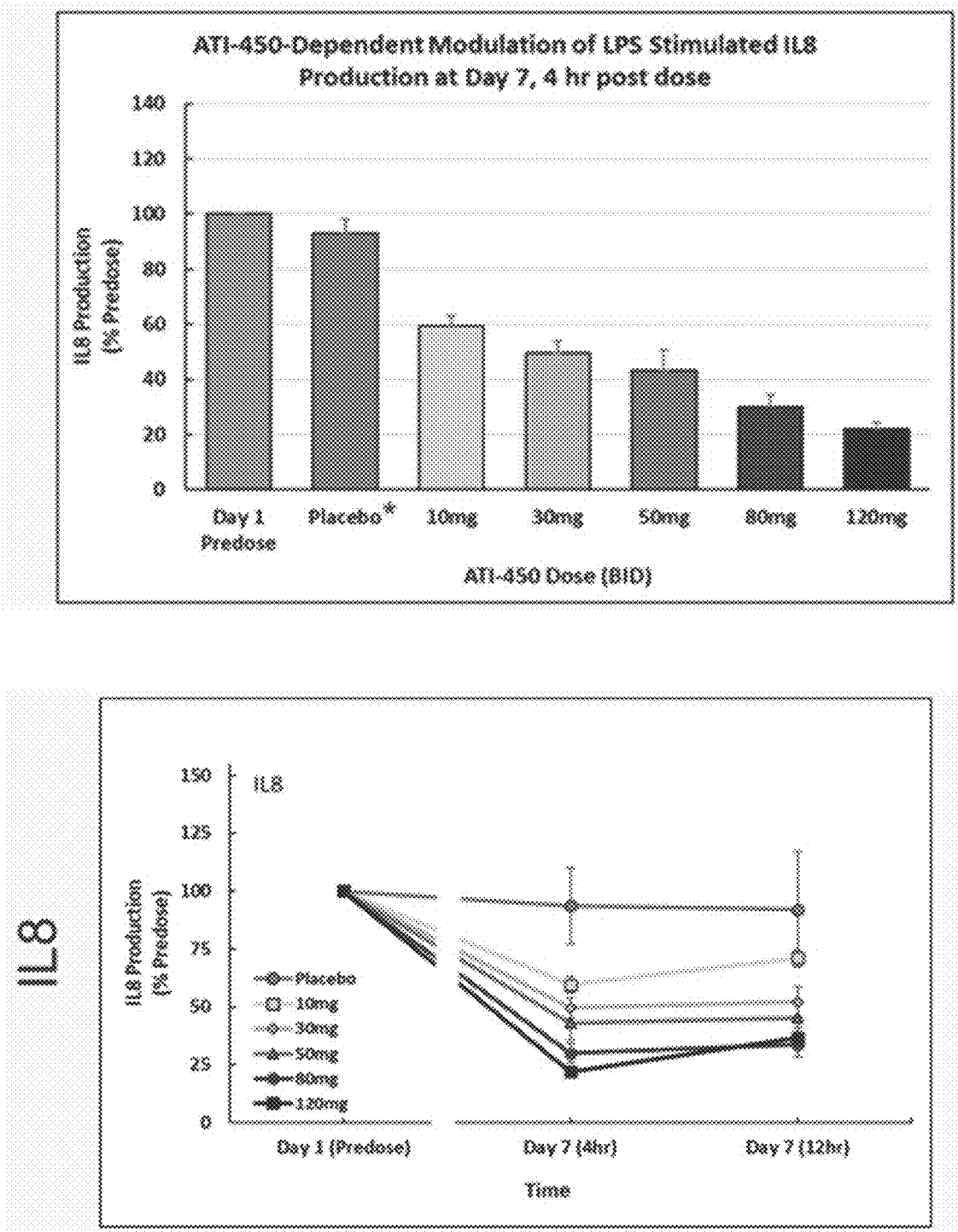
Figure 4E:
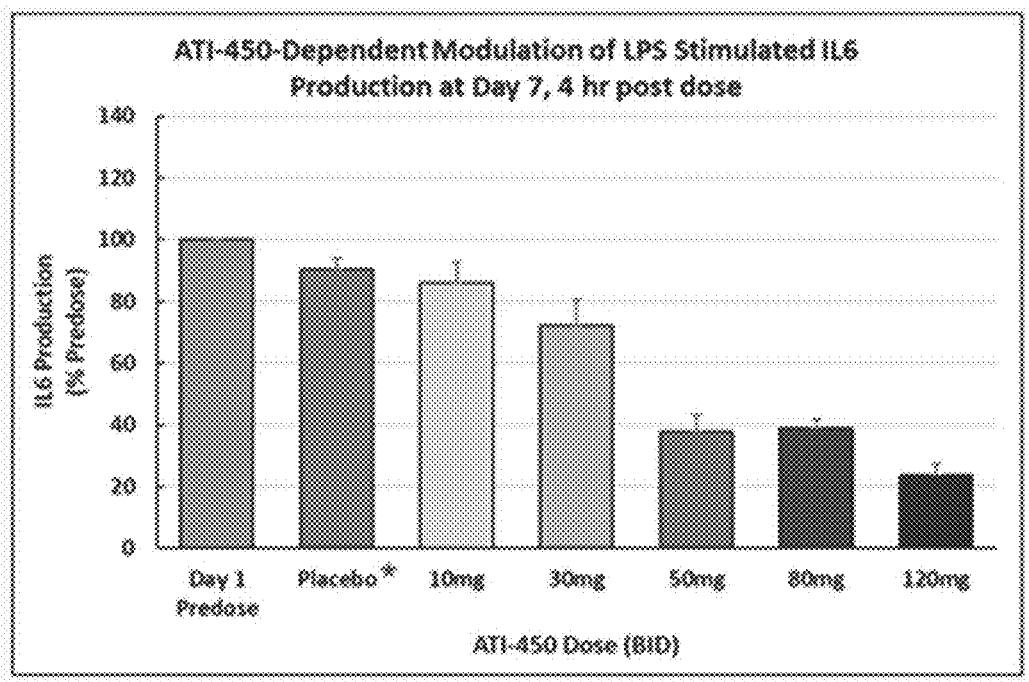
Figure 4E:
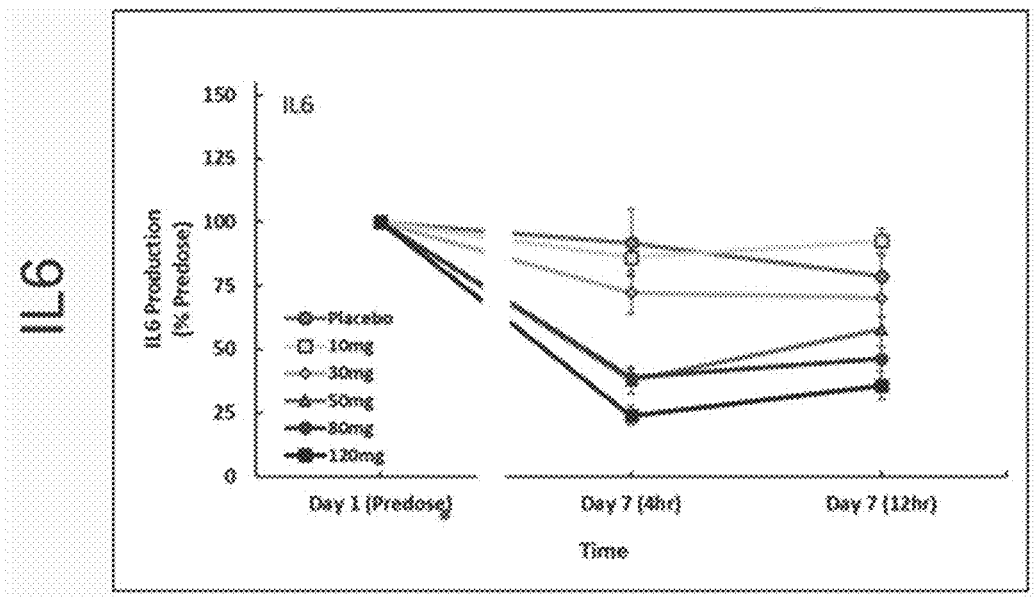

The graph of FIG. 3 shows the inhibition of LPS-stimulated cytokine and chemokine production in Day 7 blood samples taken from subjects dosed with 50 mg BID of ATI-450 (MAD cohort).

DISCUSSION

Administration of ATI-450 was generally safe and well tolerated by healthy subjects over a range of single doses up to 100 mg and multiple doses up to 50 mg BID for 7 days. All TEAEs resolved without sequelae and there were no discontinuations due to adverse events. Dizziness occurred more frequently in the active arms but there was no clear dose response; the events were generally transient in nature and almost all resolved while on study drug. A dose dependent reduction in neutrophils was observed and was consistent with the mechanism of action of ATI-450. PK parameters demonstrated that plasma concentrations of ATI-450 increased in a dose-proportional manner after administration of single or multiple ascending doses, which was also confirmed by statistical analysis with the power model for both SAD and MAD cohorts. Across all SAD and MAD cohorts, median Tmax ranged from 2 to 4 hours and mean $t_{1/2}$ ranged from approximately 9 to 12 hours with no clear relationship to dose. ATI-450 demonstrated concentration-dependent and dose-dependent modulation of the target biomarker p-HSP27 and inhibition of the production of TNF-α, IL-1β, IL-6, and IL-8.

ATI-450 presents a novel mechanism by which to inhibit MK2 and the pro-inflammatory cytokines activated by the p38MAPK pathway. As an orally administered drug, ATI-450 provides a potential alternative to injectable biologic medications that treat immune-mediated inflammatory diseases. ATI-450 has demonstrated efficacy in animal models for various immune-mediated inflammatory diseases and some types of cancer.[5, 19] Inhibition of TNF-α and IL-1β observed in healthy subjects in this study align with inhibition of the same cytokine biomarkers demonstrated in animal models for rheumatoid arthritis and cryopyrin-associated periodic syndromes.[5]

The PD responses in this study have been expressed as ratios of plasma concentrations of ATI-450 to the $IC_{50}$ for each cytokine. This measurement assists in identification of the key biomarkers that are modulated in response to ATI-450 and allows for adjustment of ATI-450 dosing to maintain plasma concentrations that are above the $IC_{80}$ for those biomarkers. ATI-450 demonstrated potent inhibition of 4 of the 5 biomarkers (p-HSP27, TNF-α, IL-1β, and IL-8). This inhibition was observed even at trough levels, as demonstrated in the 50 mg BID cohort, in which systemic drug concentrations in excess of the $IC_{50}$ were achieved for p-HSP27, TNF-α, IL-1β, and IL-8 at $C_{max}$ (3.5× to 6.0×) and $C_{trough}$ (1.4× to 2.4×). The more modest inhibition by ATI-450 of IL-6 induction in healthy subjects observed in this study may not be indicative of response in patients with rheumatoid arthritis because it does not take into account the impact of inhibiting IL-1β on downstream IL-6 release. Studies evaluating the potency of ATI-450 in human whole blood stimulated with IL-1β demonstrated potency for inhibiting IL-6 that was comparable to that for TNF-α and IL-8 (data not shown).

ATI-450 was well tolerated at the doses investigated, exhibited dose- and time-independent (i.e., linear) PK, and dose-related PD effects. Results of this study support the progression of ATI-450 into Phase 2 development for the treatment of rheumatoid arthritis and other immune-mediated inflammatory diseases.

TABLE 4

Summary of Demographic Characteristics

| | Single Ascending Dose Group | | | | | |
|---|---|---|---|---|---|---|
| | | ATI-450 | | | | |
| | Placebo (n = 8) | 10 mg (n = 6) | 30 mg (n = 6) | 50 mg (n = 6) | 100 mg (n = 6) | Overall (N = 32) |
| Sex, n (%) | | | | | | |
| Female | 6 (75.0) | 5 (83.3) | 6 (100.0) | 5 (83.3) | 5 (83.3) | 27 (84.4) |
| Male | 2 (25.0) | 1 (16.7) | 0 | 1 (16.7) | 1 (16.7) | 5 (15.6) |
| Race, n (%) | | | | | | |
| White | 3 (37.5) | 2 (33.3) | 3 (50.0) | 4 (66.7) | 3 (50.0) | 15 (46.9) |
| Black | 4 (50.0) | 3 (50.0) | 3 (50.0) | 1 (16.7) | 3 (50.0) | 14 (43.8) |
| Other | 1 (12.5) | 1 (16.7) | 0 | 1 (16.7) | 0 | 3 (9.4) |
| Ethnicity, n (%) | | | | | | |
| Hispanic or Latino | 0 | 1 (16.7) | 0 | 2 (33.3) | 1 (16.7) | 4 (12.5) |
| Not Hispanic or Latino | 8 (100.0) | 5 (83.3) | 6 (100.0) | 4 (66.7) | 5 (83.3) | 28 (87.5) |
| Age, y, mean ± SD | 37.0 ± 7.5 | 32.2 ± 13.7 | 28.7 ± 8.8 | 25.2 ± 4.0 | 31.2 ± 3.7 | 31.2 ± 8.8 |
| Weight, kg, mean ± SD | 76.4 ± 9.9 | 75.23 ± 16.78 | 72.8 ± 8.4 | 71.3 ± 8.2 | 61.5 ± 6.2 | 71.8 ± 11.2 |
| Height, cm, mean ± SD | 166.1 ± 5.9 | 172.5 ± 10.5 | 159.5 ± 10.0 | 163.8 ± 6.9 | 165.0 ± 8.6 | 165.4 ± 8.9 |
| BMI, kg/m², mean ± SD | 27.6 ± 2.6 | 25.1 ± 4.2 | 28.6 ± 2.1 | 26.6 ± 2.3 | 22.6 ± 1.1 | 26.2 ± 3.3 |

TABLE 4-continued

Summary of Demographic Characteristics

| | Multiple Ascending Dose Group | | | | |
|---|---|---|---|---|---|
| | | ATI-450 | | | |
| | Placebo (n = 6) | 10 mg BID (n = 8) | 30 mg BID (n = 8) | 50 mg BID (n = 8) | Overall (N = 30) |
| Sex, n (%) | | | | | |
| Female | 3 (50.0) | 5 (62.5) | 4 (50.0) | 5 (62.5) | 17 (56.7) |
| Male | 3 (50.0) | 3 (37.5) | 4 (50.0) | 3 (37.5) | 13 (43.3) |
| Race, n (%) | | | | | |
| White | 4 (66.7) | 3 (37.5) | 6 (75.0) | 2 (25.0) | 15 (50.0) |
| Black | 2 (33.3) | 4 (50.0) | 2 (25.0) | 5 (62.5) | 13 (43.3) |
| Other | 0 | 1 (12.5) | 0 | 1 (12.5) | 2 (6.7) |
| Ethnicity, n (%) | | | | | |
| Hispanic or Latino | 0 | 0 | 2 (25.0) | 0 | 2 (6.7) |
| Not Hispanic or Latino | 6 (100.0) | 8 (100.0) | 6 (75.0) | 8 (100.0) | 28 (93.3) |
| Age, y, mean ± SD | 35.2 ± 6.9 | 36.3 ± 7.8 | 37.9 ± 8.0 | 37.9 ± 9.0 | 36.9 ± 7.7 |
| Weight, kg, mean ± SD | 79.7 ± 17.4 | 72.7 ± 10.7 | 77.2 ± 14.4 | 75.9 ± 9.1 | 76.1 ± 12.5 |
| Height, cm, mean ± SD | 170.7 ± 7.2 | 166.6 ± 7.1 | 168.1 ± 9.6 | 170.3 ± 10.5 | 168.8 ± 8.5 |
| BMI, kg/m$^2$, mean ± SD | 27.1 ± 4.4 | 26.2 ± 3.9 | 27.1 ± 2.5 | 26.3 ± 3.7 | 26.7 ± 3.5 |

BID = twice daily;
BMI = body mass index.

TABLE 5

Most Common Treatment-Emergent Adverse Events Occurring in 2 or More Subjects (Safety Set)

| Event | ATI-450, n (%) (n = 48) | Placebo, n (%) (n = 14) |
|---|---|---|
| Dizziness | 6 (12.5) | 0 |
| Headache | 10 (20.8) | 2 (14.3) |
| Upper respiratory tract infection | 3 (6.3) | 1 (7.1) |
| Constipation | 3 (6.3) | 1 (7.1) |
| Nausea | 2 (4.2) | 1 (7.1) |
| Abdominal pain | 2 (4.2) | 0 |
| Vomiting | 0 | 2 (14.3) |

TABLE 6

Pharmacokinetic Parameters of ATI-450

| | Single Ascending Dose Group | | | | Multiple Ascending Dose Group | | |
|---|---|---|---|---|---|---|---|
| Parameter | ATI-450 10 mg (N = 6) | ATI-450 30 mg (N = 6)$^a$ | ATI-450 50 mg (N = 6) | ATI-450 100 mg (N = 6) | ATI-450 10 mg BID (N = 8) | ATI-450 30 mg BID (N = 8) | ATI-450 50 mg BID (N = 8) |
| $C_{max}$, ng/mL | 39.4 ± 10.4 | 122.0 ± 33.4 | 160.7 ± 20.4 | 426.0 ± 110.6 | 51.8 ± 15.8 | 146.5 ± 33.6 | 219.0 ± 77.8 |
| $T_{max}$, h$^b$ | 2.0 (2.0-4.0) | 4.0 (2.0-4.1) | 3.0 (2.0-4.0) | 2.0 (2.0-4.0) | 2.0 (2.0-2.0) | 2.0 (1.0-4.0) | 3.0 (1.0-4.0) |
| $AUC_{0-t}$, h*ng/mL | 276.3 ± 77.8 | 1074.0 ± 243.5$^a$ | 1430.0 ± 254.0 | 3489.8 ± 475.7 | 364.6 ± 110.7 | 1204.6 ± 309.1 | 2260.3 ± 1074.7 |
| $AUC_{0-inf}$, h*ng/mL | 285.3 ± 78.4 | 1102.4 ± 247.4$^a$ | 1464.7 ± 269.5 | 3654.8 ± 522.9 | N/A | N/A | N/A |
| $AUC_{tau}$, h*ng/mL | N/A | N/A | N/A | N/A | 287.8 ± 81.5 | 908.9 ± 163.1 | 1507.8 ± 659.9 |
| $t_{1/2}$, h | 8.5 ± 3.2 | 10.7 ± 3.3$^a$ | 9.1 ± 2.4 | 11.2 ± 5.8 | 9.6 ± 2.1 | 10.3 ± 3.2 | 11.6 ± 3.7 |
| CL/F or $CL_{ss}$/F,$^c$ L/h | 37.0 ± 8.8 | 28.4 ± 7.1$^a$ | 35.1 ± 6.3 | 27.9 ± 4.3 | 37.4 ± 10.9 | 33.9 ± 5.9 | 37.3 ± 11.7 |
| $V_z$/F or $V_{ss}$/F,$^c$ L | 430.2 ± 124.0 | 451.4 ± 201.5$^a$ | 445.0 ± 94.7 | 439.8 ± 189.7 | 517.4 ± 203.2 | 483.1 ± 85.1 | 586.4 ± 163.2 |
| $C_{trough}$, ng/mL$^d$ | | | | | | | |
| Day 2 | N/A | N/A | N/A | N/A | 10.1 ± 4.7 | 37.5 ± 18.8 | 84.0 ± 40.6 |
| Day 3 | N/A | N/A | N/A | N/A | 9.8 ± 4.5 | 44.1 ± 29.3 | 80.6 ± 44.2 |
| Day 4 | N/A | N/A | N/A | N/A | 9.2 ± 5.0 | 36.8 ± 14.9 | 81.5 ± 49.6 |
| Day 5 | N/A | N/A | N/A | N/A | 9.6 ± 4.7 | 34.9 ± 13.8 | 81.5 ± 43.9 |
| Day 6 | N/A | N/A | N/A | N/A | 10.7 ± 4.9 | 38.9 ± 16.2 | 76.4 ± 38.6 |
| Day 7 | N/A | N/A | N/A | N/A | 11.8 ± 5.2 | 41.1 ± 18.3 | 87.9 ± 49.4 |
| $C_{min}$, ng/mL | N/A | N/A | N/A | N/A | 8.1 ± 3.1 | 28.8 ± 10.7 | 58.7 ± 32.8 |

TABLE 6-continued

Pharmacokinetic Parameters of ATI-450

|  | Single Ascending Dose Group | | | | Multiple Ascending Dose Group | | |
| --- | --- | --- | --- | --- | --- | --- | --- |
| Parameter | ATI-450 10 mg (N = 6) | ATI-450 30 mg (N = 6)[a] | ATI-450 50 mg (N = 6) | ATI-450 100 mg (N = 6) | ATI-450 10 mg BID (N = 8) | ATI-450 30 mg BID (N = 8) | ATI-450 50 mg BID (N = 8) |
| $C_{avg}$, ng/mL | N/A | N/A | N/A | N/A | 24.0 ± 6.8 | 75.6 ± 13.4 | 125.6 ± 55.0 |
| $R_{ac}$, $C_{max}$ | N/A | N/A | N/A | N/A | 1.57 ± 0.62 | 1.17 ± 0.26 | 1.25 ± 0.48 |
| $R_{ac}$, $AUC_{tau}$ | N/A | N/A | N/A | N/A | 1.44 ± 0.32 | 1.36 ± 0.33 | 1.29 ± 0.37 |

Data presented are means ± SD unless otherwise indicated.
[a]One subject was excluded for $AUC_{0-t}$, $AUC_{0-inf}$, $t_{1/2}$, CL/F, and $V_z$/F measurements due to withdrawn consent. No samples were collected past 12 hours.
[b]Data presented are medians (ranges).
[c]Values for CL/F and Vz/F are for single doses and values for $CL_{ss}$/F and $V_{ss}$/F are for multiple doses.
[d]$C_{trough}$ values are presented for day 2 through day 7 for the MAD cohorts.
$AUC_{0-inf}$, area under the plasma concentration-time curve from time 0 to time infinity;
$AUC_{0-t}$, area under the plasma concentration-time curve from time 0 to time t;
$AUC_{tau}$, area under the plasma concentration-time curve over the 12-hour dosing interval, tau;
BID, twice daily;
CL/F, clearance;
$CL_{ss}$/F, clearance at steady state;
$C_{avg}$, average plasma concentration after multiple dosing, on day 7;
$C_{max}$, maximum plasma concentration;
$C_{min}$, minimum plasma concentration;
$C_{trough}$, measured concentration at the end of a dosing interval;
N/A, not applicable;
$R_{ac}$, $AUC_{tau}$, accumulation ratio for $AUC_{tau}$;
$R_{ac}$, $C_{max}$, accumulation ratio for $C_{max}$;
$t_{1/2}$, terminal elimination half-life;
$T_{max}$, time to maximum plasma concentration;
$V_{ss}$/F, volume of distribution at steady state;
$V_z$/F, volume of distribution.

TABLE 7

Cytokine and Biomarker $IC_{80}$ Values and Multiples Across the Dosing Interval in the 50 mg BID Dose Cohort

| Biomarker | $IC_{80}$[a] (ng/mL) | $C_{trough}$[b] (Multiple of $IC_{80}$) | $C_{max}$[b] (Multiple of $IC_{80}$) |
| --- | --- | --- | --- |
| p-HSP27 | 36.7 | 2.4x | 6.0x |
| TNF-α | 62.6 | 1.4x | 3.5x |
| IL-1β | 40.8 | 2.2x | 5.4x |
| IL-6 | 747.8 | 0.1x | 0.3x |
| IL-8 | 38.8 | 2.3x | 5.6x |

[a]$IC_{80}$ values generated from combined SAD and MAD ATI-450 concentration and ex vivo inhibition data using the WinNonlin inhibitory $E_{max}$ model 104.
[b]Values are from 50 mg BID MAD cohort on day 7; $C_{trough}$ = 87.9 ng/mL and $C_{max}$ = 219 ng/mL.
BID, twice daily;
$C_{max}$, maximum observed plasma concentration;
$C_{trough}$, measured concentration at the end of a dosing interval;
$IC_{80}$, concentration for 80% of maximal inhibition;
IL, interleukin;
MAD, multiple ascending dose;
p-HSP27, phosphorylated heat shock protein 27;
SAD, single ascending dose;
TNF-α, tumor necrosis factor α.

Methods

Study Design. PRA Health Sciences led the study at a clinical site in Lenexa, Kansas, and prepared the randomization scheme for all cohorts while maintaining blinding of observers associated with the study. PRA assigned randomization codes sequentially as healthy subjects became eligible for randomization after enrolling in the study. For each SAD dose cohort, subjects were randomly assigned to ATI-450 or placebo in an overall 6:2 ratio. For each MAD dose cohort, subjects were randomly assigned to ATI-450 or placebo in an overall 8:2 ratio.

Single ascending dose (SAD) cohorts. Thirty-two subjects were randomly assigned to 1 of 4 cohorts to receive ATI-450 doses of 10, 30, 50 or 100 mg (n=6 per cohort) or placebo (n=2 per cohort). Each subject received a single oral dose of ATI-450 or placebo in the morning on an empty stomach. All subjects were admitted to the clinical study facility on day −1 and stayed until 48 hours after ATI-450 or placebo administration.

Multiple ascending dose (MAD) cohorts. Thirty subjects were randomly assigned to 1 of 3 cohorts to receive ATI-450 doses of 10, 30, or 50 mg BID (n=8 per cohort) or placebo (n=2 per cohort). Subjects received each dose of ATI-450 or placebo on an empty stomach for 7 days, in the morning and the evening, with the final dose administered on the morning of day 7. Subjects were admitted to the clinical facility on day −1 and remained at the site until 72 hours after the morning dose on day 7.

Subjects. Subjects were healthy males or females between 18 and 55 years of age, inclusive; had a body mass index between 18 and 32 kg/m2, inclusive, with a minimum body weight of 50 kg; and tested negative for HIV-1 and HIV-2 antibodies, hepatitis B surface antigen, and hepatitis C virus antibody at screening. Female subjects were not pregnant or nursing and agreed to use 2 effective methods of contraception if heterosexually active and of childbearing potential.

Subjects were excluded from the study if they had a current acute or chronic disease or used medications that may have affected their safety or other study assessments within 2 weeks of admission.

The study was conducted in accordance with the principles of the Declaration of Helsinki and in compliance with the International Council for Harmonization E6 Guideline for Good Clinical Practice, and any applicable national and local laws and regulations. The clinical study protocol, informed consent forms, and amendments to all documents were reviewed and approved by Midlands Independent Review Board of Overland Park, Kansas. Informed consent was obtained from all subjects before any study-related procedures began.

Safety and Tolerability Assessments. Adverse events, clinical laboratory tests, vital signs, an electrocardiogram, Holter monitoring, and physical examination results were evaluated for each subject in both parts of the study.

Blood Sampling and Bioanalysis. Two-milliliter blood samples were collected for PK analysis. For the SAD cohorts, blood was collected before dosing and 0.5, 1, 2, 4, 6, 8, 12, 24, 36, and 48 hours after dosing. For the MAD cohorts, blood was collected on day 1 prior to the morning dose and 0.5, 1, 2, 4, 6, 8, and 12 hours after dosing (before the evening dose); before the morning dose on days 2 through 6; and on day 7, before the morning dose and 0.5, 1, 2, 4, 6, 8, 12, 13, 14, 24, 36, 48, and 72 hours after the morning dose.

Blood samples of 10 mL were collected for PD analysis. For the SAD cohorts, blood was collected before dosing and 1, 12, and 24 hours after dosing. For the MAD cohorts, on day 1 blood was collected before the morning dose and 4 and 12 hours after the morning dose (prior to the evening dose); on day 7, blood was collected before the morning dose and 4 and 12 hours after the morning dose.

ATI-450 concentrations in plasma samples were determined by PRA Health Sciences-Bioanalytical Laboratory (Lenexa, Kansas) using a validated ultra-performance liquid chromatography with tandem mass spectrometry method (details in Supplementary Information). The lower limit of quantification was 0.500 ng/mL.

PD bioanalysis (performed by Confluence Discovery Technologies, Inc. [St. Louis, Missouri]) of phosphorylated heat shock protein 27 (p-HSP27), IL-1β, IL-6, IL-8, and TNF-α levels in blood samples were analyzed under 3 conditions: (1) unstimulated, (2) ex vivo lipopolysaccharide stimulation, and (3) ex vivo lipopolysaccharide stimulation in the presence of exogenously added 10 μM ATI-450. Historical data show the percentage of maximum inhibition by ATI-450 achieved for a given analyte is consistent and therefore useful for normalization across samples. Additional details of the assays for analyzing p-HSP27 and cytokines are included in the Supplementary Information.

SAD cohort data were calculated for each subject set (day 1-pre-dosing, day 1-1 hour after dosing, day 1-12 hours after dosing, and day 2-24 hours after dosing) as the % of day 1 pre-dosing using the ex vivo lipopolysaccharide stimulation as the maximum signal and normalizing across the sample set using the day 1 ex vivo lipopolysaccharide plus 10 μM ATI-450 as maximum inhibition.

MAD cohort data were calculated for each subject set (day 1—pre-dosing, day 1-4 hours after dosing, day 1-12 hours after dosing, day 7—pre-dosing, day 7-4 hours after dosing, and day 7-12 hours after dosing) as the % of day 1 pre-dosing using the ex vivo lipopolysaccharide stimulation as the maximum signal and normalizing across the sample set using the day 1 ex vivo lipopolysaccharide plus 10 μM ATI-450 as maximum inhibition.

Pharmacokinetics. ATI-450 plasma concentrations and PK parameters were determined for all SAD and MAD cohorts. Noncompartmental analysis with Phoenix WinNonlin™, version 8.1 (Certara, Princeton, NJ) was used to determine the following PK parameters from the plasma concentration-time data for ATI-450: maximum observed plasma concentration ($C_{max}$); time to maximum observed plasma concentration ($T_{max}$); area under the plasma concentration-time curve from time 0 through time t ($AUC_{0-t}$), where t is the time of the last quantifiable concentration; area under the plasma concentration-time curve from time 0 to infinity ($AUC_{0-inf}$); apparent terminal elimination rate constant ($\lambda z$) and associated half-life ($t_{1/2}$); apparent clearance ($CL/F$); and apparent volume of distribution ($V_{z/F}$). For the MAD cohorts, several additional PK parameters were determined, including area under the plasma concentration-time curve over the 12-hour dosing interval, tau ($AUC_{tau}$); minimum observed plasma concentration in the dosing interval after multiple dosing, on day 7 ($C_{min}$); average plasma concentration after multiple dosing, on day 7 ($C_{avg}$); measured concentration at the end of a dosing interval ($C_{trough}$); accumulation ratio for $C_{max}$ and $AUC_{tau}$ ($R_{ac}$, $C_{max}$ and $R_{ac}$, $AUC_{tau}$); apparent clearance at steady state ($CL_{ss}/F$); and apparent volume of distribution at steady state ($V_{ss}/F$).

Pharmacodynamics. PD data analysis was conducted using Microsoft Excel 2010 (Microsoft, Redmond, WA), Meso Scale Discovery Workbench® analysis software (Rockville, MD), and Phoenix WinNonlin, version 8.2. For the PK/PD analysis in Phoenix WinNonlin, the ATI-450 plasma concentrations and the percentages of inhibition of production of lipopolysaccharide-stimulated p-HSP27, TNF-α, IL-1β, IL-6 and IL-8 levels in human whole blood from all SAD/MAD cohorts were simultaneously fit using an inhibitory $E_{max}$ model (WinNonlin, model 104). The parameters estimated by the model for each biomarker were the baseline effect at zero concentration ($E_0$), the maximum percent inhibition (Imax), and the ATI-450 plasma concentration at half maximal inhibition ($IC_{50}$). The ATI-450 concentrations at 80% inhibition ($IC_{80}$) were subsequently calculated from the $IC_{50}$ estimates using the following equation: $IC_x=(x/100-x)*IC_{50}$, where x is the percent inhibition (e.g., 80%). Additionally, multiples of the peak and trough concentrations of ATI-450 at 50 mg BID on day 7 to the $IC_{50}$ and $IC_{80}$ estimates for p HSP27 and each cytokine were determined.

Sample size calculations. No prospective calculations of statistical power were made for sample size. Sample sizes of 32 subjects and 30 subjects for the SAD and MAD cohorts, respectively, were selected and are typical for a first-in-human study.

Bioanalysis Assay of ATI-450. Sample processing was performed by protein precipitation using a 50.0-μL sample volume. Separation between potential metabolites and interfering endogenous compounds was achieved by liquid chromatography with tandem mass spectrometry using a Waters Acquity UPLC BEH C18 column (2.1×50 mm, 1.7 μm particle size) at 40° C. using 10 mM ammonium formate with 0.3% formic acid as mobile phase A and 50:50:0.3 acetonitrile:methanol:formic acid as mobile phase B, operating at isocratic conditions (with post-elution gradient wash-off) with a flow rate of 0.700 mL/min. A triple quadrupole 6500 mass spectrometer equipped with a turbo-ion spray source was used for detection in positive ion mode. Quantification was based on multiple reaction monitoring of the transitions of m/z 514.3→297.2 for ATI-450 and 517.3→336.2 for the internal standard, ATI-450-$^{13}C_3$. A linear calibration curve ranging from 0.500 to 500 ng/mL with a $1/x^2$ weighting factor was used. The method was minimally required to have intra- and inter-day precision (coefficients of variation) for pooled plasma quality control samples of ≤15% except at the lower limit of quantitation, where ≤20% was acceptable. The calculated concentrations (both inter- and intra-day) were required to be within 15% of nominal at all concentrations except the lower limit of quantitation, where up to 20% deviation from nominal was acceptable. The precision and accuracy of the method exceeded these minimum requirements for assay validation. In addition, stability of the analyte in frozen $K_2$-EDTA human plasma was demonstrated for periods exceeding the storage periods of the samples prior to analysis, as well as under all conditions to which study samples or working solutions were subjected.

Sample Preparation for p-HSP27 Analysis. For p-HSP27 analysis, 1-mL aliquots of each sample were transferred into six 2-mL microtubes with subsequent treatment designation: 'A' for lipopolysaccharide stimulation only (maximum signal), 'B' for ex vivo added ATI-450 samples that received lipopolysaccharide stimulation (maximum inhibition), 'C' for unstimulated. Treatment groups consisted of 3 tubes for group 'A', 2 tubes for group 'B', and 1 tube for group 'C'.

Dimethyl sulfoxide (DMSO) was added to all tubes in groups 'A' and 'C' to a final concentration of 0.1% (10 μL per mL of a 10% DMSO solution in Dulbecco's Modified Eagle Medium (DMEM) containing 10% fetal bovine serum (FBS) and 1% penicillin/streptomycin/glutamine). Samples were then rocked gently at room temperature. A stock solution of ATI-450 at 10 mM in 100% DMSO was diluted to 1 mM in DMEM containing 10% FBS and 1% penicillin/streptomycin, and 10 μL of this working solution was added per mL of blood in group 'B' samples to give a final concentration of 10 μM in 0.1% DMSO. Samples were then rocked gently at room temperature for a minimum of 1 hour.

Samples in groups 'A' and 'B' were stimulated with lipopolysaccharide at a final concentration of 100 ng/mL for 22 minutes at room temperature. A stock solution of lipopolysaccharide at 1 mg/mL in DMEM containing 10% FBS and 1% penicillin/streptomycin was diluted to 10 μg/mL in DMEM containing 10% FBS and 1% penicillin/streptomycin, and 10 μL of this working solution was added per mL of blood. Samples were gently rocked at room temperature for 11 minutes, then placed upright for 11 minutes prior to peripheral blood mononuclear cells (PBMC) isolation.

Ten μL of DMEM containing 10% FBS only was added per mL of blood in group 'C' for all patient samples (unstimulated samples). Samples were gently rocked at room temperature for 11 minutes, then placed upright for 11 minutes prior to PBMC isolation.

Upon completion of treatment (lipopolysaccharide stimulated or unstimulated) for each sample, PBMCs were isolated from each human whole blood aliquot in all treatment groups. One mL of blood from each sample was gently layered onto 0.75 mL of Histopaque-1077 in a 2-mL microcentrifuge tube. Histopaque-1077 was maintained at room temperature. The samples were centrifuged for 2 minutes at 16,000×g in an Eppendorf microcentrifuge. The interface and upper layers were removed and added to tubes containing 1 mL cold Dulbecco's phosphate-buffered saline (DPBS). These samples were then centrifuged for 30 seconds at 16,000×g in an Eppendorf microcentrifuge to pellet the cells. The buffer supernatant was removed by aspiration and the pellets were re-suspended in 1 mL of cold DPBS. The pellets from each sample were then re-pelleted, as described above. The buffer was removed by aspiration and the final pellets were lysed in 100 μL of complete lysis buffer (MSD Tris lysis buffer, 1× Halt™ Protease inhibitor cocktail, 1× phosphatase inhibitor cocktail 2, 1× phosphatase inhibitor cocktail 3, 2 mM PMSF, 2 mM sodium fluoride and 1 mM sodium vanadate). Samples were vortexed until the cell pellet fully dissolved and then were flash frozen on dry ice.

Analysis of p-HSP27 (Ser78) Levels Using Luminex Technology. The lysates were analyzed for HSP27 phosphorylation with a custom Milliplex® MAP Human Phospho-HSP27(Ser78) Cell Signaling Magnetic Bead Kit from Millipore Sigma (Burlington, MA) using the kit-prescribed immunoassay protocol for a 96-well solid plate and hand-held magnetic separation block. Once all sample lysates from a given cohort were generated, the lysates were thawed at 4° C. and transferred to a round-bottom 96-well polypropylene master plate. A daughter plate consisting of a 2-fold dilution of each lysate (17 μL of lysate plus 17 μL of Milliplex® MAP assay buffer 2) was generated for each master plate. The diluted lysates from the daughter plates were used in the assay.

The 96-well, flat-bottom, clear-bottom black plates provided in the kit were prewashed with 50 μL/well of assay buffer 2 for 10 minutes. The wash was decanted and 1× HSP27 magnetic beads in assay buffer 2 were added to each well at 25 μL/well. The diluted lysates from the daughter plates were then added at 25 μL/well. The plates were sealed and incubated overnight at 4° C. with shaking in the dark.

After the overnight incubation, using the hand-held magnetic separation block, the samples were decanted and plates were washed 2 times with assay buffer 2. Biotin-labeled detection antibody (1× in assay buffer 2) was added at 25 μL/well to all plates and incubated for 1 hour. All incubations were at room temperature with shaking in the dark. The detection antibody was then decanted using the hand-held magnetic separation block and streptavidin-phycoerythrin (PE; 1× in assay buffer 2) was added to each well at 25 μL/well. The plates were then incubated for 15 minutes. Amplification buffer (1× in assay buffer 2) was added to the streptavidin-PE-containing wells at 25 μL/well and incubated an additional 15 minutes. Using the hand-held magnetic separation block, the streptavidin-PE/amplification buffer was removed by decanting. Assay buffer 2 was added to each well at 150 μL/well. The plates were placed on the plate shaker for a minimum of 5 minutes, then analyzed using the Luminex® 100/200 Instrument (Luminex Corp, Austin, TX).

Sample Preparation for Cytokine Analysis. For each sample, 180 μL aliquots were transferred into 7 wells of a round bottom 96 well tissue culture polystyrene low evaporation plate. Of the 7 wells for each sample, 3 were designated 'A' for lipopolysaccharide stimulation only (maximum signal), 2 were designated 'B' for ex vivo added ATI-450 samples that received lipopolysaccharide stimulation (maximum inhibition), and 2 were designated 'C' for unstimulated lipopolysaccharide. No outer wells on the plates were used and all wells surrounding the samples contained 200 μL of phosphate buffered saline.

DMSO was added to all wells in groups 'A' and 'C' to a final concentration of 0.1% (10 L/well of a 2% DMSO solution in DMEM containing 10% FBS and 1% penicillin/streptomycin/glutamine). A stock solution of ATI-450 at 10 mM in 100% DMSO was diluted to 200 mM in DMEM containing 10% FBS and 1% penicillin/streptomycin, and 10 mL of this working solution was added per well to all wells in group 'B' to give a final concentration of 10 mM in 0.1% DMSO. Samples were mixed gently for 30 seconds on a plate shaker using pin tools, then placed in an incubator at 37° C./5% $CO_2$ for 1 hour.

Samples in groups 'A' and 'B' were stimulated with lipopolysaccharide at a final concentration of 100 ng/mL. A stock solution of lipopolysaccharide at 1 mg/mL in DMEM containing 10% FBS and 1% penicillin/streptomycin was diluted to 2 mg/mL in DMEM containing 10% FBS and 1% penicillin/streptomycin, and 10 mL of this working solution was added per well of blood for all samples in groups 'A' and 'B'. Ten mL of DMEM containing 10% FBS only was added per well of blood for all samples in group 'C' (unstimulated samples). Samples were mixed gently for 30 seconds on a plate shaker using pin tools, then placed in an incubator at 37° C./5% $CO_2$ for 5 hours.

Following the incubation, the plates were removed from the incubator and sealed with adhesive clear plate seals. The plates were then centrifuged for 10 minutes at 1800×g at room temperature. Seventy-five mL of plasma was removed from each well and transferred to a 96-well polypropylene round bottom master plate, which was then sealed and frozen at −80° C. until all samples from the respective cohort were generated. Once all samples from a given cohort were generated, the samples were analyzed for cytokine (TNF-α, IL-1b, IL-6, and IL-8) production using Meso Scale Discovery Technology.

Analysis of Cytokine Levels Using Meso Scale Discovery Technology. All lipopolysaccharide plasma samples were analyzed for cytokine production with a V-Plex Human Proinflammatory Panel II (4-Plex) Kit from Meso Scale Discovery (Rockville, MD). The master plates containing the plasma samples were thawed on ice, and a daughter plate consisting of a 25-fold dilution of each plasma sample (3 µL of plasma plus 72 µL of Meso Scale Discovery Diluent 2) was generated for each master plate. The diluted plasma samples from the daughter plates were used in the cytokine analysis. The Meso Scale Discovery 4-plex plates were washed 3 times with 150 µL/well of wash buffer (1×KPL phosphate buffered saline with Tween 20 from SeraCare [Milford, MA]). Prepared calibrators and the samples from the daughter plates were added to the washed Meso Scale Discovery 4-plex plates at 50 µL/well. The 4-plex plates were sealed and shaken overnight at 4° C.

After the overnight incubation, the samples were removed by decanting. The 4-plex plates were then washed 3 times with 150 µL/well of wash buffer. A detection antibody mix consisting of sulfo-tagged anti-human IL-1β, sulfo-tagged anti-human IL-6, sulfo-tagged anti-human IL-8, and sulfo-tagged anti-human TNF-α antibodies in Meso Scale Discovery Diluent 3 was added to each well at 25 µL/well, and the plates were sealed and incubated for 2 hours at room temperature with shaking. Following the incubation, the detection antibodies were removed by decanting. The 4-plex plates were washed 3 times with 150 µL/well of wash buffer after which 2× Read Buffer was added at 150 µL/well to all wells. The plates were then read using a Meso Scale Discovery Sector S 600 instrument. Calculations to establish cytokine calibration curves and to determine analyte concentrations in the samples were carried out using the Meso Scale Discovery Workbench analysis software.

TABLE 8

Statistical Analysis of Dose Proportionality of ATI-450 in SAD Cohorts

| PK Parameter | n | Intercept | Slope | 90% CI of Slope |
|---|---|---|---|---|
| $C_{max}$ (ng/mL) | 24 | 1.302 | 1.006 | (0.902, 1.111) |
| $AUC_{0-t}$ (h * ng/mL) | 23 | 3.113 | 1.088 | (0.997, 1.180) |
| $AUC_{0-inf}$ (h * ng/mL) | 23 | 3.134 | 1.091 | (0.999, 1.184) |

The dose proportionality analyses were performed using the power model: ln(PK)=intercept+slope*ln(dose)+e, where PK is the PK parameter and e is the error term. A value of slope=1 indicates dose proportionality. In Table 8, the following terms are used: AUC, area under the concentration-time curve; $C_{max}$, maximal plasma concentration; CI, confidence interval; n, number of observations; PK, pharmacokinetic.

TABLE 9

Statistical Analysis of Dose Proportionality of ATI-450 in MAD Cohorts

| PK Parameter | n | Intercept | Slope | 90% CI of Slope |
|---|---|---|---|---|
| $C_{max}$ (ng/mL) | 24 | 1.857 | 0.899 | (0.757, 1.042) |
| $AUC_{tau}$ (h * ng/mL) | 24 | 3.292 | 1.019 | (0.872, 1.167) |

The dose proportionality analyses were performed using the power model: ln(PK)=intercept+slope*ln(dose)+e, where PK is the PK parameter and e is the error term. A value of slope=1 indicates dose proportionality. In Table 9, the following terms are used: AUC, area under the concentration-time curve; $C_{max}$, maximal plasma concentration; CI, confidence interval; n, number of observations; PK, pharmacokinetic.

TABLE 10

Inhibitory $E_{max}$ Model Parameters

|  | P-HSP27 | TNF-α | IL-1β | IL-6 | IL-8 |
|---|---|---|---|---|---|
| $IC_{50}$, ng/mL | 9.2 | 15.6 | 10.2 | 186.9 | 9.7 |
| $IC_{80}$, ng/mL | 36.7 | 62.6 | 40.8 | 747.8 | 38.8 |
| $I_{max}$, % | 110.6 | 96.5 | 74.3 | 116.4 | 57.1 |

In Table 10, the following terms are used: $IC_{50}$, plasma concentration at half maximal inhibition; $IC_{80}$, plasma concentration at 80% of maximal inhibition; IL, interleukin; $I_{max}$, maximum percent inhibition; p-HSP27, phosphorylated heat shock protein 27; TNF, tumor necrosis factor.

Example 2: Extension Study of Higher Doses of Orally Administered ATI-450

This extension of the Phase I clinical study described in Example 1 was carried out to establish the safety and tolerability of higher doses (80 mg and 120 mg twice daily) of ATI-450 in healthy volunteers.

Methods: Safety, pharmacokinetics (PK) and pharmacodynamics (PD) were assessed in two cohorts of subjects in a randomized, observer-blind, placebo-controlled study in male and female healthy subjects aged 18-55 (n=77). The study consisted of twenty (20) subjects enrolled into 2 cohorts. At each dose level/cohort a total of 10 subjects were randomized to receive multiple oral doses of ATI-450, i.e., 80 mg or 120 mg (n=8), or placebo (n=2) twice daily (BID) for 7 days. The final dose was administered in the morning on Day 7. Blood samples were obtained Day 1—before dosing, Day 1-4 hours after dosing and Day 1-12 hours after dosing and Day 7—before dosing, Day 7-4 hours after dosing, day 7-12 hour after dosing and Day 7-24 hours after dosing for each subject.

Results. The graphs of FIG. 4A-4E show the continued dose-dependent inhibition of LPS-stimulated pHSP27 (FIG. 4A, top), TNF-α (FIG. 4B, top), IL-1β (FIG. 4C, top), IL-8 (FIG. 4D, top), IL-6 (FIG. 4E, top) from Day 7 blood samples taken from subjects dosed with 10 mg, 30 mg, 50 mg, 80 mg, and 120 mg of ATI-450. FIGS. 4A-4E also show mean (±SEM) levels of pHSP27 (FIG. 4A, bottom), TNF-α (FIG. 4B, bottom), IL-1β (FIG. 4C, bottom), IL-8 (FIG. 4D, bottom), IL-6 (FIG. 4E, bottom) in subjects administered 10 mg, 30 mg, 50 mg, 80 mg, and 120 mg twice daily, comparing day 1 pre-dosing values (set to 100%) with day 7 values 4 hours after dosing (approximate $C_{max}$) and 12 hours after dosing ($C_{trough}$). These results extend the findings of Example 1 to show that higher doses of ATI-450 have increased benefit in the inhibition of pro-inflammatory cytokines.

Figure 5:
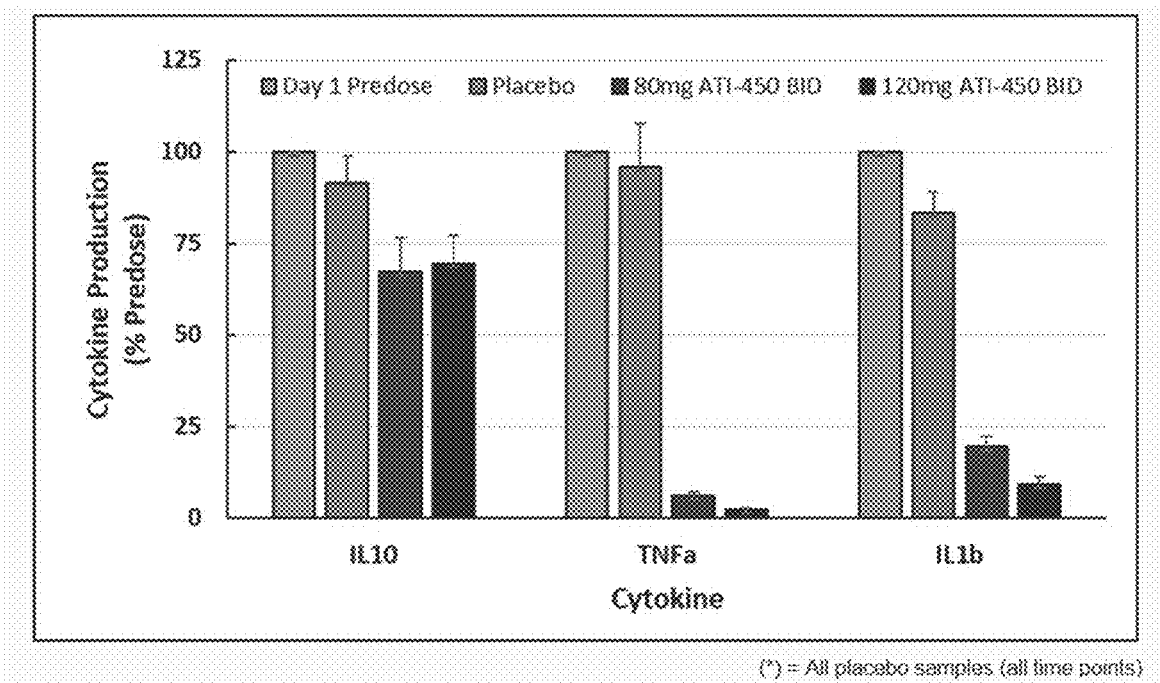
FIG. 5 is a graph showing differential modulation of ex vivo stimulated IL-1β versus TNF-α and IL-1β in blood samples taken from subjects dosed with placebo or 80 mg or 120 mg of ATI-450.

ATI-450 at the higher doses does not inhibit the regulatory anti-inflammatory cytokine IL-1β to the same extent as pro-inflammatory cytokines. FIG. 5 is a graph showing differential modulation of ex vivo stimulated IL-1β versus TNF-α and IL-1β in blood samples taken from subjects dosed with placebo or 80 mg or 120 mg of ATI-450. IL-1β was only modulated 25-30% at doses of drug that generated near maximal inhibition of proinflammatory cytokines (TNF-α and IL-1β).

Figure 6:
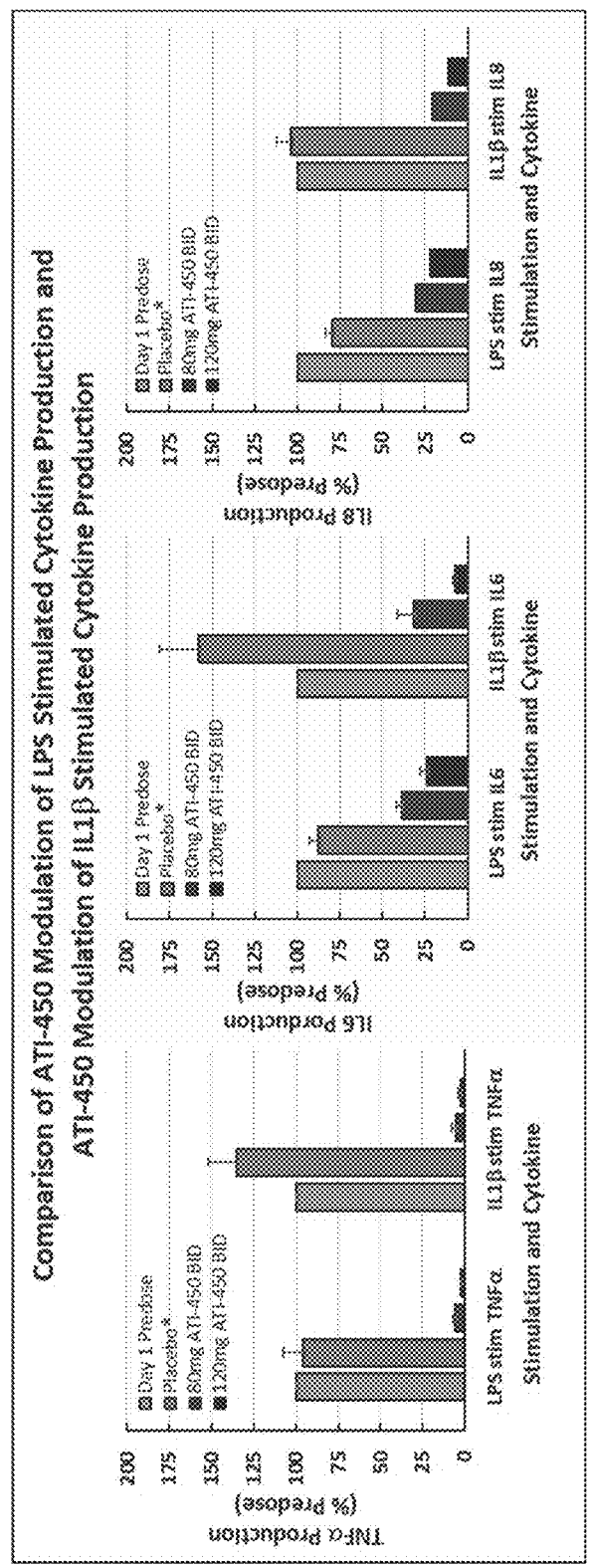
FIG. 6 depicts three graphs comparing ATI-450 modulation of LPS and IL-1β stimulated TNF-α (far left), IL-6 (middle), and IL-8 (far right) production.

ATI-450 potently inhibits ex vivo IL-1β-induced pro-inflammatory cytokines TNF-α, IL-6, and IL-8 whether stimulated by LPS or IL-1β. FIG. 6 depicts three graphs comparing ATI-450 modulation of LPS and IL-1β stimulated TNF-α (far left), IL-6 (middle), and IL-8 (far right) production.

Figure 7A:
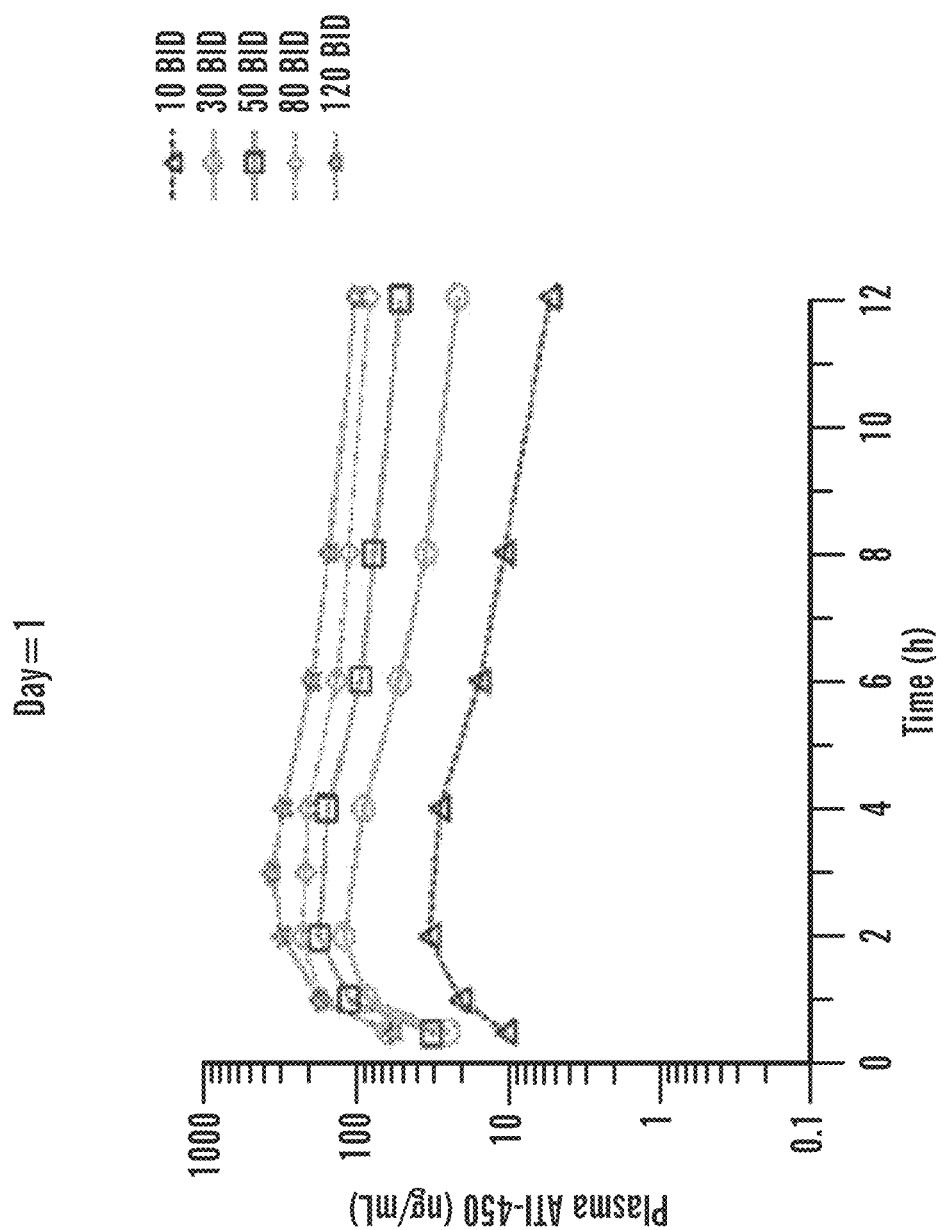
FIGS. 7A-7C show pharmacokinetic (PK) data of ATI-450 following administration of at 80 mg or 120 mg BID. The graphs of FIG. 7A show mean plasma concentration-time profiles of ATI-450 after 1 day (top) and 7 days (middle and bottom) of BID dosing, semi-log scale.
Figure 7A:
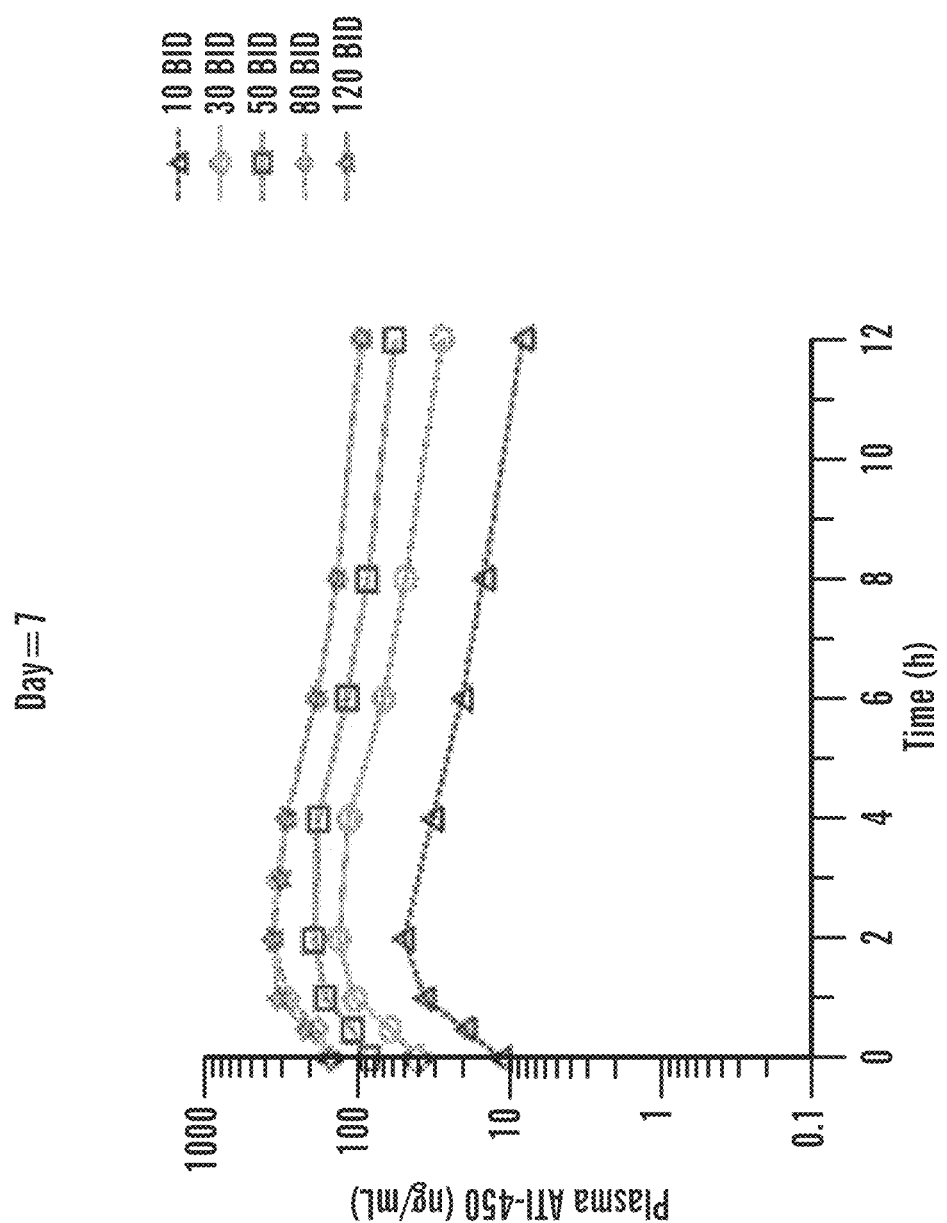
Figure 7A:
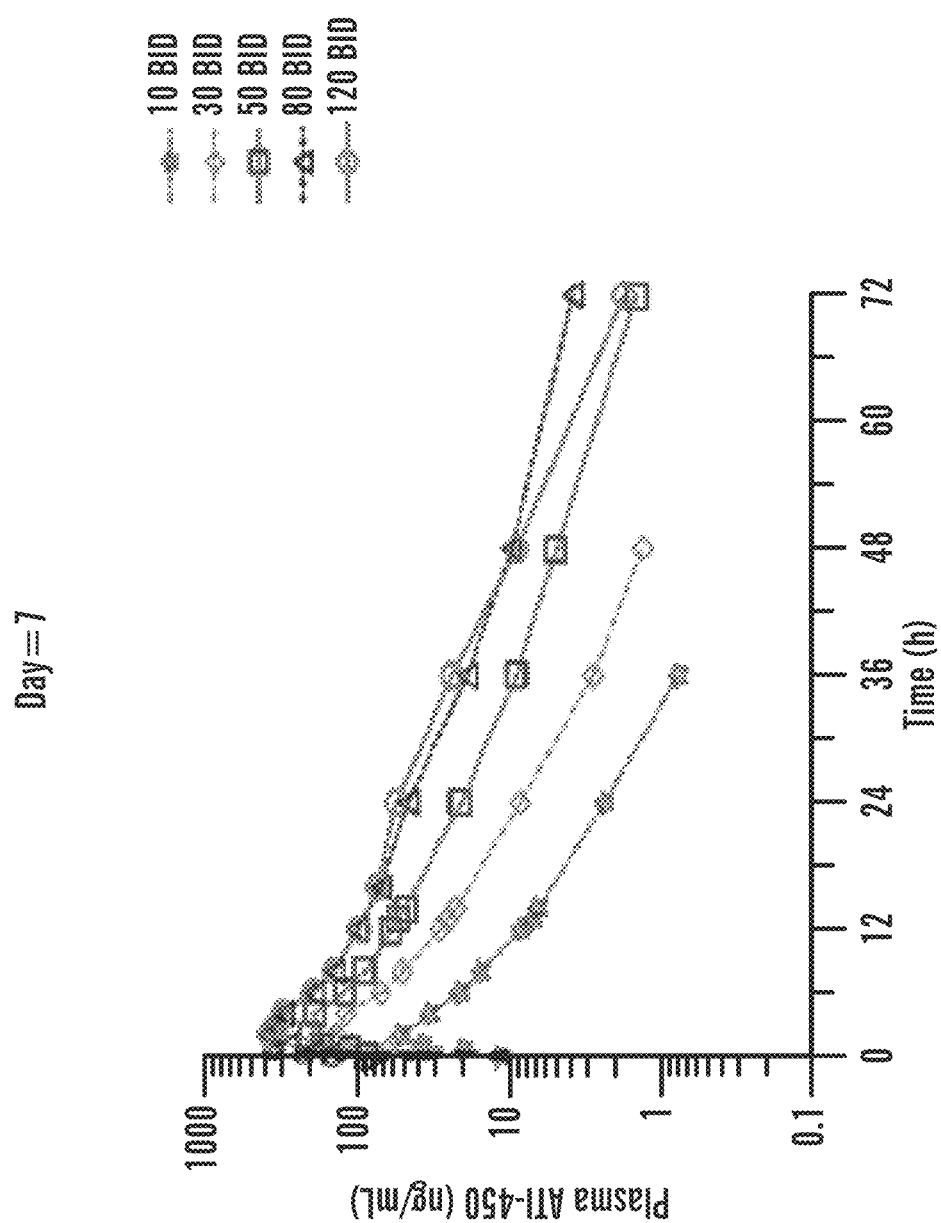
Figure 7B:
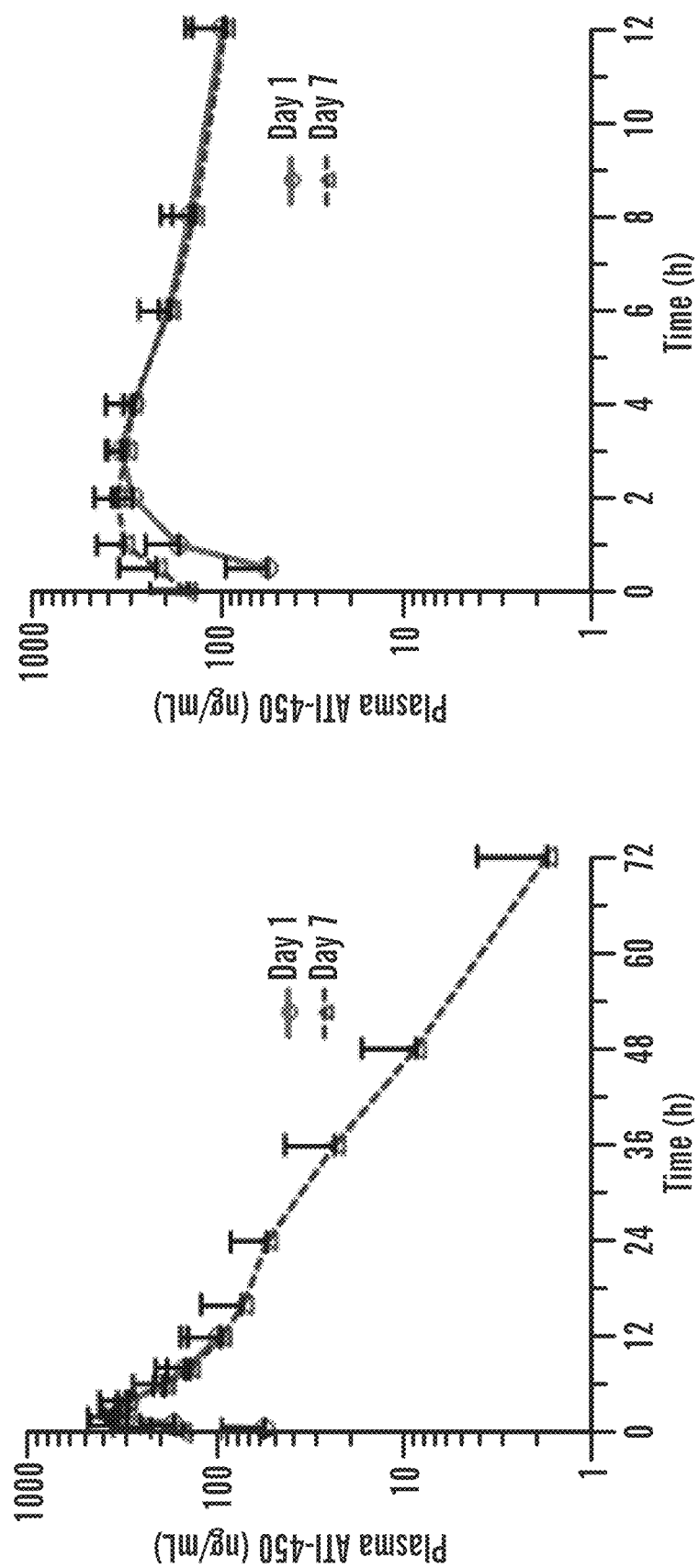
Figure 7C:
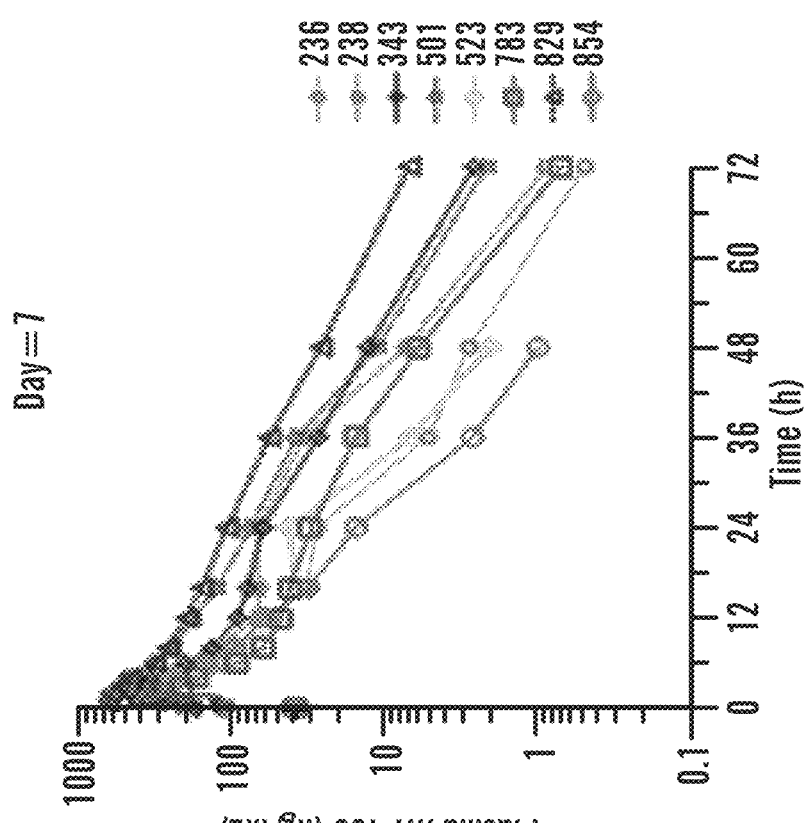
Figure 7C:
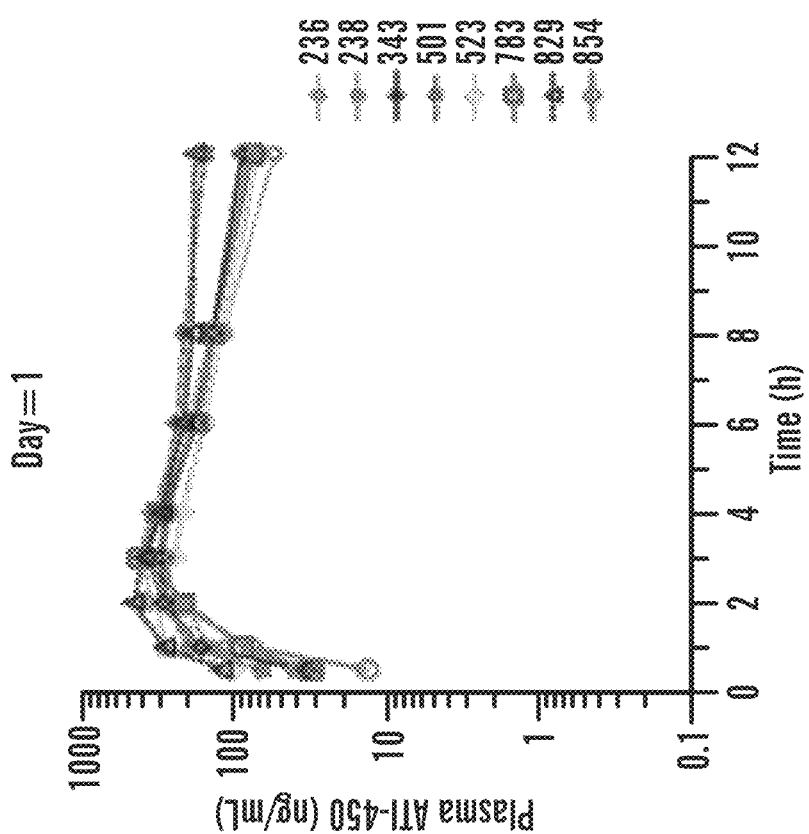

FIGS. 7A-7C and Table 8 below summarize the pharmacokinetic data of ATI-450 following 80 mg and 120 mg BID dosing. FIG. 7A depict graphs showing mean plasma concentration-time profiles of ATI-450 after 1 day (top) and 7 days (middle and bottom) of BID dosing, semi-log scale. BID, twice daily. FIG. 7B shows mean (±std. dev.) plasma concentration-time profiles of ATI-450 dosed at 120 mg BID. FIG. 7C depicts graphs showing the plasma concentration-time profiles of ATI-450 in individual subjects at days 1 (left) and 7 (right) following 120 mg BID dosing.

A summary of the mean pharmacokinetic parameters of ATI-450 80 mg and 120 mg BID dosing is provided in Table 11 below. The corresponding parameters for the 50 mg BID cohorts is included for comparison.

TABLE 11

Pharmacokinetic Parameters of ATI-450 80 mg and 120 mg BID dosing

| Parameter | Day 1 | | | Day 7 | | |
|---|---|---|---|---|---|---|
| | ATI-450 50 mg (N = 8) | ATI-450 80 mg (N = 8) | ATI-450 120 mg (N = 8) | ATI-450 50 mg BID (N = 8) | ATI-450 80 mg BID (N = 8) | ATI-450 120 mg BID (N = 8) |
| $C_{max}$, ng/mL | 186.7 ± 66.8 | 258.4 ± 83.8 | 378.9 ± 60.6 | 219.0 ± 77.8 | 388.8 ± 100.8 | 416.5 ± 122.9 |
| $t_{max}$, h[a] | 2.0 (2.0-4.0) | 2.0 (1.0-4.0) | 3.0 (2.0-3.0) | 3.0 (1.0-4.0) | 2.0 (2.0-3.0) | 2.0 (1.0-4.0) |
| $AUC_{0-t}$, h*ng/mL | 1179.5 ± 340.1 | 1679.2 ± 451.2 | 2314.5 ± 379.9 | 2260.3 ± 1074.7 | 4031.3 ± 1152.5 | 4171.0 ± 2094.4 |
| $AUC_{tau}$, h*ng/mL | 1179.5 ± 340.1 | 1685.7 ± 453.5 | 2322.1 ± 383.2 | 1507.8 ± 659.9 | 2548.0 ± 729.9 | 2577.8 ± 1030.9 |
| $t_{1/2}$, h | N/A | N/A | N/A | 11.6 ± 3.7 | 14.3 ± 5.3 | 8.7 ± 2.4 |
| $CL_{ss}/F$, L/h | N/A | N/A | N/A | 37.3 ± 11.7 | 33.2 ± 7.6 | 52.3 ± 17.4 |
| $V_{ss}/F$, L | N/A | N/A | N/A | 586.4 ± 163.2 | 690.4 ± 293.8 | 621.3 ± 182.8 |
| $C_{trough}$, ng/mL[b] | | | | | | |
| Day 2 | N/A | N/A | N/A | 84.0 ± 40.6 | 175.5 ± 67.5 | 152.5 ± 93.3 |
| Day 3 | N/A | N/A | N/A | 80.6 ± 44.2 | 148.6 ± 54.0 | 144.4 ± 98.8 |
| Day 4 | N/A | N/A | N/A | 81.5 ± 49.6 | 147.9 ± 59.9 | 126.0 ± 84.4 |
| Day 5 | N/A | N/A | N/A | 81.5 ± 43.9 | 144.7 ± 78.3 | 145.3 ± 67.5 |
| Day 6 | N/A | N/A | N/A | 76.4 ± 38.6 | 144.5 ± 64.9 | 160.8 ± 87.5 |
| Day 7 | N/A | N/A | N/A | 87.9 ± 49.4 | 158.3 ± 60.3 | 155.8 ± 93.1 |
| $C_{min}$, ng/mL | N/A | N/A | N/A | 58.7 ± 32.8 | 100.5 ± 39.8 | 96.1 ± 64.1 |
| $C_{avg}$, ng/mL | N/A | N/A | N/A | 125.6 ± 55.0 | 212.3 ± 60.8 | 214.8 ± 85.9 |
| $R_{ac}$, $AUC_{tau}$ | N/A | N/A | N/A | 1.29 ± 0.37 | 1.53 ± 0.22 | 1.08 ± 0.26 |

Data presented are means ± SD unless otherwise indicated.

[a]Data presented are medians (ranges).

[b]$C_{trough}$ values are presented for day 2 through day 7 for the MAD cohorts.

$AUC_{0-t}$, area under the plasma concentration-time curve from time 0 to time t;

$AUC_{tau}$, area under the plasma concentration-time curve over the 12-hour dosing interval, tau;

BID, twice daily;

$CL_{ss}/F$, clearance at steady state;

$C_{avg}$, average plasma concentration after multiple dosing, on day 7;

$C_{max}$, maximum plasma concentration;

$C_{min}$, minimum plasma concentration;

$C_{trough}$, measured concentration at the end of a dosing interval;

N/A, not applicable;

$R_{ac}$, $AUC_{tau}$, accumulation ratio for $AUC_{tau}$;

$t_{1/2}$, terminal elimination half-life;

$T_{max}$, time to maximum plasma concentration;

$V_{ss}/F$, volume of distribution at steady state.

Quantitation of changes in analyte concentration relative to ATI-450 dose in the five MAD cohorts is summarized in Table 12 and FIGS. 4A-4E.

TABLE 12

| Bio-marker | Dose Level (mg BID) | IC$_{50}$ $C_{trough}$ | IC$_{50}$ $C_{max}$ | IC$_{80}$ $C_{trough}$ | IC$_{80}$ $C_{max}$ | IC$_{90}$ $C_{trough}$ | IC$_{90}$ $C_{max}$ |
|---|---|---|---|---|---|---|---|
| IL-1β | 10 | 0.7 | 3.2 | 0.2 | 0.8 | 0.1 | 0.4 |
| IL-6 | 10 | 0.1 | 0.4 | 0.0 | 0.1 | 0.0 | 0.0 |
| IL-8 | 10 | 0.5 | 2.3 | 0.1 | 0.6 | 0.1 | 0.3 |
| pHSP27 | 10 | 1.3 | 5.8 | 0.3 | 1.4 | 0.1 | 0.6 |
| TNF-α | 10 | 0.7 | 3.1 | 0.2 | 0.8 | 0.1 | 0.3 |
| IL-1β | 30 | 2.6 | 9.2 | 0.6 | 2.3 | 0.3 | 1.0 |
| IL-6 | 30 | 0.3 | 1.2 | 0.1 | 0.3 | 0.0 | 0.1 |
| IL-8 | 30 | 1.8 | 6.4 | 0.5 | 1.6 | 0.2 | 0.7 |
| pHSP27 | 30 | 4.6 | 16.3 | 1.1 | 4.1 | 0.5 | 1.8 |
| TNF-α | 30 | 2.5 | 8.8 | 0.6 | 2.2 | 0.3 | 1.0 |
| IL-1β | 50 | 5.5 | 13.7 | 1.4 | 3.4 | 0.6 | 1.5 |
| IL-6 | 50 | 0.7 | 1.7 | 0.2 | 0.4 | 0.1 | 0.2 |
| IL-8 | 50 | 3.8 | 9.6 | 1.0 | 2.4 | 0.4 | 1.1 |
| pHSP27 | 50 | 9.8 | 24.3 | 2.5 | 6.1 | 1.1 | 2.7 |
| TNF-α | 50 | 5.3 | 13.1 | 1.3 | 3.3 | 0.6 | 1.5 |
| IL-1β | 80 | 9.9 | 24.3 | 2.5 | 6.1 | 1.1 | 2.7 |
| IL-6 | 80 | 1.2 | 3.1 | 0.3 | 0.8 | 0.1 | 0.3 |
| IL-8 | 80 | 6.9 | 17.0 | 1.7 | 4.3 | 0.8 | 1.9 |
| pHSP27 | 80 | 17.6 | 43.2 | 4.4 | 10.9 | 2.0 | 4.8 |
| TNF-α | 80 | 9.5 | 23.3 | 2.4 | 5.8 | 1.1 | 2.6 |
| IL-1β | 120 | 9.7 | 26.0 | 2.4 | 6.5 | 1.1 | 2.9 |
| IL-6 | 120 | 1.2 | 3.3 | 0.3 | 0.8 | 0.1 | 0.4 |
| IL-8 | 120 | 6.8 | 18.2 | 1.7 | 4.6 | 0.8 | 2.0 |
| pHSP27 | 120 | 17.3 | 46.3 | 4.3 | 11.6 | 1.9 | 5.2 |
| TNF-α | 120 | 9.3 | 24.9 | 2.3 | 6.2 | 1.0 | 2.8 |

The data in Table 12 summarizes the inhibitory concentrations of pHSP27 and the four cytokines by ATI-450 relative to the $C_{trough}$ and $C_{max}$ in the 5 MAD dose cohorts (10 mg, 30 mg, 50 mg, 80 mg and 120 mg). The data is expressed as the ratio of ATI-450 concentrations at $C_{max}$ and $C_{trough}$ within the various dose cohorts relative to the IC$_{50}$, IC$_{80}$ and IC$_{90}$ estimates for each analyte. The respective mean $C_{trough}$ and $C_{max}$ values of ATI-450 on day 7 were 11.83 and 51.8 ng/mL at 10 mg BID, 41.14 and 146.5 ng/mL at 30 mg BID, 87.94 and 219.0 ng/mL at 50 mg BID, 158.25 and 388.8 ng/mL at 80 mg BID, and 155.81 and 416.5 ng/mL at 120 mg BID. A ratio of 1.0 indicates a concentration that is equivalent to the IC value being compared. Ratios that are less than 1 are shown in normal type-face, ratios that are ≥1 are bolded. For the 50 mg BID dose cohort, concentrations at $C_{trough}$ were similar to or in excess of the relative IC$_{80}$ concentrations (1.0 to 2.5-fold) for the target biomarker pHSP27 and three of the four cytokines (TNF-α, IL-1β, and IL-8) but not for IL-6. Trough concentrations from the 80 mg BID and 120 mg BID doses produced larger, but comparable, multiples of the IC$_{80}$ concentrations for pHSP27, TNF-α, IL-1β, and IL-8 (1.7- to 4.4-fold and 1.7- to 4.3-fold, respectively) relative to 50 mg BID. The effect of ATI-450 dose on the relative concentration of each cytokine analyte in the ex vivo stimulated assay expressed as a percentage of pre-dosing analyte levels (set to 100%) for the 10 mg, 30 mg and 50 mg BID MAD cohorts on Day 7, 4 hours after dosing and 12 hours after dosing is shown in FIGS. 4A-4E. The 4-hour after dosing Day 7 samples were utilized to reflect approximate steady state $C_{max}$ ATI-450 concentrations while the 12-hour after dosing Day 7 samples were used to reflect steady-state $C_{trough}$ concentrations of the drug. A marked dose-dependent reduction in concentration is observed for all four cytokines at the four-hour timepoint and persists through twelve hours. TNF-α, IL-1β, and IL-8 all demonstrated a reduction in concentration that persisted for the entire dosing interval and did not appreciably change between 4 and 12 hours after dosing.

ATI-450 demonstrated both concentration-dependent and dose-dependent modulation of the target biomarker pHSP27 and inhibition of the production of the four cytokines analyzed, TNF-α, IL-1β, IL-6, and IL-8. Concentration-response parameters for ATI-450 reduction of pHSP27, TNF-α, IL-1β, and IL-8 were comparable, while the parameters for IL-6 were higher. At the 50 mg BID dose, concentrations at $C_{trough}$ following seven days of dosing were similar to or in excess of the IC$_{50}$ for ATI-450 reduction of pHSP27, as well as for ATI-450 inhibition of production of TNF-α, IL-1β, and IL-8. Trough concentrations from the 80 mg BID and 120 mg BID doses produced larger, but comparable, multiples of the IC80 concentrations relative to 50 mg BID suggesting that a greater level of target inhibition may be achieved at these higher doses.

The higher dosing regimens, i.e., 80 mg and 120 mg BID, were well tolerated with no severe adverse effects reported. A summary of the safety data is provided in Table 13 below.

TABLE 13

Preliminary Safety Data in Patients Administered 80 mg or 120 mg BID

| AE | Cohort 1 (80 mg BID, n = 8) | Cohort 1 (placebo) | Cohort 2 (120 mg BID, n = 8) | Cohort 2 (placebo) | Intensity |
|---|---|---|---|---|---|
| Headache | 2 (25%) | 1 (50%) | 7 (88%) | 1 (50%) | Mild |
| Dizziness | 2 (25%) | | 6 (75%) | | Mild |
| Xerosis | 1 (13%) | | 5 (63%) | | Mild |
| Constipation | 1 (14%) | | | | Mild |
| Nausea | | | 2 (25%) | | Mild |
| Parasthesia | | | 2 (25%) | | Mild |
| Abdominal Pain | | | 1 (13%) | | Mild |
| Loose stools | | | 1 (13%) | | Mild |
| Pharyngitis | | | 1 (13%) | | Mild |

\# only 1$^{st}$ or 2$^{nd}$ day
+ 7 cases resolved on drug
* After stopping drug Example 3: Non-Clinical Safety Assessment of 13-Week Oral Administration of ATI-450

Study Design. In this study, 13-week oral administration of ATI-450 was tested in rate and mini-pigs. Rats were administered 0 (vehicle), 3, 10 and 30 mg/kg/day, and Mini-pigs were administered 0 (vehicle) 10, 30 and 60 mg/kg/day Results: The no-observed adverse effect level (NOAEL) for rat was 30 mg/kg/day, and for mini-pig was 60 mg/kg/day. No study drug-related mortality was observed.

Rat non adverse findings: minimal ulceration/mixed cell inflammation was observed around nasal area in several animals at mid and high dose. Minimal to moderate degeneration of myocytes at all doses, including control animals. However, complete recovery following 28-day non-dosing period was observed.

Mini-pig non-adverse findings: clinical observations at ≥30 mg/kg/day. Slightly increased neutrophil, lymphocyte and platelet counts were observed along with decreased red cell mass in males at ≥10 mg/kg/day and females at 60 mg/kg/day.

TABLE 14

Mean Systemic Exposures ($C_{max}$ and $AUC_{0-24}$) in Rats and Minipigs Given Daily
Oral Doses of Study Drug for 13-weeks Compared to Preliminary Mean Systemic Exposures
($C_{max}$ and $AUC_{0-12}$) in Healthy Human Subjects Given Twice Daily Oral Doses
of 50 mg, 80 mg, and 120 mg Study Drug for 6.5 days.

| Species | Dose | Study Day | $C_{max}$ (ng/mL) | $AUC_{0-24}$ (ng · h/mL) | Exposure Multiples Rat/Human $C_{max}$ | AUC | Minipig/Human $C_{max}$ | AUC |
|---|---|---|---|---|---|---|---|---|
| Rat | 30 mg/kg/day | 88 | M = 3260 F = 5440 | M = 36400 F = 43500 | — | — | — | — |
| Minipig | 60 mg/kg/day | 90 | M = 1670 F = 2360 | M = 14400 F = 22600 | — | — | — | — |
| Human | 50 mg BID | 7 | 219.0 | 3042[a] | 15-25 | 12-14 | 7.6-11 | 4.7-7.4 |
|  | 80 mg BID | 7 | 388.8 | 5096[a] | 8.4-14 | 7.1-8.5 | 4.3-6.1 | 2.8-4.4 |
|  | 120 mg BID | 7 | 416.5 | 5156[a] | 7.8-13 | 7.1-8.4 | 4.0-5.7 | 2.8-4.4 |

[a]Human AUC value represents the total daily exposure calculated as $AUC_{0-12} \times 2$ Example 4: Oral Composition of ATI-450 for Treatment of Rheumatoid Arthritis A Phase 2a, randomized, investigator and patient-blind, sponsor-unblinded, parallel group, placebo-controlled study was conducted to investigate the safety, tolerability, PK, and PD of ATI-450 plus MTX versus MTX alone in patients with moderate to severe RA.

Approximately 19 patients were enrolled with the expectation that at least 15 patients would complete the 12-weeks of treatment. The study consists of an up to 28-day screening period, a 12-week treatment period, and a 4-week follow-up period. The total duration of the study for patients remaining until their final follow-up assessment is 20 weeks.

The primary objective was to evaluate the safety and tolerability of ATI-450 plus MTX in patients with moderate to severe rheumatoid arthritis (RA). The secondary objective of the study was to assess (i) the PD profiles of ATI-450 plus MTX in patients with moderate to severe RA, and (ii) the pharmacokinetics of ATI-450 in patients with moderate to severe RA who are receiving concomitant MTX. In addition to the primary and secondary objectives, the PD profiles of ATI-450 plus MTX in patients with moderate to severe RA was assessed.

Patient eligibility was assessed based on the following criteria: (i) a diagnosis of adult onset RA (ACR/EULAR classification criteria); (ii) DAS28-CRP≥3.2 defined as moderate to high disease activity; (iii) moderately to severely active RA defined by at least 4/28 tender and 4/28 swollen joints; (iv) hsCRP≥5 mg/L at screening; (v) definitive intra-articular synovitis or osteitis defined as a score of 1 or greater on a Hand-Wrist MRI (using RAMRIS); (vi) stable MTX dose (defined as 7.5 mg to 25 mg weekly) for at least 4 weeks prior to the screening visit. Patients whose eligibility was confirmed at baseline were randomized in a 3:1 ratio to receive either ATS-450 tablets (50 mg twice daily [BID]) plus MTX, or matching placebo tablets plus MTX. Study medications were administered orally for 12 weeks. Patients were required to remain on a stable dose of MTX (7.5 mg to 25 mg/week) and a stable dose of folic or folinic acid (≥5 mg/week) for the duration of the study.

Patients attended clinic visits on Days 7, 14, 28, 42, 56, and 84 (±1 day) for safety, efficacy, PK, and PD assessments. The morning dose of study medication was administered in the clinic on each study visit day.

At the completion of 4 weeks of treatment (Day 28), each patient's safety data (e.g., AEs, laboratory values, vital signs, and ECGs) will be reviewed to ensure that the patient is tolerating the treatment regimen and is deemed suitable to continue treatment for the next 8 weeks.

On Day 84 (Week 12), patients will complete the end of study assessments. A safety follow-up visit will be conducted 30 days (+7) after the last dose of study medication.

Efficacy Assessments and Results

A summary of patient demographic is provided in Table 15 below.

TABLE 15

Patient Demographics

| Parameter | Statistic/Category | Placebo | ATI-450 |
|---|---|---|---|
| Age (year) | n | 3 | 16 |
|  | Mean (SD) | 55.33 (6.807) | 55.88 (9.926) |
|  | Median | 53 | 59.5 |
|  | Min-Max | 50-63 | 32-65 |
| Sex | Female | 3/3 (100%) | 11/16 (68.75%) |
|  | Male | 0/0 (0%) | 5/16 (31.25%) |
| Weight (kg) | n | 3 | 16 |
|  | Mean (SD) | 98.93 (14.616) | 92.74 (25.504) |
|  | Median | 105.4 | 88.15 |
|  | Min-Max | 82.2-109.2 | 52.7-141.5 |
| BMI | n | 3 | 16 |
|  | Mean (SD) | 36.53 (4.737) | 33.37 (8.829) |
|  | Median | 38.7 | 30.6 |
|  | Min-Max | 31.1-39.8 | 20.6-51.7 |
| Duration of Disease | n | 3 | 16 |
|  | Mean (SD) | 7.5 (11.364) | 9.98 (9.554) |
|  | Median | 1.6 | 6.45 |
|  | Min-Max | 0.3-20.6 | 0.3-33.4 |
| hsCRP (mg/L) | n | 3 | 16 |
|  | Median | 21.3 | 11.7 |
|  | Min-Max | 12.6-31.2 | 2.6-29.5 |
| DAS-28 | n | 3 | 16 |
|  | Median | 5.3 | 5.65 |
|  | Min-Max | 5.3-6.7 | 3.9-7.4 |
|  | Mean (SD) | 5.77 (0.808) | 5.71 (0.937) |
| Race | Black Or African American | 1/3 (33.33%) |  |
|  | Asian |  | 1/16 (6.25%) |
|  | White | 2/3 (66.67%) | 15/16 (93.75%) |
| Ethnicity | Hispanic Or Latino |  | 4/16 (25%) |
|  | Not Hispanic Or Latino | 3/3 (100%) | 12/16 (75%) |

Overall the patient population exhibited high disease activity as indicated by the median Disease Activity Score for 28 Joint Count (DAS-28) (see Smolen et al., "Validity and reliability of the twenty-eight-joint count for the assessment of rheumatoid arthritis activity." *Arthritis Rheum* 38(1):38-43 (1995), which is hereby incorporated by reference in its entirety) for both the treatment group (5.65) and the placebo group (6.0). In addition, the patient population exhibited a broad range of disease duration of 0.3-34 years, with many patient having high hsCRP despite long history and multiple treatment option. This suggests a relatively refractory group of patients.

Disease Activity Score for 28 Joint Count. Assessments of RA by the Disease Activity Score (modified to include the 28 joint counts according to Smolen et al., "Validity and reliability of the twenty-eight-joint count for the assessment of rheumatoid arthritis activity." *Arthritis Rheum* 38(1):38-43 (1995), which is hereby incorporated by reference in its entirety (DAS28)) were conducted prior to the commencement of the study and at study days 1, 7, 14, 28, 42, 56, 84, and at the follow-up visit. The DAS28 consists of a composite score of the following variables: tender joint count, swollen joint count, CRP, and Patient's Global Assessment of Disease Activity score (Prevoo et al., "Modified Disease Activity Scores that include twenty-eight joints," *Arthritis & Rheumatism* 38(1):44-48 (1995), which is hereby incorporated by reference in its entirety).

The following equation was used to calculate the DAS28 (CRP):

$$DAS28(CRP)=0.56\sqrt{TJC28}+0.28\sqrt{SJC28}+0.36\cdot\ln(CRP+1)+0.014\times(\text{Patient's Global Assessment of Disease Activity})+0.96, \text{ where:}$$

TJC28=number of joints tender out of 28
SJC28=number of joints swollen out of 28
CRP=C-reactive protein
Patient's Global Assessment of Disease Activity on a 100 mm visual analog scale (VAS) recorded by the patient Interpretation of the DAS28 (CRP) disease activity measure is on a scale of 0 to 9.4, where: <2.6 is considered remission, ≥2.6 to <3.2 is considered low/minimal, ≥3.2 to ≤5.1 is considered moderate, and >5.1 is considered high/severe (Anderson et al., "Rheumatoid arthritis disease activity measures: American College of Rheumatology recommendations for use in clinical practice," *Arthritis Care Res* (Hoboken) 64(5):640-7 (2012), which is hereby incorporated by reference in its entirety).

Figure 8:
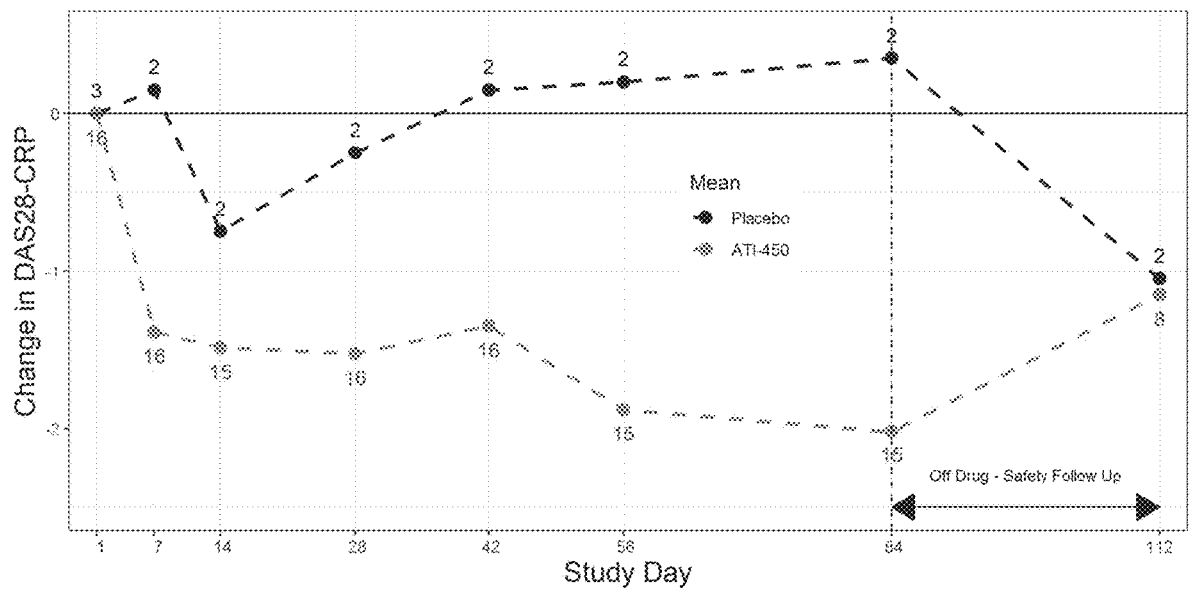
FIG. 8 is a graph showing the median change in DAS28-CRP from baseline for all patients in placebo and ATI-450 (50 mg/BID) treatment groups at days 1, 7, 14, 28, 42, 56, and 84 of treatment and after treatment ended at day 112. The numbers on each line represent the number of patients at each timepoint.
Figure 9:
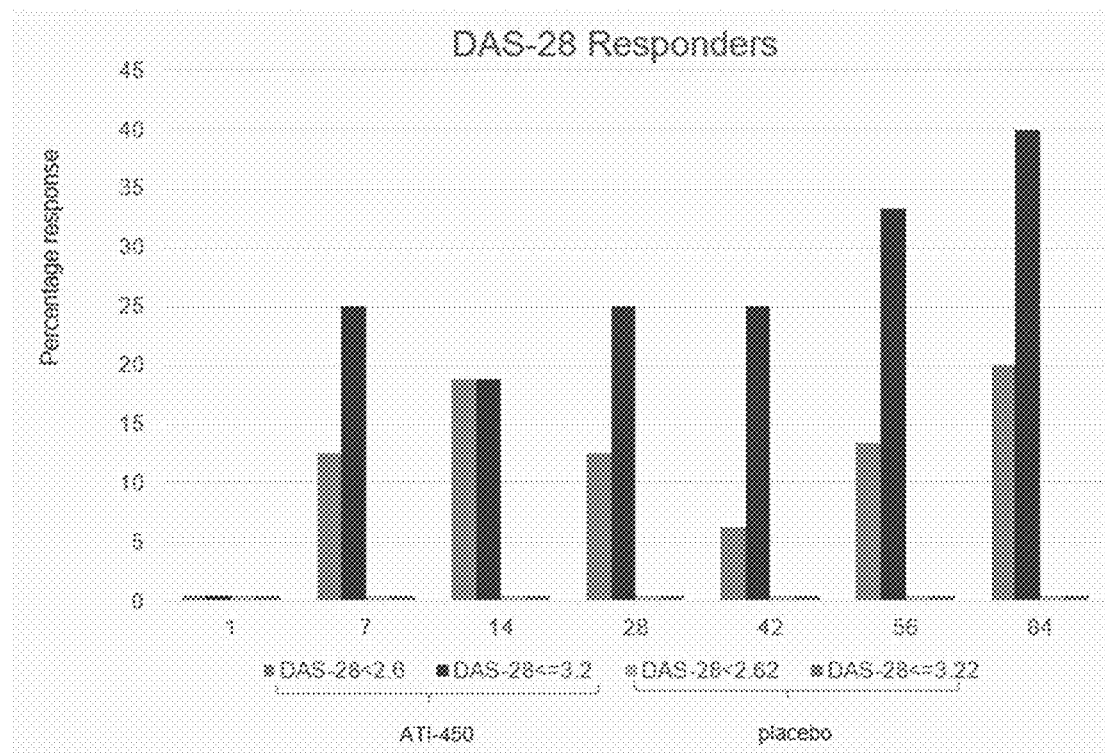
FIG. 9 is a graph showing the percent of patients having DAS-28<2.6 and <3.2 over the course of treatment (through day 84).

Results of this assessment are provided in FIG. 8 and FIG. 9. FIG. 8 is a graph showing the median change in DAS28-CRP from baseline for all patients as of the assessment date. This data shows a rapid and sustained onset of efficacy, which is markedly different from other p38 inhibitors. The increase in DAS28-CRP observed in the follow-up patients (i.e., at day 112) is expected because treatment has stopped and indicates a drug-specific effect. Overall, the maintained decrease in DAS28-CRP observed in all patients through day 84 indicates clinically relevant decrease in disease activity without any evidence of tachyphylaxis. FIG. 9 is a graph showing the percent of patients having a DAS28-CRP below 2.6 and below 3.2 at each of days 1, 7, 24, 28, 42, 56, and 84.

ACR20/50/70. The ACR20 (50/70) response criteria is an endpoint that indicates the proportion of patients with at least a 20% (50%/70%) improvement in the number of swollen and tender joints (66/68 joint counts) and at least a 20% (50%/70%) improvement in 3 or more of the following ACR core measures:

To meet the ACR20 criteria, the patient must have at least a 20% improvement in the following ACR Core Set:
Swollen joint count (66 joint count)
Tender joint count (68 joint count)
An improvement of at least 20% in at least 3 of the following 5 measures:
Patient's Global Assessment of Disease Activity (VAS)
Patient's Assessment of Arthritis Pain (VAS)
Patient's Assessment of Physical Function/Health Assessment Questionnaire-Disability Index (HAQ-DI)
Physician's Global Assessment of Disease Activity (VAS)
Acute phase reactant as measured by hsCRP
ACR50=50% improvement in the swollen and tender joint count and at least 50% improvement in at least 3 of the 5 measures.
ACR70=70% improvement in the swollen and tender joint count and at least 70% improvement in at least 3 of the 5 measures.

Figure 11:
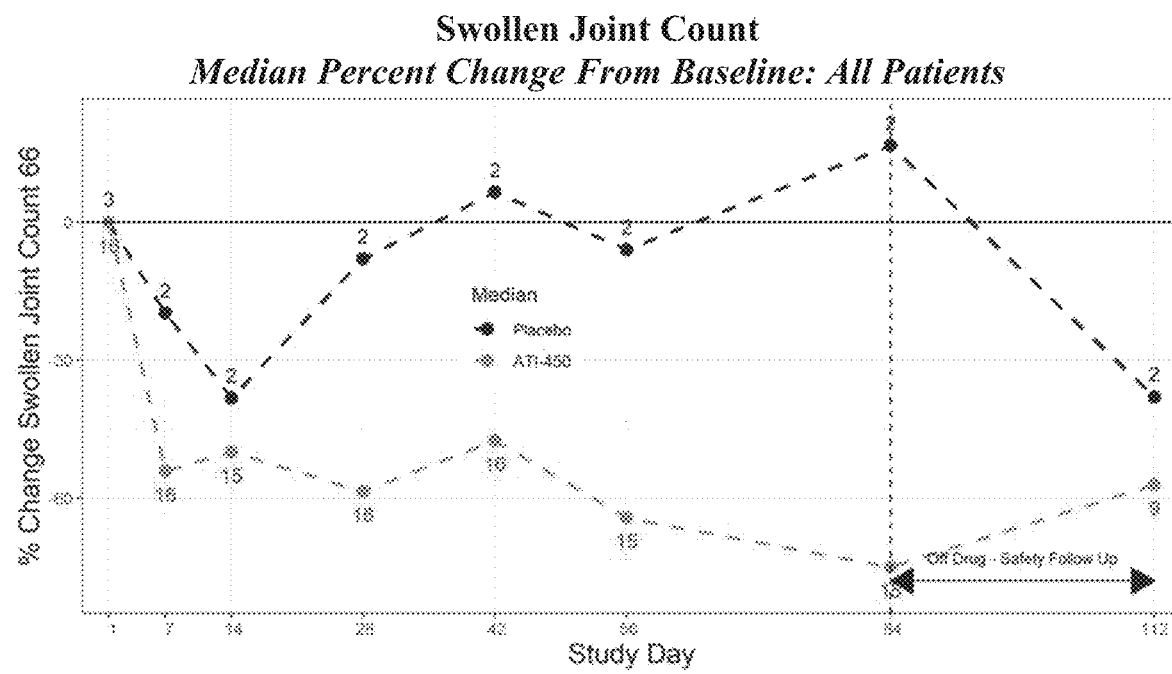
FIG. 11 is a graph showing the median percent change in swollen joint count from baseline for all patients in placebo and ATI-450 (50 mg/BID) treatment groups at days 1, 7, 14, 28, 42, 56, and 84 of treatment and after treatment ended at day 112. The numbers on each line represent the number of patients at each timepoint.
Figure 12:
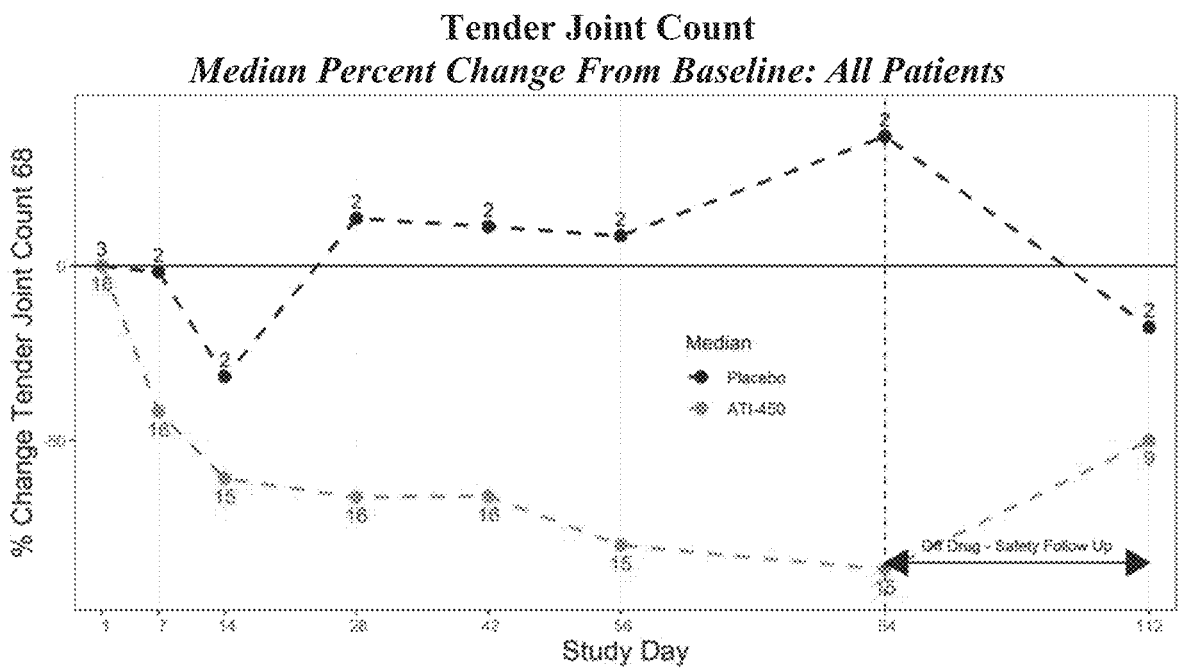
FIG. 12 is a graph showing the median percent change in tender joint count from baseline for all patients in placebo and ATI-450 (50 mg/BID) treatment groups at days 1, 7, 14, 28, 42, 56, and 84 of treatment and after treatment ended at day 112. The numbers on each line represent the number of patients at each timepoint.

Results for this assessment are shown in FIGS. 11-12. The graph of FIG. 11 show the median change from baseline in swollen joint count, and the graph of FIG. 12 shows the median change from baseline in tender joint count for all patients as of the assessment date. The sustained decrease in swollen joint count and tender joint count over the entirety of the treatment period (84 days) shows clinically significant decrease in disease activity without any evidence of tachyphylaxis. The increase in swollen and tender joint count (or decrease in change from baseline) observed in the follow-up patients at day 112 was expected because treatment had ceased.

The graph of FIG. 14 shows the responder analysis at days 1, 28, 56, 84 of treatment and after treatment at day 112. As noted above the ACR values represent the proportion of patients in each group meeting ACR20, ACR50, and ACR70 criteria as described above.

RAMRIS and CARLOS Hand MRI Assessments. The Hand-Wrist MRI RAMRIS is a validated and well-accepted objective imaging measure in RA trials. RAMRIS has sub-scores for synovitis (scored 0 to 3), osteitis (0 to 3), and bone erosions (0 to 10). The CARLOS is a 9-point cartilage loss scale (Perterfy et al., "Monitoring cartilage loss in the hands and wrists in rheumatoid arthritis with magnetic resonance imaging in a multi-center clinical trial: IMPRESS (NCT00425932)," *Arthritis Research & Therapy*, 15:R44 (2013), which is hereby incorporated by reference in its entirety) that has been used successfully in four randomized controlled clinical trials of RA. The RAMRIS synovitis score changes rapidly with effective RA therapies and changes can be detected even in small group sizes. In randomized controlled trials, statistically significant decrease in synovitis scores have been observed within 2 weeks of onset of effective treatment with approximately 30 patients per arm (Beals et al. "Magnetic resonance imaging of the hand and wrist in a randomized, double-blind, multicenter, placebo-controlled trial of infliximab for rheumatoid arthritis: Comparison of dynamic contrast enhanced assessments with semi-quantitative scoring," *PLoS ONE* 12(12):e0187297 (2017), which is hereby incorporated by reference in its entirety).

These studies also showed significant inhibition of progression of joint damage (RAMRIS bone erosion and CARLOS cartilage loss) demonstrated within only 12 weeks. The Hand-Wrist MRI scans will be done by the site (or a suitable local facility designated by the site) and will be centrally read. Instructions outlining scan collection parameters submission requirements will be provided in a separate site instruction manual from the MRI central laboratory.

The result of the Hand-Wrist MRI RAMRIS assessments for the current study are provided in FIGS. 15-17 and the tables below. FIG. 15 is a graph showing the percent of patients responsive to ATI-450 treatment as assessed by CARLOS (cartilage loss), erosion, osteitis, synovitis. The graph of FIG. 15 is showing percent responsiveness in these endpoints by treatment and hand. A patient was deemed responsive if a ≥1-point improvement in any hand was observed.

FIG. 16 is a graph showing the change in baseline at day 84 for CARLOS, erosion, osteitis, and synovitis in both hands of placebo and ATI-450 (50 mg BID) treated patients. The data represents the average of both hands as assessed by the Hand-Wrist MRI RAMRIS. FIG. 17 is a similar graph showing the change in baseline at day 84 for CARLOS, erosion, osteitis, and synovitis for each hand in placebo and ATI-450 (50 mg BID) patients. Diamonds represent mean values.

Tables 16 and 17 below provide MRI RAMIS assessment scores for CARLOS, erosion, osteitis, and synovitis at baseline and after 12 weeks of treatment with ATI-450 (50 mg BID) or placebo. The results of this analysis collectively demonstrate that ATI 450 treatment prevents the progression of joint destruction and provides significant improvement in synovitis.

TABLE 16

Hand-Wrist MRI RAMIS Assessment for the Most Severe Hand

| Parameter | ATI-450 | Placebo |
|---|---|---|
| RAMRIS Synovitis Score | | |
| Baseline, n | 15 | 2 |
| Mean (SD) | 6.1 (4.703) | 8.5 (11.314) |
| Week 12, n | 15 | 2 |
| Mean (SD) | 5.93 (4.625) | 9 (12.021) |
| Change from baseline, Mean (SD) | −0.17 (2.059) | 0.5 (0.707) |
| RAMRIS Osteitis Score | | |
| Baseline, n | 15 | 2 |
| Mean (SD) | 2.93 (4.754) | 4.5 (6.364) |
| Week 12, n | 15 | 2 |
| Mean (SD) | 3.83 (5.063) | 6.25 (8.839) |
| Change from baseline, Mean (SD) | 0.9 (2.055) | 1.75 (2.475) |
| RAMRIS Erosion Score | | |
| Baseline, n | 15 | 2 |
| Mean (SD) | 13.27 (13.625) | 17.5 (24.749) |
| Week 12, n | 15 | 2 |
| Mean (SD) | 13.9 (14.311) | 19 (26.87) |
| Change from baseline, Mean (SD) | 0.63 (1.42) | 1.5 (2.121) |
| Carlos Cartilage Loss | | |
| Baseline, n | 15 | 2 |
| Mean (SD) | 7.6 (10.677) | 18.25 (25.809) |
| Week 12, n | 15 | 2 |
| Mean (SD) | 7.63 (10.451) | 18.25 (25.809) |
| Change from baseline, Mean (SD) | 0.03 (0.481) | 0 (0) |

TABLE 17

Hand-Wrist MRI RAMIS Assessment for the Other Hand

| Parameter | ATI-450 | Placebo |
|---|---|---|
| RAMRIS Synovitis Score | | |
| Baseline, n | 15 | 2 |
| Mean (SD) | 4.07 (3.914) | 7.25 (10.253) |
| Week 12, n | 15 | 2 |
| Mean (SD) | 4.4 (4.826) | 9.75 (13.789) |
| Change from baseline, Mean (SD) | 0.33 (2.059) | 2.5 (3.536) |
| RAMRIS Osteitis Score | | |
| Baseline, n | 15 | 2 |
| Mean (SD) | 2.4 (4.544) | 10.25 (14.496) |
| Week 12, n | 15 | 2 |
| Mean (SD) | 3.4 (5.562) | 10.25 (14.496) |
| Change from baseline, Mean (SD) | 1 (2.283) | 0 (0) |
| RAMRIS Erosion Score | | |
| Baseline, n | 15 | 2 |
| Mean (SD) | 13.3 (13.749) | 25.5 (36.062) |
| Week 12, n | 15 | 2 |
| Mean (SD) | 13.03 (13.2) | 25.5 (36.062) |
| Change from baseline, Mean (SD) | −0.27 (1.178) | 0 (0) |
| Carlos Cartilage Loss | | |
| Baseline, n | 15 | 2 |
| Mean (SD) | 7.45 (16.287) | 18.88 (26.693) |
| Week 12, n | 15 | 2 |
| Mean (SD) | 7.45 (16.287) | 18.88 (26.693) |
| Change from baseline, Mean (SD) | 0 (0) | 0 (0) |

The Patient's Global Assessment of Disease Activity Visual Analog Scale. The Patient's Global Assessment of Disease Activity VAS is used to measure the patient's global assessment of disease activity. The VAS is 100 mm in length with "0" (no activity at all, very well) on the left end of the line and "100" (worst activity imaginable, very poor) on the right end of the line. The participant draws a vertical line through the horizontal line to indicate their level of disease activity. Study staff measure from the left end of the line to the line marked by the participant and record this length in mm (0 to 100). The results of this assessment for treatment (n=13) and placebo (n=2) groups through day 84 of the study are show in the graph of FIG. 13A.

Patient's Assessment of Arthritis Pain Visual Analog Scale. The Patient's Assessment of Arthritis Pain VAS is used to measure the patient's level of arthritis pain. The VAS is 100 mm in length with "0" (no pain at all, no pain) on the left and "100" (worst pain imaginable, the worst possible pain) on the right end of the line. The participant draws a vertical line through the horizontal line to indicate how much pain they are experiencing that day. Study staff measure from the left end of the line to the line marked by the participant and record this length in mm (0 to 100). The results of this assessment for treatment (n=13) and placebo (n=2) groups through day 84 of the study are show in graph of FIG. 13B.

Patient's Assessment of Physical Function/Health Assessment Questionnaire-Disability Index. The Patient's Assessment of Physical Function/HAQ-DI is utilized to assess the participant's physical function or disability. The HAQ-DI asks about the degree of difficulty a person has in accomplishing tasks in 8 functional areas (dressing, arising, eating, walking, hygiene, reaching, gripping, and activities [errands and chores]). Responses in each functional area are scored from "0" indicating no difficulty to "3" indicating inability to perform a task in that area. Study staff should not clarify any of the questions for the participant. The results of this assessment for treatment (n=13) and placebo (n=2) groups through day 84 of the study are shown in FIG. 13C.

Figure 13D:
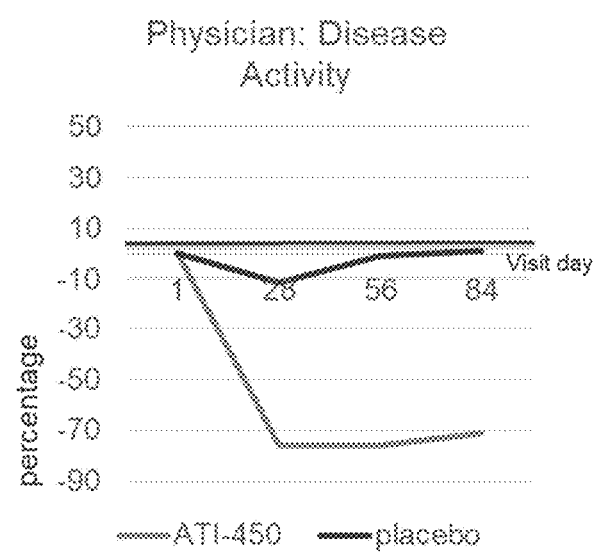

Physician Completed Efficacy Questionnaire. When this assessment is completed at study days 1, 28, 56, 84 and at follow-up, it will be one of the first assessments done at the visit, and must be completed prior to drug dosing. The Physician's Global Assessment of Disease Activity VAS is a measure completed by the investigator or designee. The VAS is 100 mm in length with "0" (no activity at all, no arthritis activity) on the left end of the line and "100" (worst activity imaginable, extremely active arthritis) at the other end of the line. The investigator or designee draws a vertical line through the horizontal line to indicate the patient's disease activity. Study staff measure the line from the left end to the investigator's (or designee) line and record this length in mm (0 to 100 mm). The results of this assessment for treatment (n=13) and placebo (n=2) groups through day 84 of the study are show in the graph of FIG. 13D.

High Sensitivity C-reactive Protein (hsCRP). Blood samples for evaluation of hsCRP were collected prior to the commencement of the study, and at study days 1, 7, 14, 28, 42, 56, 84, and at the time of follow-up (day 112). Samples were shipped to a central laboratory. Specific instructions for collection, processing, storage and shipment of samples for hsCRP were provided in a separate laboratory manual.

Figure 10:
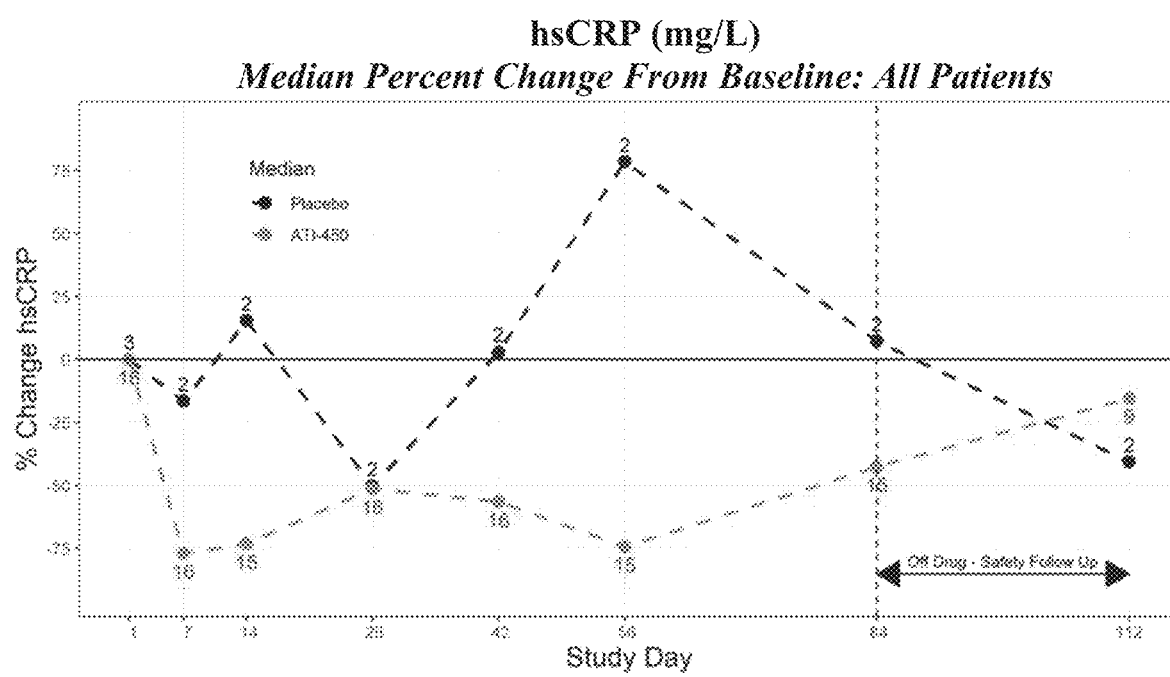
FIG. 10 is a graph showing the median percent change in high sensitivity C-reactive protein (hsCRP) (mg/mL) from baseline for all patient in placebo and ATI-450 (50 mg/BID) treatment groups at days 1, 7, 14, 28, 42, 56, and 84 of treatment and after treatment ended at day 112. The numbers on each line represent the number of patients at each timepoint.

Results of this assessment are provided in FIG. 10. The graph of FIG. 10 shows median change in hsCRP from baseline through day 84 for all patients and through day 112 (i.e., after treatment ceased) for some patients. The slight increase in hsCRP observed in the follow-up patients was expected, because treatment had stopped and was indicative of a drug-specific treatment effect. Overall, the rapid and sustained reduction in hsCRP from baseline observed in all patients through day 84 indicates clinically relevant decrease in disease activity without any evidence of tachyphylaxis.

Pharmacodynamics. Venous blood samples of approximately 10 mL was collected for measurement of ex vivo stimulated cytokine levels (e.g., TNF-α, IL-1β, IL-6, IL-8, IFNγ, IL-17, IL-18, IL-1β, IL-1RA, and IL-1α), and phosphoprotein PD parameters at study dates 1, 7, 14, 28, 42, 56, 84, and at the follow-up. For the endogenous cytokine levels (e.g., TNF-α, IL-1β, IL-6, IL-8, IFNγ, IL-17, IL-18, IL-1β, IL-1α, and IL-1RA), 1 mL of serum will be drawn at each identified time point.

p38 inhibitor compounds as a class have shown a lack of durable efficacy in RA studies. It is thought that dosing with a p38 inhibitor over 12 weeks results in pathway reprogramming and inhibitor induced p38 independent cytokine production over time. In contrast, administration of ATI-450 for 12 weeks in RA patients result in sustained inhibition of proinflammatory cytokines as shown in the graphs of FIGS. 18A and 18B. Blood was analyzed from RA patients on day 1 of dosing and day 84 of dosing, following ex vivo stimulation with LPS and evaluated for the ability of ATI-450 to inhibit TNF-α, IL-1β, IL-6, and IL-8 compared with placebo. As demonstrated by the last two bars in each cytokine group shown in FIGS. 18A and 18B, ATI-450 inhibition of each cytokine after 84 days of dosing was very similar to ATI-450 inhibition of each cytokine of each cytokine after 1 day of dosing. This data shows that inhibitor dependent pathway reprogramming and tachyphylaxis is not observed with the MK2 inhibitor ATI-450, in contrast to what has been hypothesized with p38 inhibitors.

Endogenous cytokines were evaluated in plasma from the RA patients over the course of dosing ATI-450 for 12 weeks. The data for TNF-α and IL-1RA are provided in FIGS. 19A and 19B, respectively. These data are expressed as median % change relative to pre-dosing for both drug-treated and placebo-treated patients. Samples were evaluated at trough drug levels through day 84 and the last point is near $C_{max}$ following the final dose on day 84. The horizontal line (-■-) in FIG. 19A depicts TNF-α levels in blood from normal volunteer subjects that were evaluated in the same assay. TNF-α levels are rapidly reduced by 4 weeks of dosing (trough) and this reduction was maintained throughout the 12 weeks of dosing. The horizontal line (-■-) in FIG. 19B represents IL-1RA levels in healthy subjects. In contrast the anti-inflammatory cytokine IL-1RA was elevated in RA patients and is not impacted by ATI-450 across the 12 weeks. This data indicates that ATI-450 cytokine inhibition is skewed toward proinflammatory cytokines relative to anti-inflammatory cytokines.

Figure 20A:
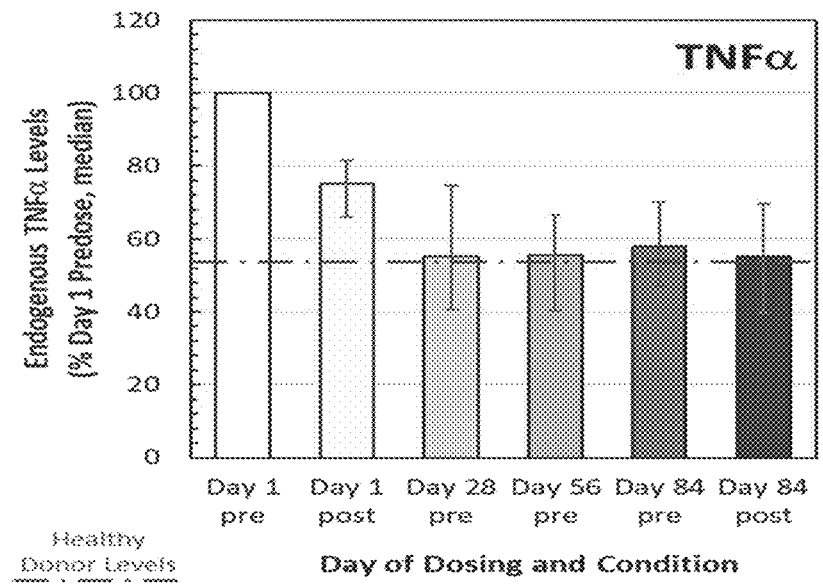
Figure 20B:
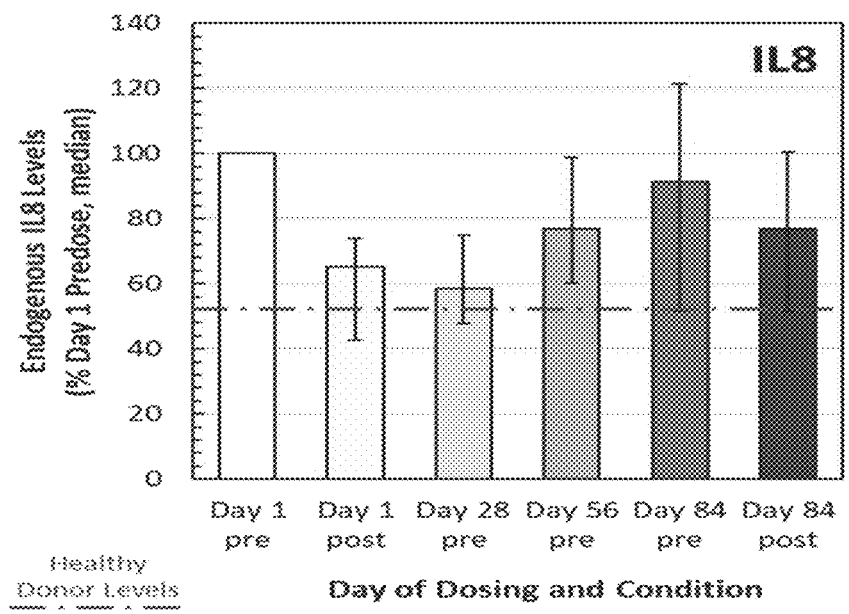
Figure 20C:
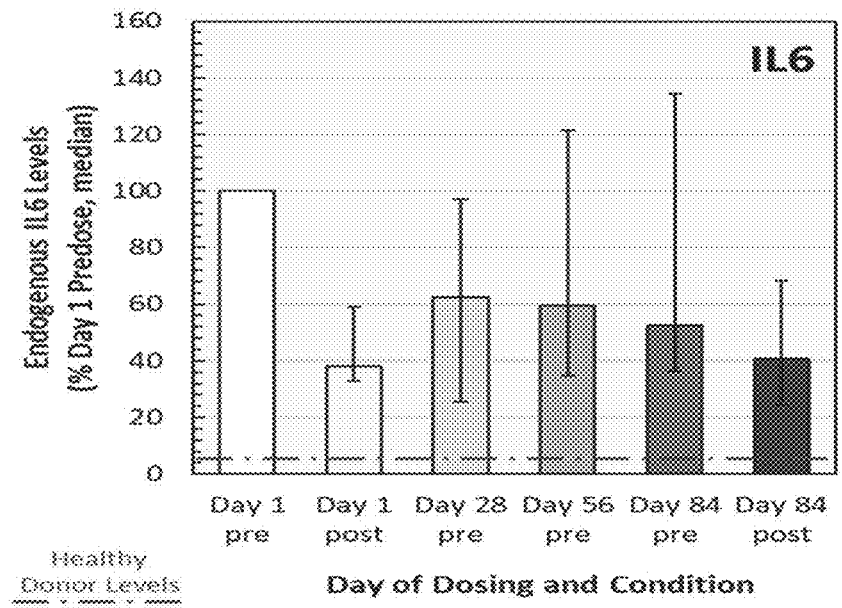
Figure 20D:
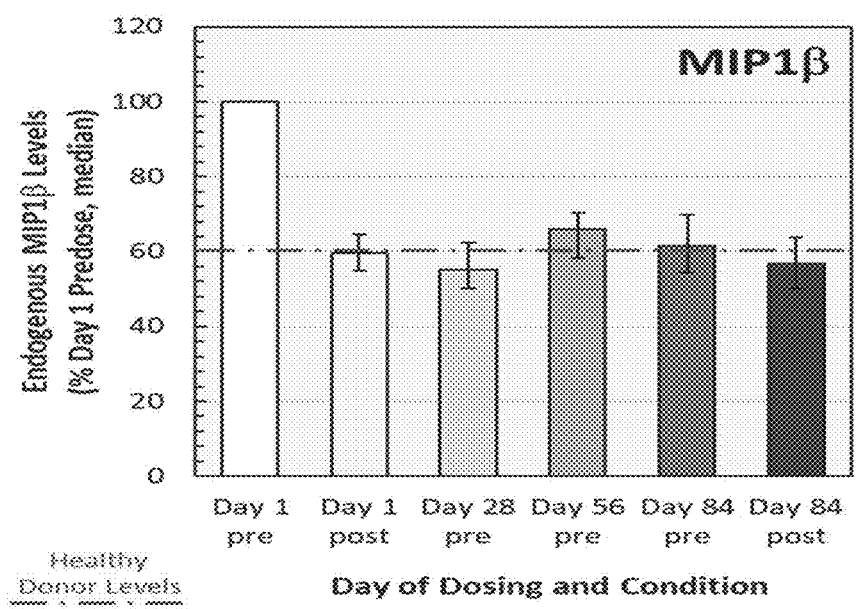

FIGS. 20A-20D provide a broader look at the impact of ATI-450 on endogenous cytokine levels in plasma from the RA patients over the course of dosing ATI-450 for 12 weeks. Plasma levels of three proinflammatory cytokines (TNF-α (FIG. 20A), IL-6 (FIG. 20C), IL-8 (FIG. 20B)), from a 13-plex tested are shown in this Figure, along with the chemokine MIP1β (FIG. 20D). The data are expressed as median % change relative to pre-dosing for drug treated patients. Samples were evaluated at trough drug levels after 4, 8 and 12 weeks of dosing and 4 hours after the final dose on day 84. The horizontal line (-■-) describes cytokine/chemokine level in plasma from normal healthy volunteer subjects. TNF-α levels are significantly reduced after 4 weeks of dosing and this reduction was maintained throughout the 12 weeks and approached the level of cytokine present in healthy volunteers. Similarly, IL-6, IL-8, and MIP1β levels are reduced at week 4 and this reduction was maintained through the 12 weeks of the study. This analysis further demonstrates the durable anti-inflammatory activity of ATI-450 dosed at 50 mg BID in RA patients over 12 weeks.

Safety. Overall, the study drug was very well tolerated, with no serious or severe adverse events reported. Only one subject withdrew for investigation of palpitations and elevated CPK. Table 18 below summarizes the reported events.

TABLE 18

Adverse Events Reported by Study Subject

| | Preferred Term | | | |
|---|---|---|---|---|
| | ATI-450 50 mg BID (n = 16) | | Placebo (n = 3) | |
| | Mild (n %) | Moderate (n %) | Mild (n %) | Moderate (n %) |
| Blood cholesterol increased | 1 (6.25) | 0 | | |
| Blood creatine phosphokinase increased | 0 | 1 (6.25) | | |
| Constipation | 1 (6.25) | 0 | | |
| Dental caries | | | 1 (33.33) | 0 |
| Ear infection | 1 (6.25) | 0 | | |
| Abnormal ECG | 1 (6.25) | 0 | | |
| Essential hypertension | 0 | 1 (6.25) | | |

TABLE 18-continued

Adverse Events Reported by Study Subject

| | Preferred Term | | | |
|---|---|---|---|---|
| | ATI-450 50 mg BID (n = 16) | | Placebo (n = 3) | |
| | Mild (n %) | Moderate (n %) | Mild (n %) | Moderate (n %) |
| Hyperliidaemia | 0 | 1 (6.25) | | |
| Hypokalaemia | 0 | 1 (6.25) | | |
| Ligament sprain | 1 (6.25) | 0 | | |
| Low density lipoprotein increased | 1 (6.25) | 0 | | |
| Mouth ulceration | 1 (6.25) | 0 | | |
| Muscle strain | | | 0 | 1 (33.33) |
| Palpitations | 1 (6.25) | 0 | | |
| Rash erythematous | 1 (6.25) | 0 | | |
| Sinusitis | 0 | 1 (6.25) | | |
| Skin abrasion | 1 (6.25) | 0 | | |
| Urinary tract infection | 0 | 2 (12.5) | | |
| Ventricular extrasystoles | 1 (6.25) | 0 | | |
| White blood cell count increased | 1 (6.25) | 0 | | |

SUMMARY OF THE RESULTS

ATI-450 was generally well tolerated. One subject in the treatment arm withdrew due to palpitations, which were unrelated to the study medication, and an elevated CPK, which was determined by the site investigator to be drug-related. One subject in the placebo arm withdrew as a result of prohibited medication needed to treat muscle strain. No serious adverse events were reported and all adverse events were mild to moderate. The most common adverse events (reported by at least 2 subjects) were urinary tract infection and elevated lipids.

In this trial, ATI-450 demonstrated durable clinical activity, as defined by a marked and sustained reduction in DAS28-CRP and evaluation of ACR20/50/70 responses over 12 weeks. The mean change from baseline in DAS28-CRP at week 12 was a 2.0 reduction in the treatment arm and a 0.35 increase in the placebo arm. The proportion of subjects with a DAS28-CRP score at week 12 of ≤ to 3.2 (low disease activity or remission) was 40% and 0% in the 15 subjects in the treatment arm and 2 subjects in the placebo arm, respectively, of which the proportion of subjects with a DAS28-CRP score of <2.6 (remission) was 20% and 0% in the treatment and placebo arms, respectively.

ACR20/50/70 was observed at week 12 in 60%, 33% and 20%, respectively, of the 15 subjects in the treatment arm, and in 0% of two subjects in the placebo arm. The median reduction from baseline in hsCRP was >40% throughout the 12 weeks of the trial in the treatment arm. An interim analysis (11 treatments, two placebo) of ex vivo stimulated cytokines from blood samples taken from the treatment arm showed a marked and durable inhibition of TNF-α, IL-1β, IL-6, and IL-8 over the 12 week dosing period. Similarly, analysis of endogenous cytokines also demonstrated a marked and sustained inhibition of median concentrations of TNF-α, IL-6, IL-8, and MIP1β in the treatment arm over the 12-week period.

ATI-450 was generally well tolerated. No serious adverse events were reported and all adverse events were mild to moderate. The most common adverse events (each reported in 2 subjects) were urinary tract infection (UTI), elevated lipids and ventricular extrasystoles, all of which were determined to be unrelated to treatment except for one UTI. Two subjects withdrew from the trial, one in the treatment arm and one in the placebo arm.

Example 5: Phase 2B, Randomized, Double-Blind, Parallel Group, Placebo-Controlled Study to Investigate Efficacy, Safety, Tolerability, Pharmacokinetics, and Pharmacodynamics of Multiple Doses of ATI-450 Plus MTX Versus MTX Alone in Patients with Moderate to Severe RA This is a Phase 2b, randomized, double-blind, parallel group, placebo-controlled study to investigate the efficacy, safety, tolerability, pharmacokinetics (PK), and pharmacodynamics (PD) of multiple doses of ATI-450 plus MTX versus MTX alone in patients with moderate to severe RA who have had an inadequate response to methotrexate alone.

Subjects whose eligibility is confirmed at baseline will be randomized in a 1:1:1:1 ratio to receive either ATI-450 tablets (20 mg, 50 mg, and 80 mg twice daily [BID]) plus MTX, or matching placebo tablets BID plus MTX. The randomization of patients to treatment groups will be stratified by two separate factors. The first stratification factor will be patients who test positive for rheumatoid factor (RF) and/or anti-cyclic citrullinated peptide (CCP) at screening versus those patients who do not test positive for both of these antibodies. The second stratification factor will be those patients who have experience with either a biologic RA treatment or a JAK RA treatment versus those with no such experience. Enrollment will be limited such that no more than 25% of the study population will have tested negative for either RF or anti-CPP or both. Likewise, enrollment will be limited such that no more than 25% of the population has prior experience with either a biologic RA therapy or a JAK RA therapy. Study medications will be administered orally for 12 weeks. Patients will be required to remain on a stable dose of MTX (15 mg to 25 mg/week for 4 weeks prior to screen or 10 mg/week for 4 weeks prior to screening for patients with documented intolerance) for the duration of the study.

Patients will attend clinic visits on Days 1, 8, 15, 29, 43, 57, and 85 (±1 day) for safety, efficacy, trough PK, and PD assessments. The morning dose of study medication will be administered in the clinic on each study visit day.

On Day 85 (Week 12), patients will complete the end of study assessments. A safety follow-up visit will be conducted 30 days (+7) after the last dose of study medication.

Inclusion criteria for subjects include 1) a diagnosis of adult-onset rheumatoid arthritis (RA) as defined by the 2010 American College of Rheumatology/European League Against Rheumatism classification criteria; 2) Disease Activity Score using 28 join count-C-reactive protein (CRP) (DAS28-CRP) greater than 3.2 defined as moderate or high disease activity; 3) have moderate to severe RA defined by a minimum disease activity criteria (6 or more swollen joints at screening and baseline visits; 6 or more tender joints at screening and baseline visits; and a high-sensitivity C-reactive protein (hsCRP) level greater than the upper limit of normal (ULN) or positive for both RF and/or anti-cyclic citrullinated peptide (CCP) at screening visit); 4) a minimum of 12 weeks on MTX with a stable MTX dose (of 15 mg to 25 mg/week or 10 mg/week for patients with documented intolerance) for at least 4 weeks prior to screening; 5) male or non-pregnant, non-nursing female aged 18-75 years old (inclusive); and 6) screening laboratory evaluations falling within the normal range of the central laboratory's reference ranges.

Efficacy Analyses

All efficacy summaries will be conducted on both the Intent-to-treat (ITT) and Per-protocol (PP) populations.

The primary endpoint assessed in this study is the proportion of subjects achieving American College of Rheumatology (ACR) 20 at 12 weeks.

Secondary endpoints to be assess in this study include: 1) proportion of subjects with ACR 50/70 at week 12; 2) proportion of subjects with ACR 20/50/70 over time; 3) Mean change from baseline in Disease Activity Score using 28 joint count-C-reactive protein (CRP) (DAS28-CRP) over time; 4) Proportion of patients achieving DAS 28 remission (score <2.6) over time and at week 12; 5) Mean change from baseline in Clinical Disease Activity Index (CDAI) over time; 6) Median percent change from baseline in high sensitivity C-reactive protein (hsCRP) levels over time; 7) Health Assessment Questionnaire Disability Index (HAQ-DI) over time; 8) ATI-450 concentrations at clinic visits (trough and 2-hour post dose sampling for all patients; and additional serial sampling for noncompartmental PK analysis for patients in PK sub-study); 9) Mean change from baseline in endogenous cytokine levels (e.g., TNF-α, IL-1β, IL-6, IL-9, IFNγ, IL-17, IL-18, IL-1β, IL-1α, and IL-1RA).

ACR 20/50/70 responder rates as well as the proportion of patients with DAS28-CRP<2.6 will be analyzed using a logistic regression. Patients with missing ACR values or missing DAS28-CRP values will be considered non-responders. Patients with negative intercurrent events (such as requiring rescue) will also be considered non-responders for ACR 20/50/70 and DAS28-CRP<2.6.

The DAS28-CRP, CDAI, 66/68 swollen/tender joint count, Patient's Global Assessment of Disease Activity, Patient's Assessment of Arthritis Pain, and Physicians Global Assessment of Disease Activity, as well as their corresponding changes from baseline will be analyzed over time (for all scheduled time points) using mixed model repeated measures. Model based point estimates and 95% confidence intervals will be provided for treatment effects. Point estimates, 95% confidence intervals and p-values will be provided for treatment differences versus placebo.

The hsCRP levels, change from baseline in hsCRP and percent change from baseline in hsCRP will be summarized over time using continuous statistical summary measures. Determination of sustained treatment effect for hsCRP will be based upon the median percent change from baseline in hsCRP over time in the PP population. Exploratory dose response modeling will be conducted for ACR 20/50/70 responder rates, the change from baseline in DAS28-CRP, 66/68 swollen/tender joint count, Patient's Global Assessment of Disease Activity, Patient's Assessment of Arthritis Pain, the Physicians Global Assessment of Disease Activity, as well as percent change from baseline in hsCRP, separately.

Safety of treatment will be based on 1) number and frequency of adverse events (AEs), 2) vital signs, 3) ECG, 4) serum chemistry, 5) hematology, 6) urinalysis, and 7) coagulation.

Plasma concentrations of ATI-450 and its primary circulating metabolite (CDD-2164) will be measured on each assessment day.

Example 6: Phase 2B, Randomized, Double-Blind, Parallel Group, Placebo-Controlled Study to Investigate Efficacy, Safety, Tolerability, Pharmacokinetics, and Pharmacodynamics of Multiple Doses of ATI-450 vs Placebo in Patients with Moderate to Severe Active Psoriatic Arthritis This is a Phase 2b, randomized, double-blind, parallel group, placebo-controlled study to investigate the safety, tolerability, PK, and PD of multiple doses of ATI-450 versus placebo in patients with moderate to severe active psoriatic arthritis (PSoA) who have had an inadequate response to MTX alone.

Subjects meeting eligibility criteria will receive 50 mg ATI-450 twice daily or a matching placebo tablet twice daily. Treatment will continue for 12 weeks while remaining on a stable dose of MTX (15 mg to 25 mg per week) prior to and for the duration of the study. PK and PD assessments occurred on days 1, 8, 15, 29, 43, 57 and 85 days. Subject groups are stratified based on prior use of DMARDs (Disease Modifying Anti-Rheumatic Drug).

Inclusion criteria for subjects include 1) a clinical diagnosis of PSoA with symptom onset at least 6 months prior to the screening visit and fulfillment of the Classification Criteria for PsA (CASPAR criteria); 2) An active disease at baseline defined as at least 3 tender joints and at least 3 swollen joints at screening and baseline visits; 3) Presence of either at screening: (a) at least one erosion on X-ray as determined by central imaging review; or (b) hsCRP level higher than the laboratory-defined ULN; 4) A diagnosis of active plaque psoriasis or documented history of plaque psoriasis; 5) An inadequate response (lack of efficacy after a minimum 12 week duration of therapy) to previous or current treatment with at least 1 non-biologic DMARD at a maximally tolerated dose (MTX, sulfasalazine, leflunomide, cyclosporine, apremilast, bucillamine, or iguratimod), or an intolerance or contraindicated for DMARDs; and 6) Subjects being treated concurrently with non-biologic DMARDs at study entry must be on less than or equal to 2 non-biologic DMARDs (except the combination of MTX and leflunomide). The following DMARDs are permitted: MTX, sulfasalazine, leflunomide, apremilast, hydroxychloroquine, bucillamine, and iguratimod. Treatments must have been ongoing for at least 12 weeks at a stable dose for at least 4 weeks prior to the baseline visit. Finally, screening laboratory evaluations (hematology, chemistry, coagulation, and urinalysis) must fall within the normal range of the central laboratory's reference ranges.

Exclusion Criteria for subjects include: 1) Current treatment with more than two non-biologic DMARDs; the use of DMARDs other than methotrexate, sulfasalazine, leflunomide, apremilast, hydroxychloroquine, bucillamine, and iguratimod; or the use of methotrexate in combination with leflunomide. 2) A history of fibromyalgia, any arthritis with onset prior to age 17 years, or current diagnosis of inflammatory joint disease other than PsA (including, but not limited to rheumatoid arthritis, gout, overlap connective tissue diseases, scleroderma, polymyositis, dermatomyositis, systemic lupus erythematosus). A prior history of reactive arthritis or axial spondyloarthritis including ankylosing spondylitis and non-radiographic axial spondyloarthritis is permitted if documentation of change in diagnosis to PsA or additional diagnosis of PsA is made. A prior history of fibromyalgia is permitted if documentation of change in diagnosis to PsA or documentation that the diagnosis of fibromyalgia was made incorrectly. 3) a current acute or chronic immunoinflammatory disease other than PSoA which may impact the course or assessment of PSoA. 4) An uncontrolled non-immunoinflammatory disease that may place the patient at increased risk during the study or impact the interpretation of results. 5) A history or evidence of active or latent tuberculosis. 6) A history of alcoholism/current alcoholic, alcoholic liver disease, or other chronic liver disease; active treatment of an infection with antibiotics. 7) Positive for HIV or hepatitis B or C. 8) a white blood cell count of less than $3.0 \times 10^3$ cells/mm$^3$; an absolute neutrophil count of less than $1.5 \times 10^3$ cells/mm$^3$; a lymphocyte count of less than $0.5 \times 10^3$ cells/mm$^3$; a platelet count of less than $100 \times 10^3$ cells/mm$^3$; a hemoglobin level less than 10 g/dL; an aspartate aminotransferase (AST) or alanine aminotransferase (ALT) level equal to or greater than 1.5× ULN; a total bilirubin level equal to or greater than 2×ULN unless patient has been diagnosed with Gilberts' disease and this is clearly documented; an estimated glomerular filtration rate (eGFR) of less than 40 mL/min/1.73 m$^2$ based on Modification of Diet and Renal Disease formula. 9) A blood pressure level (in supine position after at least 5 minutes rest) less than 90 mmHg or greater than 140 mmHg for systolic blood pressure or less than 40 mmHg or greater than 90 mmHg for diastolic blood pressure. 10) Has taken rituximab or other B cell inhibitor within 6 months; has taken a biologic DMARD within 8 weeks; has taken enteracept or anakinra within 4 weeks; has taken a conventional DMARD (leflunomide, cyclosporine, azathioprine) or JAK inhibitors within one month. 11) Has had an intra-articular corticosteroid injection within 30 days; has taken an investigational small molecule within 30 days; are currently receiving corticosteroids at doses greater than 10 mg per day of prednisone (or equivalent) or have been receiving an unstable dosing regimen of corticosteroids within 2 weeks of the screening visit; have started treatment with non-steroidal anti-inflammatory drugs (NSAIDs) or have been receiving an unstable dosing regimen of NSAIDs within 2 weeks of the screening visit. 12) a history of stroke; a significant cardiac disease that would affect interpretation of study data or the safety of the patient's participation in the study, per judgment of the investigator, including recent myocardial infarction or unstable angina, or heart failure with New York Heart Association Class III or IV symptoms; evidence of atrial fibrillation, atrial flutter, complete right or left bundle branch block, Wolff-Parkinson-White Syndrome, or other significant rhythm disturbance; evidence of acute ischemia; screening or pre-dosing baseline mean QTcF greater than 450 msec; a personal or family history of long QT syndrome or sudden death. 13) any joint procedure within 90 days of screening.

Efficacy Analyses:

The primary objective of this study is to assess the efficacy of multiple doses of ATI-450 in patients with moderate to severe PSoA. This objective will be assessed by determining the proportion of subjects achieving ACR (American College of Rheumatology) 20 at week 12 in the ITT population. Response defined as at least 20% reduction (improvement) compared with baseline in tender joint count (TJC), swollen joint count (SJC), and at least 3 of the 5 remaining ACR core set measures: patient's assessment of pain, patient's global assessment of disease activity (PtGA); physician's global assessment of disease activity (PhGA), Health Assessment Questionnaire-Disability Index (HAQ-DI), and high sensitivity C-reactive protein (hsCRP).

The secondary objective of this study is to assess the pharmacodynamics (PD) of ATI-450 in patients with moderate to severe PSoA. This objective will be assessed by determining 1) proportion of patients with ACR 50/70 at week 12; 2) proportion of patients with ACR 20/50/70 over time; 3) proportion of patients achieving a static Investigator Global Assessment (sIGA) of Psoriasis of 0 or 1 and at least a 2-point improvement from baseline; 4) a psoriasis area severity index (PASI) 75 response (for participants with at least a 3% BSA psoriasis as baseline); 5) proportion of participants achieving minimal disease activity (MDA), determined based on subjects fulfilling 5 of 7 outcome measures: TJC≤1; SJC≤1; PASI≤1 or BSA-Ps≤3%; Patient's Assessment of Pain NRS≤1.5; PtGA-Disease Activity NRS≤2.0; HAQ-DI score≤0.5; and tender entheseal points ≤1; 5) a change from baseline in HAQ-DI over 12 weeks; 6) a change from baseline in short-form (SF)-36 Physical Component Summary (PCS); 7) a change from baseline FACIT-Fatigue Questionnaire; 8) a change from baseline in Self-Assessment of Psoriasis Symptoms (SAPS) Questionnaire; and 9) safety (adverse effects, ECG, laboratory values). Another secondary objective of this study is to assess the pharmacokinetics (PK) of ATI-450 in patients with moderate to severe PSoA who are receiving concomitant MTX. This objective will be assessed by determining the ATI-450 concentrations at clinic visits (trough PK analysis).

An exploratory objective of this study is to assess the PD of ATI-450 plus MTX in patients with moderate to severe PSoA. This objective will be assessed by determining Mean change from baseline in endogenous cytokine levels (e.g., tumor necrosis factor-α [TNF-α], interleukin [IL]-1β, IL-6, IL-8, IFNγ, IL 17, IL-18, IL-1β, IL-1α and IL-1RA)

All efficacy summaries will be conducted on both the ITT and PP populations.

The primary efficacy analysis will be the treatment comparison of the percentage of patients achieving ACR20 at week 12 in the ITT population. This analysis will be conducted within the context of a logistic regression model. Treatment group will enter the model as a class variable and baseline severity will be included as a covariate. The hypothesis test and corresponding p-value will be a one-sided test with an alpha level of 0.05. Point estimates and 90% confidence intervals for the odds ratio will be provided in addition to the p-values.

Treatment comparisons for all secondary endpoints will be conducted using a logistic regression like that of the primary analysis. This will be done on both the ITT and PP populations.

Treatment comparisons for all continuous secondary endpoints will be conducted using a Mixed Model Repeated Measures (MMRM). This model will include factors for treatment group, time, and time by treatment interaction as well as a baseline covariate, where appropriate. Subject identifier will be included in the model in a manner that allows observations within a given subject over time to be treated as repeated measures. All treatment comparisons will be based on a one-sided hypothesis test with a 0.05 alpha level. Point estimates and 90% confidence intervals for the difference in least square means will be provided in addition to the p-values. These analyses will be done for both the ITT and PP populations.

Safety of treatment will be based on 1) incidence and severity of AEs, vital signs, ECG measurements, clinical laboratory values (hematology, serum chemistry, coagulation, urinalysis).

Example 7: A Phase 2a, Randomized, Double-Blind, Parallel Group, Placebo-Controlled Dose Ranging Study to Investigate the Efficacy, Safety, Tolerability, Pharmacokinetics, and Pharmacodynamics of ATI-450 Vs Placebo in Patients with Moderate to Severe Hidradenitis Suppurativa (HS)

This is a Phase 2b, randomized, double-blind, parallel group, placebo-controlled study to investigate the efficacy, safety, tolerability, PK, and PD of ATI-450 50 mg BID versus placebo in patients with moderate to severe HS who have had an inadequate response or intolerance to an adequate trial of oral antibiotics. Subjects meeting eligibility criteria will receive 50 mg or 80 mg ATI-450 (oral tablet) twice daily or a matching placebo tablet twice daily. PK and PD assessments occurred on days 1, 8, 15, 29, 43, 57 and 85 days.

Inclusion criteria include: 1) subject diagnosed with moderate to severe Hidradenitis Suppurativa (HS) for at least one year prior to baseline visit; 2) subject exhibits HS lesions (Hurley stage II or III) present in at least two distinct anatomical areas; 3) draining fistula count of <=20 at Baseline visit; 4) total abscesses and nodule count (AN count) of >=5 at Baseline visit; 5) subject agrees to use a daily antiseptic wash on their HS lesions; 6) subject must have a history of inadequate response or intolerance to an adequate trial of oral antibiotics for treatment of HS.

Exclusion criteria include a history of active skin disease other than HS that could interfere with the assessment of HS; an uncontrolled non-immunoinflammatory disease that may place the patient at increased risk during the study or impact the interpretation of results; a history or evidence of active or latent tuberculosis; a history of alcoholism/current alcoholic, alcoholic liver disease, or other chronic liver disease; active treatment of an infection with antibiotics; positive for HIV or hepatitis B or C; a white blood cell count of less than $3.0 \times 10^3$ cells/mm3; an absolute neutrophil count of less than $1.5 \times 10^3$ cells/mm3; a lymphocyte count of less than $0.5 \times 10^3$ cells/mm3; a platelet count of less than $100 \times 10^3$ cells/mm3; a hemoglobin level less than 10 g/dL; an aspartate aminotransferase (AST) or alanine aminotransferase (ALT) level equal to or greater than 1.5×ULN; 12) a total bilirubin level equal to or greater than 2×ULN unless patient has been diagnosed with Gilberts' disease and this is clearly documented; an estimated glomerular filtration rate (eGFR) of less than 40 mL/min/1.73 m2 based on Modification of Diet and Renal Disease formula; a blood pressure level (in supine position after at least 5 minutes rest) less than 90 mmHg or greater than 140 mmHg for systolic blood pressure or less than 40 mmHg or greater than 90 mmHg for diastolic blood pressure; has taken rituximab or other B cell inhibitor within 6 months; has taken a biologic DMARD within 8 weeks; has taken enteracept or anakinra within 4 weeks; has taken a conventional DMARD (leflunomide, cyclosporine, azathioprine) or JAK inhibitors within one month; an intra-articular corticosteroid injection within 30 days; has taken an investigational small molecule within 30 days; is currently receiving corticosteroids at doses greater than 10 mg per day of prednisone (or equivalent) or have been receiving an unstable dosing regimen of corticosteroids within 2 weeks of the screening visit; have started treatment with non-steroidal anti-inflammatory drugs (NSAIDs) or have been receiving an unstable dosing regimen of NSAIDs within 2 weeks of the screening visit; a history of stroke; a significant cardiac disease that would affect interpretation of study data or the safety of the patient's participation in the study, per judgment of the investigator, including recent myocardial infarction or unstable angina, or heart failure with New York Heart Association Class III or IV symptoms; evidence of atrial fibrillation, atrial flutter, complete right or left bundle branch block, Wolff-Parkinson-White Syndrome, or other significant rhythm disturbance; evidence of acute ischemia; screening or pre-dosing baseline mean QTcF greater than 450 msec; a personal or family history of long QT syndrome or sudden death; and any joint procedure within 90 days of screening.

Efficacy Analysis

The primary objective of this study is assess the efficacy of multiple doses of ATI-450 in patients with moderate to severe HS. This objective will be assessed by determining percentage of patients achieving Hidradenitis Suppurativa Clinical Response (HiSCR) at week-12 (HiSCR is defined as at least a 50% reduction from Baseline in the total abscess and inflammatory nodule (AN) count, with no increase in abscess or draining fistula counts).

A secondary objective of this study is to assess the efficacy and safety of ATI-450 in patients with moderate to severe HS. This objective will be assessed by determining 1) percentage of patients achieving at least 30% reduction from Baseline in Numerical Rating Scale (NRS30) in Patient's Global Assessment of Skin Pain (PGA Skin Pain) at week 12 among patients with baseline NRS30≥3 (NRS30 is evaluated based on worst skin pain in a 24-hour recall period (maximal daily pain)); 2) percentage of patients achieving at least 30% reduction from baseline in NRS30 in PGA Skin Pain at week 12 among patients with baseline NRS30≥3; 3) percentage of patients who experience at least 25% increase in AN counts with a minimum increase of 2 relative to baseline over the 12-week treatment period; 4) change from baseline in Dermatology Life Quality Index (DLQI) over 12 weeks (the DLQI is a 10-item validated questionnaire used to assess the impact of HS disease symptoms and treatment on quality of life (QoL). It consists of 10 questions evaluating impact of skin diseases on different aspects of a participant's QoL over the prior week, including symptoms and feelings, daily activities, leisure, work or school, personal relationships, and the side effects of treatment); 5) change from baseline in HS-related swelling assessed based on the Hidradenitis Suppurativa Symptom Assessment (HSSA) over 12 weeks (HSSA is a 9-item patient reported outcome (PRO) questionnaire developed to assess the symptoms of HS on a 0 to 11-point NRS, where 0 represents no symptoms and 10 represents extreme symptom experience); 6) change from baseline in HS-related odor assessed based on the HSSA over 12-weeks; 7) change from baseline in HS-related worst drainage assessed based on the HSSA over 12-weeks; and 8) safety (AEs, SAEs, laboratory values, ECG). Another secondary objective of this study is to assess the pharmacokinetics (PK) and pharmacodynamics (PD) of ATI-450 in patients with HS. This objective will be assessed by determining ATI-450 concentrations at clinic visits (trough PK analysis).

Pharmacodynamics of ATI-450 in patients with moderate to severe HS will also be assessed by determining the mean change from baseline in endogenous cytokine levels (e.g., TNF-α IL-1β, IL-6, IL-8, IFNγ, IL 17, IL-18, IL-1β, IL-1α, and IL-1RA).

All efficacy summaries will be conducted on both the ITT and PP populations.

The primary efficacy analysis will be the treatment comparison of the percentage of patients achieving HiSCR at week 12 in the ITT population. This analysis will be conducted within the context of a logistic regression model.

Treatment group will enter the model as a class variable and baseline severity will be included as a covariate. The hypothesis test and corresponding p-value will be a one-sided test with an alpha level of 0.05. Point estimates and 90% confidence intervals for the odds ratio will be provided in addition to the p-values.

Treatment comparisons for all secondary responder endpoints (percentage of patients achieving at least 30% reduction from Baseline in NRS30 in PGA Skin Pain and percentage of patients who experience at least 25% increase in AN count with a minimum increase of 2 relative to baseline over the 12-week treatment period) will be conducted using a logistic regression like that of the primary analysis. This will be done on both the ITT and PP populations.

Treatment comparisons for all continuous secondary endpoints will be conducted using a Mixed Model Repeated Measures (MMRM). This model will include factors for treatment group, time, and time by treatment interaction as well as a baseline covariate, where appropriate. Subject identifier will be included in the model in a manner that allows observations within a given subject over time to be treated as repeated measures. All treatment comparisons will be based on a one-sided hypothesis test with a 0.05 alpha level. Point estimates and 90% confidence intervals for the difference in least square means will be provided in addition to the p-values. These analyses will be done for both the ITT and PP populations.

Example 8: A Phase 2a, Open-Label, Single-Arm Study to Investigate the Safety and Efficacy of ATI-450 for the Maintenance of Remission in Patients with Cryopyrin-Associated Periodic Syndrome (CAPS) Previously Managed with Anti-IL-1 Therapy CAPS is a rare hereditary autoinflammatory disease caused by a gain-of-function mutation of the NLRP3 gene coding for cryopyrin, which is a component of the NLRP3 inflammasome. Dysregulation of the NLRP3 inflammasome results in an overproduction of interleukin-1 (IL-1), and consequently the inflammatory symptoms seen in CAPS. Current anti-IL-1 therapies have been shown to induce rapid and sustained disease remission in CAPS patients and are generally well tolerated.

ATI-450 has been shown to cause a marked inhibition of IL-1 in both pre-clinical and clinical studies. Current anti-IL-1 therapies for treatment of CAPS are biologics that are administered either intravenously or subcutaneously. ATI-450, an orally administered small molecule, has the potential to have a similar safety and efficacy profile compared to currently available therapies with a differentiated route of administration that may be preferred by some CAPS patients.

This study is being conducted to determine the safety, tolerability, pharmacokinetics (PK), pharmacodynamics (PD), and preliminary efficacy of ATI-450 in patients with CAPS.

The primary objective of this study is to assess the safety and tolerability of ATI-450 to maintain remission in patients with CAPS previously managed with anti-IL-1 therapy. This objective will be assessed by investigating the number and percent of adverse events (AEs) and serious adverse events (SAEs); mean change from baseline in laboratory values, vital signs, and electrocardiograms (ECGs).

The secondary objective of this study is to assess the efficacy of ATI-450 to maintain remission in patients previously managed with anti-IL-1 therapy. To assess this objective, several endpoints will be assessed. These endpoints include (i) determining the proportion of participants in disease remission over time. Disease remission is defined as having a Physician Global Assessment (PGA) score of absent or minimal and a high sensitivity C-reactive protein (hsCRP) and serum amyloid A (SAA) value within the normal range (≤10 mg/L) or within 30 percent of the baseline value. (ii) Determining the proportion of participants in clinical remission over time. Clinical remission is defined as having a PGA score of absent or minimal. (iii) Determining the time to relapse; where relapse is defined as a two-point worsening on the PGA scale. (iv) Determining the proportion of participants who experience re-emergence of disease symptoms after discontinuation of ATI-450. Re-emergence is defined as a daily Key Symptom Score (KSS) ≥3 points higher than baseline for at least 2 consecutive days. KSS is derived from the patient-administered daily health assessment form (DHAF). (v) Determining the proportion of participants with a mean KSS no more than 2 points higher than baseline for at least 6 out of 8 weeks during the treatment period. (vi) Determine change from baseline in PGA. (vii) Determine change from baseline in KSS. (viii) Determine change from baseline in hsCRP and SAA.

In addition to the above, the study will also investigate the following two exploratory objectives: (i) assessing the pharmacodynamics (PD) of ATI-450 in patients with CAPS, and (ii) assessing the Pharmacokinetics (PK) of ATI-450 in patients with CAPS. These objectives will be assessed by determining the change from baseline in serum cytokines IL-1β, IL-1α, IL-6, IL-18, and TNF-α and the ATI-450 concentrations at trough.

This is a Phase 2a, open-label, single-arm study to investigate the safety, tolerability, efficacy, PK, and PD of ATI 450 to maintain remission in patients with CAPS previously managed with anti-IL-1 therapy. Up to 10 patients are planned to be enrolled in the study. The study will consist of an up to 8-week screening period, a 12-week treatment period, and a 4-week safety follow-up period. The total duration of the study for patients remaining in the study until their final safety follow up assessment will be up to 24 weeks.

The investigator will obtain signed informed consent from the patient before any study procedures are performed. For further details regarding the informed consent process, see Section 9.3. During the screening visit each patient will be required to have all assessments performed as outlined in the Schedule of Assessments (Table 13).

Patients eligible for the study include those with (1) Diagnosis of Familial Cold Autoinflammatory Syndrome, Muckle-Wells Syndrome, or Neonatal Onset Multisystem Inflammatory Disease. Prior agreement between the Investigator and Aclaris for study eligibility is required for patients who do not have a molecular diagnosis of NLRP3 mutations available (either testing not performed, or testing performed, but negative) upon study entry. For those patients who have not been molecularly tested for NLRP3 mutations, molecular testing should be performed during the study; (2) Patients with a PGA score of "minimal" or less and who are considered to have achieved that response as a result of successful anti-IL-1 therapy; and (3) Continuous Treatment with anti-IL-1 therapy for at least 6 months.

Patients whose eligibility is confirmed at baseline will begin dosing ATI-450 tablets (50 mg BID). Such patients will be in protocol-defined remission due to prior treatment with an anti-IL-1 biologic. Dosing will begin on the day that the next dose of their anti-IL-1 therapy is scheduled at which time anti-IL-1 therapy will be discontinued.

The first dose of ATI-450 (50 mg BID) will be taken at the following times (based on anti-IL-1 therapy):

Anakinra: 24 hours (+/−1 hour) after last administration or at approximate time of regular anakinra dose.

Canakinumab: 8 weeks (+/−1 week) after last administration.

Rilonacept: 1 week (+/−1 day) after last administration.

ATI-450 will be administered orally for 12-weeks. Patients will attend clinic visits on Days 14, 28, 56, and 84 (+/−1 day) for safety, efficacy, PK and PD assessments. Patients will begin recording disease symptoms in their daily diary card 7 days prior to beginning administration of ATI-450, or immediately starting at the screening visit if the Day 1 visit is scheduled to occur less than 7 days after the screening visit. Patients will continue to complete their diary until completion of the safety follow up Day 7 visit.

At the end of 12-weeks, Day 84 (+/−1 day), patients will stop ATI-450 and conduct end of study assessments. Patients will complete safety follow-up visits on site 7 Days (+4 days) after the last dose of ATI-450 and via a phone call 30 Days (+/−3 days) after the last dose.

The study is designed to assess the safety, tolerability, efficacy, PK, and PD of ATI-450 in patients with CAPS.

Many patients with CAPS achieve complete or near complete disease remission with currently available anti-IL-1 therapies. Therefore, the study is designed to minimize patient's time off anti-IL-1 therapy due to potentially harmful long-term complications that can result from prolonged relapse of disease symptoms.

The study is open-label and there is no washout period for anti-IL-1 therapy; patients enrolled in the trial will begin treatment with study medication (Day 1) on the day of their next scheduled dose of anti-IL-1 therapy. At the end of the 12-week treatment period, ATI-450 administration will be discontinued, and patients will delay administration of anti-IL-1 therapy until 7 days (+4 days) after the last dose of ATI-450.

The 12-week treatment period was selected to allow sufficient time to explore the efficacy of ATI-450 in maintaining disease remission, and to adequately rule out the potential for prolonged disease remission caused by the last dose of anti-IL-1 therapy. Due to its long $t_{1/2}$, this is particularly relevant in instances when canakinumab is used.

The start of the study will be the date on which the first patient provides informed consent, and the end of the study will be the date of the last patient's last assessment. It is anticipated that total duration could be up to 24 weeks.

TABLE 19

| Assessment | Screening Visit 1 Day −56 to Day −1 | 12-Week Treatment Period | | | | | 4-Week Safety Follow-up | |
|---|---|---|---|---|---|---|---|---|
| | | Visit 2 Baseline Day 1 | Visit 3 Day 14 | Visit 4 Day 28 (+/−1 day) | Visit 5 Day 56 | Visit 6 Day 84 EOS | Visit 7 Day 7[6] (+4 days) | Visit 8 Phone Call Day 30 (+/−3 days) |
| Informed Consent | X | | | | | | | |
| Eligibility Review | X | X | | | | | | |
| CAPS and Other Medical History and Demographics | X | | | | | | | |
| QuantiFERON Gold Test for TB | X | | | | | | | |
| Height | X | | | | | | | |
| Weight | X | | | | | | | |
| Physical Exam[1] | X | | | | | | | |
| Limited Physical Exam | | X | X | X | X | X | X | |
| Physicians Global Assessment of Disease Activity[2] | X | X | X | X | X | X | X | |
| Patient Diary (daily)[2,8] | X | X | X | X | X | X | X | |
| Key Symptom Score[2,8] | X | X | X | X | X | X | X | |
| HIV and Hep Screen | X | | | | | | | |
| SARS-CoV-2 Testing by RT-PCR | | X | | | | | | |
| Vital Signs[2,3] | X | X | X | X | X | X | X | |
| 12-Lead ECG[2,4] | X | X | | | | X | | |
| Hematology, Coagulation, Chemistry, Lipids, and Urinalysis | X | X | X | X | X | X | X | |
| PD Blood Sampling[2] | | X | X | X | X | X | X | |
| PK Blood Sampling[2] | | X | X | X | X | X | X | |
| Serum Pregnancy | X | | | | | | | |
| Urine Pregnancy | | X | X | X | X | X | X | |
| Dispense Study Medication | | X | X | X | X | | | |
| Administration of Morning Dose of ATI-450 in Clinic[7] | | X | X | X | X | X | | |

TABLE 19-continued

|  | Screening Visit 1 Day −56 to Day −1 | 12-Week Treatment Period | | | | | 4-Week Safety Follow-up | |
|---|---|---|---|---|---|---|---|---|
| Assessment | | Visit 2 Baseline Day 1 | Visit 3 Day 14 | Visit 4 Day 28 (+/−1 day) | Visit 5 Day 56 | Visit 6 Day 84 EOS | Visit 7 Day 7[6] (+4 days) | Visit 8 Phone Call Day 30 (+/−3 days) |
| Drug Accountability | | | X | X | X | X | | |
| Adverse Events[5] | X | X | X | X | X | X | X | X |
| Prior and Concomitant Medications | X | X | X | X | X | X | X | X |

ECG = electrocardiogram,
Hep = hepatitis,
PD = pharmacodynamic,
TB = tuberculosis,
EOS = end of study

[1] A full physical examination will be performed at screening. The brief physical examination (including signs of CAPS) will be performed at visit 6 and follow-up. Body mass index will be derived in the eCRF.
[2] On dosing day(s), patient diary, PGA, KSS, vitals, clinical laboratory parameters, PK, and PD will be performed before the administration of study medication.
[3] Vital signs will be measured prior to dosing and immediately following dosing in a semi supine position after 5 minutes' rest and will include temperature, systolic and diastolic blood pressure, pulse, and respiratory rate.
[4] A triplicate 12-lead ECG will be recorded after the subject has been resting for at least 5 minutes in a supine position.
[5] Serious adverse event reporting will start at the time of consent. Any AE that occurs between the time of consent and dosing on Day 1 will be recorded as medical history. Treatment-emergent AEs will be collected following the first dose of study medication on Day 1.
[6] Patients should not start their anti-IL-1 therapy until all safety follow-up Day 7 assessments have been completed. However, in the event of a safety concern, patients will be allowed to return early or restart their anti-IL-1 therapy early prior to completing the safety follow-up Day 7 visit at the discretion of the investigator.
[7] The last dose of ATI-450 will be administered in clinic on Day 84. The second dose of ATI-450 is not to be administered on Day 84.
[8] Patients will be instructed on how to complete their patient diary at the screening visit. Patients will begin completing the patient diary 7 days prior to beginning ATI-450 administration (Day 1), or immediately beginning at the screening visit if the Day 1 visit is scheduled to occur less than 7 days after screening.

Statistical Methods:

Determination of Sample Size—The sample size for this study was determined based upon feasibility constraints as opposed to a formal power computation. Up to 10 patients are planned to be enrolled.

Analysis Populations. The Intent-to-treat (ITT) population will include all patients who have been administered at least one dose of study medication. The Per-Protocol (PP) population will include all patients who complete 12-weeks of treatment and 4-weeks of safety follow-up and have completed study assessments.

Efficacy Analyses—All efficacy summaries will be conducted on both the ITT and PP populations.

Proportion of participants in disease remission over time; where disease remission is defined as having a PGA score of minimal or better and a hsCRP and SAA value within the normal range or within 30 percent of the baseline value (ITT and PP population).

Proportion of participants in clinical remission over time; where clinical remission is defined as having a PGA score of minimal or better (ITT and PP population).

Proportion of participants who experience an increase over baseline in daily KSS of ≥3 for at least two days after discontinuation of ATI-450 over time (PP population).

Proportion of participants who maintain a mean KSS of no more than 2 points higher than baseline in at least 6 out of 8 weeks in the ITT and PP population.

Change from baseline in PGA and KSS scores will be reported descriptively over time (ITT and PP population).

Change from baseline in hsCRP and SAA and percent change from baseline in hsCRP and SAA will be summarized over time using continuous statistical summary measures. Determination of sustained treatment effect for hsCRP and SAA will be based upon the median percent change from baseline in the ITT and PP population.

Efficacy Assessments

Physician Completed Efficacy Questionnaire. The Physician's Global Assessment of Autoinflammatory Disease Activity (PGA) is a measure to be completed by the investigator or designee. The PGA uses a 5-point rating scale: absent, minimal, mild, moderate, and severe. The investigator will select a rating based on the patient's current disease activity at the time of the visit.

Maintenance of Disease Remission and Clinical Remission. Maintenance of disease remission will be assessed during the treatment period. Disease remission is defined as having a PGA score of absent or minimal and a hsCRP and SAA value within the normal range (≤10 mg/L) or within 30 percent of the baseline value.

Maintenance of clinical remission will be assessed during the treatment period. Clinical remission is defined as having a PGA score of absent or minimal.

Time to Relapse Time to relapse will be assessed during the treatment period. Relapse is defined as a two-point worsening on the PGA scale.

Patient Completed Efficacy Questionnaires. When these assessments are required at the times outlined in Table 13, they should be the first tasks done at any visit, and prior to study medication dosing.

The Key Symptom Score (KSS) is derived from the patient-administered daily health assessment form (DHAF), and is the average on a 0 to 10 scale (0=None, 10=Very Severe) of 5 separate scales—rash, feeling of fever and chills, joint pain, eye redness and pain, and fatigue.

The DHAF is designed using a linear rating scale of circles in half-step units (e.g., 0.5, 1.0, 1.5, 2.0, etc.), which are marked 0 (none, no severity) to 10 (very severe). Patients will select the circle on the scale that they determine most accurately represents severity of the symptom that they have experienced during the last 24 hours.

The DHAF will be completed daily by the patient. Daily KSS will be calculated by averaging the sum of the 5 individual symptom scores. KSS during a specified time period will further be calculated by averaging the sum of daily KSS scores during the time period.

Patients will be provided a quiet, private place to complete the assessments. Patients will be instructed to answer all the questions to the best of their ability and without help from others (study staff, family, or friends). The study staff should review the questionnaires after they are completed and encourage patients to complete any missing information. Patients can refrain from answering any question. Study staff will record the refusal of patients to answer any question in the source documents.

Re-emergence of CAPS Symptoms Re-emergence of CAPS symptoms will be assessed after ATI-450 is discontinued following completion of the treatment period. Re-emergence is defined as an increase in daily KSS of ≥3 from baseline for at least two consecutive days.

High Sensitivity C-reactive Protein and Serum Amyloid A. Blood samples for evaluation of hsCRP and SAA will be collected at the times specified in Table 13. Samples will be shipped to a central laboratory. Specific instructions for collection, processing, storage and shipment of blood samples will be provided in a separate laboratory manual. The normal range for serum hsCRP and SAA is defined as <10 mg/L for both.

Safety Assessments

Adverse Events: AEs will be followed, recorded, and reported.

Clinical Laboratory Evaluations: Laboratory assessments during treatment will be performed by a central laboratory. Blood and urine samples will be collected at the times indicated in Table 13. On dosing day(s), sampling for the analysis of clinical laboratory parameters will be performed before the administration of study medication.

Unless indicated otherwise, all laboratory samples will be processed and shipped to the central laboratory, as described in the central laboratory manual. The central laboratory will analyze the samples or send them to reference laboratory(ies) for analysis, as indicated in the manual. Refer to the central laboratory manual for the maximum total volume of blood to be collected per patient throughout the study.

The following parameters will be assessed:

Hematology: hemoglobin, hematocrit, red blood cells, platelets, total WBC count, differential WBC count, and ANC Coagulation: INR, partial thromboplastin time, and prothrombin time Biochemistry: albumin, alkaline phosphatase (ALP), ALT, amylase, AST, blood urea nitrogen (BUN), calcium, creatine phosphokinase, hsCRP, creatinine, gamma glutamyltransferase, glucose, inorganic phosphatase, lactate dehydrogenase, lipase, magnesium, potassium, SAA, sodium, chloride, bicarbonate, total bilirubin, total protein, and uric acid Lipids: total cholesterol, high-density lipoprotein, low-density lipoprotein, and triglycerides Urinalysis: pH, specific gravity, creatinine, glucose, bilirubin, blood, and protein Potential Drug-induced Liver Injury. Hy's Law cases have the following 3 components: (1) The drug causes hepatocellular injury, generally shown by a higher incidence of ≥3-fold elevations above the ULN of ALT or AST than the placebo; (2) Among study patients showing such aminotransferase elevations, often with aminotransferases much greater than 3×ULN, one or more also shows elevation of serum total bilirubin to >2×ULN or INR>1.5, without initial findings of cholestasis (elevated ALP); (3) No other reason can be found to explain the combination of increased aminotransferase and total bilirubin, such as viral hepatitis A, B, or C; evidence for biliary obstruction; acute alcoholic hepatitis (recent drinking and AST>2×ALT are supportive); recent history of severe hypotension or congestive heart failure; other underlying viral disease; pre-existing or acute liver disease; or another drug (including non-prescription products such as herbal supplements) capable of causing the observed injury Example 9: ATI-450 Inhibits Inflammatory Cytokines Involved in Autoimmune Conditions ATI-450 Increases Regulatory T (Treg) Cells in Mouse Collagen-Induced Arthritis Model: To investigate the utility of ATI-450 for the treatment of autoimmune conditions, the effect of ATI-450 on T cell subsets was evaluated in a murine model of collagen-induced arthritis (CIA). In this model DBA/1 mice (12/group) were immunized with bovine collagen/CFA to induce arthritis. At day 18, animals were administered vehicle, ENBREL (10 mg/kg QD), or ATI-450 (1000 ppm chow). At day 21, mice were boosted with bovine collagen/CFA, and at day 35 the study was terminated. Popliteal lymph nodes were dissected from mice, cleaned of any trace fat, mechanically dissociated and filtered through 70 micron cell strainers. Live lymphocytes were counted using a Moxi GO II cell counter (Orflo). One million lymphocytes were plated, treated with Fc block, and stained with antibodies targeting surface receptors (including CD45, CD3, CD4) along with a fixable live/dead dye. Cells were fixed/permeabilized (eBioscience Transcription Factor Staining kit) and stained with anti-Foxp3 antibody. The cells were collected via flow cytometry analysis on an Attune NxT instrument. T-regulatory cells were gated as lymphocyte-sized, live, CD45+ CD3+ CD4+ Foxp3+ cells.

As shown in FIG. 21, ATI-450 treatment in the murine CIA model significantly increased the number of regulatory T cells (TREGs). Given TREG cells known involvement in the suppressing the immune response and prevention of autoimmune disease, this data indicates the utility of ATI-450 for the treatment of autoimmune conditions, such as inflammatory bowel disease, systemic lupus nephritis (SLE), and others.

ATI-450 blocks Lipopolysaccharide (LPS) stimulated TNF-α, IL-1β and IL-6 production in Human Whole Blood. Venous blood from healthy human volunteers was collected in tubes containing sodium heparin and aliquoted (180 µL per well) into 96 well round-bottom tissue culture plates. Compounds were serially diluted in 100% DMSO (Sigma-Aldrich, D2650) followed by a 50× dilution into DMEM/110% FBS (Gibco, 11965/26140). The diluted compounds were then added to each plate in duplicate 10 µL aliquots for final concentrations as indicated in FIG. 22A. Vehicle consisted of DMSO at a final assay concentration of 0.1%. Pin tools (V&P Scientific, Inc., VP246) were placed in the wells and the plate was placed at 37° C. with 5% $CO_2$, with gently shaking for five minutes, then pin tools were removed and saved. After a one-hour incubation at 37° C. with 5% $CO_2$, 10 µL of LPS (Sigma-Aldrich, L2630), in DMEM/10% FBS (Gibco, 11965/26140) was added for a final concentration of 100 ng/mL to each well except for the no stimulus wells. Pin tools were placed in the wells in the same orientation as the previous step and gently shook for five minutes at 37° C. with 5% $CO_2$, then removed. After five hours of incubation with LPS at 37° C. with 5% $CO_2$, each reaction plate of blood was centrifuged at 1,800×g for five minutes. The plasma was harvested and assayed for TNF-α, IL-1β, and IL-6 using Meso Scale Discovery Technology V-plex human cytokine kits according to the kit protocol. The kit plates were read using an MSD Sector S 6000 instrument. Calculations to establish cytokine calibration curves and to determine analyte concentrations in the samples were carried out using the MSD DISCOVERY WORKBENCH® analysis software.

LPS stimulates Toll-like receptor 4 (TLR4) release of a number of pro-inflammatory cytokines. As show in FIG. 22A, ATI-450 potently inhibited LPS-stimulated IL-6, TNF-α, and IL-1β with $IC_{50}$ values of between 0.01-0.1 µM. While ATI-450 mediated inhibition of TLR4 stimulated cytokine release was expected given ATI-450's role MK2 inhibition, it was unknown whether ATI-450 would similarly block cytokine release triggered by other stimuli, such as TLR3 and TLR 7,8 activation.

ATI-450 Inhibited Poly(I:C) stimulated IP10, IFNγ, IL-6, IL-8 and TNF-α production in Human Whole Blood. Human whole blood assays were performed as described above with the exceptions listed below. Human whole blood was aliquoted (175 µL per well) into 96 well round-bottom tissue culture plates. Compounds were serially diluted in 100% DMSO (Sigma-Aldrich, D2650) followed by a 25× dilution into DMEM/10% FBS (Gibco, 11965/26140). The diluted compounds were then added to each plate in duplicate 5 µL aliquots for final concentrations as indicated in FIG. 22B. After the one-hour incubation with the compounds or vehicle, 20 µL of poly(I:C) (InvivoGen, HMW, tlrl-pic), in DPBS (Gibco, 14190-136) was added for a final concentration of 100 µg/mL to each well except for the no stimulus wells. After twenty-four hours of incubation with poly(I:C), plasma was harvested and assayed for IP10, IFNγ, IL-6, IL-8 and TNF-α using Meso Scale Discovery Technology V-plex human cytokine kits according to the kit protocol.

Poly(I:C) is a TLR3 agonist that induces the activation of the proinflammatory cytokines, IL-6, TNF-α, interferon-γ and the inflammatory chemokines, IL-8 and interferon-γ inducible protein (IP10). As shown in FIG. 22B, ATI-450 was able to potently inhibit in vitro TLR3 stimulated cytokines and chemokines with $IC_{50}$ values of between 0.01-0.1p M.

ATI-450 Inhibited R848 stimulated TNF-α, IL-1β, IL-6 and IL-8 production in Human Whole Blood. Human whole blood assays were performed as described above with the exceptions listed below. Human whole blood was aliquoted (200 µL per well) into 96 well round-bottom tissue culture plates. Compounds were serially diluted in 100% DMSO (Sigma-Aldrich, D2650) followed by a 10× dilution into RPMI (Gibco, 11875). The diluted compounds were then added to each plate in duplicate 2 µL aliquots for final concentrations as indicated in FIG. 22C. After the one-hour incubation with the compounds or vehicle, 2 µL of R848 (InvivoGen, tlrl-r848) in RPMI (Gibco, 11875) was added for a final concentration of 0.5 µg/mL to each well except for the no stimulus wells. After five hours of incubation with R848, plasma was harvested and assayed for TNF-α, IL-1β, IL-6 and IL-8 using Meso Scale Discovery Technology V-plex human cytokine kits according to the kit protocol.

R848 (resiquimod) is a potent agonist of TLR 7 and TLR8. TLR7 and TLR8 activation induces expression and activity of various inflammatory cytokines and chemokines including IL-6, IL-8, TNF-α, and IL-1β. As shown in FIG. 22C, ATI-450 was able to potently inhibit in vitro TLR7- and TLR8-stimulated cytokines and chemokines with $IC_{50}$ values of ~0.1 µM.

While ATI-450 mediated inhibition of TLR4 stimulated cytokine release was expected given ATI-450's role in MK2 inhibition of pro-inflammatory signaling pathways, it was unexpected that ATI-450 would similarly block cytokine release triggered by multiple other stimuli, such as TLR3 and TLR7 and TLR8 receptor activation. These data indicated that ATI-450 has therapeutic utility for the treatment of autoimmune disease and other disorder that have a strong anti-nuclear antibody drive, e.g., lupus, scleroderma, Sjogren's syndrome, juvenile arthritis, etc.

To further assess ATI-450 inhibition of various cellular cytokines, multiple cell types and various stimuli were tested as described below. The results of these studies are presented in Table 14 below.

U937 Cell differentiation and LPS stimulated cytokine assay: The U937 human pre-monocytic cell line (ATCC, CRL-1593.2) was grown in complete media: RPMI 1640 (Gibco, A10491) with penicillin-streptomycin (10 U/mL)-glutamine (2 mM) (Gibco, 10378016) and 10% FBS(Gibco, 26140-079). Cells were differentiated to a monocyte/macrophage phenotype with the addition of PMA (Sigma-Aldrich, P1585) (20 ng/mL, 24 hours), washed with DPBS (Gibco, 14190-136) and incubated in complete media for 24 hours at 37° C., 5% $CO_2$. Following recovery, the cells were scraped, counted, re-plated in complete media in accordance with the experimental design and incubated for an additional 24 hours at 37° C., 5% $CO_2$ prior to stimulation with LPS (Sigma-Aldrich, L2630) as described below.

Differentiated U937 cells were pretreated for one hour in the presence of serially diluted compound or vehicle then stimulated with LPS at a final concentration of 100 ng/mL for four hours. Culture media was then collected for determination of cytokine levels using Meso Scale Technology.

A549 IL-1β stimulated IL-6 Assay—A549 cells (American Type Culture Collection, ATCC CRL-1593.2) were grown in Ham's F-12K (Kaighn's) (Gibco, 21127-022) with penicillin-streptomycin (10 U/mL) (Gibco, 15140-122) and 10% fetal bovine serum (Gibco, 26140-079). Cells were grown to 80% confluence then trypsinized to remove cells. Cells were plated in 96 well flat bottom plates in complete media and allowed to recover overnight. Cells were pre-treated for one hour in the presence of serially diluted compound or vehicle (0.5% DMSO) (Sigma-Aldrich, D2650) then stimulated with IL-1β (1 ng/mL) (R&D Systems, 201-LB-005) for 18 hours. Culture media was then collected for determination of IL-6 levels using Meso Scale Technology.

Human PBMC LPS Stimulated IL-1β Assay—Frozen Human PBMC stocks were rapidly thawed, resuspended in DMEM/10% FBS (Gibco, 11965/26140), pelleted at 130×g for 5 minutes then resuspended in DMEM/10% FBS and plated at 200,000 cells per well (180 µl) in flat bottom 96 well plates. The cells were allowed to recover for several hours at 37° C. with 5% $CO_2$. Compounds were serially diluted in 100% DMSO (Sigma-Aldrich, D2650) followed by a 50× dilution into DMEM/10% FBS (Gibco, 11965/26140). The diluted compounds were then added to each plate in duplicate 10 µL aliquots. Vehicle consisted of DMSO at a final assay concentration of 0.1%. After a one-hour incubation at 37° C. with 5% $CO_2$, 10 µL of LPS (Sigma-Aldrich, L2630), in DMEM/10% FBS (Gibco, 11965/26140) was added for a final concentration of 100 ng/mL to each well except for the no stimulus wells. After twenty-four hours of incubation with LPS at 37° C. with 5% $CO_2$, each reaction plate of PBMC was centrifuged at 130×g for five minutes. The supernatant/conditioned media was harvested and assayed for IL-1β using Meso Scale Discovery Technology V-plex human cytokine kits according to the kit protocol.

Porcine LPS stimulated TNF-α Assay—Porcine whole blood was collected into heparinized vacutainers then transferred into conical tubes and shipped overnight on wet ice. Porcine whole blood was aliquoted (160 µL/well) into round bottom 96 well tissue culture plates. Compounds were serially diluted in 100% DMSO (Sigma-Aldrich, D2650) followed by a 100× dilution into RPMI/10% FBS (Gibco, 11875/26140). The diluted compounds were then added to each plate in duplicate 20 µL aliquots for final concentrations ranging from 10 µM to 1 µM. DMSO final concentration was 0.1%. After a one-hour incubation at 37° C. with 5% $CO_2$, 20 µL of LPS (Sigma-Aldrich, L2630), in RPMI/10% FBS (Gibco, 11875/26140) was added for a final concentration of 10 µg/mL to each well except for the no stimulus wells. After four hours of incubation with LPS, plasma was harvested by centrifugation at 1,800×g for five minutes. The plasmas were assayed for TNF-α levels using a porcine specific TNF-α Quantikine ELISA kit (R&D, PTA00) according to the kit protocol.

ATI-450 Inhibits IL-17 Production in vitro: To investigate whether ATI-450 mediated inhibition of the TLR2 pathway also plays a role in modulating IL-17 production, total CD4+ cells were isolated from human PBMCs using the CD4 StemCell Isolation Kit. CD4+ cells were cultured for 3 days under TH17 skewing conditions (anti-CD3, anti-CD28, anti-IL-4, anti-IFNγ, rIL-6, rIL-1β, rIL-23, rTGFβ). On day 3, cells were harvested, washed, re-plated, and treated with compound or DMSO only. After 1 hr incubation, cells were re-stimulated overnight with anti-CD3 dynabeads at a 1:1 cell:bead ratio. After 18-20 hours, supernatants were collected and assayed for IL-17A levels using MSD. As shown in FIG. 24, ATI-450 partially inhibits IL-17 production in CD4+ cells.

Inhibition of Il-17 has demonstrated utility in the treatment of psoriasis, psoriatic arthritis, and spondylitis. The observed partial inhibition of IL-17 by ATI-450 may also render ATI-450 particular suitable for the treatment of IBD,

TABLE 20

| | | $IC_{50}$ (nM, Mean ± Standard Deviation) | | |
|---|---|---|---|---|
| Cell System | Stimulant | TNF-α | IL-1α/β | IL-6 |
| U937 cells | LPS, 100 ng/mL, 4 hr | 1.55 ± 0.35 | | |
| A549 cells | IL-1β, 1 ng/mL, 18 hr | | | 11.1 ± 7.6 |
| hPBMC | LPS, 100 ng/mL, 24 hr | | 31.1 (IL-1α) | |
| mPMN | IL-1α, 10 ng/mL, 4 hr | 5.0 | | |
| Rat Whole Blood | LPS, 100 ng/mL, 4 hr | 14.3 ± 1.9 | | 28.3 ± 1.2 |
| Human Whole Blood | LPS, 100 ng/mL, 4 or 24 hr | 29.0 ± 9.0 | 6.1 (IL-1β) | 135 ± 97 |
| Human Whole Blood | IL-1β, 10 ng/mL, 5 hr | 12.2 ± 4.0 | | 11.1 ± 3.8 |
| Human Whole Blood | R848, 0.5 ug/mL, 5 hr | 34.8 ± 5.0 | 95.6 ± 34.8 (IL-1β) | 79.2 ± 17.2 |
| Human Whole Blood | Poly I:C, 100 ug/mL, 24 hr | 20.8 ± 12.8 | | 13.2 ± 12.8 |
| Pig Whole Blood | LPS, 10 mg/mL, 4 hr | 7.4 | | |

Example 10: ATI-450 Inhibits Cytokines Involved in Inflammatory Skin Conditions ATI-450 Inhibits TLR2 Stimulated Cytokine Signaling in vitro: Significant literature suggest that TLR2 agonists drive TH17 differentiation and suppress regulatory T cells (see e.g., Nyirenda et al., "TLR2 Stimulation Drives Human Naïve and Effector Regulatory T Cells into a Th17-Like Phenotype with Reduced Suppressive Function," *J Immunol.* 187(5):2278-90 (2021), which is hereby incorporated by reference in its entirety). To investigate whether ATI-450 mediated induction of Treg cells involved inhibition of TLR2 agonist signaling, the ability of ATI-450 to inhibit LPS or PAM3 (TLR2 agonist) TNF-α levels in vitro was examined. To this end, peripheral blood mononuclear cells were pre-incubated for 1 hour with ATI-450 at final concentrations of 10-10,000 nM (or DMSO to give a final of 0.1% in all wells). LPS or Pam3 were then added to the designated wells for a final concentration of 100 ng/mL for both (or medium for unstimulated control). After 30 min MSU was added to the designated wells for final concentration of 100 µg/mL (or medium for no-MSU control). After a 6-hour incubation, plates were centrifuged at 500×g for 5 min, and medium was collected from each well for assay.

Released TNF-α was measured using Meso Scale Discovery technology, an ELISA-like format with capture and detection antibodies, but with a final readout using electrochemiluminescence.

As shown in FIG. 23, ATI-450 dose dependently inhibits TLR2 ligand induced TNF-α production. As noted above TLR2 signaling drives TH17 cell differentiation.

where only partial IL-17 inhibition is thought to provide efficacy without exacerbating IBD.

ATI-450 Inhibits IL-1β stimulated TNF-α, IL-6 and IL-8 production in Human Whole Blood—Human whole blood assays were performed as described above with the exceptions listed below. Human whole blood was aliquoted (200 µL per well) into 96 well round-bottom tissue culture plates. Compounds were serially diluted in 100% DMSO (Sigma-Aldrich, D2650) followed by a 10× dilution into RPMI (Gibco, 11875). The diluted compounds were then added to each plate in duplicate 2 µL aliquots for final concentrations as indicated in FIG. 25. After the one-hour incubation with the compounds or vehicle, 2 µL of IL-1β (R&D, 201-LB-010) in RPMI (Gibco, 11875) was added for a final concentration of 0.5 µg/mL to each well except for the no stimulus wells. After six hours of incubation with IL-1β, plasma was harvested and assayed for TNF-α, IL-6 and IL-8 using Meso Scale Discovery Technology V-plex human cytokine kits according to the kit protocol.

As shown in FIG. 25, ATI-450 dose dependently inhibits IL-1β-stimulated TNF-α ($IC_{80}$ 31±6 ng/mL), IL-6 ($IC_{80}$ 41±20 ng/mL), and for IL-8 ($IC_{80}$ 40±12 ng/mL) in human whole blood.

ATI-450 Inhibits IL-1α biosynthesis and activity in human immune cells. Human PBMCs were pre-treated with ATI-450 for 1 hour, and then stimulated with LP for 24 hours. Biosynthesis of IL-1α was quantified using MSD technology. In a separate study, mouse neutrophils were isolated from CD-1 mouse bone marrow, plated, and rested for one hour prior to addition of various concentrations of ATI-450 which was added and incubated for 1 hour at 37° C. Cells and compound were stimulated with mouse IL-1α to a final concentration of 10 ng/mL and incubated for 4 hours at 37° C. Supernatants were collected and TNF-α levels quantitated using MSD technology.

As shown in FIG. 26A, ATI-450 dose dependently inhibited LPS induced IL-1α biosynthesis, with an $IC_{50}$ value of 31.1 nM. ATI-450 also dose dependently inhibits IL-1α mediated TNF-α signaling in neutrophils as shown in FIG. 26B.

Example 11: Formulations of ATI-450 Tablets

The compositions of the tablets comprising ATI-450 and tablets comprising placebo used in the Examples herein are provided in Table 21 below. The excipients used in the drug tables and their function are provided in Table 22 below.

TABLE 21

Composition of ATI-450 tablets

| Component | 10 mg Strength | | Placebo | | 50 mg Strength | | Placebo | |
|---|---|---|---|---|---|---|---|---|
| | % w/w | mg/tab | % w/w | mg/tab | % w/w | mg/tab | % w/w | mg/tab |
| ATI-450 | 12.5 | 10 | — | — | 12.5 | 50 | — | — |
| Silicified microcrystalline cellulose | 71 | 56.8 | 83.5 | 66.8 | 71 | 284 | 83.5 | 334 |
| Mannitol | 10 | 8 | 10 | 8 | 10 | 40 | 10 | 40 |
| Crospovidone | 5 | 4 | 5 | 4 | 5 | 20 | 5 | 20 |
| Hydrophilic fumed silica | 0.75 | 0.6 | 0.75 | 0.6 | 0.75 | 3 | 0.75 | 3 |
| Magnesium stearate | 0.75 | 0.6 | 0.75 | 0.6 | 0.75 | 3 | 0.75 | 3 |
| Total | 100 | 80 | 100 | 80 | 100 | 400 | 100 | 400 |

TABLE 22

Excipients in Tablets Comprising ATI-450

| Excipient | Chemical Name | Function | Quality Standard |
|---|---|---|---|
| ProSolv HD 90 | Silicified microcrystalline cellulose | Filler/Binder | NF/EP/JP |
| Perlitol 200 SD | Mannitol | Diluent | USP/EP |
| Polyplasdone XL | Crospovidone | Disintegrant | NF/EP/JP |
| Aerosil 200 | Colloidal silicone dioxide | Glidant | NF/EP/JP |
| Magnesium stearate | Magnesium stearate | Lubricant | NF/EP/JP |

Example 12: Separation of Compound (P)-I

Racemic 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (250 mg, 0.49 mmol) may be prepared according to the methods described in U.S. Pat. No. 9,115,089, which is hereby incorporated by reference in its entirety. Chiral resolution of 3-chloro-4-((3,5-difluoropyridin-2-yl)methoxy)-2'-(2-(2-hydroxypropan-2-yl)pyrimidin-4-yl)-5', 6-dimethyl-2H-[1,4'-bipyridin]-2-one to obtain the P atropisomer, i.e., Compound (P)-I as disclosed herein, is carried out as described below.

Racemic 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (250 mg, 0.49 mmol) was separated using supercritical fluid chromatography (Thar 80, preparative SFC, ChiralCel OD-H, 250×30 mm ID column) with a mobile phase of carbon dioxide and ethanol. The separation method used an isocratic method of 40% ethanol with a flow rate of 50 mL/min and a cycle time of 10 min. Optical rotation was determined using a WZZ-2S polarimeter.

The faster isomer ((P)-I) eluted at 1.77 minutes yielded 115 mg of (−)-3-chloro-4-((3,5-difluoropyridin-2-yl)methoxy)-2'-(2-(2-hydroxypropan-2-yl)pyrimidin-4-yl)-5', 6-dimethyl-2H-[1,4'-bipyridin]-2-one in ethylene glycol: $[\alpha]_D^{20}$ −46° ($CH_3OH$); $^1H$ NMR (400 MHz, DMSO-$d_6$) δ ppm 8.97 (d, J=5.09 Hz, 1H), 8.86 (s, 1H), 8.69 (s, 1H), 8.61 (s, 1H), 8.24 (d, J=5.08 Hz, 1H), 8.10 (t, 1H), 6.85 (s, 1H), 5.50 (s, 2H), 5.26 (s, 1H), 2.11 (s, 3H), 1.98 (s, 3H), 1.54 (s, 3H), 1.52 (s, 3H); MS (ES) m/e 514 (M+H).

The slower isomer ((M)-I) eluted at 3.68 minutes yielded 112 mg of (+)-3-chloro-4-((3,5-difluoropyridin-2-yl)methoxy)-2'-(2-(2-hydroxypropan-2-yl)pyrimidin-4-yl)-5', 6-dimethyl-2H-[1,4'-bipyridin]-2-one in ethylene glycol: $[\alpha]_D^{20}$ +45° ($CH_3OH$); $^1H$ NMR (400 MHz, DMSO-$d_6$) δ ppm 8.97 (d, J=5.09 Hz, 1H), 8.86 (s, 1H), 8.69 (s, 1H), 8.61 (s, 1H), 8.24 (d, J=5.08 Hz, 1H), 8.10 (t, 1H), 6.85 (s, 1H), 5.50 (s, 2H), 5.26 (s, 1H), 2.11 (s, 3H), 1.98 (s, 3H), 1.54 (s, 3H), 1.52 (s, 3H); MS (ES) m/e 514 (M+H).

Example 13: Crystal Form Screen of Compound (P)-I

The crystal-form screening study involved a total of 48 neat and binary solvent systems which addressed the moderate solubility of the input material and provided a diverse set of polarities, dielectric constants, dipole moments, and hydrogen-bond donor/acceptor attributes. Water-containing solvents with a variety of water activities ($a_w$)[1] were also included to probe for the formation of hydrates. Temperatures ranging between 40° C. to −20° C.

The screening studies were comprised of the following crystallization modes:

Temperature-cycled ripening of API slurries between 5-40° C. for four days (TC)

Rapid cooling clarified saturated solutions from 40 to −20° C. and holding at −20° C. for three days (RC)

Slow evaporation of clarified solutions at RT over 14 days.

Rapid evaporation of solvents under reduced pressure from solutions that did not produce solids during slow evaporation after 14 days (EV).

A summary of the outcomes of the screening study are shown in Table 23.

TABLE 23

Results of the Crystal Form Screen

| # | Solvent | TC | RC | EV | Water Activity |
|---|---|---|---|---|---|
| 1 | Water | Form A | | | 1.00 |
| 2 | Methanol | | | Form A | |
| 3 | 2-Methoxyethanol:Isopropyl ether (20:80) | Form A | | Form A | |
| 4 | 1-Propanol | | | Form A | |
| 5 | Nitromethane | Form A | Form A | Form A | |
| 6 | Acetonitrile | Form A | Form A | Form A | |
| 7 | DMSO:t-butyl methyl ether (20:80) | | | Form A | |
| 8 | Acetone | | | Form A | |
| 9 | 2-Butanone | | | Form A | |
| 10 | Dichloromethane | | | Form A | |
| 11 | Methyl acetate:Heptane (20:80) | Form A | | | |
| 12 | 4-Methyl-2-pentanone | Form A | | Form A | |
| 13 | Chloroform | | | | |
| 14 | Ethyl acetate | | | Form A | |
| 15 | Chlorobenzene:Cyclohexane (20:80) | Form A | | | |
| 16 | Tetrahydrofuran | | | Form A | |
| 17 | 1,4-Dioxane | | | Form A | |
| 18 | Isopropyl ether | Form A | | | |
| 19 | Toluene | Form A | | Form A | |
| 20 | Cyclohexane | Form A | | | |
| 21 | Heptane | Form A | | | |
| 22 | 1-Butanol | Form A | | | |
| 23 | 2-Propanol | Form A | | Form A | |
| 24 | Trifluoroethanol:Isopropyl ether (20:80) | Form A | | | |
| 25 | Dimethyl carbonate | Form A | | Form A | |
| 26 | t-Butyl methyl ether | Form A | | | |
| 27 | Isopropyl acetate | Form A | | Form A | |
| 28 | Ethanol | | | Form A | |
| 29 | 1-Methoxy-2-propanol:Isopropyl ether (20:80) | Form A | | | |
| 30 | Cyclohexanone | | | | |
| 31 | N,N-Dimethylformamide:Water (20:80) | Form A | | | 0.95 |
| 32 | 2-Methoxyethyl ether:Heptane (20:80) | Form A | | | |
| 33 | Methanol:Water (95:5) | Form A | | Form A | 0.20 |
| 34 | Acetonitrile:Water (95:5) | Form A | | | 0.94 |
| 35 | Acetone:Water (20:80) | Form A | | Form A | 0.96 |
| 36 | Tetrahydrofuran::Water (20:80) | Form A | | Form A | 0.82 |
| 37 | 2-propanol:Water (95:5) | Form A | | Form A | 0.55 |
| 38 | Methanol:Water (90:10) | Form A | Form A | Form A | 0.33 |
| 39 | Acetonitrile:Water (90:10) | Form A | | Form A | 0.76 |
| 40 | Acetone:Water (90:10) | | | Form A | 0.70 |
| 41 | Tetrahydrofuran:Water (90:10) | | | Form A | 0.83 |
| 42 | 1,4-Dioxane:Water (90:10) | | | Form A | 0.70 |
| 43 | 2-propanol:Water (90:10) | | Form A | Form A | 0.65 |
| 44 | Acetone:Water (80:20) | | Form A | Form A | 0.77 |
| 45 | Ethanol:Water (20:80) | Form A | | | 0.93 |
| 46 | Ethyl acetate:cyclohexane (20:80) | Form A | | | |
| 47 | Acetonitrile:isopropyl ethyl ether (20:80) | Form A | | | |
| 48 | 4-Methyl-2-pentanone:heptane (20:80) | Form A | | | |

Example 14: Single Crystal Structure Determination of Compound (P)-I (Form A)

The crystalline form of Compound (P)-I has been characterized relative to the absolute stereochemical configuration of the spatial arrangement of the atoms using single crystal X-ray diffraction. A detailed description of structure determination by X-ray diffraction is provided in Stout & Jensen, X-Ray Structure Determination: A Practical Guide, Macmillan Co., New York (1968), Chapter 3, which is herein incorporated by reference. Alternatively, the unique spatial arrangements of atoms in three dimensions within the crystalline lattice may be characterized by X-ray powder diffraction analysis. A detailed description of X-ray powder diffraction is provided in Cullity, B. D. Elements of X-ray Diffraction. Addison-Wesley, (1978) ISBN 0-201-01174-3 Chapter 14), which is herein incorporated by reference. PXRD data consists of experimentally determined values of the two-theta position, the intensity values of multiple crystallographic reflections, also known as Bragg reflections, and their peak shape. The PXRD data may be analyzed computational, including by the method of Rietveld refinement. A detailed description of Rietveld refinement of X-ray powder diffraction data is provided in Pecharsky, Vitalij K.; Zavalij, Peter Y. (2009) Fundamentals of powder diffraction and structural characterization of materials (2nd ed.). New York: Springer. ISBN 978-0-387-09579-0. OCLC 314182615, which is herein incorporated by reference.

PXRD data may be collected at various temperatures or pressures in order to facilitate Rietveld refinement. The experimental PXRD data including 2-theta values, d-spacing, Bragg reflections and intensity values may be compared to a simulated PXRD pattern derived from the single crystal structure determination which represents an idealized pure powder, using a computational method such as described in Macrae, Clare F., et al. "Mercury 4.0: from visualization to analysis, design and prediction." Journal of Applied Crystallography vol. 53, 226-235. 1 Feb. 2020, doi:10.1107/516005767 19014092.

One of ordinary skill in the art will appreciate that an X-ray powder diffraction pattern may be obtained with a measurement error that is dependent upon the measurement conditions employed in the data collection. It is generally accepted that the peak shape, intensity values and two-theta positions derived from an X-ray powder diffraction pattern can fluctuate depending upon the type of instrument used, the measurement conditions and the method of computational analysis performed. It should be further understood that that the two-theta values and their relative intensities may also vary and accordingly, the exact order of intensity values should not be taken into account.

Additionally, the experimental error for diffraction angle measurements for a conventional X-ray powder diffraction pattern is typically about 5% or less. Assessment of the extent of measurement error should be taken into account when describing the position of the two-theta diffraction peaks. Consequently, it is to be understood that the crystal forms described in this invention are not limited to the crystal forms that provide X-ray powder diffraction patterns completely identical to the X-ray powder diffraction patterns depicted in the FIG. 27 disclosed herein. Any crystal forms that provide X-ray powder diffraction patterns substantially identical to those disclosed in the accompanying Figures fall within the scope of the present invention. The ability to ascertain substantial identities of X-ray diffraction patterns is within the purview of one of ordinary skill in the art. Likewise, it is to be understood that any crystal forms that provide differential scanning calorimetry (DSC) and/or thermogravimetric analysis (TGA) substantially identical to those disclosed in the accompanying FIG. 28 fall within the scope of the present invention. The ability to ascertain substantial identities of these patterns is within the purview of one of ordinary skill in the art.

Crystalline Form A of Compound (P)-I is anhydrous and was obtained from crystallization conditions described in Example 13 utilizing various organic solvents and organic/water solvent systems.

X-Ray Powder Diffraction (PXRD) diffractograms were acquired on PANalytical X'Pert Pro diffractometer using Ni-filtered Cu Kα (45 kV/40 mA) radiation and a step size of 0.02° 2θ and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers.

Values of significant Bragg reflections, their 2-theta positions and d-spacing values, as compared to results from simulated PXRD data of crystalline Form A of Compound (P)-I are shown in Table 24 as derived from the PXRD spectrum, shown in FIG. 27.

TABLE 24

Experimental and simulated PXRD data

| Experimental PXRD | | Simulated PXRD | | | |
|---|---|---|---|---|---|
| 2-Theta Angles (°) | d (Å) | Bragg Reflections | | | 2-Theta Angles (°) | d (Å) |
| | | h | k | l | | |
| 5.21 | 16.946 | 0 | 0 | 1 | 5.20 | 17.2385 |
| 9.78 | 9.0362 | 0 | 1 | 0 | 9.80 | 8.99183 |
| 10.27 | 8.6059 | 0 | 1 | 1 | 10.26 | 8.48713 |
| 13.00 | 6.8073 | 0 | 1 | 2 | 13.16 | 6.92863 |
| 15.34 | 5.7705 | 0 | 1 | -2 | 15.22 | 5.81934 |
| 15.51 | 5.7099 | 0 | 0 | 3 | 15.41 | 5.74618 |
| 16.92 | 5.2351 | 0 | 1 | 3 | 17.07 | 5.33869 |
| 17.92 | 4.9473 | 1 | 1 | -2 | 17.91 | 4.94901 |
| 18.86 | 4.7017 | 1 | -1 | 1 | 18.85 | 4.70444 |
| 19.60 | 4.5254 | 0 | 2 | 1 | 19.66 | 4.58616 |
| 20.57 | 4.3147 | 1 | -1 | -2 | 20.65 | 4.30016 |
| 21.01 | 4.2259 | 0 | 2 | 2 | 20.92 | 4.24356 |
| 23.60 | 3.7675 | 0 | 2 | -2 | 23.58 | 3.77065 |
| 24.29 | 3.6608 | 0 | 1 | 4 | 24.13 | 3.65807 |
| 25.92 | 3.4341 | 2 | 2 | 2 | 25.70 | 3.46431 |
| 29.05 | 3.0712 | 1 | -1 | 2 | 29.19 | 3.0598 |
| 29.48 | 3.0275 | 0 | 3 | 1 | 29.48 | 3.02715 |

Differential Scanning Calorimetry (DSC) was conducted with a TA Instruments Q100 differential scanning calorimeter equipped with an auto sampler and a refrigerated cooling system under 40 mL/min N2 purge. DSC thermograms were obtained at 15° C./min in crimped Al pans. FIG. 28 depicts one such thermogram (bottom trace), obtained from a sample of (P)-I.

Thermogravimetric Analysis (TGA) thermograms were obtained with a TA Instruments Q500 thermogravimetric analyzer under 40 mL/min N2 purge at 15° C./min in Pt or Al pans.

DSC analysis, depicted in FIG. 28 (top trace) indicates crystalline Form A of Compound (P)-I exhibits a melting/racemization event at 187.92° C., followed by a recrystallization event at 195.8° C., and finally a sharp endotherm at 253.5° C. (melt of racemate). Negligible weight loss (0.7%) is observed between 25° C. and 256° C. by TGA.

Fourier Transform Infrared Spectroscopy (FT-IR): Characteristic spectral absorbance data from FT-JR of Form A of Compound (P)-I showing the location of significant IR-active regions and their functional group assignments is shown in Table 25.

TABLE 25

FT-IR Absorbance Data

| Wavenumber (cm-1) | Functional Group Assignment |
|---|---|
| 3486 | —OH stretch |
| 3072 | C—H (aromatic) stretch |
| 2982 | C—H (CH3) stretch |
| 1656 | C=O stretch |
| 1605 | C=N stretch |
| 1592 | C=N stretch |
| 1571 | C=C stretch |
| 1546 | C=N stretch |
| 1525 | C=C stretch |
| 1476 | C—H (CH2) bend |
| 1457 | CH2 scissor |
| 1429 | C—H (CH3) bend |
| 1385 | C—H (gem dimethyl) bend |
| 1380 | —O—H bend |
| 1350 | C—N(pyridone) stretch |
| 1296 | C—F stretch |
| 1237 | C—O (conjugated, alkyl ether) stretch |
| 1214 | C—H (aromatic) bend |
| 1184 | C—O (tertiary alcohol) stretch |
| 1130 | C—F stretch |
| 1103 | C—H (aromatic) bend |
| 1051 | C—F stretch |
| 1044 | C—F stretch |
| 1005 | C—H (aromatic) bend |
| 978 | C—H (aromatic) bend |
| 964 | C—H (aromatic) bend |
| 860 | C—H (aromatic) bend |
| 840 | C—H (aromatic) bend |
| 810 | C—H (aromatic) bend |
| 793 | C—H (aromatic) bend |
| 781 | C—H (aromatic) bend |
| 755 | C—Cl stretch |
| 741 | C—H (aromatic) bend |
| 703 | C—H (aromatic) bend |
| 669 | N—C=O bend |

Example 15: p38 Inhibitory Potency and p38/MK2 Substrate Selectivity of Compound (P)-I Inhibition of MK2 and PRAK by Compound (P)-I and (M)-I, respectively, was investigated to understand selectivity of Compound (P)-I and/or Compound (M)-I in reducing inflammatory response. Compound (P)-I and (M)-I were evaluated in enzyme assays that compared inhibitor potency in blocking p38/MK2 versus p38/PRAK-induced phosphorylation of an HSP-27-derived peptide substrate. The ability of Compound (P)-I and (M)-I to inhibit activated phospho-p38α was evaluated using a p38α/MK2 and a p38α/PRAK cascade assay format. The kinase activity of p38α was determined by its ability to phosphorylate GST-MK2 or GST-PRAK. Activation of MK2 or PRAK by p38α was quantitated by measuring the phosphorylation of a fluorescently-labeled, MK2/PRAK specific peptide substrate, Hsp27 peptide. The phosphorylation of the Hsp27 peptide was quantified using IMAP technology (Molecular Devices, Sunnyvale CA). Kinase reactions were carried out in a 384-well plate (Greiner, 781280) in 20 mM HEPES pH 7.5, 10 mM MgCl$_2$, 0.01% Triton X-100, 0.01% BSA, 1 mM DTT, and 2% DMSO. The concentration of inhibitor in the assays was varied between 0.02 nM to 30,000 nM, while the Hsp27 peptide substrate and MgATP were held constant at 1 μM and 10 μM, respectively. Activated p38α was added to a final concentration of 30 μM for reactions with non-phosphorylated 1 nM GST-MK2 in the cascade reaction. For the p38α/PRAK cascade, the concentration of non-activated GST-PRAK was held constant at 10 nM while p38α was added to a final concentration of 200 μM. Kinase reactions were incubated at room temperature and quenched after 120 minutes by the addition of IMAP Binding Solution. Under these conditions, approximately 20% of the substrate Hsp27 peptide was phosphorylated. Reactions were initiated by the addition of activated p38α except for pre-incubation experiments, where reactions were initiated by the addition of Hsp27 peptide and MgATP. Pre-incubation of p38α with inhibitor or p38α with non-activated GST-MK2 or non-activated GST-PRAK and inhibitor were performed at 2× final assay concentrations at room temperature 240 minutes prior to adding ATP and Hsp27 peptide to initiate catalysis. The inhibitory potency of Compounds (P)-I and (M)-I was quantitated from dose-response $IC_{50}$ values or $K_i$ values from p38α/MK2 cascade assays while the substrate selectivity was calculated as a ratio of p38α/PRAK:p38α/MK2 $IC_{50}$ values.

Compound (P)-I and Compound (M)-I were tested in accordance with the above described assay, yielding $IC_{50}$ values described in Table 26 below:

TABLE 26

| Compound | Structure | p38/MK2 $IC_{50}$ (μM) | p38/PRAK $IC_{50}$ (μM) | Selectivity Ratio |
| --- | --- | --- | --- | --- |
| (P)-I | 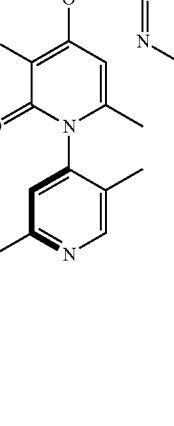 | 0.021 | 8.1 | 385× |
| (M)-I | 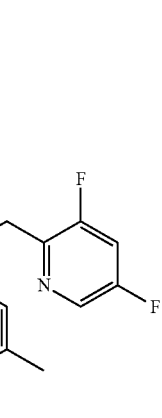 | 3.48 | 12.5 | 3.6 |

Example 16: Cytokine Regulation in Human Monocytes by Compound (P)-I

The p38 pathway has been shown to be critical for the biosynthesis of a number of pro-inflammatory cytokines including TNFα, IL-1β and IL-6. Therefore, inhibition of the p38 MAP Kinase pathway will lower the inflammatory response by decreasing biosynthesis of pro-inflammatory cytokines. This study shows the amount of Compound (P)-I and Compound (M)-I necessary to inhibit biosynthesis of TNFα, IL-6, and IL-1β (pro-inflammatory cytokines) by half, demonstrating the effectiveness of each compound in reducing inflammation. Evaluation of the potency and efficacy of Compound (P)-I and Compound (M)-I to block cytokine production were carried out using the human U937 cell line. The U937 human pre-monocytic cell line was obtained from the American Type Culture Collection (Rockville, MD). These cells were differentiated to a monocytic/macrophage phenotype as described by Burnette (Burnette et al, (2009). SD0006: a potent, selective and orally available inhibitor of p38 MAP Kinase, Pharmacology 84(1):42-60). Differentiated U937 cells (human peripheral blood mononuclear cells (hPBMC)) were seeded into 96-well tissue culture plates (200,000 cells/well) in complete media. After 24 hours, the cells were pretreated for 60 minutes in the presence or absence of Compound (P)-I and Compound (M)-I and then stimulated with LPS (0.1 µg/mL) for 4 hours. Culture media was then collected for determination of TNFα, IL-6 or IL-1β levels by ELISA. Cytokine concentrations were extrapolated from recombinant protein standard curves using a four-parameter logistic model and solving for $IC_{50}$ after iterating to the best least-squares fit.

Both atropisomers of ATI-450 (Compounds (M)-I and (P)-I) were tested in accordance with the above described assay, yielding $IC_{50}$ values described in Table 27 below:

TABLE 27

| Compound | hPBMC TNFα $IC_{50}$ (µM) | hPBMC IL-1β $IC_{50}$ (µM) | hPBMC IL-6 $IC_{50}$ (µM) |
|---|---|---|---|
| (P)-ATI-450 | 0.004 | 0.012 | 0.145 |
| (M)-ATI-450 | >10,000 | >10,000 | >10,000 |

Although embodiments herein have been described in considerable detail with reference to certain preferred embodiments thereof, other versions are possible. Therefore, the spirit and scope of the appended claims should not be limited to the description and the preferred versions contained within this specification.

The invention claimed is:

1. A method for treating p38 MAPK associated cancer, said method comprising:
administering, to a human subject having a p38 MAPK mediated cancer, an oral dose of 5 mg/day to 300 mg/day of Compound I

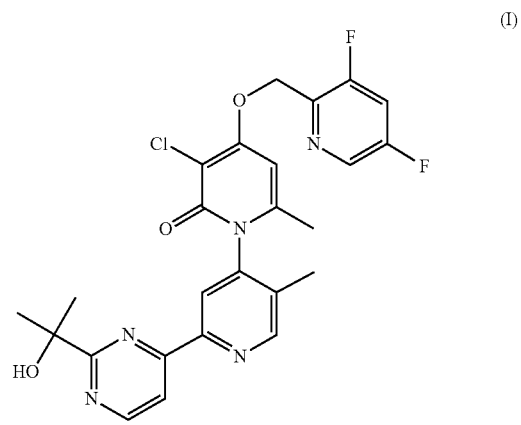 [SMILES: Cc1cnc(-c2ccnc(C(C)(C)O)n2)cc1-n1c(C)cc(OCc2ncc(F)cc2F)c(Cl)c1=O]

(I)

or a pharmaceutically acceptable salt thereof to treat said p38 MAPK mediated cancer;
wherein Compound I comprises Compound (P)-I and Compound (M)-I;
wherein Compound (P)-I is crystalline Form A characterized by an PXRD pattern having
a peak expressed in degrees 2θ at about 9.78±0.2 and wherein said p38 MAPK mediated cancer is treated.

2. The method of claim 1, wherein Compound I comprises the Compound (P)-I

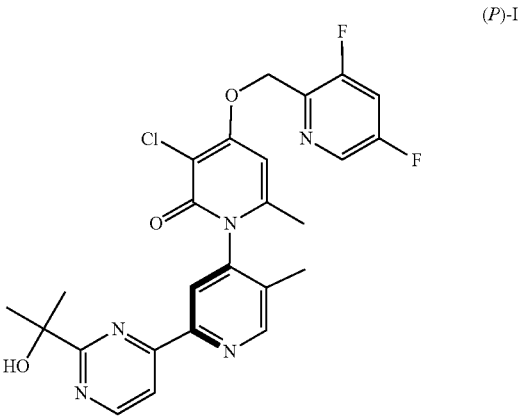

(P)-I and the Compound (M)-I

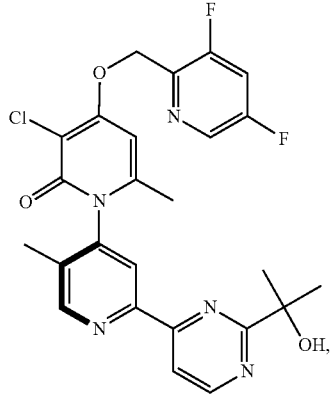

(M)-I in a molar ratio of (P)-I to (M)-I of about 4:1.

3. The method of claim 1, wherein Compound I comprises Compound (P)-I substantially free of Compound (M)-I.

4. The method of claim 1, wherein Compound I is a free base.

5. The method of claim 1, wherein Compound I is administered twice daily.

6. The method of claim 1, wherein the p38 MAPK mediated cancer is selected from bone cancer, breast cancer, metastatic breast cancer, and pancreatic cancer.

7. The method of claim 6, wherein breast cancer is metastatic breast cancer.

8. The method of claim 1, wherein the method further comprises administering one or more additional therapeutic agents in conjunction with Compound I.

9. The method of claim 8, wherein the one or more additional therapeutic agents is selected from the group consisting of an anti-inflammatory drug, an immunosuppressive drug, an immunomodulatory drug, an immunotherapeutic agent, a cytostatic drug, an angiogenesis inhibitor, a kinase inhibitor, a cytokine blocker, an inhibitor of cell adhesion molecules, a chemotherapeutic agent, alkylating agents, anti-metabolites, plant alkaloids and terpenoids, topoisomerase inhibitors, cytotoxic antibiotics, angiogenesis inhibitors, tyrosine kinase inhibitors, and immune checkpoint inhibitors.

10. The method of claim 8, wherein the one or more additional therapeutic agents is selected from the group consisting of cisplatin, carboplatin, oxaliplatin, streptozocin, busulfan, cyclophosphamide, mercaptopurine, thioguanine, pentostatin, cytosine arabinoside, gemcitabine, fluorouracil, leucovorin, methotrexate, vincristine, vinblastine, paclitaxel, irinotecan, topotecan, etoposide, actinomycin D, doxorubicin, bleomycin, mitomycin, sunitinib, bevacizumab, imatinib, erlotinib, lapatininb, axitinib, atezolizumab, avelumab, durvalumab, ipilimumab, pembrolizumab, nivolumab, and tremelimumab.

11. The method of claim 1, wherein Compound I is formulated as a solid dosage form selected from a tablet, a capsule, a lozenge, a sachet, a powder, granules, and orally dispersible film.

12. The method of claim 11, wherein the solid dosage form is a tablet.

13. A method for treating bone cancer in a human subject in need thereof comprising administering to the human subject an oral dose of 5 mg/day to 300 mg/day of Compound I

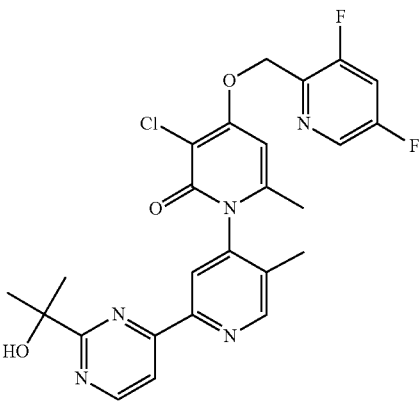

(I)

or a pharmaceutically acceptable salt thereof, wherein Compound I comprises crystalline Form A of Compound (P)-I characterized by an PXRD pattern having a peak expressed in degrees 2θ at about 9.78±0.2, wherein the bone cancer in the human subject is treated.

14. The method of claim 13, wherein Compound I comprises the Compound (P)-I

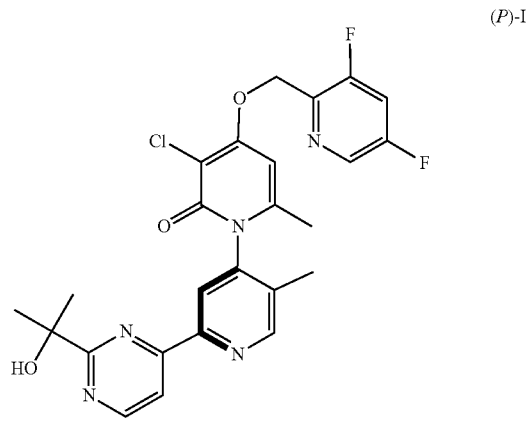

(P)-I and the Compound (M)-I

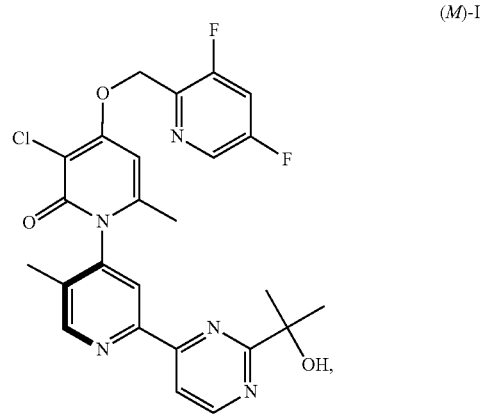

(M)-I in a molar ratio of (P)-I to (M)-I of about 4:1.

15. The method of claim 13, wherein Compound I is administered twice daily.

16. A method for treating breast cancer in a human subject in need thereof comprising administering to the human subject an oral dose of 5 mg/day to 300 mg/day of Compound I

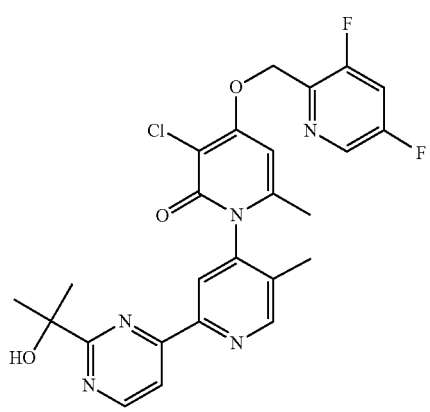

(I)

or a pharmaceutically acceptable salt thereof, wherein Compound I comprises crystalline Form A of Compound (P)-I characterized by an PXRD pattern having a peak expressed in degrees 2θ at about 9.78±0.2, wherein the breast cancer in the human subject is treated.

17. The method of claim 16, wherein Compound I comprises the Compound (P)-I

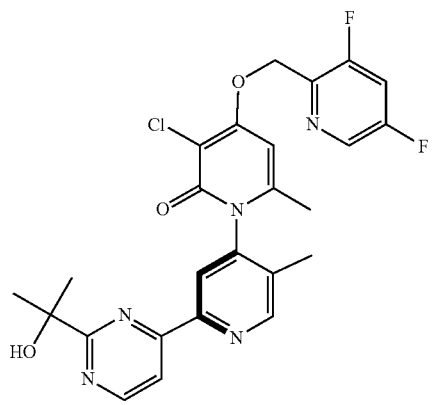

(P)-I and the Compound (M)-I

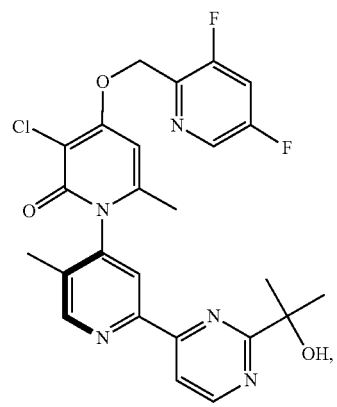

(M)-I in a molar ratio of (P)-I to (M)-I of about 4:1.

18. The method of claim 16, wherein Compound I comprises Compound (P)-I substantially free of Compound (M)-I.

19. The method of claim 16, wherein Compound I is administered twice daily.

20. The method of claim 16, wherein the breast cancer is metastatic breast cancer.

21. A method for treating pancreatic cancer in a human subject in need thereof comprising administering to the human subject an oral dose of 5 mg/day to 300 mg/day of Compound I

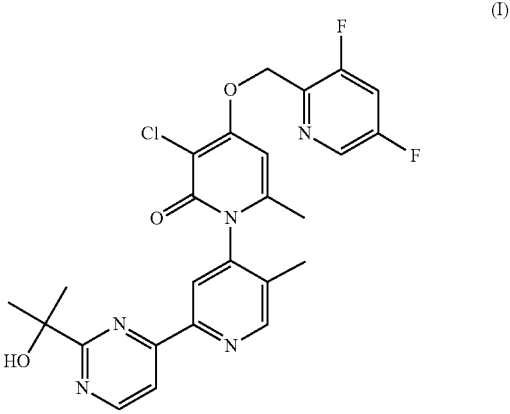 [SMILES: Cc1cnc(-c2ccnc(C(C)(C)O)n2)cc1-n1c(C)cc(OCc2ncc(F)cc2F)c(Cl)c1=O]

(I)

or a pharmaceutically acceptable salt thereof, wherein Compound I comprises crystalline Form A of Compound (P)-I characterized by an PXRD pattern having a peak expressed in degrees 2θ at about 9.78±0.2, wherein the pancreatic cancer in the human subject is treated.

22. The method of claim 21, wherein Compound I comprises the Compound (P)-I
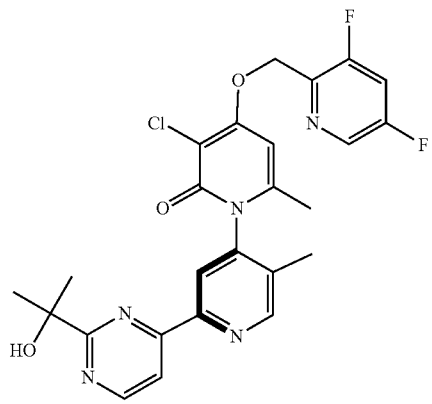
(P)-I
and the Compound (M)-I
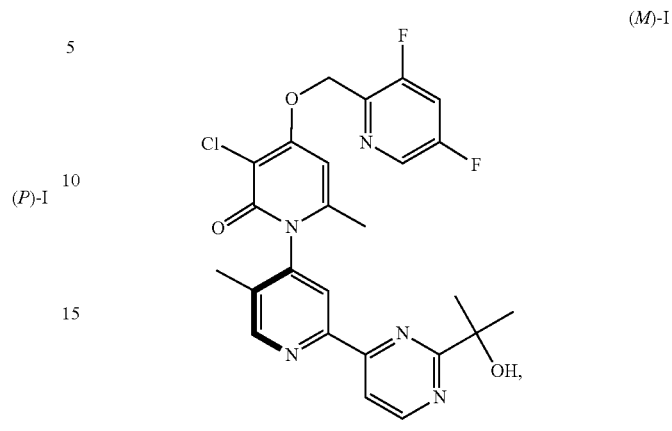
(M)-I
in a molar ratio of (P)-I to (M)-I of about 4:1.
23. The method of claim 21, wherein Compound I comprises Compound (P)-I substantially free of Compound (M)-I.
24. The method of claim 21, wherein Compound I is administered twice daily.
* * * * *